US010683311B2

(12) United States Patent
Dufour et al.

(10) Patent No.: US 10,683,311 B2
(45) Date of Patent: Jun. 16, 2020

(54) TRISUBSTITUTEDSILYLPHENOXY-HETEROCYCLES AND ANALOGUES

(71) Applicant: Bayer CropScience Aktiengesellschaft, Monheim am Rhein (DE)

(72) Inventors: Jérémy Dufour, Lyons (FR); Philippe Desbordes, Lyons (FR); Christophe Dubost, La tour de Salvagny (FR); Mathieu Gourgues, Lyons (FR); Ruth Meissner, Leverkusen (DE); Andrew Pettinger, Lyons (FR); Philippe Rinolfi, Chatillon d Azergues (FR); Valérie Toquin, Saint-Romain-au-Mont-d'Or (FR); Ulrike Wachendorff-Neumann, Neuwied (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 15/771,846

(22) PCT Filed: Oct. 28, 2016

(86) PCT No.: PCT/EP2016/076048
§ 371 (c)(1),
(2) Date: Apr. 27, 2018

(87) PCT Pub. No.: WO2017/072283
PCT Pub. Date: May 4, 2017

(65) Prior Publication Data
US 2019/0233444 A1 Aug. 1, 2019

(30) Foreign Application Priority Data
Oct. 29, 2015 (EP) ..................................... 15290278

(51) Int. Cl.
*C07D 215/38* (2006.01)
*C07F 7/08* (2006.01)
*C07D 471/04* (2006.01)
*C07D 495/04* (2006.01)
*C07D 241/44* (2006.01)
*C07D 215/20* (2006.01)
*C07D 401/12* (2006.01)
*C07D 487/04* (2006.01)
*C07D 241/42* (2006.01)
*A61P 31/00* (2006.01)
*C07D 241/18* (2006.01)
*C07D 413/12* (2006.01)
*C07F 7/18* (2006.01)

(52) U.S. Cl.
CPC ............ *C07F 7/0812* (2013.01); *A61P 31/00* (2018.01); *C07D 215/20* (2013.01); *C07D 215/38* (2013.01); *C07D 241/18* (2013.01); *C07D 241/42* (2013.01); *C07D 241/44* (2013.01); *C07D 401/12* (2013.01); *C07D 413/12* (2013.01); *C07D 471/04* (2013.01); *C07D 487/04* (2013.01); *C07D 495/04* (2013.01); *C07F 7/0816* (2013.01); *C07F 7/18* (2013.01)

(58) Field of Classification Search
CPC . C07D 413/12; C07D 241/218; C07F 7/0812; C07F 7/18
USPC ......................................................... 514/63
See application file for complete search history.

(56) References Cited

U.S. PATENT DOCUMENTS

2012/0165369 A1  7/2012  Ablordeppey

FOREIGN PATENT DOCUMENTS

| EP | 0326330 A2 | 8/1989 |
|---|---|---|
| EP | 0410762 A1 | 1/1991 |
| EP | 2657225 A2 | 12/2011 |
| JP | 2014166991 A | 9/2014 |
| WO | 03080580 A2 | 10/2003 |
| WO | 2007072093 A1 | 7/2007 |
| WO | 2008116831 A1 | 10/2008 |
| WO | 2008155588 A1 | 12/2008 |
| WO | 2009019286 A1 | 2/2009 |
| WO | 2014065710 A1 | 5/2014 |

OTHER PUBLICATIONS

International Search Report dated Dec. 19, 2016, issued in counterpart international application No. PCT/EP2016/076048.
Database Registry; Chemical Abstract [Online] (May 25, 2001), "Quinoline, 3-(2-cholorophenoxy)-2-(4-cholorophenyl)-" XP002752899, retrieved from Registry Database access No. 338400-85-4.
Database Registry; Chemical Abstract [Online] (Dec. 31, 2002), "4-Quinolinecarboxylic acid, 3-(2-chlorophenoxy)-2-(4-chlorophenyl)-", XP002752900, retrieved from Registry Database accession No. 477886-56-9.
Database Registry; Chemical Abstract [Online] (Mar. 16, 2011), "Quinolinium, 3-[(2-chlorophenyl)amino]-1-methyl-", XP002752901, retrieved from Registry Database accession No. 1268668-17-2.

(Continued)

*Primary Examiner* — Kahsay Habte
(74) *Attorney, Agent, or Firm* — McBee Moore & Vanik, IP LLC

(57) ABSTRACT

The present disclosure relates to fungicidal active compounds, more specifically to trisubstitutedsilylphenoxyhetero-cycles and analogues thereof, processes and, intermediates for their preparation and use thereof as fungicidal active compound, particularly in the form of fungicide compositions. The present disclosure also relates to methods for the control of phytopathogenic fungi of plants using these compounds or compositions comprising thereof.

18 Claims, No Drawings

(56) References Cited

OTHER PUBLICATIONS

Database Registry; Chemical Abstract [Online] (Mar. 16, 2011), "Quinolinium, 3-[(2-chlorophenyl)(5-cyclohexylpentyl)ami no]-1-methyl-", XP002752902, retrieved from Registry Database accession No. 1268668-23-0.
Database Registry; Chemical Abstract [Online] (Nov. 27, 2012), "Benzonitrile, 3-cholro-4-(3-quinolinylamino)-", XP002752906,retrieved from REGISTRYDatabase accession No. 1407301-89-6.
Database Registry; Chemical Abstract [Online] (Feb. 21, 2014), "Benzonitrile, 3-bromo-4-(quinolinylamino)-", XP002752917,retrieved from REGISTRYDatabase accession No. 1551935-00-2.
Database Registry; Chemical Abstract [Online] (Jul. 1, 2003), "I,2-Benzenedicarbonitrile, 4-[(7-methoxy-3-quinolinyl)amino]-5-nitro-" XP002752921, retrieved from Registry Database accession No. 540512-77-4.
Database Registry; Chemical Abstract [Online] (Dec. 2, 2012), "3-Quinolinamine, N-(4-bromo-2-nitrophenyl)-", XP002752922, retrieved from Registry Database accession No. 1408734-82-6.
Abbasi M M et al: "Synthesis of some quino[2,3-b] [1,4]benzoxazines", Gazzetta Chimica Italiana, Societ GBP A Chimica Italiana, IT, vol. 116, No. 7, (Jan. 1, 1986), pp. 373-375, XP009187934.
George Roger Clemo et al., "CCLXXIII. The synthesis of isoindenoquinolines. Part I" , Journal of the Chemical Society, vol. 0, No. 0, (Jan. 1, 1930) , pp. 2133-2138, XP055326714.
Mazu T K et al., "Identification of 3-phenylaminoquinolinium and3-phenylaminopyridinium salts as new agents against opportunistic fungal pathogens" , Bioorganic & Medicinal Chemistry, Pergamon, GB, vol. 19, No. 1, (Jan. 1, 2011), pp. 524-533, XP027577788.
Abbas Hebat-Allah Set al., "Molecular modeling studies and synthesis of novel quinoxaline derivatives with potential anticancer activity as inhibitors of c-Met kinase", Bioorganic & Medicinal Chemistry, vol. 23, No. 20, (Jan. 1, 2015), pp. 6560-6572, XP029284146.
Comfort A Boateng et al., "Optimization of 3-(phenylthio)quinolinium compounds against opportunistic fungal pathogens" , European Journal of Medicinal Chemistry, Editions Scientifique Elsevier, Paris, FR, vol. 46, No. 5, (Feb. 15, 2011), pp. 1789-1797, XP028370947.
Nirogi R V S et al., "Synthesis and structure activity relationship of 3-(arylsulfonyl)-8-(piperidin-4-yl-amino)quinoline derivatives as 5-HT6 receptor antagonists", Asian Journal of Chemi, Chemic Publishing, Sah I Badad, IN , vol. 26, No. 13, (Jan. 1, 2014), pp. 3779-3784, XP009192729.
Database Registry; Chemical Abstract [Online] (Jun. 28, 2001), "Phen-4-d-ol, 2-(trimethylsilyl)-", XP002752923, retrieved from Registry.
James E. Van Epp et al: Aromatization of arene 1,2-oxides. 1-(Trimethylsilyl)benzene I,2-oxide, The Journal of Organic Chemistry, vol. 46, No. 9, (Apr. 1, 1981), pp. 1817-1820, XP055240674.
Yoshiro Ohmomo et al., "Radioiodinated Phenoxyacetic Acid Derivatives as potential Brain Imaging Agents. i. Efficient Synthesis via Trimethylsilyl intermediates", Chemical and Pharmaceutical Bulletin, vol. 37, No. 9, (Jan. 1, 1989) pp. 2276-2281, XP055327007.
James E. M. Booker et al., "Approaches to the quaternary stereocentre and to the heterocyclic core in diazonamide A using the Heck reaction and related coupling reactions", Organic & Biomolecular Chemistry, vol. 4, No. 22, (Jan. 1, 2006), p. 4193, XP055327010.
Seung Hwan Cho et al., "Iridium-catalyzed diborylation of benzylic C—H bonds directed by a hydrosilyl group: synthesis of 1,1-benzyldiboronate esters", Chemical Science, vol. 5, No. 2, 1 (Jan. 1, 2014) , pp. 694-698, XP055327012.
Timothy S. De Vries et al., "Superelectrophilic Intermediates in Nitrogen-Directed Aromatic Borylation", Journal of the American Chemical Society, vol. 131, No. 41, (Oct. 21, 2009), pp. 14679-14687, XP055327013.

TRISUBSTITUTEDSILYLPHENOXY-HETEROCYCLES AND ANALOGUES

TECHNICAL FIELD

The present disclosure relates to fungicidal active compounds, more specifically to trisubstitutedsilylphenoxyheterocycles and analogues thereof, processes and intermediates for their preparation and use thereof as fungicidal active compound, particularly in the form of fungicide compositions. The present disclosure also relates to methods for the control of phytopathogenic fungi of plants using these compounds or compositions comprising thereof.

BACKGROUND

In Japanese patent application JP-2014/124411 and in international patent application WO 2013/002205, certain phenoxyquinolines are generically embraced in a broad disclosure of numerous compounds of the following formula:

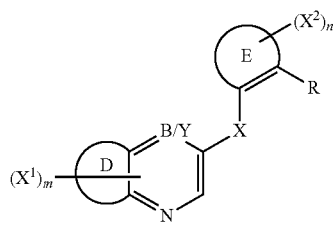

wherein D and E represent a 5- to 7-membered ring, X represents O, NH or N—$C_1$-$C_8$-alkyl, B (or Y) represents C or N, and R represents among various groups, an optionally substituted alkoxy group, an optionally disubstituted amino group, an optionally substituted and optionally oxidized alkylsulfanyl group, or a nitro group. However, JP-2014/124411 and WO2013/002205 do not disclose nor suggest providing compounds wherein R represents a substituted silylated group.

In Japanese patent application JP-2014/166991 certain phenoxyquinolines are generically embraced in a broad disclosure of numerous compounds of the following formula:

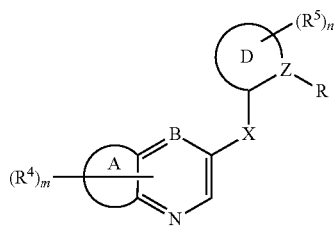

wherein A represents a 5- to 7-membered ring, D represents a 5- to 7-membered hydrocarbon or heterocycle ring, X represents O, S, NH or N—$C_1$-$C_8$-alkyl, Z and B independently represent C or N, and R represents among various groups, an optionally substituted alkyl group such as a trisubstitutedsilylalkyl group, an optionally substituted ketone group, an optionally substituted $C_6$-$C_{10}$-aryl group, an optionally substituted $C_2$-$C_8$-alkynyl group, or a cyano group. However, JP-2014/166991 does not disclose nor suggest providing compounds wherein R represents a substituted silylated group.

In international patent application WO 2011/081174 certain phenoxyquinolines are generically embraced in a broad disclosure of numerous compounds of the following formula:

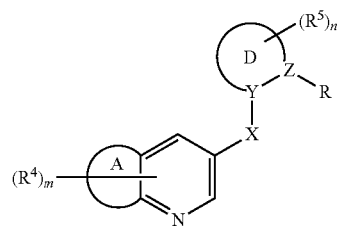

wherein A and D represent a 5- to 7-membered hydrocarbon or heterocycle ring, X represents O, S, S(O), S(O)$_2$, an optionally substituted C, or an optionally substituted N, Y and Z independently represent C or N, and R represents an optionally substituted alkyl group, an optionally substituted $C_6$-$C_{10}$-aryl group, or a cyano group. However, WO 2011/081174 does not disclose nor suggest providing compounds wherein R represents a substituted silylated group.

In international patent application WO 2012/161071 certain phenoxyquinolines are generically embraced in a broad disclosure of numerous compounds of the following formula:

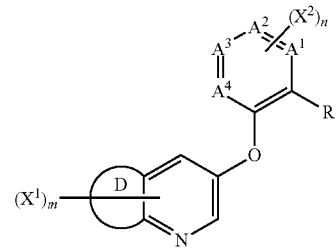

wherein D represents a 5- to 7-membered ring, $A^1$, $A^2$, $A^3$ and $A^4$ independently represent C or N provided at least one of $A^n$ is N, and R represents an optionally substituted alkyl group or a cyano group. However, WO 2012/161071 does not disclose nor suggest providing compounds wherein R represents a substituted silylated group.

In international patent application WO 2013/058256 certain phenoxyquinolines are generically embraced in a broad disclosure of numerous compounds of the following formula:

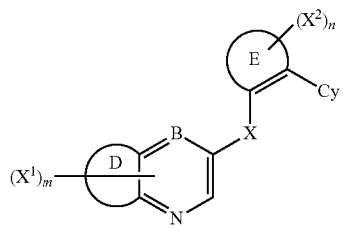

wherein D and E represent a 5- to 7-membered hydrocarbon or heterocycle ring, X represents O, S, C(O) or CH(OH), B represents C or N, and Cy represents an optionally substituted oxiranyl, or an optionally substituted 5- or 6-membered heterocyclyl group. However, WO 2013/058256 does not disclose nor suggest providing compounds wherein Cy represents a substituted silylated cycle.

In European patent application EP 0326330 certain phenoxyquinolines are generically embraced in a broad disclosure of numerous compounds of the following formula:

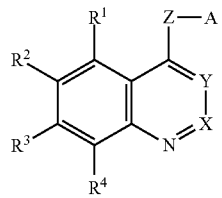

wherein X and Y can represent $CR^5$ and $R^5$ represents H, Cl or Br, Z can represent O, $NR^6$ and $R^6$ can represent various substituents among which an hydrogen or an alkyl group, and A can represent various groups among which an ortho-trisubstitutedsilylphenyl group. However, EP 0326330 does not disclose nor suggest providing compounds wherein the ortho-trisubstitutedsilylphenoxy —Z-A group is attached in the 3-position of the quinoline moiety.

In European patent application EP 0410762 certain phenoxyquinolines are generically embraced in a broad disclosure of numerous compounds of the following formula:

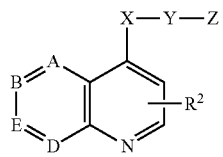

wherein one of the A, B, E or D is N and the others are $CR^1$, $R^1$ and $R^2$ are independently a hydrogen or a halogen atom, X can represent O, $NR^3$ or $CR^4R^5$, Y can be a direct bond, and Z can represent various groups among which an ortho-trisubstitutedsilylphenyl group. However, EP 0410762 does not disclose nor suggest providing compounds wherein the ortho-trisubstitutedsilylphenoxy —X—Y—Z group is attached in the 3-position of the naphthyridine moiety.

Nowadays, environmental and economic demands are continuously increasing with regard for instance to the spectrum of action, toxicity, selectivity, application rate, formation of residues, and preparation processes of fungicides. Some pathogens have also been found to develop resistance to used fungicides. Therefore, in agriculture, there is a continuous need to provide new fungicide compounds that may answer these environmental and economic requirements and/or alleviate the problems associated with pathogens resistance.

DETAILED DESCRIPTION

Accordingly, the present invention provides trisubstitutedsilylphenoxyquinolines and analogues thereof as described herein below that may be used as microbicide, preferably as fungicide active compounds.

Active Compounds
The present invention provides compounds of formula (I)

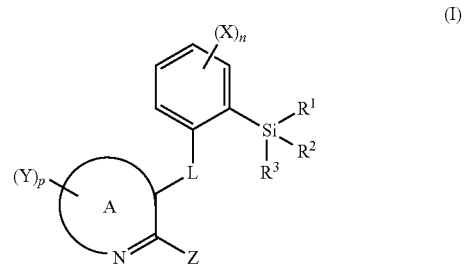

wherein
A represents a partially saturated or unsaturated fused bicyclic 9-, 10- or 11-membered heterocyclyl ring comprising at least 1 nitrogen atom and from 0 to 4 more heteroatoms independently selected in the list consisting of N, O and S;
Z is selected from the group consisting of hydrogen atom, halogen atom, unsubstituted or substituted $C_1$-$C_8$-alkyl, $C_1$-$C_8$-halogenoalkyl comprising up to 9 halogen atoms that can be the same or different, unsubstituted or substituted $C_2$-$C_8$-alkenyl, $C_2$-$C_8$-halogenoalkenyl comprising up to 9 halogen atoms that can be the same or different, unsubstituted or substituted $C_2$-$C_8$-alkynyl, $C_2$-$C_8$-halogenoalkynyl comprising up to 9 halogen atoms that can be the same or different, unsubstituted or substituted $C_3$-$C_7$-cycloalkyl, unsubstituted or substituted $C_4$-$C_7$-cycloalkenyl, hydroxyl, unsubstituted or substituted $C_1$-$C_8$-alkoxy, $C_1$-$C_8$-halogenoalkoxy comprising up to 9 halogen atoms that can be the same or different, unsubstituted or substituted aryl, unsubstituted or substituted heterocyclyl, formyl, unsubstituted or substituted $C_1$-$C_8$-alkylcarbonyl, unsubstituted or substituted (hydroxyimino)$C_1$-$C_8$-alkyl, unsubstituted or substituted ($C_1$-$C_8$-alkoxyimino)$C_1$-$C_8$-alkyl, carboxyl, unsubstituted or substituted $C_1$-$C_8$-alkoxycarbonyl, carbamoyl, unsubstituted or substituted $C_1$-$C_8$-alkylcarbamoyl, unsubstituted or substituted di-$C_1$-$C_8$-alkylcarbamoyl, amino, unsubstituted or substituted $C_1$-$C_8$-alkylamino, unsubstituted or substituted di-$C_1$-$C_8$-alkylamino, sulfanyl, unsubstituted or substituted $C_1$-$C_8$-alkylsulfanyl, unsubstituted or substituted $C_1$-$C_8$-alkylsulfinyl, unsubstituted or substituted $C_1$-$C_8$-alkylsulfonyl, unsubstituted or substituted $C_1$-$C_6$-trialkylsilyl, cyano and nitro, preferably Z is selected from the group consisting of hydrogen atom, halogen atom, unsubstituted or substituted $C_1$-$C_8$-alkyl, $C_1$-$C_8$-halogenoalkyl comprising up to 9 halogen atoms that can be the same or different, unsubstituted or substituted $C_2$-$C_8$-alkenyl, hydroxyl, unsubstituted or substituted $C_1$-$C_8$-alkoxy, $C_1$-$C_8$-halogenoalkoxy comprising up to 9 halogen atoms that can be the same or different, unsubstituted or substituted aryl, unsubstituted or substituted heterocyclyl and cyano;
n represents 0, 1, 2, 3 or 4;
p represents 0, 1, 2, 3, 4 or 5;
L represents O, S, SO, $SO_2$, $CR^4R^5$ or $NR^6$ wherein
$R^4$ and $R^5$ are independently selected from the group consisting of hydrogen atom, halogen atom, hydroxyl, unsubstituted or substituted $C_1$-$C_8$-alkoxy and unsubstituted or substituted $C_1$-$C_8$ alkyl, or they may form together with the carbon atom to which they are linked a carbonyl group;

$R^6$ is selected from the group consisting of hydrogen atom, substituted or non-substituted $C_1$-$C_8$-alkyl, $C_1$-$C_8$-halogenoalkyl comprising up to 9 halogen atoms that can be the same or different, unsubstituted or substituted $C_2$-$C_8$-alkenyl, $C_2$-$C_8$-halogenoalkenyl comprising up to 9 halogen atoms that can be the same or different, unsubstituted or substituted $C_3$-$C_8$-alkynyl, $C_3$-$C_8$-halogenoalkynyl comprising up to 9 halogen atoms that can be the same or different, unsubstituted or substituted $C_3$-$C_7$-cycloalkyl, $C_3$-$C_7$-halogenocycloalkyl comprising up to 9 halogen atoms that can be the same or different, unsubstituted or substituted $C_3$-$C_7$-cycloalkyl-$C_1$-$C_8$-alkyl, formyl, unsubstituted or substituted $C_1$-$C_8$-alkylcarbonyl, $C_1$-$C_8$-halogenoalkylcarbonyl comprising up to 9 halogen atoms that can be the same or different, unsubstituted or substituted $C_1$-$C_8$-alkoxycarbonyl, $C_1$-$C_8$-halogenoalkoxycarbonyl comprising up to 9 halogen atoms that can be the same or different, unsubstituted or substituted $C_1$-$C_8$-alkylsulfonyl, $C_1$-$C_8$-halogenoalkylsulfonyl comprising up to 9 halogen atoms that can be the same or different, unsubstituted or substituted aryl-$C_1$-$C_8$-alkyl and unsubstituted or substituted phenylsulfonyl;

X is independently selected from the group consisting of halogen atom, unsubstituted or substituted $C_1$-$C_8$-alkyl, $C_1$-$C_8$-halogenoalkyl comprising up to 9 halogen atoms that can be the same or different, unsubstituted or substituted $C_2$-$C_8$-alkenyl, $C_2$-$C_8$-halogenoalkenyl comprising up to 9 halogen atoms that can be the same or different, unsubstituted or substituted $C_2$-$C_8$-alkynyl, $C_2$-$C_8$-halogenoalkynyl comprising up to 9 halogen atoms that can be the same or different, unsubstituted or substituted $C_3$-$C_7$-cycloalkyl, unsubstituted or substituted $C_4$-$C_7$-cycloalkenyl, hydroxyl, unsubstituted or substituted $C_1$-$C_8$-alkoxy, $C_1$-$C_8$-halogenoalkoxy comprising up to 9 halogen atoms that can be the same or different, unsubstituted or substituted aryl, unsubstituted or substituted heterocyclyl, formyl, unsubstituted or substituted $C_1$-$C_8$-alkylcarbonyl, unsubstituted or substituted (hydroxyimino)$C_1$-$C_8$-alkyl, unsubstituted or substituted ($C_1$-$C_8$-alkoxyimino)$C_1$-$C_8$-alkyl, carboxyl, unsubstituted or substituted $C_1$-$C_8$-alkoxycarbonyl, carbamoyl, unsubstituted or substituted $C_1$-$C_8$-alkylcarbamoyl, unsubstituted or substituted di-$C_1$-$C_8$-alkylcarbamoyl, amino, unsubstituted or substituted $C_1$-$C_8$-alkylamino, unsubstituted or substituted di-$C_1$-$C_8$-alkylamino, sulfanyl, unsubstituted or substituted $C_1$-$C_8$-alkylsulfanyl, unsubstituted or substituted $C_1$-$C_8$-alkylsulfinyl, unsubstituted or substituted $C_1$-$C_8$-alkylsulfonyl, unsubstituted or substituted $C_1$-$C_6$-trialkylsilyl, cyano, nitro, hydroxymethyl and (tetrahydro-2H-pyran-2-yloxy)methyl, preferably X is independently selected from the group consisting of halogen atom, unsubstituted or substituted $C_1$-$C_8$-alkyl, $C_1$-$C_8$-halogenoalkyl comprising up to 9 halogen atoms that can be the same or different, unsubstituted or substituted $C_1$-$C_8$-alkoxy, $C_1$-$C_8$-halogenoalkoxy comprising up to 9 halogen atoms that can be the same or different, amino, cyano and nitro;

Y is independently selected from the group consisting of halogen atom, unsubstituted or substituted $C_1$-$C_8$-alkyl, $C_1$-$C_8$-halogenoalkyl comprising up to 9 halogen atoms that can be the same or different, unsubstituted or substituted $C_2$-$C_8$-alkenyl, $C_2$-$C_8$-halogenoalkenyl comprising up to 9 halogen atoms that can be the same or different, unsubstituted or substituted $C_2$-$C_8$-alkynyl, $C_2$-$C_8$-halogenoalkynyl comprising up to 9 halogen atoms that can be the same or different, unsubstituted or substituted $C_3$-$C_7$-cycloalkyl, unsubstituted or substituted $C_4$-$C_7$-cycloalkenyl, hydroxyl, unsubstituted or substituted $C_1$-$C_8$-alkoxy, $C_1$-$C_8$-halogenoalkoxy comprising up to 9 halogen atoms that can be the same or different, unsubstituted or substituted aryl, unsubstituted or substituted heterocyclyl, formyl, unsubstituted or substituted $C_1$-$C_8$-alkylcarbonyl, unsubstituted or substituted (hydroxyimino)$C_1$-$C_8$-alkyl, unsubstituted or substituted ($C_1$-$C_8$-alkoxyimino)$C_1$-$C_8$-alkyl, carboxyl, unsubstituted or substituted $C_1$-$C_8$-alkoxycarbonyl, carbamoyl, unsubstituted or substituted $C_1$-$C_8$-alkylcarbamoyl, unsubstituted or substituted di-$C_1$-$C_8$-alkylcarbamoyl, amino, unsubstituted or substituted $C_1$-$C_8$-alkylamino, unsubstituted or substituted di-$C_1$-$C_8$-alkylamino, sulfanyl, unsubstituted or substituted $C_1$-$C_8$-alkylsulfanyl, unsubstituted or substituted $C_1$-$C_8$-alkylsulfinyl, unsubstituted or substituted $C_1$-$C_8$-alkylsulfonyl, unsubstituted or substituted $C_1$-$C_6$-trialkylsilyl, cyano and nitro, preferably Y is independently selected from the group consisting of halogen atom, unsubstituted or substituted $C_1$-$C_8$-alkyl, $C_1$-$C_8$-halogenoalkyl comprising up to 9 halogen atoms that can be the same or different, unsubstituted or substituted $C_1$-$C_8$-alkoxy, $C_1$-$C_8$-halogenoalkoxy comprising up to 9 halogen atoms that can be the same or different, hydroxyl and cyano;

$R^1$ is selected from the group consisting of unsubstituted or substituted $C_1$-$C_8$-alkyl, unsubstituted or substituted $C_2$-$C_8$-alkenyl, unsubstituted or substituted $C_2$-$C_8$-alkynyl, unsubstituted or substituted $C_3$-$C_7$-cycloalkyl, unsubstituted or substituted $C_4$-$C_7$-cycloalkenyl, unsubstituted or substituted aryl and unsubstituted or substituted heterocyclyl, preferably $R^1$ is selected from the group consisting of unsubstituted or substituted $C_1$-$C_8$-alkyl;

$R^2$ is selected from the group consisting of hydroxyl, unsubstituted or substituted $C_1$-$C_8$-alkoxy, unsubstituted or substituted $C_1$-$C_8$-alkyl, unsubstituted or substituted $C_2$-$C_8$-alkenyl, unsubstituted or substituted $C_2$-$C_8$-alkynyl, unsubstituted or substituted $C_3$-$C_7$-cycloalkyl, unsubstituted or substituted $C_4$-$C_7$-cycloalkenyl, unsubstituted or substituted aryl and unsubstituted or substituted heterocyclyl, preferably $R^2$ is selected from the group consisting of unsubstituted or substituted $C_1$-$C_8$-alkyl and unsubstituted or substituted aryl;

When $R^1$ and $R^2$ represent an unsubstituted or substituted $C_1$-$C_8$ alkyl or an unsubstituted or substituted $C_2$-$C_8$ alkenyl, they can form, together with the silicon atom to which they are linked, an unsubstituted or substituted $C_3$-$C_8$-silacycloalkyl ring or an unsubstituted or substituted $C_4$-$C_8$-silacycloalkenyl ring;

$R^3$ is selected from the group consisting of hydrogen atom, halogen atom, unsubstituted or substituted $C_1$-$C_8$-alkyl, $C_1$-$C_8$-halogenoalkyl comprising up to 9 halogen atoms that can be the same or different, unsubstituted or substituted $C_2$-$C_8$-alkenyl, unsubstituted or substituted $C_2$-$C_8$-alkynyl, unsubstituted or substituted $C_3$-$C_7$-cycloalkyl, unsubstituted or substituted $C_4$-$C_7$-cycloalkenyl, hydroxyl, unsubstituted or substituted $C_1$-$C_8$-alkoxy, unsubstituted or substituted aryl, unsubstituted or substituted aryl-$C_1$-$C_8$-alkyl, unsubstituted or substituted heterocyclyl, unsubstituted or substituted heterocyclyl-$C_1$-$C_8$-alkyl, unsubstituted or substituted hydroxy-$C_1$-$C_8$-alkyl, unsubstituted or substituted $C_1$-$C_8$-alkoxy-$C_1$-$C_8$-alkyl, unsubstituted or substituted $C_1$-$C_8$-alkylcarbonyloxy-$C_1$-$C_8$-alkyl, unsubstituted or substituted aryloxy-$C_1$-$C_8$-alkyl, unsubstituted or substituted heterocyclyloxy-$C_1$-$C_8$-alkyl, unsubstituted or substituted amino-$C_1$-$C_8$-alkyl, unsubstituted or substituted $C_1$-$C_8$-alkylamino-$C_1$-$C_8$-alkyl, unsubstituted or substituted di-$C_1$-$C_8$-alkylamino-$C_1$-$C_8$-alkyl, unsubstituted or substituted arylamino-$C_1$-$C_8$-alkyl, unsubstituted or substituted di-arylamino-$C_1$-$C_8$-alkyl, unsubstituted or substituted heterocyclylamino-$C_1$-$C_8$-alkyl, unsubstituted or substituted $C_1$-$C_8$-alkylcarbonylamino-$C_1$-$C_8$-alkyl, unsubstituted or substituted $C_1$-$C_8$-alkoxycarbonylamino-$C_1$-$C_8$-alkyl, unsubstituted or substituted $C_1$-$C_8$-alkylsulfanyl-$C_1$-$C_8$-alkyl, unsubstituted or substituted $C_1$-$C_8$-alkylsulfinyl-$C_1$-$C_8$-alkyl, unsubstituted or substituted $C_1$-$C_8$-alkylsulfonyl-$C_1$-$C_8$-alkyl and unsubstituted or substituted cyano-$C_1$-$C_8$-alkyl, preferably $R^3$ is selected from the group consisting of hydrogen atom, halogen atom, unsubstituted or substituted $C_1$-$C_8$-alkyl, $C_1$-$C_8$-halogenoalkyl comprising up to 9 halogen atoms that can be the same or different, unsubstituted or substituted $C_3$-$C_7$-cycloalkyl, unsubstituted or substituted $C_2$-$C_8$-alkenyl, unsubstituted or substituted aryl, unsubstituted or substituted aryl-$C_1$-$C_8$-alkyl, hydroxyl, unsubstituted or substituted heterocyclyl and unsubstituted or substituted heterocyclyl-$C_1$-$C_8$-alkyl;

$R^3$ and X, when said X is vicinal to $SiR^1R^2R^3$, may form, together with the silicon and carbon atoms to which they are respectively attached, an unsubstituted or substituted 5-, 6- or 7-membered, partially saturated, heterocycle;

When $R^2$ represents an unsubstituted or substituted $C_1$-$C_8$-alkoxy and $R^3$ represents an unsubstituted or substituted $C_1$-$C_8$-alkoxy or an unsubstituted or substituted $C_1$-$C_8$ alkyl, they can form, together with the silicon atom to which they are linked an unsubstituted or substituted 5-, 6- or 7-membered heterocycle;

as well as their salts, N-oxides, metal complexes, metalloid complexes and optically active isomers or geometric isomers.

As used herein, when a group is said to be "substituted", the one or more substituents of said substituted group may be independently selected from the group consisting of halogen atom, nitro, hydroxyl, cyano, amino, sulfanyl, pentafluoro-$\lambda^6$-sulfanyl, formyl, carbamoyl, carbamate, $C_1$-$C_8$-alkyl, tri($C_1$-$C_8$-alkyl)silyl, $C_3$-$C_7$-cycloalkyl, $C_1$-$C_8$-halogenoalkyl having 1 to 5 halogen atoms, $C_3$-$C_8$-halogenocycloalkyl having 1 to 5 halogen atoms, $C_2$-$C_8$-alkenyl, $C_2$-$C_8$-alkynyl, $C_1$-$C_8$-alkylamino, di-$C_1$-$C_8$-alkylamino, $C_1$-$C_8$-alkoxy, $C_1$-$C_8$-halogenoalkoxy having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylcarbonyl, $C_1$-$C_8$-halogenoalkylcarbonyl having 1 to 5 halogen atoms, $C_1$-$C_8$-alkylcarbamoyl, di-$C_1$-$C_8$-alkylcarbamoyl, $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, $C_1$-$C_8$-alkylsulfanyl, $C_1$-$C_8$-halogenoalkylsulfanyl having 1 to 5 halogen atoms, $C_1$-$C_8$-alkylsulfinyl, $C_1$-$C_8$-halogenoalkylsulfinyl having 1 to 5 halogen atoms, $C_1$-$C_8$-alkylsulfonyl and $C_1$-$C_8$-halogenoalkylsulfonyl having 1 to 5 halogen atoms.

As used herein, halogen means fluorine, chlorine, bromine or iodine; formyl means —CH(=O); carboxyl means —C(=O)OH; carbonyl means —C(=O)—; carbamoyl means —C(=O)NH$_2$; N-hydroxycarbamoyl means —C(=O)NHOH; triflyl means —SO$_2$—CF$_3$; SO represents a sulfoxide group; SO$_2$ represents a sulfone group; heteroatom means sulfur, nitrogen or oxygen; methylene means the diradical —CH$_2$—; aryl typically means phenyl or naphthyl; unless provided differently, heterocyclyl means a 5- to 7-membered ring, preferably a 5- to 6-membered ring, which may be saturated, partially saturated or unsaturated, comprising from 1 to 4 heteroatoms independently selected in the list consisting of N, O, S.

The term "membered" as used herein in the expression "9-, 10- or 11-membered heterocyclyl ring" or "5- to 6-membered ring" designates the number of skeletal atoms that constitutes the ring.

As used herein, the expression "partially saturated or unsaturated fused bicyclic "9-, 10- or 11-membered heterocyclyl ring" designates fused bicyclic ring systems comprising a saturated ring fused with an unsaturated ring or two fused unsaturated rings, the bicyclic ring system being constituted from 9 to 11 skeletal atoms.

As used herein, an alkyl group, an alkenyl group and an alkynyl group as well as moieties containing these terms, can be linear or branched.

When an amino group or the amino moiety of any other amino-containing group is substituted by two substituents that can be the same or different, the two substituents together with the nitrogen atom to which they are linked can form a heterocyclyl group, preferably a 5- to 7-membered heterocyclyl group, that can be substituted or that can include other hetero atoms, for example a morpholino group or piperidinyl group.

Any of the compounds of the present invention can exist in one or more optical or chiral isomer forms depending on the number of asymmetric centres in the compound. The invention thus relates equally to all optical isomers and racemic or scalemic mixtures thereof (the term "scalemic" denotes a mixture of enantiomers in different proportions) and to mixtures of all possible stereoisomers, in all proportions. The diastereoisomers and/or the optical isomers can be separated according to methods which are known per se by the man ordinary skilled in the art.

Any of the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

Any of the compounds of the present invention can also exist in one or more geometric isomer forms depending on the relative position (syn/anti or cis/trans) of the substituents of the chain or ring. The invention thus relates equally to all syn/anti (or cis/trans) isomers and to all possible syn/anti (or cis/trans) mixtures, in all proportions. The syn/anti (or cis/trans) isomers can be separated according to general methods, which are known per se by the man ordinary skilled in the art.

When a compound of the invention can be present in tautomeric form, the invention also encompasses any tautomeric forms of such compound, even when this is not expressly mentioned.

Compounds of formula (I) are herein referred to as "active compound(s)".

In the above formula (I), Z is preferably selected from the group consisting of hydrogen atom, halogen atom, hydroxyl, unsubstituted or substituted $C_1$-$C_6$-alkyl, $C_1$-$C_6$-halogenoalkyl comprising up to 9 halogen atoms that can be the same or different, unsubstituted or substituted $C_1$-$C_6$-alkoxy, $C_1$-$C_6$-halogenoalkoxy comprising up to 9 halogen atoms that can be the same or different and cyano, more preferably Z is a hydrogen atom or an unsubstituted or substituted $C_1$-$C_6$-alkyl, even more preferably Z is a hydrogen atom or a methyl group.

In the above formula (I), n is preferably 0 or 1.

In the above formula (I), p is preferably 0, 1, 2 or 3.

In the above formula (I), L is preferably 0 or $CH_2$.

In the above formula (I), X is preferably independently a halogen atom or an unsubstituted or substituted $C_1$-$C_6$-alkyl group, more preferably X is independently a chlorine atom, a fluorine atom or a methyl group.

In the above formula (I), Y is preferably independently selected from the group consisting of halogen atom, unsubstituted or substituted $C_1$-$C_6$-alkyl, $C_1$-$C_6$-halogenoalkyl comprising up to 9 halogen atoms that can be the same or different, unsubstituted or substituted $C_1$-$C_6$-alkoxy, $C_1$-$C_6$-halogenoalkoxy comprising up to 9 halogen atoms that can be the same or different and cyano, more preferably Y is independently selected from the group consisting of halogen atom and unsubstituted or substituted $C_1$-$C_6$-alkyl, even more preferably Y is independently a fluorine atom, a chlorine atom or a methyl group.

In the above formula (I), $R^1$ is preferably an unsubstituted or substituted $C_1$-$C_6$-alkyl, more preferably a methyl group.

In the above formula (I), $R^2$ is preferably an unsubstituted or substituted $C_1$-$C_6$-alkyl, more preferably a methyl group.

In the above formula (I), $R^3$ is preferably selected from the group consisting of hydrogen atom, unsubstituted or substituted $C_1$-$C_6$-alkyl, unsubstituted or substituted $C_3$-$C_7$-cycloalkyl, unsubstituted or substituted aryl, unsubstituted or substituted aryl-$C_1$-$C_6$-alkyl, unsubstituted or substituted heterocyclyl, unsubstituted or substituted heterocyclyl-$C_1$-$C_6$-alkyl and hydroxyl, more preferably $R^3$ is selected from the group consisting of hydrogen atom, unsubstituted or substituted $C_1$-$C_6$-alkyl, unsubstituted or substituted aryl, unsubstituted or substituted aryl-$C_1$-$C_6$-alkyl and hydroxyl, even more preferably $R^3$ is a hydrogen atom, a hydroxyl, a methyl group, a phenyl group or a benzyl group.

In some embodiments, the compounds of the present invention are compounds of formula (I) wherein:

Y is independently selected from the group consisting of halogen atom, unsubstituted or substituted $C_1$-$C_6$-alkyl, $C_1$-$C_6$-halogenoalkyl comprising up to 9 halogen atoms that can be the same or different, unsubstituted or substituted $C_1$-$C_6$-alkoxy, $C_1$-$C_6$-halogenoalkoxy comprising up to 9 halogen atoms that can be the same or different and cyano;

Z is selected from the group consisting of hydrogen atom, halogen atom, hydroxyl, unsubstituted or substituted $C_1$-$C_6$-alkyl, $C_1$-$C_6$-halogenoalkyl comprising up to 9 halogen atoms that can be the same or different, unsubstituted or substituted $C_1$-$C_6$-alkoxy, $C_1$-$C_6$-halogenoalkoxy comprising up to 9 halogen atoms that can be the same or different and cyano; and A, $R^1$, $R^2$, $R^3$, X, n, p and L are disclosed herein.

Some preferred compounds according to the invention are compounds of formula (I) wherein A is selected in the list consisting of:

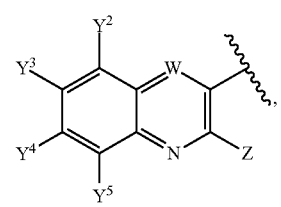
(A$^1$)

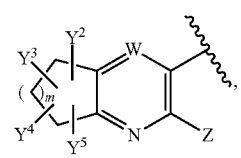
(A$^2$)

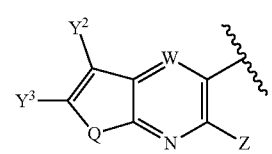
(A$^3$)

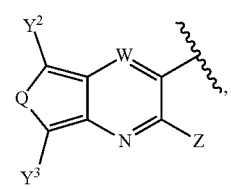
(A$^4$)

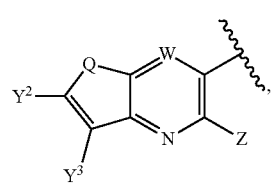
(A$^5$)

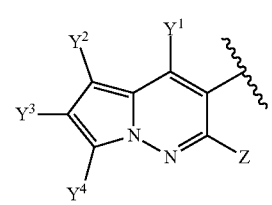
(A$^6$)

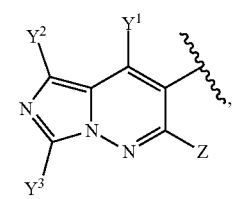
(A$^7$)

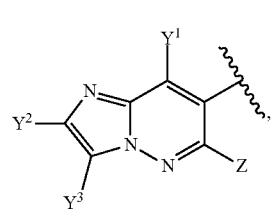
(A$^8$)

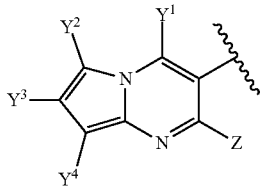 (A⁹)

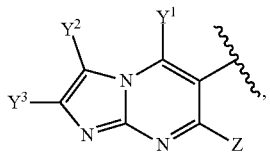 (A¹⁰)

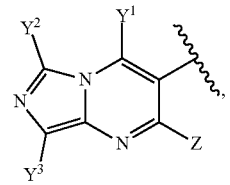 (A¹¹)

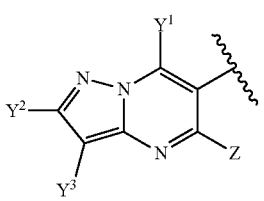 (A¹²)

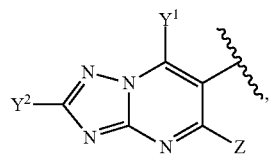 (A¹³)

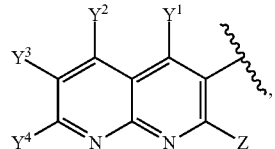 (A¹⁴)

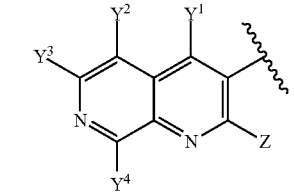 (A¹⁵)

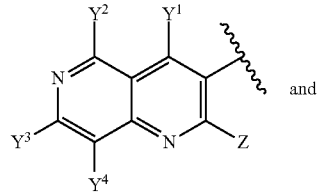 (A¹⁶) and

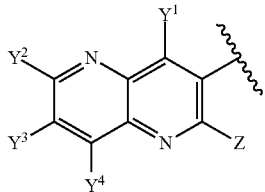 (A¹⁷)

wherein:
W is $CY^1$ or N;
Q is O, S or $NY^6$ with $Y^6$ being a hydrogen atom or an unsubstituted or substituted $C_1$-$C_8$-alkyl;
$Y^1$, $Y^2$, $Y^3$, $Y^4$ and $Y^5$ are independently a hydrogen atom or Y as disclosed above, preferably, $Y^1$, $Y^2$, $Y^3$, $Y^4$ and $Y^5$ are independently selected from the group consisting of hydrogen atom, halogen atom, substituted or unsubstituted $C_1$-$C_6$-alkyl, $C_1$-$C_6$-halogenoalkyl comprising up to 9 halogen atoms that can be the same or different, unsubstituted or substituted $C_1$-$C_6$-alkoxy, $C_1$-$C_6$-halogenoalkoxy comprising up to 9 halogen atoms that can be the same or different and cyano, more preferably $Y^1$, $Y^2$, $Y^3$, $Y^4$ and $Y^5$ are independently selected from the group consisting of hydrogen atom, halogen atom and unsubstituted or substituted $C_1$-$C_6$-alkyl, even more preferably $Y^1$, $Y^2$, $Y^3$, $Y^4$ and $Y^5$ are independently a hydrogen atom, a fluorine atom, a chlorine atom or a methyl group;
Z is as disclosed above, preferably Z is selected from the group consisting of hydrogen atom, halogen atom, hydroxyl, unsubstituted or substituted $C_1$-$C_6$-alkyl, $C_1$-$C_6$-halogenoalkyl comprising up to 9 halogen atoms that can be the same or different, unsubstituted or substituted $C_1$-$C_6$-alkoxy, $C_1$-$C_6$-halogenoalkoxy comprising up to 9 halogen atoms that can be the same or different and cyano, more preferably Z is a hydrogen atom or an unsubstituted or substituted $C_1$-$C_6$-alkyl, even more preferably Z is a hydrogen atom or a methyl group;
m is 1, 2 or 3; and
n, X, L, $R^1$, $R^2$ and $R^3$ are as disclosed herein.
Preferably, in these embodiments wherein A is selected in the list consisting of $A^1$ to $A^{17}$,
L is O or $CH_2$, more preferably O; and/or
$R^1$ is an unsubstituted or substituted $C_1$-$C_6$-alkyl, more preferably a methyl group; and/or
$R^2$ is an unsubstituted or substituted $C_1$-$C_6$-alkyl, more preferably a methyl group; and/or
$R^3$ is selected from the group consisting of hydrogen atom, unsubstituted or substituted $C_1$-$C_6$-alkyl, unsubstituted or substituted $C_3$-$C_7$-cycloalkyl, unsubstituted or substituted aryl, unsubstituted or substituted aryl-$C_1$-$C_6$-alkyl, unsubstituted or substituted heterocyclyl, unsubstituted or substituted heterocyclyl-$C_1$-$C_6$-alkyl and hydroxyl, more preferably $R^3$ is selected from the group consisting of hydrogen atom, unsubstituted or substituted $C_1$-$C_6$-alkyl, unsubstituted or substituted aryl, unsubstituted or substituted aryl-$C_1$-$C_6$-alkyl and hydroxyl, even more preferably $R^3$ is a hydrogen atom, a hydroxyl, a methyl group, a phenyl group or a benzyl group; and/or
n represents 0 or 1; and/or
X is a halogen atom or an unsubstituted or substituted $C_1$-$C_6$-alkyl group, more preferably X is a chlorine atom, a fluorine atom or a methyl group.

Some preferred compounds according to the invention are compounds of formula (I) wherein A is selected from the list consisting of $A^1$, $A^2$, $A^3$, $A^5$, $A^{10}$, $A^{12}$ and $A^{17}$ as disclosed above, wherein W, Q, $Y^1$, $Y^2$, $Y^3$, $Y^4$, $Y^5$, m, n, X, L, $R^1$, $R^2$ and $R^3$ are as disclosed herein.

Some preferred compounds according to the invention are compounds of formula (I) wherein A is a heterocycle of formula $A^1$ as disclosed above wherein W, $Y^1$, $Y^2$, $Y^3$, $Y^4$, $Y^5$, n, X, L, $R^1$, $R^2$ and $R^3$ are as disclosed herein.

Some more preferred compounds according to the invention are compounds of formula (I) wherein:

A represents a heterocycle of formula ($A^1$) wherein:
W is $CY^1$ or N;
$Y^1$ to $Y^5$ independently represent a hydrogen atom, a fluorine atom or a methyl group, preferably a hydrogen atom or fluorine atom, more preferably Y, $Y^2$ and $Y^3$ represent a hydrogen atom and $Y^4$ and $Y^5$ independently represent a hydrogen atom or a fluorine atom;
Z represents a hydrogen atom or a methyl group;
$R^1$, $R^2$, $R^3$, X, n and L are as defined above, preferably $R^1$ and $R^2$ represent an unsubstituted or a substituted $C_1$-$C_6$-alkyl, $R^3$ is selected in the group consisting of unsubstituted or substituted $C_1$-$C_6$-alkyl, unsubstituted or substituted $C_3$-$C_7$-cycloalkyl, unsubstituted or substituted aryl, unsubstituted or substituted heterocyclyl and hydroxyl, preferably $R^3$ is an unsubstituted or substituted $C_1$-$C_6$-alkyl or a hydroxyl, and X is a chlorine atom, a fluorine atom or a methyl group. Preferably, in some embodiments of these more preferred compounds, n represents 0 or 1 with X being vicinal to $SiR^1R^2R^3$ when n represents 1.

The above mentioned preferences with regard to the substituents of the compounds according to the invention can be combined in various manners. These combinations of preferred features thus provide sub-classes of compounds according to the invention. Examples of such sub-classes of preferred compounds according to the invention are:

preferred features of A with one or more preferred features of L, $R^1$, $R^2$, $R^3$, n, p, X, Y and Z;
preferred features of L with one or more preferred features of A, $R^1$, $R^2$, $R^3$, n, p, X, Y and Z;
preferred features of $R^1$ with one or more preferred features of A, L, $R^2$, $R^3$, n, p, X, Y and Z;
preferred features of $R^2$ with one or more preferred features of A, L, $R^1$, $R^3$, n, p, X, Y and Z;
preferred features of $R^3$ with one or more preferred features of A, L, $R^1$, $R^2$, n, p, X, Y and Z;
preferred features of n with one or more preferred features of A, L, $R^1$, $R^2$, $R^3$, p, X, Y and Z;
preferred features of p with one or more preferred features of A, L, $R^1$, $R^2$, $R^3$, n, X, Y and Z;
preferred features of X with one or more preferred features of A, L, $R^1$, $R^2$, $R^3$, n, p, Y and Z;
preferred features of Y with one or more preferred features of A, L, $R^1$, $R^2$, $R^3$, n, p, X and Z;
preferred features of Z with one or more preferred features of A, L, $R^1$, $R^2$, $R^3$, n, p, X and Y.

In these combinations of preferred features of the substituents of the compounds according to the invention, the said preferred features can also be selected among the more preferred features of each of A, L, $R^1$, $R^2$, $R^3$, n, p, X, Y and Z so as to form most preferred subclasses of compounds according to the invention.

Processes for the Preparation of the Active Compounds

The present invention also relates to processes for the preparation of compounds of formula (I).

Compounds of formula (I) as herein-defined can be prepared by a process P1 which comprises the step of reacting a halogenoaryl of formula (II) or one of its salts:

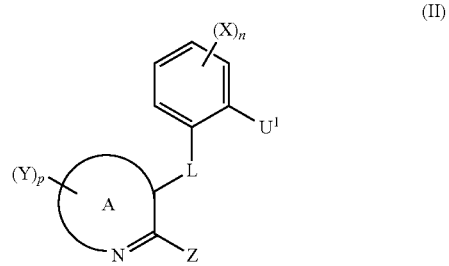

(II)

wherein A, L, n, p, X, Y and Z are as herein-defined and $U^1$ represents a chlorine atom, a bromine atom, an iodine atom, a mesyl group, a tosyl group or a triflyl group, with a disilyl derivative of formula (IIIa):

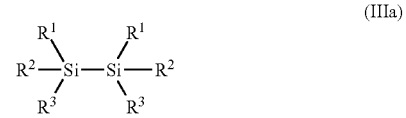

(IIIa)

wherein $R^1$, $R^2$ and $R^3$ are as herein-defined.

Process P1 can be performed in the presence of a transition metal catalyst such as palladium and if appropriate in the presence of a phosphine ligand or a N-heterocyclic carbene ligand, if appropriate in the presence of a base and if appropriate in the presence of a solvent according to known processes (Organic Letters (2003), 5, 3483, Organic Letters (2007), 9, 3785 and cited references therein).

Derivatives of formula (II) wherein wherein A, L, n, p, X, Y and Z are as herein-defined and $U^1$ represents a chlorine atom, a bromine atom or an iodine atom, can be prepared by diazotation of an aniline of formula (IV) or one of its salts:

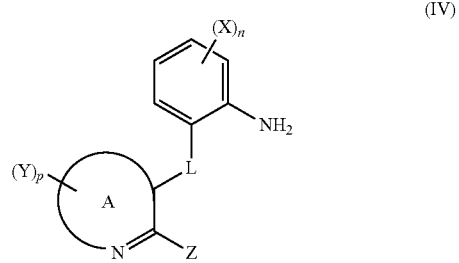

(IV)

wherein A, L, n, p, X, Y and Z are as herein-defined, according to known processes (Patai's Chemistry of Functional Groups—Amino, Nitroso, Nitro and Related Groups—1996).

Derivatives of formula (II) can also be prepared by aromatic nucleophilic substitution according to known processes (Journal of Heterocyclic Chemistry (2008), 45, 1199 and Synthetic Communications (1999), 29, 1393).

Derivatives of formula (II) can also be prepared from compounds of formula (VIII) by condensation of the corresponding ortho-substituted [thio]phenols or anilines according to known processes (US-2012/289702).

Derivatives of formula (II) can also be prepared by process P6 described below.

Anilines of formula (IV) wherein wherein A, L, n, p, X, Y and Z are as herein-defined can be prepared by reduction of a nitro group of formula (V) or one of its salts:

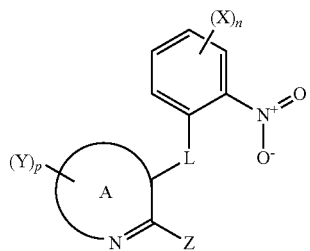

wherein A, L, n, p, X, Y and Z are as herein-defined according to known processes (Patai's Chemistry of Functional Groups—Amino, Nitroso, Nitro and Related Groups—1996).

Disilyl derivatives of formula (IIIa) are known or can be prepared by known processes.

Compounds of formula (I) wherein $R^3$ represents a hydroxyl can be prepared from compounds of formula (I) wherein $R^3$ represents an unsubstituted or substituted $C_1$-$C_6$-alkoxy (themselves prepared by process P1) by an acidic hydrolysis according to known processes (Organic Letters (2003), 5, 3483)

Compounds of formula (I) wherein $R^3$ represents a fluorine atom can be prepared from compounds of formula (I) wherein $R^3$ represents an unsubstituted or substituted $C_1$-$C_6$-alkoxy (themselves prepared by process P1) by known processes (Synlett (2012), 23, 1064 and cited references therein) or can be prepared from compounds of formula (I) wherein $R^3$ represents a hydroxyl by known processes (EP1908472)

Process P1 can be carried out in the presence of a catalyst, such as a metal salt or complex. Suitable metal derivatives for this purpose are transition metal catalysts such as palladium. Suitable metal salts or complexes for this purpose are for example, palladium chloride, palladium acetate, tetrakis(triphenylphosphine)palladium(0), bis(dibenzylideneacetone)palladium(0), tris(dibenzylideneacetone)dipalladium(0), bis(triphenylphosphine)palladium(II) dichloride, [1,1'-bis(diphenylphosphino)ferrocene]dichloropalladium (II), bis(cinnamyl)dichlorodipalladium(II), bis(allyl)-dichlorodipalladium(II) or [1,1'-Bis(di-tert-butylphosphino)ferrocene]dichloropalladium(II).

It is also possible to generate a palladium complex in the reaction mixture by separate addition to the reaction of a palladium salt and a ligand or salt, such as triethylphosphine, tri-tert-butylphosphine, tri-tert-butylphosphonium tetrafluoroborate, tricyclohexylphosphine, 2-(dicyclohexylphosphino)biphenyl, 2-(di-tert-butylphosphino)biphenyl, 2-(dicyclohexylphosphino)-2'-(N,N-dimethylamino)biphenyl, 2-(tert-butylphosphino)-2'-(N,N-dimethylamino)biphenyl, 2-di-tert-butylphosphino-2',4',6'-triisopropylbiphenyl 2-dicyclohexylphosphino-2',4',6'-triisopropylbiphenyl, 2-dicyclohexylphosphino-2,6'-dimethoxybiphenyl, 2-dicyclohexylphosphino-2',6'-diisopropoxybiphenyl, triphenylphosphine, tris-(o-tolyl)phosphine, sodium 3-(diphenylphosphino)benzenesulfonate, tris-2-(methoxyphenyl)phosphine, 2,2'-bis(diphenylphosphino)-1,1'-binaphthyl, 1,4-bis(diphenylphosphino)butane, 1,2-bis(diphenylphosphino) ethane, 1,4-bis(dicyclohexylphosphino) butane, 1,2-bis(dicyclohexylphosphino)-ethane, 2-(dicyclohexylphosphino)-2'-(N,N-dimethylamino)-biphenyl, 1,1'-bis(diphenylphosphino)-ferrocene, (R)-(–)-1-[(S)-2-diphenyl-phosphino)ferrocenyl]ethyldicyclohexylphosphine, tris-(2,4-tert-butyl-phenyl)phosphite, di(1-adamantyl)-2-morpholinophenylphosphine or 1,3-bis(2,4,6-trimethylphenyl)imidazolium chloride.

It is also advantageous to choose the appropriate catalyst and/or ligand from commercial catalogues such as "Metal Catalysts for Organic Synthesis" by Strem Chemicals or "Phosphorous Ligands and Compounds" by Strem Chemicals.

Suitable bases for carrying out process P1 can be inorganic and organic bases which are customary for such reactions. Preference is given to using alkaline earth metal or alkali metal hydroxides, such as sodium hydroxide, calcium hydroxide, potassium hydroxide or other ammonium hydroxide derivatives; alkaline earth metal, alkali metal or ammonium fluorides such as potassium fluoride, caesium fluoride or tetrabutylammonium fluoride; alkaline earth metal or alkali metal carbonates, such as sodium carbonate, potassium carbonate, potassium bicarbonate, sodium bicarbonate or caesium carbonate; alkali metal or alkaline earth metal acetates, such as sodium acetate, lithium acetate, potassium acetate or calcium acetate; alkali metal or alkaline earth metal phosphate, such as tripotassium phosphate alkali; alkali metal alcoholates, such as potassium tert-butoxide or sodium tert-butoxide; tertiary amines, such as trimethylamine, triethylamine, tributylamine, N,N-dimethylaniline, N,N-dicyclohexylmethylamine, N,N-diisopropylethylamine, N-methylpiperidine, N,N-dimethylaminopyridine, diazabicyclooctane (DABCO), diazabicyclononene (DBN) or diazabicycloundecene (DBU); and also aromatic bases, such as pyridine, picolines, lutidines or collidines.

Suitable solvents for carrying out process P1 can be customary inert organic solvents. Preference is given to using optionally halogen atomated aliphatic, alicyclic or aromatic hydrocarbons, such as petroleum ether, pentane, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; ureas, such as 1,3-dimethyl-3,4,5,6-tetrahydro-2 (1H)-pyrimidinone; esters, such as methyl acetate or ethyl acetate, sulfoxides, such as dimethyl sulfoxide, or sulfones, such as sulfolane; and a mixture thereof.

It can also be advantageous to carry out process P1 with a co-solvent such as water or an alcohol such as methanol, ethanol, propanol, isopropanol or tert-butanol.

Process P1 may be performed in an inert atmosphere such as argon or nitrogen atmosphere. When carrying out process P1, 1 mole or an excess of compound of formula (III) and from 1 to 5 moles of base and from 0.01 to 20 mole percent of a palladium complex can be employed per mole of compound of formula (II). It is also possible to employ the reaction components in other ratios. Work-up is carried out by known methods.

Compounds of formula (I) as herein-defined can be prepared by a process P2 which comprises the step of reacting a compound of formula (VI) or one of its salts:

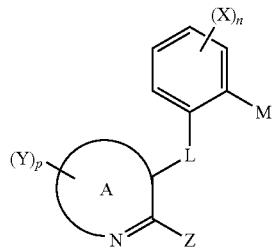

wherein A, L, n, p, X, Y and Z are as herein-defined and M represents an alkali metal such as lithium that can be complexed by 1 to 2 ligands or a halogenomagnesium that can be complexed by 1 to 2 ligands, with a silyl derivative of formula (IIIb) or a silyl derivative of formula (IIIc):

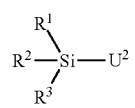

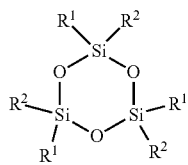

wherein $R^1$, $R^2$ and $R^3$ are as herein-defined and $U^2$ represents a chlorine atom, a bromine atom, an iodine atom or an unsubstituted or substituted $C_1$-$C_6$-alkoxy.

A compound of formula (VI) can be obtained from a halogenoaryl derivative of formula (II) by the reaction with magnesium metal or lithium metal; or by halogen/metal exchange using an alkyllithium reagent or a Grignard reagent or a manufactured complex prepared from an alkyl-lithium reagent or a Grignard reagent preferably under anhydrous conditions. Optionally lithium chloride can be used in pre-formed combination with these reagents.

Examples of alkyllithium reagents used in the lithiation process include methyllithium, phenyllithium, n-butyl-lithium, sec-butyllithium, iso-butyllithium, tert-butyl-lithium, and the like.

Examples of Grignard reagents used in the magnesium complexation process include methylmagnesium chloride, ethylmagnesium chloride, n-butylmagnesium chloride, iso-propylmagnesium chloride, chloro-(2,2,6,6-tetramethyl-1-piperidyl)magnesium and the like. A manufactured complex prepared from n-butylmagnesium chloride and n-butyl-lithium may also be used.

Examples of ligands used in the lithiation process or magnesium complexation process include tetramethylethyl-enediamine, hexamethylphosphotriamide, (+) or (−)-sparteine or 1,3-dimethyl-3,4,5,6-tetrahydro-2(1H)-pyrimi-dinone.

A solvent used in the lithiation or magnesium complex-ation is not particularly limited as long as it forms an anhydrous reaction system without dissolving the compound to react therewith or exhibit any particular interaction there-with. Preference is given to using non-halogenated aliphatic, alicyclic or aromatic hydrocarbons, such as petroleum ether, pentane, hexane, heptane, cyclohexane, methylcyclohexane, benzene, toluene, xylene, decalin, ISOPAR (registered trademark) E or ISOPAR (registered trademark) G; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane or 1,2-di-ethoxyethane; and a mixture thereof.

The lithiation or magnesium complexation may be performed in an inert atmosphere and prepared at a temperature of 0° C. to −78° C.

Alternatively, a compound of formula (VI) can be prepared from a compound of formula (VII) or one of its salts:

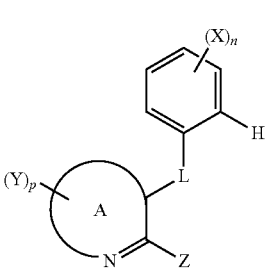

wherein A, L, n, p, X, Y and Z are as herein-defined by reaction with a base such as n-butyllithium, lithium di-isopropylamine, lithium tetramethylpiperidide, lithium bis(trimethylsilyl)amine, methyllithium or chloro-(2,2,6,6-te-tramethyl-1-piperidyl)magnesium and the like, preferably under anhydrous conditions. Optionally lithium chloride can be used in pre-formed combination with these reagents.

The solvent used in the reaction of compounds (VII) with a base is not particularly limited as long as it forms an anhydrous reaction system without dissolving the compound to react therewith or exhibit any particular interaction there-with. Preference is given to using non-halogenated aliphatic, alicyclic or aromatic hydrocarbons, such as petroleum ether, pentane, hexane, heptane, cyclohexane, methylcyclohexane, benzene, toluene, xylene, decalin, ISOPAR (registered trademark) E or ISOPAR (registered trademark) G; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane or 1,2-di-ethoxyethane; and a mixture thereof.

The reaction may be performed in an inert atmosphere and prepared at a temperature of 0° C. to −78° C.

Compounds of formula (VII) are known and can be prepared by known processes (Organic Letters (2012), 14, 173, Bioorganic & Medicinal Chemistry, 19, 939 and cited references therein).

Silyl derivatives of formula (IIIb) and (IIIc) are known or can be prepared by known processes.

Compounds of formula (I) wherein $R^3$ represents a hydroxyl can also be prepared from compounds of formula (I) wherein $R^3$ represents an hydrogen atom (themselves prepared by process P2) by known processes (Chemis-try—A European Journal (2012), 18, 9789, WO-2013/058825 and EP1908472).

Suitable solvents for carrying out process P2 are not particularly limited as long as it forms an anhydrous reaction system without dissolving the compound to react therewith or exhibit any particular interaction therewith. Preference is given to using non-halogenated aliphatic, alicyclic or aromatic hydrocarbons, such as petroleum ether, pentane, hexane, heptane, cyclohexane, methylcyclohexane, benzene, toluene, xylene, decalin, ISOPAR (registered trademark) E or ISOPAR (registered trademark) G; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane or 1,2-diethoxyethane or a mixture thereof.

Process P2 may be performed in an inert atmosphere. When carrying out process P2, 1 mole or an excess of compound of formula (IIIb) or compound of formula (IIIc) can be employed per mole of compound of formula (VII). It is also possible to employ the reaction components in other ratios. Work-up is carried out by known methods.

Compounds of formula (I) as herein-defined can be prepared by a process P3 which comprises the step of reacting a compound of formula (VIII) or one of its salts with a compound of formula (IX) as illustrated by the following reaction scheme:

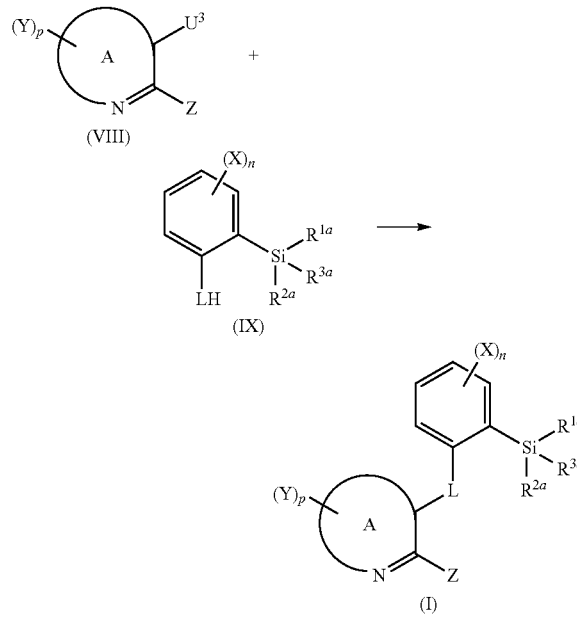

wherein L represents O, S or $NR^6$;

$U^3$ represents a chlorine atom, a bromine atom, an iodine atom, a mesyl group, a tosyl group or a triflyl group;

$R^{1a}$ and $R^{2a}$ independently represent an unsubstituted or substituted $C_1$-$C_8$-alkyl, an unsubstituted or substituted $C_2$-$C_8$-alkenyl, an unsubstituted or substituted $C_3$-$C_7$-cycloalkyl, an unsubstituted or substituted aryl or an unsubstituted or substituted heterocyclyl; and $R^{3a}$ represents a hydrogen atom, an unsubstituted or substituted $C_1$-$C_8$-alkyl; a $C_1$-$C_8$-halogenoalkyl comprising up to 9 halogen atoms that can be the same or different; an unsubstituted or substituted $C_2$-$C_8$-alkenyl; an unsubstituted or substituted $C_2$-$C_8$-alkynyl; an unsubstituted or substituted $C_3$-$C_7$-cycloalkyl; an unsubstituted or substituted $C_4$-$C_7$-cycloalkenyl; an unsubstituted or substituted aryl; an unsubstituted or substituted aryl-$C_1$-$C_8$-alkyl; an unsubstituted or substituted heterocyclyl; an unsubstituted or substituted heterocyclyl-$C_1$-$C_8$-alkyl; an unsubstituted or substituted hydroxy-$C_1$-$C_8$-alkyl; an unsubstituted or substituted $C_1$-$C_8$-alkoxy-$C_1$-$C_8$-alkyl; an unsubstituted or substituted $C_1$-$C_8$-alkylcarbonyloxy-$C_1$-$C_8$-alkyl; an unsubstituted or substituted aryloxy-$C_1$-$C_8$-alkyl; an unsubstituted or substituted heterocyclyloxy-$C_1$-$C_8$-alkyl; an unsubstituted or substituted amino-$C_1$-$C_8$-alkyl; an unsubstituted or substituted $C_1$-$C_8$-alkylamino-$C_1$-$C_8$-alkyl; an unsubstituted or substituted di-$C_1$-$C_8$-alkylamino-$C_1$-$C_8$-alkyl; an unsubstituted or substituted arylamino-$C_1$-$C_8$-alkyl; an unsubstituted or substituted di-arylamino-$C_1$-$C_8$-alkyl; an unsubstituted or substituted heterocyclylamino-$C_1$-$C_8$-alkyl; an unsubstituted or substituted $C_1$-$C_8$-alkylcarbonylamino-$C_1$-$C_8$-alkyl; an unsubstituted or substituted $C_1$-$C_8$-alkoxycarbonylamino-$C_1$-$C_8$-alkyl; an unsubstituted or substituted $C_1$-$C_8$-alkylsulfanyl-$C_1$-$C_8$-alkyl; an unsubstituted or substituted $C_1$-$C_8$-alkylsulfinyl-$C_1$-$C_8$-alkyl; an unsubstituted or substituted $C_1$-$C_8$-alkylsulfonyl-$C_1$-$C_8$-alkyl; or an unsubstituted or substituted cyano-$C_1$-$C_8$-alkyl; and A, n, p, X, Y, $R^6$ and Z are as herein-defined.

Compounds of formula (IX) are commercially available or can be prepared by well known processes.

Process P3 can be performed in the presence of a transition metal catalyst such as palladium and if appropriate in the presence of a phosphine ligand or a N-heterocyclic carbene ligand; or copper and if appropriate in the presence of a ligand; and if appropriate in the presence of a base and if appropriate in the presence of a solvent according to known processes (Organic Letters (2012), 14, 170, Organic Letters (2002), 4, 1623 and cited references therein).

Suitable palladium-based catalyst can be as disclosed in connection with process P1.

Suitable copper salts or complexes and their hydrates for this purpose are for example, copper metal, copper(I) iodide, copper(I) chloride, copper(I) bromide, copper(II) chloride, copper(II) bromide, copper(II) oxide, copper(I) oxide, copper(II) acetate, copper(I) acetate, copper(I) thiophene-2-carboxylate, copper(I) cyanide, copper(II) sulfate, copper bis(2,2,6,6-tetramethyl-3,5-heptanedionate), copper(II) trifluoromethanesulfonate, tetrakis(acetonitrile)copper(I) hexafluorophosphate, tetrakis(acetonitrile)-copper(I) tetrafluoroborate.

It is also possible to generate a copper complex in the reaction mixture by separate addition to the reaction of a copper salt and a ligand or salt, such as ethylenediamine, N,N-dimethylethylenediamine, N,N'-dimethylethylenediamine, rac-trans-1,2-diaminocyclohexane, rac-trans-N,N'-dimethylcyclohexane-1,2-diamine, 1,1'-binaphthyl-2,2'-diamine, N,N,N',N'-tetramethylethylenediamine, proline, N,N-dimethylglycine, quinolin-8-ol, pyridine, 2-aminopyridine, 4-(dimethylamino)pyridine, 2,2'-bipyridyl, 2,6-di(2-pyridyl)pyridine, 2-picolinic acid, 2-(dimethylaminomethyl)-3-hydroxypyridine, 1,10-phenanthroline, 3,4,7,8-tetramethyl-1,10-phenanthroline, 2,9-dimethyl-1,10-phenanthroline, 4,7-dimethoxy-1,10-phenanthroline, N,N'-bis[(E)-pyridin-2-ylmethylidene]cyclohexane-1,2-diamine, N-[(E)-phenylmethylidene], N-[(E)-phenylmethylidene]-cyclohexanamine, 1,1,1-tris(hydroxymethyl)ethane, ethylene glycol, 2,2,6,6-tetramethylheptane-3,5-dione, 2-(2,2-dimethylpropanoyl)cyclohexanone, acetylacetone, dibenzoylmethane, 2-(2-methylpropanoyl)cyclohexanone, biphenyl-2-yl(di-tert-butyl)phosphane, ethylenebis-(diphenylphosphine), N,N-diethylsalicylamide, 2-hydroxybenzaldehyde oxime, oxo[(2,4,6-trimethylphenyl)amino]acetic acid or 1H-pyrrole-2-carboxylic acid.

It is also advantageous to choose the appropriate catalyst and/or ligand from commercial catalogues such as "Metal Catalysts for Organic Synthesis" by Strem Chemicals or from reviews (Chemical Society Reviews (2014), 43, 3525, Coordination Chemistry Reviews (2004), 248, 2337 and references therein).

Suitable bases for carrying out process P3 can be as disclosed in connection with process P1.

Suitable solvents for carrying out process P3 can be as disclosed in connection with process P1.

Process P3 may be performed in an inert atmosphere. When carrying out process P3, 1 mole or an excess of compound of formula (IX) and from 1 to 5 moles of base and from 0.01 to 20 mole percent of a transition metal complex can be employed per mole of compound of formula (VIII). It is also possible to employ the reaction components in other ratios. Work-up is carried out by known methods.

Compounds of formula (I) as herein-defined can be prepared by a process P4 which comprises the step of reacting a compound of formula (X) or one of its salts with a compound of formula (XI) as illustrated by the following reaction scheme:

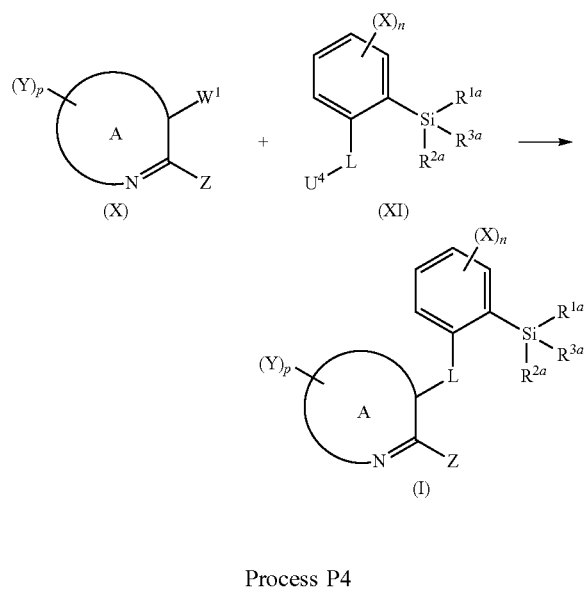

Process P4 wherein L represents $CR^4R^5$;

$R^4$ and $R^5$ independently represent a hydrogen atom or an unsubstituted or substituted $C_1$-$C_8$ alkyl;

$U^4$ represents a bromine atom, a chlorine atom, an iodine atom, a mesyl group, a tosyl group or a triflyl group;

$W^1$ represents a boron derivative such as a boronic acid, a boronic ester or a potassium trifluoroborate derivative;

$R^{1a}$ and $R^{2a}$ independently represent an unsubstituted or substituted $C_1$-$C_8$-alkyl, an unsubstituted or substituted $C_2$-$C_8$-alkenyl, an unsubstituted or substituted $C_3$-$C_7$-cycloalkyl, an unsubstituted or substituted aryl or an unsubstituted or substituted heterocyclyl;

$R^{3a}$ represents a hydrogen atom; an unsubstituted or substituted $C_1$-$C_8$-alkyl; a $C_1$-$C_8$-halogenoalkyl comprising up to 9 halogen atoms that can be the same or different; an unsubstituted or substituted $C_2$-$C_8$-alkenyl; an unsubstituted or substituted $C_2$-$C_8$-alkynyl; an unsubstituted or substituted $C_3$-$C_7$-cycloalkyl; an unsubstituted or substituted $C_4$-$C_7$-cycloalkenyl; an unsubstituted or substituted aryl; an unsubstituted or substituted aryl-$C_1$-$C_8$-alkyl; an unsubstituted or substituted heterocyclyl; an unsubstituted or substituted heterocyclyl-$C_1$-$C_8$-alkyl; an unsubstituted or substituted hydroxy-$C_1$-$C_8$-alkyl; an unsubstituted or substituted $C_1$-$C_8$-alkoxy-$C_1$-$C_8$-alkyl; an unsubstituted or substituted $C_1$-$C_8$-alkylcarbonyloxy-$C_1$-$C_8$-alkyl; an unsubstituted or substituted aryloxy-$C_1$-$C_8$-alkyl; an unsubstituted or substituted heterocyclyloxy-$C_1$-$C_8$-alkyl; an unsubstituted or substituted amino-$C_1$-$C_8$-alkyl; an unsubstituted or substituted $C_1$-$C_8$-alkylamino-$C_1$-$C_8$-alkyl; an unsubstituted or substituted di-$C_1$-$C_8$-alkylamino-$C_1$-$C_8$-alkyl; an unsubstituted or substituted arylamino-$C_1$-$C_8$-alkyl; an unsubstituted or substituted di-arylamino-$C_1$-$C_8$-alkyl; an unsubstituted or substituted heterocyclylamino-$C_1$-$C_8$-alkyl; an unsubstituted or substituted $C_1$-$C_8$-alkylcarbonylamino-$C_1$-$C_8$-alkyl; an unsubstituted or substituted $C_1$-$C_8$-alkoxycarbonylamino-$C_1$-$C_8$-alkyl; an unsubstituted or substituted $C_1$-$C_8$-alkylsulfanyl-$C_1$-$C_8$-alkyl; an unsubstituted or substituted $C_1$-$C_8$-alkylsulfinyl-$C_1$-$C_8$-alkyl; an unsubstituted or substituted $C_1$-$C_8$-alkylsulfonyl-$C_1$-$C_8$-alkyl or an unsubstituted or substituted cyano-$C_1$-$C_8$-alkyl; and A, n, p, X, Y and Z are as herein-defined.

Compounds of formula (XI) can be prepared by known processes (Journal of the American Chemical Society (1957), 79, 6540; Journal of Organic Chemistry (2000), (65), 4913; Tetrahedron Letters (2002), 43, 8569).

Process P4 can be performed in the presence of a transition metal catalyst such as palladium and if appropriate in the presence of a phosphine ligand or a N-heterocyclic carbene ligand and if appropriate in the presence of a base and if appropriate in the presence of a solvent. Suitable palladium salts or complexes for this purpose can be as disclosed in connection with process P1.

Suitable bases for carrying out process P4 can be as disclosed in connection with process P1.

Suitable solvents for carrying out process P4 can be as disclosed in connection with process P1.

It can also be advantageous to carry out process P4 according to the invention, with a co-solvent such as water or an alcohol such as methanol, ethanol, propanol, isopropanol or tert-butanol.

Process P4 may be performed in an inert atmosphere. When carrying out process P4, 1 mole or an excess of compound of formula (XI) and from 1 to 5 moles of base and from 0.01 to 20 mole percent of a transition metal complex can be employed per mole of compound of formula (X). It is also possible to employ the reaction components in other ratios. Work-up is carried out by known methods.

Compounds of formula (I) as herein-defined can be prepared by a process P5 which comprises the step of reacting a compound of formula (VIII) or one of its salts with a compound of formula (XII) as illustrated by the following reaction scheme:

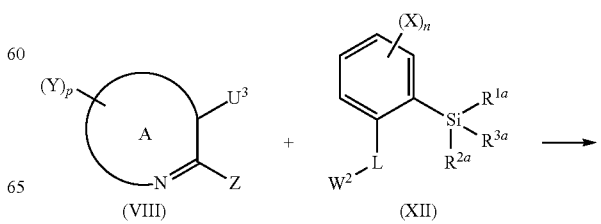

-continued

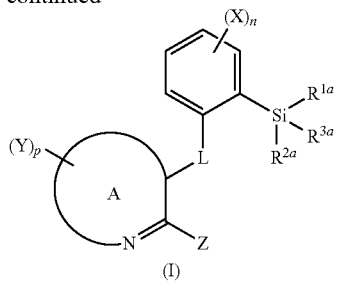

Process P5 wherein L represents $CR^4R^5$;

$R^4$ and $R^5$ independently represent a hydrogen atom, an unsubstituted or substituted $C_1$-$C_8$-alkoxy or an unsubstituted or substituted $C_1$-$C_8$ alkyl;

$U^3$ represents a bromine atom, a chlorine atom, an iodine atom, a mesyl group, a tosyl group or a triflyl group;

$W^2$ represents a boron derivative such as a boronic acid, a boronic ester or a potassium trifluoroborate derivative;

$R^{1a}$ and $R^{2a}$ independently represent an unsubstituted or substituted $C_1$-$C_8$-alkyl, an unsubstituted or substituted $C_2$-$C_8$-alkenyl, an unsubstituted or substituted $C_3$-$C_7$-cycloalkyl, an unsubstituted or substituted aryl or an unsubstituted or substituted heterocyclyl;

$R^{3a}$ represents a hydrogen atom or an unsubstituted or substituted $C_1$-$C_8$-alkyl; a $C_1$-$C_8$-halogenoalkyl comprising up to 9 halogen atoms that can be the same or different; an unsubstituted or substituted $C_2$-$C_8$-alkenyl; an unsubstituted or substituted $C_2$-$C_8$-alkynyl; an unsubstituted or substituted $C_3$-$C_7$-cycloalkyl; an unsubstituted or substituted $C_4$-$C_7$-cycloalkenyl; an unsubstituted or substituted aryl; an unsubstituted or substituted aryl-$C_1$-$C_8$-alkyl; an unsubstituted or substituted heterocyclyl; an unsubstituted or substituted heterocyclyl-$C_1$-$C_8$-alkyl; an unsubstituted or substituted hydroxy-$C_1$-$C_8$-alkyl; an unsubstituted or substituted $C_1$-$C_8$-alkoxy-$C_1$-$C_8$-alkyl; an unsubstituted or substituted $C_1$-$C_8$-alkylcarbonyloxy-$C_1$-$C_8$-alkyl; an unsubstituted or substituted aryloxy-$C_1$-$C_8$-alkyl; an unsubstituted or substituted heterocyclyloxy-$C_1$-$C_8$-alkyl; an unsubstituted or substituted amino-$C_1$-$C_8$-alkyl; an unsubstituted or substituted $C_1$-$C_8$-alkylamino-$C_1$-$C_8$-alkyl; an unsubstituted or substituted di-$C_1$-$C_8$-alkylamino-$C_1$-$C_8$-alkyl; an unsubstituted or substituted arylamino-$C_1$-$C_8$-alkyl; an unsubstituted or substituted di-arylamino-$C_1$-$C_8$-alkyl; an unsubstituted or substituted heterocyclylamino-$C_1$-$C_8$-alkyl; an unsubstituted or substituted $C_1$-$C_8$-alkylcarbonylamino-$C_1$-$C_8$-alkyl; an unsubstituted or substituted $C_1$-$C_8$-alkoxycarbonylamino-$C_1$-$C_8$-alkyl; an unsubstituted or substituted $C_1$-$C_8$-alkylsulfanyl-$C_1$-$C_8$-alkyl; an unsubstituted or substituted $C_1$-$C_8$-alkylsulfinyl-$C_1$-$C_8$-alkyl or an unsubstituted or substituted $C_1$-$C_8$-alkylsulfonyl-$C_1$-$C_8$-alkyl or an unsubstituted or substituted cyano-$C_1$-$C_8$-alkyl; and A, n, p, X, Y and Z are as herein-defined.

Compounds of formula (XII) can be prepared from compounds of formula (XI) by known processes (Tetrahedron Letters (2003), 44, 233 and Chemistry Letters (2002), 780).

Process P5 can be performed in the presence of a transition metal catalyst such as palladium and if appropriate in the presence of a phosphine ligand or a N-heterocyclic carbene ligand and if appropriate in the presence of a base and if appropriate in the presence of a solvent. Suitable palladium salts or complexes for this purpose can be as disclosed in connection with process P1.

Suitable bases for carrying out process P5 can be as disclosed in connection with process P1.

Suitable solvents for carrying out process P5 can be as disclosed in connection with process P1.

It can also be advantageous to carry out process P5 according to the invention, with a co-solvent such as water or an alcohol such as methanol, ethanol, propanol, isopropanol or tert-butanol.

Process P5 may be performed in an inert atmosphere. When carrying out process P5, 1 mole or an excess of compound of formula (XII) and from 1 to 5 moles of base and from 0.01 to 20 mole percent of a transition metal complex can be employed per mole of compound of formula (VIII). It is also possible to employ the reaction components in other ratios. Work-up is carried out by known methods.

Compounds of formula (I) as herein-defined can be prepared by a process P6 which comprises the step of reacting a compound of formula (XIII) or one of its salts with a compound of formula (XIV) as illustrated by the following reaction scheme:

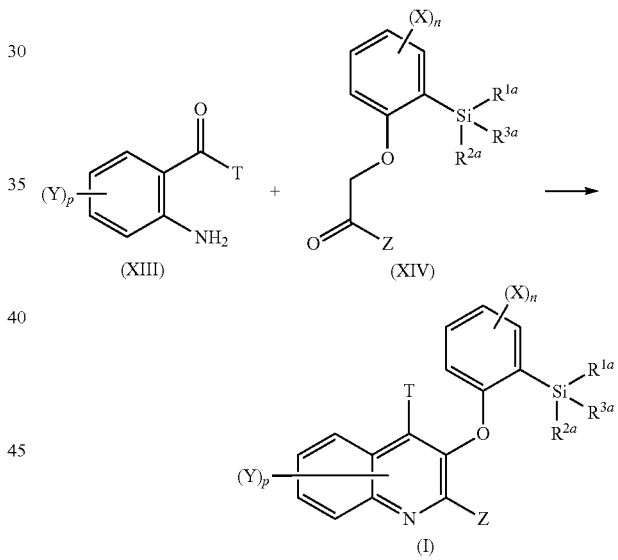

Process P6 wherein T represents a hydrogen atom, an unsubstituted or substituted $C_1$-$C_8$ alkyl, an unsubstituted or substituted $C_3$-$C_7$-cycloalkyl, an unsubstituted or substituted aryl or an unsubstituted or substituted heterocyclyl;

p represents 0, 1, 2, 3 or 4;

Z represents an unsubstituted or substituted $C_1$-$C_8$-alkyl, an unsubstituted or substituted $C_3$-$C_7$-cycloalkyl, an unsubstituted or substituted aryl or an unsubstituted or substituted heterocyclyl;

$R^{1a}$ and $R^{2a}$ independently represent an unsubstituted or substituted $C_1$-$C_8$-alkyl, an unsubstituted or substituted $C_2$-$C_8$-alkenyl, an unsubstituted or substituted $C_3$-$C_7$-cycloalkyl, an unsubstituted or substituted aryl or an unsubstituted or substituted heterocyclyl;

$R^{3a}$ represents a hydrogen atom or an unsubstituted or substituted $C_1$-$C_8$-alkyl; a $C_1$-$C_8$-halogenoalkyl comprising up to 9 halogen atoms that can be the same or different; an unsubstituted or substituted $C_2$-$C_8$-alkenyl; an unsubstituted or substituted $C_2$-$C_8$-alkynyl; an unsubstituted or substituted $C_3$-$C_7$-cycloalkyl; an unsubstituted or substituted $C_4$-$C_7$-cycloalkenyl; an unsubstituted or substituted aryl; an unsubstituted or substituted aryl-$C_1$-$C_8$-alkyl; an unsubstituted or substituted heterocyclyl; an unsubstituted or substituted heterocyclyl-$C_1$-$C_8$-alkyl; an unsubstituted or substituted hydroxy-$C_1$-$C_8$-alkyl; an unsubstituted or substituted $C_1$-$C_8$-alkoxy-$C_1$-$C_8$-alkyl; an unsubstituted or substituted $C_1$-$C_8$-alkylcarbonyloxy-$C_1$-$C_8$-alkyl; an unsubstituted or substituted aryloxy-$C_1$-$C_8$-alkyl; an unsubstituted or substituted heterocyclyloxy-$C_1$-$C_8$-alkyl; an unsubstituted or substituted amino-$C_1$-$C_8$-alkyl; an unsubstituted or substituted $C_1$-$C_8$-alkylamino-$C_1$-$C_8$-alkyl; an unsubstituted or substituted di-$C_1$-$C_8$-alkylamino-$C_1$-$C_8$-alkyl; an unsubstituted or substituted arylamino-$C_1$-$C_8$-alkyl; an unsubstituted or substituted di-arylamino-$C_1$-$C_8$-alkyl; an unsubstituted or substituted heterocyclylamino-$C_1$-$C_8$-alkyl; an unsubstituted or substituted $C_1$-$C_8$-alkylcarbonylamino-$C_1$-$C_8$-alkyl; an unsubstituted or substituted $C_1$-$C_8$-alkoxycarbonylamino-$C_1$-$C_8$-alkyl; an unsubstituted or substituted $C_1$-$C_8$-alkylsulfanyl-$C_1$-$C_8$-alkyl; an unsubstituted or substituted $C_1$-$C_8$-alkylsulfinyl-$C_1$-$C_8$-alkyl; an unsubstituted or substituted $C_1$-$C_8$-alkylsulfonyl-$C_1$-$C_8$-alkyl or an unsubstituted or substituted cyano-$C_1$-$C_8$-alkyl; and n, X and Y are as herein-defined.

Process P6 can be performed, if appropriate, in the presence of a suitable base or, if appropriate, in the presence of a suitable Brønsted or Lewis acid, and if appropriate in the presence of a solvent.

Compounds of formula (XIII) are commercially available or can be prepared by well known processes.

Compounds of formula (XIV) can be prepared by known processes from corresponding phenols (IX) and corresponding alpha-halo ketones (Organic and Biomolecular Chemistry (2006), 4, 4193).

Process P6 can as well be used for the preparation 3-phenoxynaphthyridines.

Suitable bases for carrying out process P6 can be as disclosed in connection with process P1.

Suitable Lewis acids for carrying out process P6 can be inorganic and organic Lewis acids which are customary for such reactions. Preference is given to using metal halides, such as aluminium(III) chloride, iron(III) chloride, zinc(II) chloride, titanium tetrachloride, boron trifluoride; triflates, such as scandium(III) triflate, bismuth(III) triflate or ytterbium(III) triflate and also iodine.

Suitable Brønsted acids for carrying out process P6 can be inorganic and organic Lewis acids which are customary for such reactions. Preference is given to using hydrogen halides, such as hydrogen chloride or hydrogen bromide; sulfonic acids such as p-toluenesulfonic acid, camphorsulfonic acid, methanesulfonic acid or trifluoromethanesulfonic acid and also polyphosphoric acid, phosphoric acid sulfuric acid, potassium bisulfite, trifluoroacetic acid or acetic acid.

Suitable solvents for carrying out process P6 can be customary inert organic solvents. Preference is given to using water, an alcohol such as methanol, ethanol, propanol, isopropanol, tert-butanol or tert-amyl alcohol, optionally halogen atomated aliphatic, alicyclic or aromatic hydrocarbons, such as petroleum ether, pentane, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 2-methyltetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; ureas, such as 1,3-dimethyl-3,4,5,6-tetrahydro-2(1H)-pyrimidinone; esters, such as methyl acetate or ethyl acetate, sulfoxides, such as dimethyl sulfoxide, or sulfones, such as sulfolane; and a mixture thereof.

Process P6 may be performed in an inert atmosphere. When carrying out process P6, 1 mole or an excess of compound of formula (XIV) and from 0.01 to 5 moles of base or from 0.01 to 5 moles percent of suitable acid can be employed per mole of compound of formula (XIII). It is also possible to employ the reaction components in other ratios. Work-up is carried out by known methods.

Processes P1, P2, P3, P4, P5 and P6 are generally carried out under atmospheric pressure. It is also possible to operate under elevated or reduced pressure.

When carrying out processes P1, P2, P3, P4, P5 and P6, the reaction temperatures can be varied within a relatively wide range. In general, these processes are carried out at temperatures from −78° C. to 200° C., preferably from −78° C. to 150° C. A way to control the temperature for the processes is to use microwave technology.

In general, the reaction mixture is concentrated under reduced pressure. The residue that remains can be freed by known methods, such as chromatography or crystallization, from any impurities that can still be present.

Work-up is carried out by customary methods. Generally, the reaction mixture is treated with water and the organic phase is separated off and, after drying, concentrated under reduced pressure. If appropriate, the remaining residue can, be freed by customary methods, such as chromatography, crystallization or distillation, from any impurities that may still be present.

The compounds of formula (I) can be prepared according to the general processes of preparation described above. It will nevertheless be understood that, on the basis of his general knowledge and of available publications, the skilled worker will be able to adapt the methods according to the specifics of each compound, which it is desired to synthesize.

Intermediates for the Preparation of the Active Compounds

The present invention also relates to intermediates for the preparation of compounds of formula (I).

Thus, the present invention relates to compounds of formula (IIa) as well as their acceptable salts:

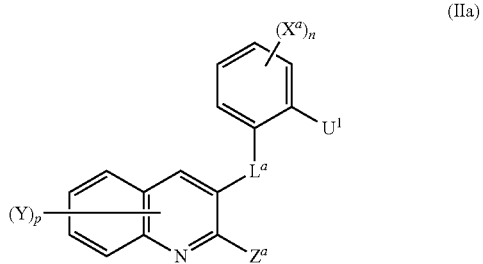

wherein:
L$^a$ represents O, S, CH$_2$ or NR$^6$;
U$^1$ represents a chlorine atom, a bromine atom, a iodine atom, a mesyl group, a tosyl group or a triflyl group;
X$^a$ represents a halogen atom, a C$_1$-C$_8$-alkyl group, a C$_1$-C$_8$-halogenoalkyl group comprising 2 to 9 halogen atoms that can be the same or different, a C$_1$-C$_8$-alkoxy group, a C$_1$-C$_8$-halogenoalkoxy group comprising up to 9 halogen atoms that can be the same or different, a C$_1$-C$_8$-alkylsulfanyl group, a C$_1$-C$_8$-halogenoalkylsulfanyl group comprising up to 9 halogen atoms that can be the same or different, or cyano;
Z$^a$ represents a hydrogen atom, a halogen atom, a C$_1$-C$_8$-alkyl group, a C$_1$-C$_8$-halogenoalkyl group comprising up to 9 halogen atoms that can be the same or different, a C$_1$-C$_8$-alkoxy group, a C$_1$-C$_8$-halogenoalkoxy group comprising up to 9 halogen atoms that can be the same or different, a C$_1$-C$_8$-alkylsulfanyl group, or a C$_1$-C$_8$-halogenoalkylsulfanyl group comprising up to 9 halogen atoms that can be the same or different; and
n, p, Y and R$^6$ are as herein-defined,
provided that the compound of formula (IIa) does not represent:
3-(2-chlorobenzyl)-2-methoxy-6-(pyridin-3-yl)quinoline [1574532-60-7],
3-chloro-4-(quinolin-3-ylamino)benzonitrile [1407301-89-6],
8-fluoro-3-(3-fluoro-2-iodophenoxy)quinoline [1314012-45-7],
3-[(2-bromophenyl)sulfanyl]quinoline [1299398-51-8],
N-(2-chlorophenyl)quinolin-3-amine [1021328-11-9],
6-bromo-3-(2-chlorobenzyl)-2-methoxyquinoline [930406-96-5],
2-chloro-3-(2-chlorobenzyl)-6-fluoroquinoline [924658-62-8],
2-chloro-3-(2-chlorobenzyl)quinoline [924658-58-2],
N-[2-bromo-5-(trifluoromethyl)phenyl]quinolin-3-amine [891779-92-3],
N-(2-bromo-4-chlorophenyl)quinolin-3-amine [891779-90-1],
N-(2-bromo-4-methylphenyl)quinolin-3-amine [891779-88-7],
3-(2-bromo-4,5-dimethoxybenzyl)quinolin-4-ol [856100-31-7],
3-(2-bromo-4,5-dimethoxybenzyl)-4-chloroquinoline [856089-71-9],
3-(2-chlorobenzyl)-4-phenyl-8-(trifluoromethyl)quinoline [854770-03-9],
N-(2-bromophenyl)quinolin-3-amine [848086-11-3], and
3-[(2-chlorophenyl)sulfanyl]-8-nitroquinoline [607743-29-3].
The following compounds of formula (IIa) are also mentioned in chemical databases and/or suppliers' databases but without any references or information which enable these to be prepared and separated
3-chloro-4-(quinolin-3-yloxy)benzonitrile [1965167-19-4],
3-bromo-4-(quinolin-3-yloxy)benzonitrile [1925480-59-6],
3-bromo-4-(quinolin-3-ylamino)benzonitrile [1551935-00-2],
6-bromo-2-chloro-3-(2-chlorobenzyl)quinoline [1429750-26-4],
6-bromo-3-(2,4-dichlorobenzyl)-2-methoxyquinoline [930445-54-8], and
6-bromo-3-(2,3-dichlorobenzyl)-2-methoxyquinoline [930406-99-8].
Preferred compounds of formula (IIa) according to the invention are:

3-(3-fluoro-2-iodophenoxy)quinoline,
3-(2-iodophenoxy)quinoline,
3-(2-bromophenoxy)quinoline,
3-(2-bromophenoxy)-8-fluoroquinoline,
3-(2-bromophenoxy)-8-fluoro-2-methylquinoline,
3-(2-bromophenoxy)-7,8-difluoroquinoline,
3-(2-bromophenoxy)-7,8-difluoro-2-methylquinoline,
3-(2-bromophenoxy)-2-methylquinoline,
3-(2-bromo-6-fluorophenoxy)-7,8-difluoro-2-methylquinoline,
3-(2-bromo-5-fluorophenoxy)-7,8-difluoro-2-methylquinoline,
3-(2-bromo-4-fluorophenoxy)-8-chloroquinoline,
3-(2-bromo-4-fluorophenoxy)-7,8-difluoro-2-methylquinoline,
3-(2-bromo-4-fluorophenoxy)-2-methylquinoline,
3-(2-bromo-3-methoxyphenoxy)-7,8-difluoro-2-methylquinoline,
3-(2-bromo-3-fluorophenoxy)-7,8-difluoroquinoline,
3-(2-bromo-3-fluorophenoxy)-7,8-difluoro-2-methylquinoline,
3-(2-bromo-3-fluorophenoxy)-4-methylquinoline,
3-(2-bromo-3-fluorophenoxy)-2-methylquinoline,
3-(2-bromo-3-fluorophenoxy)-2-(difluoromethyl)quinoline,
3-(2-bromo-3-chlorophenoxy)-7,8-difluoro-2-methylquinoline,
3-(2-bromo-3-chlorophenoxy)-2-methylquinoline,
N-(2-bromo-3-fluorophenyl)-2-(difluoromethyl)quinolin-3-amine,
8-chloro-3-(2-chloro-4-fluorophenoxy)quinoline,
3-[2-bromo-3-(trifluoromethoxy) phenoxy]-7,8-difluoro-2-methylquinoline,
3-[2-bromo-3-(trifluoromethoxy)phenoxy)phenyl]-2-methylquinoline, and
3-(2-bromo-4-chlorophenoxy)-2-methylquinoline.
Other preferred compounds of formula (II) according to the invention are:
2-iodo-3-(quinolin-3-yloxy)benzaldehyde,
[2-iodo-3-(quinolin-3-yloxy)phenyl]methanol,
2-{2-bromo-3-[(2-methylquinolin-3-yl)oxy] phenyl}ethanol,
N-{2-bromo-3-[(tetrahydro-2H-pyran-2-yloxy)methyl] phenyl}quinolin-3-amine,
3-{2-iodo-3-[(tetrahydro-2H-pyran-2-yloxy)methyl] phenoxy}quinoline,
3-(2-bromo-5-nitrophenoxy)-7,8-difluoro-2-methylquinoline,
(2-bromophenyl)(quinolin-3-yl)methanone, and
3-[2-bromo-3-(2-chloroethyl)phenoxy]-2-methylquinoline.
The present invention also relates to compounds of formula (IIb) as well as their acceptable salts:

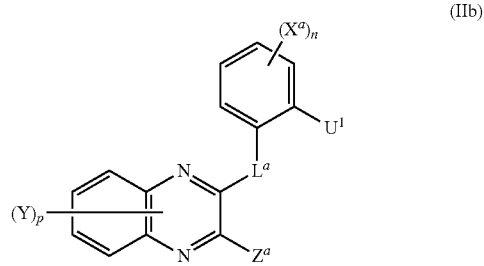

wherein:
L$^a$ represents O, S, CH$_2$ or NR$^6$; U$^1$ represents a chlorine atom, a bromine atom, a iodine atom, a mesyl group, a tosyl group or a triflyl group;

X$^a$ represents a halogen atom, a C$_1$-C$_8$-alkyl group, a C$_1$-C$_8$-halogenoalkyl group comprising 2 to 9 halogen atoms that can be the same or different, a C$_1$-C$_8$-alkoxy group, a C$_1$-C$_8$-halogenoalkoxy group comprising up to 9 halogen atoms that can be the same or different, a C$_1$-C$_8$-alkylsulfanyl group, a C$_1$-C$_8$-halogenoalkylsulfanyl group comprising up to 9 halogen atoms that can be the same or different, or cyano;

Z$^a$ represents a hydrogen atom, a halogen atom, a C$_1$-C$_8$-alkyl group, a C$_1$-C$_8$-halogenoalkyl group comprising up to 9 halogen atoms that can be the same or different, a C$_1$-C$_8$-alkoxy group, a C$_1$-C$_8$-halogenoalkoxy group comprising up to 9 halogen atoms that can be the same or different, a C$_1$-C$_8$-alkylsulfanyl group, or a C$_1$-C$_8$-halogenoalkylsulfanyl group comprising up to 9 halogen atoms that can be the same or different; and n, p, Y and R$^6$ are as herein-defined, provided that the compound of formula (IIb) does not represent:

2-(2-chlorophenoxy)-3-methylquinoxaline [1792986-07-2],
2-bromo-3-[(2-bromo-4-chlorophenyl)sulfanyl]quinoxaline [1674381-01-1],
2-bromo-3-(2-bromo-4-chlorophenoxy)quinoxaline [1674380-91-6],
2-(2-iodophenoxy)quinoxaline [1055190-73-2],
N-[2,6-dichloro-4-(trifluoromethyl)phenyl]-3-(trifluoromethyl)quinoxalin-2-amine [803726-02-5],
N-(2-chlorophenyl)-3-methylquinoxalin-2-amine [438481-21-1],
2-[(2-chlorophenyl)sulfanyl]-3-(trifluoromethyl)quinoxaline [338773-65-2],
2-[(2-chlorophenyl)sulfanyl]quinoxaline [338394-57-3],
2-(2-bromophenoxy)quinoxaline [223592-42-5],
2-(2-chlorophenoxy)quinoxaline [223592-28-7],
N-(2,4-dichlorophenyl)quinoxalin-2-amine [128499-91-2], and
2-(2-chlorobenzyl)quinoxaline [108852-34-2].

The following compounds of formula (IIb) are also mentioned in chemical databases and/or suppliers' databases but without any references or information which enable these to be prepared and separated 2-(2-bromo-4-methoxyphenoxy)-3-methylquinoxaline [1921330-33-7],
2-(2-bromo-4-methoxyphenoxy)quinoxaline [1918929-81-3],
2-(2-bromophenoxy)-3-chloroquinoxaline [1546723-03-8],
2-(2-bromo-5-fluorophenoxy)-3-methylquinoxaline [1540198-72-8],
2-(2-bromo-5-fluorophenoxy)quinoxaline [1503431-97-7],
2-(5-bromo-2-chlorophenoxy)quinoxaline [1468741-12-9],
2-(2-bromo-4-fluorophenoxy)quinoxaline [1460342-41-9],
2-(2-bromo-4-fluorophenoxy)-3-methylquinoxaline [1458220-97-7],
2-(2-iodophenoxy)-3-methylquinoxaline [1457170-20-5],
2-(2-bromo-4-methylphenoxy)-3-methylquinoxaline [1455256-50-4],
2-(5-bromo-2-chlorophenoxy)-3-methylquinoxaline [1406847-74-2],
2-(2-bromo-4-chlorophenoxy)quinoxaline [1356750-37-2],
2-(2-bromophenoxy)-3-methylquinoxaline [1285665-15-7],
2-(2-bromo-4-methylphenoxy)quinoxaline [1275144-84-7],
2-(2-chloro-4-fluorophenoxy)-3-methylquinoxaline [1181513-80-3],
N-(2-chloro-4-fluorophenyl)quinoxalin-2-amine [1029754-17-3],
N-(2-chloro-4-methylphenyl)quinoxalin-2-amine [933029-23-3],
2-chloro-3-(2-chlorophenoxy)quinoxaline [930037-00-6],
6,7-dichloro-2-(2,4,6-trichlorophenoxy)-3-(trifluoromethyl)quinoxaline [478040-16-3],
6,7-dichloro-2-(2,6-dichlorophenoxy)-3-(trifluoromethyl)quinoxaline [478040-14-1],
N-(2,4-dichlorophenyl)-3-methylquinoxalin-2-amine [438481-37-9], and
3-chloro-N-(2-chlorophenyl)quinoxalin-2-amine [372172-51-5].

Preferred compounds of formula (IIb) according to the invention are:

2-(2-bromophenoxy)-5,6-difluoroquinoxaline,
2-(2-bromophenoxy)-5,6-difluoro-3-methylquinoxaline,
2-(2-bromo-6-methylphenoxy)-5,6-difluoro-3-methylquinoxaline,
2-(2-bromo-6-fluorophenoxy)-5,6-difluoro-3-methylquinoxaline,
2-(2-bromo-6-chlorophenoxy)-5,6-difluoro-3-methylquinoxaline,
2-(2-bromo-5-methylphenoxy)-5,6-difluoro-3-methylquinoxaline,
2-(2-bromo-5-fluorophenoxy)-5,6-difluoro-3-methylquinoxaline,
2-(2-bromo-5-chlorophenoxy)-5,6-difluoro-3-methylquinoxaline,
2-(2-bromo-4-methylphenoxy)-5,6-difluoro-3-methylquinoxaline,
2-(2-bromo-4-fluorophenoxy)-5,6-difluoro-3-methylquinoxaline,
2-(2-bromo-4-chlorophenoxy)-5,6-difluoro-3-methylquinoxaline,
2-(2-bromo-3-methylphenoxy)-5,6-difluoro-3-methylquinoxaline,
2-(2-bromo-3-methoxyphenoxy)-5,6-difluoro-3-methylquinoxaline,
2-(2-bromo-3-fluorophenoxy)quinoxaline,
2-(2-bromo-3-fluorophenoxy)-5,6-difluoroquinoxaline,
2-(2-bromo-3-fluorophenoxy)-5,6-difluoro-3-methylquinoxaline,
2-(2-bromo-3-fluorophenoxy)-3-methylquinoxaline,
2-(2-bromo-3-chlorophenoxy)-5,6-difluoro-3-methylquinoxaline,
5-bromo-4-[(5,6-difluoroquinoxalin-2-yl)oxy]-2-fluorobenzonitrile,
4-bromo-3-[(5,6-difluoro-3-methylquinoxalin-2-yl)oxy]benzonitrile,
3-bromo-2-[(5,6-difluoroquinoxalin-2-yl)oxy]-4-fluorobenzonitrile,
2-bromo-3-[(5,6-difluoro-3-methylquinoxalin-2-yl)oxy]benzonitrile, and
2-[2-bromo-3-(trifluoromethoxy) phenoxy]-5,6-difluoro-3-methylquinoxaline.

Another preferred compound of formula (II) according to the invention is 2-bromo-3-[(5,6-difluoroquinoxalin-2-yl)oxy]benzaldehyde.

The present invention also relates to compounds of formula (IVa) as well as their acceptable salts:

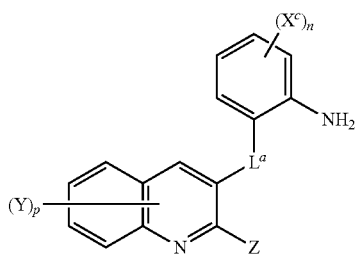

(IVa)

wherein:

$L^a$ represents O, S, $CH_2$ or $NR^6$;

X represents a halogen atom, a $C_1$-$C_8$-alkyl group, a $C_1$-$C_8$-halogenoalkyl group comprising up to 9 halogen atoms that can be the same or different, a $C_1$-$C_8$-alkoxy group, a $C_1$-$C_8$-halogenoalkoxy group comprising up to 9 halogen atoms that can be the same or different, a $C_1$-$C_8$-alkylsulfanyl group, a $C_1$-$C_8$-halogenoalkylsulfanyl group comprising up to 9 halogen atoms that can be the same or different, or cyano; and n, p, Y, Z and $R^6$ are as herein-defined, provided that the compound of formula (IVa) does not represent:

2-chloro-6-[(8-fluoroquinolin-3-yl)oxy]aniline [1417192-69-8], 2-fluoro-6-[(8-fluoroquinolin-3-yl)oxy]aniline [1417192-68-7], 4-[3-(2-aminophenoxy)-7-chloroquinolin-4-yl]-5-methoxy-2-methyl-2,4-dihydro-3H-1,2,4-triazol-3-one [1099507-90-0], 3-[(2-aminophenyl)sulfanyl]-6-chloro-4-phenylquinolin-2(1H)-one [727373-79-7], and 2-[(2-methylquinolin-3-yl)methyl]aniline [412336-26-6].

The following compounds of formula (IVa) are also mentioned in chemical databases and/or suppliers' databases but without any references or information which enable these to be prepared and separated:

2-chloro-6-(quinolin-3-yloxy)aniline [1965174-36-0],
2-ethoxy-6-(quinolin-3-yloxy)aniline [1962433-63-1],
3-amino-4-(quinolin-3-yloxy)benzonitrile [1962433-62-0],
3,4-difluoro-2-(quinolin-3-yloxy)aniline [1961697-86-8],
4-chloro-5-fluoro-2-(quinolin-3-yloxy)aniline [1936776-00-9],
2-methyl-6-(quinolin-3-yloxy)aniline [1931475-56-7],
3-methyl-2-(quinolin-3-yloxy)aniline [1929234-81-0],
5-chloro-4-fluoro-2-(quinolin-3-yloxy)aniline [1929234-79-6],
4-chloro-2-(quinolin-3-yloxy)aniline [1929231-29-7],
2-amino-3-(quinolin-3-yloxy)benzonitrile [1929005-25-3],
4-methoxy-2-(quinolin-3-yloxy)aniline [1928990-92-4],
5-methyl-2-(quinolin-3-yloxy)aniline [1928990-89-9],
4-bromo-2-(quinolin-3-yloxy)aniline [1928857-57-1],
5-bromo-2-(quinolin-3-yloxy)aniline [1928857-56-0],
5-chloro-2-(quinolin-3-yloxy)aniline [1928857-55-9],
4-methyl-2-(quinolin-3-yloxy)aniline [1928857-54-8],
5-fluoro-2-(quinolin-3-yloxy)aniline [1928620-30-7],
5-fluoro-4-methoxy-2-(quinolin-3-yloxy)aniline [1928620-20-5],
4,5-dichloro-2-(quinolin-3-yloxy)aniline [1927506-45-3],
2-methoxy-6-(quinolin-3-yloxy)aniline [1927506-43-1],
4-amino-3-(quinolin-3-yloxy)benzonitrile [1927506-39-5],
4-fluoro-5-iodo-2-(quinolin-3-yloxy)aniline [1927139-87-4],
2-(quinolin-3-yloxy)aniline [1927139-86-3],
2-fluoro-6-(quinolin-3-yloxy)aniline [1927074-28-9],
2,4-difluoro-6-(quinolin-3-yloxy)aniline [1926935-19-4],
4-fluoro-2-(quinolin-3-yloxy)aniline [1926934-99-7],
3-chloro-2-(quinolin-3-yloxy)aniline [1925620-69-4],
4-bromo-5-fluoro-2-(quinolin-3-yloxy)aniline [1925620-65-0],
5-bromo-4-fluoro-2-(quinolin-3-yloxy)aniline [1925620-60-5],
5-iodo-2-(quinolin-3-yloxy)aniline [1925480-40-5],
5-fluoro-4-methyl-2-(quinolin-3-yloxy)aniline [1925480-34-7], and
5-methoxy-2-(quinolin-3-yloxy)aniline [1925480-32-5].

Preferred compounds of formula (IVa) according to the invention are:

N-(quinolin-3-yl)benzene-1,2-diamine,
2-fluoro-6-[(2-methylquinolin-3-yl)oxy]aniline,
2-[(7,8-difluoroquinolin-3-yl)oxy]aniline,
2-[(7,8-difluoroquinolin-3-yl)oxy]-6-fluoroaniline,
2-[(7,8-difluoro-2-methylquinolin-3-yl)oxy]aniline,
2-[(7,8-difluoro-2-methylquinolin-3-yl)oxy]-6-fluoroaniline and
2-[(2-methylquinolin-3-yl)oxy]aniline.

The present invention also relates to compounds of formula (Va) as well as their acceptable salts:

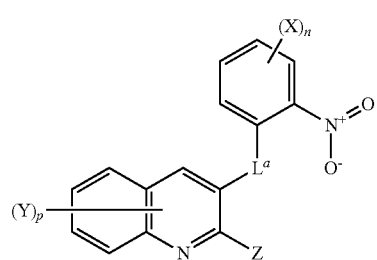

(Va)

wherein $L^a$ represents O, S, $CH_2$ or $NR^6$; and n, p, X, Y, Z and $R^6$ are as herein-defined, provided that the compound of formula (Va) does not represent:

N-[2,6-dinitro-4-(trifluoromethyl)phenyl]quinolin-3-amine [1638502-56-3],

N-(2,4-dinitrophenyl)quinolin-3-amine [1638502-54-1], 3-(3-chloro-2-nitrophenoxy)-8-fluoroquinoline [1417192-66-5], 8-fluoro-3-(3-fluoro-2-nitrophenoxy)quinoline [1417192-65-4], 3-(2-nitrophenoxy)quinoline [1417192-64-3], N-(4,6-dimethyl-2-oxo-1,2-dihydroquinolin-3-yl)-N-(5-methyl-2,4-dinitrophenyl)acetamide [107403-93-0], N-(4,6-dimethyl-2-oxo-1,2-dihydroquinolin-3-yl)-N-(2-nitrophenyl)acetamide [107403-92-9], 4,6-dimethyl-3-[(5-methyl-2,4-dinitrophenyl)amino]quinolin-2(1H)-one [107403-91-8], 4,6-dimethyl-3-[(2-nitrophenyl)amino]quinolin-2(1H)-one [107403-90-7], and 3-[(2-nitrophenyl)sulfanyl]quinoline [100461-52-7].

The following compounds of formula (Va) are also mentioned in chemical databases and/or suppliers' databases but without any references or information which enable these to be prepared and separated:

3-(4-bromo-2-nitrophenoxy)quinoline [1973729-88-2],
2-nitro-3-(quinolin-3-yloxy)aniline [1961752-50-0],
3-(3-chloro-2-nitrophenoxy)quinoline [1928857-81-1], 3-(3-fluoro-2-nitrophenoxy)quinoline [1928857-78-6],
N-(4-bromo-2-nitrophenyl)quinolin-3-amine [1408734-82-6],
4-hydroxy-3-[(2-nitrophenyl)sulfanyl]quinolin-2(1H)-one [685890-60-2], and
4-[(7-methoxyquinolin-3-yl)amino]-5-nitrophthalonitrile [540512-77-4].

Preferred compounds of formula (Va) according to the invention are:
7,8-difluoro-3-(3-fluoro-2-nitrophenoxy)quinoline,
7,8-difluoro-3-(3-fluoro-2-nitrophenoxy)-2-methylquinoline,
7,8-difluoro-3-(2-nitrophenoxy)quinoline,
7,8-difluoro-2-methyl-3-(2-nitrophenoxy)quinoline,
3-(3-fluoro-2-nitrophenoxy)quinoline,
3-(3-fluoro-2-nitrophenoxy)-2-methylquinoline, and
2-methyl-3-(2-nitrophenoxy)quinoline.

The present invention also relates to compounds of formula (IXa):

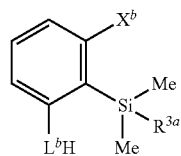

(IXa)

wherein:
$X^b$ represents a hydrogen atom, a chlorine atom or a fluorine atom;
$L^b$ represents O, S and NH; and
$R^{3a}$ represents a hydrogen atom or an unsubstituted or substituted $C_1$-$C_8$-alkyl; a $C_1$-$C_8$-halogenoalkyl comprising up to 9 halogen atoms that can be the same or different; an unsubstituted or substituted $C_2$-$C_8$-alkenyl; an unsubstituted or substituted $C_2$-$C_8$-alkynyl; an unsubstituted or substituted $C_3$-$C_7$-cycloalkyl; an unsubstituted or substituted $C_4$-$C_7$-cycloalkenyl; an unsubstituted or substituted aryl; an unsubstituted or substituted aryl-$C_1$-$C_8$-alkyl; an unsubstituted or substituted heterocyclyl; an unsubstituted or substituted heterocyclyl-$C_1$-$C_8$-alkyl; an unsubstituted or substituted hydroxy-$C_1$-$C_8$-alkyl; an unsubstituted or substituted $C_1$-$C_8$-alkoxy-$C_1$-$C_8$-alkyl; an unsubstituted or substituted $C_1$-$C_8$-alkylcarbonyloxy-$C_1$-$C_8$-alkyl; an unsubstituted or substituted aryloxy-$C_1$-$C_8$-alkyl; an unsubstituted or substituted heterocyclyloxy-$C_1$-$C_8$-alkyl; an unsubstituted or substituted amino-$C_1$-$C_8$-alkyl; an unsubstituted or substituted $C_1$-$C_8$-alkylamino-$C_1$-$C_8$-alkyl; an unsubstituted or substituted di-$C_1$-$C_8$-alkylamino-$C_1$-$C_8$-alkyl; an unsubstituted or substituted arylamino-$C_1$-$C_8$-alkyl; an unsubstituted or substituted di-arylamino-$C_1$-$C_8$-alkyl; an unsubstituted or substituted heterocyclylamino-$C_1$-$C_8$-alkyl; an unsubstituted or substituted $C_1$-$C_8$-alkylcarbonylamino-$C_1$-$C_8$-alkyl; an unsubstituted or substituted $C_1$-$C_8$-alkoxycarbonylamino-$C_1$-$C_8$-alkyl; an unsubstituted or substituted $C_1$-$C_8$-alkylsulfanyl-$C_1$-$C_8$-alkyl; an unsubstituted or substituted $C_1$-$C_8$-alkylsulfinyl-$C_1$-$C_8$-alkyl; an unsubstituted or substituted $C_1$-$C_8$-alkylsulfonyl-$C_1$-$C_8$-alkyl; or an unsubstituted or substituted cyano-$C_1$-$C_8$-alkyl;

provided that the compound of formula (IXa) does not represent:

2-[dimethyl(phenyl)silyl]aniline [1819368-37-0],
3-fluoro-2-(trimethylsilyl)phenol [1808920-27-5],
3-chloro-2-(trimethylsilyl)phenol [1808920-08-2],
2-[heptyl(dimethyl)silyl]aniline [1427772-62-0],
2-[hexyl(dimethyl)silyl]aniline [217662-68-5],
2,2'-(dimethylsilanediyl)diphenol [122397-35-7],
2,2'-(dimethylsilanediyl)dibenzenethiol [117526-69-9],
2-{dimethyl[(trimethylsilyl)methyl]silyl}benzenethiol [117526-66-6],
2-[tert-butyl(dimethyl)silyl]benzenethiol [117526-58-6],
2-[tert-butyl(dimethyl)silyl]phenol [82772-29-0],
2-(trimethylsilyl)aniline [57792-17-3],
2-(dimethylsilyl) phenol [33367-00-9],
2-(trimethylsilyl)benzenethiol [33356-45-5], and
2-(trimethylsilyl)phenol [15288-53-6].

The following compounds of formula (IXa) are also mentioned in chemical databases and/or suppliers' databases but without any references or information which enable these to be prepared and separated:
2-[{4-[(2-ethylhexyl)oxy]phenyl}(dimethyl)silyl]phenol [1398044-32-0], and
2-[allyl(dimethyl)silyl]benzenethiol [699532-17-7].

Preferred compounds of formula (IXa) according to the invention are: 3-fluoro-2-[isopropyl(dimethyl)silyl]phenol,
2-[isopropyl(dimethyl)silyl]phenol,
2-[isobutyl(dimethyl)silyl]phenol,
2-[ethyl(dimethyl)silyl]phenol,
2-[cyclohexyl(dimethyl)silyl]phenol, and
2-[benzyl(dimethyl)silyl]phenol.

Other preferred compounds of formula (IXa) according to the invention are 2-(triethylsilyl)phenol and 3-fluoro-2-(triethylsilyl)phenol.

The present invention also relates to compounds of formula (XIa):

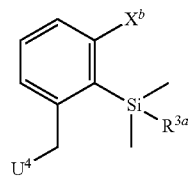

(XIa)

wherein:
$X^b$ represents a hydrogen atom, a chlorine atom or a fluorine atom;
$U^4$ represents a bromine atom, a chlorine atom, an iodine atom, a mesyl group, a tosyl group or a triflyl group; and
$R^{3a}$ represents a hydrogen atom or an unsubstituted or substituted $C_1$-$C_8$-alkyl; a $C_1$-$C_8$-halogenoalkyl comprising up to 9 halogen atoms that can be the same or different; an unsubstituted or substituted $C_2$-$C_8$-alkenyl; an unsubstituted or substituted $C_2$-$C_8$-alkynyl; an unsubstituted or substituted $C_3$-$C_7$-cycloalkyl; an unsubstituted or substituted $C_4$-$C_7$-cycloalkenyl; an unsubstituted or substituted aryl; an unsubstituted or substituted aryl-$C_1$-$C_8$-alkyl; an unsubstituted or substituted heterocyclyl; an unsubstituted or substituted heterocyclyl-$C_1$-$C_8$-alkyl; an unsubstituted or substituted hydroxy-$C_1$-$C_8$-alkyl; an unsubstituted or substituted $C_1$-$C_8$-alkoxy-$C_1$-$C_8$-alkyl; an unsubstituted or substituted $C_1$-$C_8$-alkylcarbonyloxy-$C_1$-$C_8$-alkyl; an unsubstituted or substituted aryloxy-$C_1$-$C_8$-alkyl; an unsubstituted or substituted heterocyclyloxy-$C_1$-$C_8$-alkyl; an unsubstituted or substituted amino-$C_1$-$C_8$- alkyl; an unsubstituted or substituted C₁-C₈-alkylamino-C₁-C₈-alkyl; an unsubstituted or substituted di-C₁-C₈-alkylamino-C₁-C₈-alkyl; an unsubstituted or substituted arylamino-C₁-C₈-alkyl; an unsubstituted or substituted di-arylamino-C₁-C₈-alkyl; an unsubstituted or substituted heterocyclylamino-C₁-C₈-alkyl; an unsubstituted or substituted C₁-C₈-alkylcarbonylamino-C₁-C₈-alkyl; an unsubstituted or substituted C₁-C₈-alkoxycarbonylamino-C₁-C₈-alkyl; an unsubstituted or substituted C₁-C₈-alkylsulfanyl-C₁-C₈-alkyl; an unsubstituted or substituted C₁-C₈-alkylsulfinyl-C₁-C₈-alkyl; an unsubstituted or substituted C₁-C₈-alkylsulfonyl-C₁-C₈-alkyl; or an unsubstituted or substituted cyano-C₁-C₈-alkyl;

provided that the compound of formula (XIa) does not represent:

[2-(chloromethyl)phenyl](trimethyl)silane [1379234-14-6],
[2-(bromomethyl)phenyl](3-chloropropyl)dimethylsilane [130284-14-9],
[2-(iodomethyl)phenyl](trimethyl)silane [126328-94-7],
[2-(bromomethyl)phenyl](chloromethyl)dimethylsilane [54848-87-2],
bis[2-(bromomethyl)phenyl](dimethyl)silane [19421-15-9], and
[2-(bromomethyl)phenyl](trimethyl)silane [17903-43-4].

Preferred compounds of formula (XIa) according to the invention are: 5-{[2-(bromomethyl)phenyl](dimethyl)silyl}-2-chloropyridine,
[2-(iodomethyl)phenyl](dimethyl)phenylsilane,
[2-(bromomethyl)phenyl](dimethyl)phenylsilane,
[2-(bromomethyl)phenyl](dimethyl)2-thienylsilane,
[2-(bromomethyl)phenyl](dimethyl)(4-phenoxyphenyl)silane,
[2-(bromomethyl)phenyl](4-chlorophenyl)dimethylsilane,
benzyl[2-(bromomethyl)phenyl]dimethylsilane,
biphenyl-4-yl[2-(bromomethyl)phenyl]dimethylsilane, and
(4-benzylphenyl)[2-(bromomethyl)phenyl]dimethylsilane.

The present invention also relates to compounds of formula (XIIa):

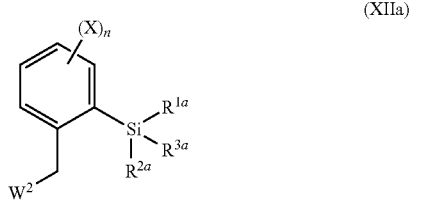

wherein:
W² represents a boron derivative such as a boronic acid, a boronic ester or a potassium trifluoroborate derivative; $R^{1a}$ and $R^{2a}$ independently represent an unsubstituted or substituted C₁-C₈-alkyl, an unsubstituted or substituted C₂-C₈-alkenyl, an unsubstituted or substituted C₃-C₇-cycloalkyl, an unsubstituted or substituted aryl, an unsubstituted or substituted heterocyclyl;
$R^{3a}$ represents a hydrogen atom or an unsubstituted or substituted C₁-C₈-alkyl; a C₁-C₈-halogenoalkyl comprising up to 9 halogen atoms that can be the same or different; an unsubstituted or substituted C₂-C₈-alkenyl; an unsubstituted or substituted C₂-C₈-alkynyl; an unsubstituted or substituted C₃-C₇-cycloalkyl; an unsubstituted or substituted C₄-C₇-cycloalkenyl; an unsubstituted or substituted aryl; an unsubstituted or substituted aryl-C₁-C₈-alkyl; an unsubstituted or substituted heterocyclyl; an unsubstituted or substituted heterocyclyl-C₁-C₈-alkyl; an unsubstituted or substituted hydroxy-C₁-C₈-alkyl; an unsubstituted or substituted C₁-C₈-alkoxy-C₁-C₈-alkyl; an unsubstituted or substituted C₁-C₈-alkylcarbonyloxy-C₁-C₈-alkyl; an unsubstituted or substituted aryloxy-C₁-C₈-alkyl; an unsubstituted or substituted heterocyclyloxy-C₁-C₈-alkyl; an unsubstituted or substituted amino-C₁-C₈-alkyl; an unsubstituted or substituted C₁-C₈-alkylamino-C₁-C₈-alkyl; an unsubstituted or substituted di-C₁-C₈-alkylamino-C₁-C₈-alkyl; an unsubstituted or substituted arylamino-C₁-C₈-alkyl; an unsubstituted or substituted di-arylamino-C₁-C₈-alkyl; an unsubstituted or substituted heterocyclylamino-C₁-C₈-alkyl; an unsubstituted or substituted C₁-C₈-alkylcarbonylamino-C₁-C₈-alkyl; an unsubstituted or substituted C₁-C₈-alkoxycarbonylamino-C₁-C₈-alkyl an unsubstituted or substituted C₁-C₈-alkylsulfanyl-C₁-C₈-alkyl; an unsubstituted or substituted C₁-C₈-alkylsulfinyl-C₁-C₈-alkyl; an unsubstituted or substituted C₁-C₈-alkylsulfonyl-C₁-C₈-alkyl; or an unsubstituted or substituted cyano-C₁-C₈-alkyl; and n and X are as herein-defined, provided that the compound of formula (XIIa) does not represent:
dimethyl{2-[(4,4,5,5-tetramethyl-1,3,2-dioxaborolan-2-yl)methyl]phenyl}silane [1639367-72-8],
methyl(phenyl){2-[(4,4,5,5-tetramethyl-1,3,2-dioxaborolan-2-yl)methyl]phenyl}silane [1639367-73-9], and
diphenyl{2-[(4,4,5,5-tetramethyl-1,3,2-dioxaborolan-2-yl)methyl]phenyl}silane [1639367-74-0].

A preferred compound of formula (XIIa) according to the invention is
trimethyl{2-[(4,4,5,5-tetramethyl-1,3,2-dioxaborolan-2-yl)methyl]phenyl}silane.

The present invention also relates to compounds of formula (VIIa) as well as their acceptable salts:

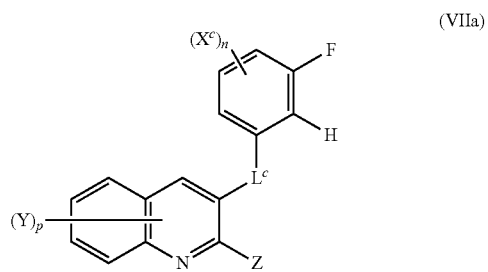

wherein:
$L^c$ represents O or S;
$X^c$ represents a halogen atom, a C₁-C₈-alkyl group, a C₁-C₈-halogenoalkyl group comprising up to 9 halogen atoms that can be the same or different, a C₁-C₈-alkoxy group, a C₁-C₈-halogenoalkoxy group comprising up to 9 halogen atoms that can be the same or different, a C₁-C₈-alkylsulfanyl group, a C₁-C₈-halogenoalkylsulfanyl group comprising up to 9 halogen atoms that can be the same or different, or cyano;
$Z^a$ represents a hydrogen atom, a halogen atom, a C₁-C₈-alkyl group, a C₁-C₈-halogenoalkyl group comprising up to 9 halogen atoms that can be the same or different, a C₁-C₈-alkoxy group, a C₁-C₈-halogenoalkoxy group comprising up to 9 halogen atoms that can be the same or different, a C₁-C₈-alkylsulfanyl group, or a C₁-C₈- halogenoalkylsulfanyl group comprising up to 9 halogen atoms that can be the same or different; and n, p and Y are as herein-defined, provided that the compound of formula (VIIa) does not represent:

3-[(3-fluorophenyl)sulfanyl]quinoline [1299398-31-4], 8-chloro-3-[(3-fluorophenyl)sulfanyl]quinoline [1060579-26-1], 3-[(3-fluorophenyl)sulfanyl]-8-iodoquinoline [607743-40-8], 3-[(3-fluorophenyl)sulfanyl]quinolin-8-amine [607743-39-5], and 3-[(3-fluorophenyl)sulfanyl]-8-nitroquinoline [607743-33-9].

The following compounds of formula (VIIa)

are also mentioned in chemical databases and/or suppliers' databases but without any references or information which enable these to be prepared and separated:

3-fluoro-5-(quinolin-3-yloxy)benzonitrile [1961698-21-4], and

3-[3-(chloromethyl)-5-fluorophenoxy]quinoline [1927507-05-8].

Preferred compounds of formula (VIIa) according to the invention are:—2-chloro-3-(3-fluorophenoxy)quinoline, 2-ethoxy-3-(3-fluorophenoxy)quinoline, 3-(3-fluorophenoxy)-2-(methylsulfanyl)quinoline, 3-(3-fluorophenoxy)-2-methylquinoline, 3-(3-fluorophenoxy)quinoline, and 3-(3-fluorophenoxy)quinoline 1-oxide.

Other preferred compounds of formula (VII) according to the invention are:

(3-fluorophenyl)(quinolin-3-yl)methanol, (3-fluorophenyl)(quinolin-3-yl)methanone, 2-(difluoromethyl)-N-(3-fluorophenyl)quinolin-3-amine, 3-[(3-fluorophenyl)sulfinyl]quinoline, and 3-[(3-fluorophenyl)sulfonyl]quinoline.

The present invention also relates to compounds of formula (VIIb) as well as their acceptable salts:

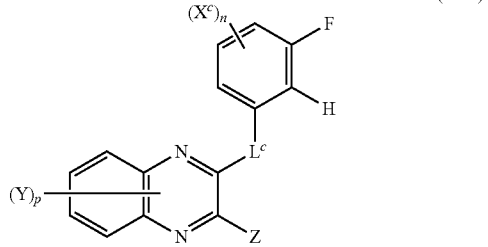

(VIIb)

wherein:

$L^c$ represents O or S;

$X^c$ represents a halogen atom, a $C_1$-$C_8$-alkyl group, a $C_1$-$C_8$-halogenoalkyl group comprising up to 9 halogen atoms that can be the same or different, a $C_1$-$C_8$-alkoxy group, a $C_1$-$C_8$-halogenoalkoxy group comprising up to 9 halogen atoms that can be the same or different, a $C_1$-$C_8$-alkylsulfanyl group, a $C_1$-$C_8$-halogenoalkylsulfanyl group comprising up to 9 halogen atoms that can be the same or different, or cyano;

$Z^a$ represents a hydrogen atom, a halogen atom, a $C_1$-$C_8$-alkyl group, a $C_1$-$C_8$-halogenoalkyl group comprising up to 9 halogen atoms that can be the same or different, a $C_1$-$C_8$-alkoxy group, a $C_1$-$C_8$-halogenoalkoxy group comprising up to 9 halogen atoms that can be the same or different, a $C_1$-$C_8$-alkylsulfanyl group, or a $C_1$-$C_8$-halogenoalkylsulfanyl group comprising up to 9 halogen atoms that can be the same or different; and n, p and Y are as herein-defined, provided that the compound of formula (VIIb) does not represent 2-(4-chloro-3-fluorophenoxy)-3-methylquinoxaline [477870-89-6].

The following compounds of formula (VIIb)

are also mentioned in chemical databases and/or suppliers' databases but without any references or information which enable these to be prepared and separated:

2-(2-bromo-5-fluorophenoxy)-3-methylquinoxaline [1540198-72-8], 2-(3-bromo-5-fluorophenoxy)-3-methylquinoxaline [1506611-98-8], 2-(3-bromo-5-fluorophenoxy)quinoxaline [1504501-15-8], 2-(2-bromo-5-fluorophenoxy)quinoxaline [1503431-97-7], 2-(4-bromo-3-fluorophenoxy)-3-methylquinoxaline [1486151-04-5], 2-(4-bromo-3-fluorophenoxy)quinoxaline [1478282-37-9], and 6,7-dichloro-2-(4-chloro-3-fluorophenoxy)-3-(trifluoromethyl)quinoxaline [478039-58-6].

The present invention also relates to compounds of formula (XIV) as well as their acceptable salts:

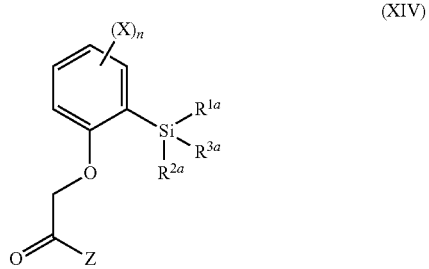

(XIV)

wherein:

$R^{1a}$ and $R^{2a}$ independently represent an unsubstituted or substituted $C_1$-$C_8$-alkyl, an unsubstituted or substituted $C_2$-$C_8$-alkenyl, an unsubstituted or substituted $C_3$-$C_7$-cycloalkyl, an unsubstituted or substituted aryl, an unsubstituted or substituted heterocyclyl;

$R^{3a}$ represents a hydrogen atom or an unsubstituted or substituted $C_1$-$C_8$-alkyl; a $C_1$-$C_8$-halogenoalkyl comprising up to 9 halogen atoms that can be the same or different; an unsubstituted or substituted $C_2$-$C_8$-alkenyl; an unsubstituted or substituted $C_2$-$C_8$-alkynyl; an unsubstituted or substituted $C_3$-$C_7$-cycloalkyl; an unsubstituted or substituted $C_4$-$C_7$-cycloalkenyl; an unsubstituted or substituted aryl; an unsubstituted or substituted aryl-$C_1$-$C_8$-alkyl; an unsubstituted or substituted heterocyclyl; an unsubstituted or substituted heterocyclyl-$C_1$-$C_8$-alkyl; an unsubstituted or substituted hydroxy-$C_1$-$C_8$-alkyl; an unsubstituted or substituted $C_1$-$C_8$-alkoxy-$C_1$-$C_8$-alkyl; an unsubstituted or substituted $C_1$-$C_8$-alkylcarbonyloxy-$C_1$-$C_8$-alkyl; an unsubstituted or substituted aryloxy-$C_1$-$C_8$-alkyl; an unsubstituted or substituted heterocyclyloxy-$C_1$-$C_8$-alkyl; an unsubstituted or substituted amino-$C_1$-$C_8$-alkyl; an unsubstituted or substituted $C_1$-$C_8$-alkylamino-$C_1$-$C_8$-alkyl; an unsubstituted or substituted di-$C_1$-$C_8$-alkylamino-$C_1$-$C_8$-alkyl; an unsubstituted or substituted arylamino-$C_1$-$C_8$-alkyl; an unsubstituted or substituted di-arylamino-$C_1$-$C_8$-alkyl; an unsubstituted or substituted heterocyclylamino-$C_1$-$C_8$-alkyl; an unsubstituted or substituted $C_1$-$C_8$-alkylcarbonylamino-$C_1$-$C_8$-alkyl; an unsubstituted or substituted $C_1$-$C_8$-alkoxycarbonylamino-$C_1$-$C_8$-alkyl; an unsubstituted or substituted $C_1$-$C_8$-alkylsulfanyl-$C_1$-$C_8$-alkyl; an unsubstituted or substituted $C_1$-$C_8$-alkylsulfinyl-$C_1$-$C_8$-alkyl; an unsubstituted or substituted $C_1$-$C_8$-alkylsulfonyl-$C_1$-$C_8$-alkyl; or an unsubstituted or substituted cyano-$C_1$-$C_8$-alkyl;

and n, X and Z are as herein-defined, provided that the compound of formula (XIV) does not represent:

2-[2-bromo-6-(trimethylsilyl)phenoxy]-1-phenylethanone [918304-52-6], methyl {2-[methoxy(dimethyl)silyl]phenoxy}acetate [187871-83-6], N-[2-(dimethylamino)ethyl]-2-[2-(trimethylsilyl)phenoxy]acetamide [126485-69-6], 2-(dimethylamino)ethyl [2-(trimethylsilyl)phenoxy]acetate [126485-64-1], butyl {2-[methoxy(dimethyl)silyl]phenoxy}acetate [122397-19-7], ethyl [2-(trimethylsilyl)phenoxy]acetate [104653-63-6], and [2-(trimethylsilyl)phenoxy]acetic acid [104653-62-5].

A preferred compound of formula (XIV) according to the invention is 1-[2-(trimethylsilyl)phenoxy]acetone.

Compositions and Formulations

The present invention further relates to a composition, in particular a composition for controlling unwanted microorganisms, comprising one or more compounds of formula (I). The composition is preferably is a fungicidal composition.

The composition typically comprises one or more compounds of formula (I) and one or more acceptable carriers, in particular one or more agriculturally acceptable carriers.

A carrier is a natural or synthetic, organic or inorganic substance with which the active ingredients are mixed or combined for better applicability, in particular for better application to plants, plant parts or seeds. The carrier, which may be solid or liquid, is generally inert.

Examples of suitable solid carriers include, but are not limited to, ammonium salts, natural rock flours, such as kaolins, clays, talc, chalk, quartz, attapulgite, montmorillonite or diatomaceous earth, and synthetic rock flours, such as finely divided silica, alumina and silicates. Examples of typically useful solid carriers for preparing granules include, but are not limited to, crushed and fractionated natural rocks such as calcite, marble, pumice, sepiolite and dolomite, synthetic granules of inorganic and organic flours and granules of organic material such as paper, sawdust, coconut shells, maize cobs and tobacco stalks.

Examples of suitable liquid carriers include, but are not limited to, water, polar and nonpolar organic chemical liquids, for example from the classes of aromatic and nonaromatic hydrocarbons (such as cyclohexane, paraffins, alkylbenzenes, xylene, toluene alkylnaphthalenes, chlorinated aromatics or chlorinated aliphatic hydrocarbons such as chlorobenzenes, chloroethylenes or methylene chloride), alcohols and polyols (which may optionally also be substituted, etherified and/or esterified, such as butanol or glycol), ketones (such as acetone, methyl ethyl ketone, methyl isobutyl ketone cyclohexanone), esters (including fats and oils) and (poly)ethers, unsubstituted and substituted amines, amides (such as dimethylformamide), lactams (such as N-alkylpyrrolidones) and lactones, sulphones and sulphoxides (such as dimethyl sulphoxide). The carrier may also be a liquefied gaseous extender, i.e. liquid which is gaseous at standard temperature and under standard pressure, for example aerosol propellants such as halohydrocarbons, butane, propane, nitrogen and carbon dioxide.

The composition may further comprise one or more acceptable auxiliaries which are customary for formulating compositions (e.g. agrochemical compositions), such as one or more surfactants.

Examples of suitable surfactants include emulsifiers and/or foam formers, dispersants or wetting agents having ionic or nonionic properties, or mixtures thereof. Examples thereof are salts of polyacrylic acid, salts of lignosulphonic acid, salts of phenolsulphonic acid or naphthalenesulphonic acid, polycondensates of ethylene and/or propylene oxide with fatty alcohols, fatty acids or fatty amines (polyoxyethylene fatty acid esters, polyoxyethylene fatty alcohol ethers, for example alkylaryl polyglycol ethers), substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. A surfactant is typically used when the active ingredient and/or the carrier is insoluble in water and the application is made with water. Then, the amount of surfactants typically ranges from 5 to 40% by weight of the composition.

Further examples of auxiliaries which are customary for formulating agrochemical compositions include water repellent, siccatives, binder (adhesive, tackifier, fixing agent, such as carboxymethylcellulose, natural and synthetic polymers in the form of powders, granules or latices, such as gum arabic, polyvinyl alcohol and polyvinyl acetate, natural phospholipids such as cephalins and lecithins and synthetic phospholipids, polyvinylpyrrolidone, polyvinyl acetate, polyvinyl alcohol and tylose), thickeners, stabilizers (e.g. cold stabilizers, preservatives, antioxidants, light stabilizers, or other agents which improve chemical and/or physical stability), dyes or pigments (such as inorganic pigments, e.g. iron oxide, titanium oxide and Prussian Blue; organic dyes, e.g. alizarin, azo and metal phthalocyanine dyes), antifoams (e.g. silicone antifoams and magnesium stearate), preservatives (e.g. dichlorophene and benzyl alcohol hemiformal), secondary thickeners (cellulose derivatives, acrylic acid derivatives, xanthan, modified clays and finely divided silica), stickers, gibberellins and processing auxiliaries, mineral and vegetable oils, perfumes, waxes and nutrients (including trace nutrients, such as salts of iron, manganese, boron, copper, cobalt, molybdenum and zinc), protective colloids, thixotropic substances, penetrants, sequestering agents and complex formers.

The choice of the carriers and/or auxiliaries will depend on the intended mode of application of the composition and/or on the physical properties of the active ingredient(s).

The compositions may be formulated in the form of any customary formulations, such as solutions (e.g aqueous solutions), emulsions, wettable powders, water- and oil-based suspensions, powders, dusts, pastes, soluble powders, soluble granules, granules for broadcasting, suspoemulsion concentrates, natural products impregnated with the active ingredient(s), synthetic substances impregnated with the active ingredient(s), fertilizers and also microencapsulations in polymeric substances. In the formulation of the composition, the active ingredient may be present in suspended, emulsified or dissolved form.

The compositions may be ready-for-use compositions, i.e. the compositions can be directly applied to the plant or seed by a suitable device, such as a spraying or dusting device. Alternatively, the compositions may be in the form of commercial concentrates which have to be diluted, preferably with water, prior to use.

The compositions can be prepared in conventional manners, for example by mixing the active ingredient(s) with one or more carriers and/or one or more suitable auxiliaries, such as disclosed herein above.

The compositions contain generally from 0.05 to 99% by weight, from 0.01 to 98% by weight, preferably from 0.1 to 95% by weight, more preferably from 0.5 to 90% by weight, most preferably from 10 to 70% by weight of the active ingredient or mixture thereof.

The compositions described above can be used for controlling unwanted microorganisms. The compositions may be applied to the microorganisms and/or in their habitat.

The compounds of formula (I) can be used as such or in formulations thereof. They can also be mixed or used in combination with known fungicides, bactericides, acaricides, nematicides, insecticides or mixtures thereof. The use of known fungicides, bactericides, acaricides, nematicides or insecticides, may allow to broaden the activity spectrum or to prevent development of resistance. Examples of known fungicides, insecticides, acaricides, nematicides or bactericides are disclosed in Pesticide Manual, 14th ed. The compounds of formula (I) can also be mixed or used in combination with other known active agents, such as herbicides, or with fertilizers, growth regulators, safeners and/or semiochemicals.

Thus, in some embodiments, the composition further comprises an additional active agent selected from fungicides, bactericides, acaricides, nematicides, insecticides, herbicides, fertilizers, growth regulators, safeners, semiochemicals and mixtures thereof.

Examples of especially preferred fungicides which could be mixed with the compound and the composition of the invention are:

1) Inhibitors of the ergosterol biosynthesis, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) Pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1 S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1 S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[[rel(2R,3R)-3-(2-chlorophenyl)-2-(2,4-difluorophenyl)oxiran-2-yl]methyl}-1H-1,2,4-triazol-5-yl thiocyanate, (1.041) 1-{[rel(2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)-ethoxy]-2-methylpyridin-3-yl}-N-ethyl-N-methylimidoformamide, (1.077) N'-{5-bromo-6-[(i S)-1-(3,5-difluoro phenyl)ethoxy]-2-methylpyridin-3-yl}-N-ethyl-N-methylimidoformamide, (1.078) N'-{5-bromo-6-[(cis-4-iso propylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) Mefentrifluconazole, (1.082) Ipfentrifluconazole.

2) Inhibitors of the respiratory chain at complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) Isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of syn-epimeric racemate 1RS,4SR,9RS and anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) Pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoro-methyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide.

3) Inhibitors of the respiratory chain at complex Ill, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadone, (3.010) fenamidone, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-

2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate.

4) Inhibitors of the mitosis and cell division, for example (4.001) carbendazim, (4.002) diethofencarb, (4.003) ethaboxam, (4.004) fluopicolide, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds capable to have a multisite action, for example (5.001) bordeaux mixture, (5.002) captafol, (5.003) captan, (5.004) chlorothalonil, (5.005) copper hydroxide, (5.006) copper naphthenate, (5.007) copper oxide, (5.008) copper oxychloride, (5.009) copper (2+) sulfate, (5.010) dithianon, (5.011) dodine, (5.012) folpet, (5.013) mancozeb, (5.014) maneb, (5.015) metiram, (5.016) metiram zinc, (5.017) oxine-copper, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable to induce a host defence, for example (6.001) acibenzolar-S-methyl, (6.002) isotianil, (6.003) probenazole, (6.004) tiadinil.

7) Inhibitors of the amino acid and/or protein biosynthesis, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

8) Inhibitors of the ATP production, for example (8.001) silthiofam.

9) Inhibitors of the cell wall synthesis, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl) prop-2-en-1-one.

10) Inhibitors of the lipid and membrane synthesis, for example (10.001) propamocarb, (10.002) propamocarb hydrochloride, (10.003) tolclofos-methyl.

11) Inhibitors of the melanin biosynthesis, for example (11.001) tricyclazole, (11.002) 2,2,2-trifluoroethyl {3-methyl-1-[(4-methylbenzoyl)amino]butan-2-yl}carbamate.

12) Inhibitors of the nucleic acid synthesis, for example (12.001) benalaxyl, (12.002) benalaxyl-M (kiralaxyl), (12.003) metalaxyl, (12.004) metalaxyl-M (mefenoxam).

13) Inhibitors of the signal transduction, for example (13.001) fludioxonil, (13.002) iprodione, (13.003) procymidone, (13.004) proquinazid, (13.005) quinoxyfen, (13.006) vinclozolin.

14) Compounds capable to act as an uncoupler, for example (14.001) fluazinam, (14.002) meptyldinocap.

15) Further compounds, for example (15.001) Abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenone, (15.017) mildiomycin, (15.018) natamycin, (15.019) nickel dimethyldithiocarbamate, (15.020) nitrothal-isopropyl, (15.021) oxamocarb, (15.022) Oxathiapiprolin, (15.023) oxyfenthiin, (15.024) pentachlorophenol and salts, (15.025) phosphorous acid and its salts, (15.026) propamocarb-fosetylate, (15.027) pyriofenone (chlazafenone), (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts, (15.046) 3-(4,4,5-trifluoro-3,3-dimethyl-3,4-dihydroisoquinolin-1-yl) quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butanoic acid, (15.050) 5-amino-1,3,4-thiadiazole-2-thiol, (15.051) 5-chloro-N'-phenyl-N'-(prop-2-yn-1-yl)thiophene-2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl] pyridin-2-yl}carbamate, (15.062) 5-fluoro-4-imino-3-methyl-1-[(4-methylphenyl)sulfonyl]-3,4-dihydropyrimidin-2(1H)-one.

All named mixing partners of the classes (1) to (15) as described here above can be present in the form of the free compound and/or, if their functional groups enable this, an agriculturally acceptable salt thereof.

Methods and Uses

The compounds of formula (I) have potent microbicidal activity. Thus, the compounds of formula (I) or compositions comprising thereof can be used for controlling unwanted microorganisms, such as fungi and bacteria. They can be particularly useful in crop protection—they control microorganisms that cause plants diseases- or in the protection of timber, storage goods or various materials, as described in more details herein below. More specifically, the compounds of formula (I) or compositions comprising thereof can be used to protect seeds, germinating plants, emerged seedlings, plants, plant parts, fruits and the soil in which the plants grow from unwanted microorganisms.

The term "control" or "controlling" as used herein encompasses curative and protective control of unwanted microorganisms. The unwanted microorganisms may be pathogenic bacteria or pathogenic fungi, more specifically phytopathogenic bacteria or phytopathogenic fungi. As detailed herein below, these phytopathogenic microorganisms are the causal agents of a broad spectrum of plants diseases More specifically, the compounds of the formula (I) or compositions comprising thereof can be used as fungicide. In particular, they can useful in crop protection, for example for the control of unwanted fungi, such as Plasmodiophoromycetes, Oomycetes, Chytridiomycetes, Zygomycetes, Ascomycetes, Basidiomycetes and Deuteromycetes.

The compounds of the formula (I) or compositions comprising thereof can also be used as bactericide. In particular, they can be used in crop protection, for example for the control unwanted bacteria, such as Pseudomonadaceae, Rhizobiaceae, Enterobacteriaceae, Corynebacteriaceae and Streptomycetaceae.

Therefore, the present invention also relates to a method for controlling unwanted phytopathogenic microorganisms, such as fungi and bacteria, comprising the step of applying one or more compound of formula (I) or a composition comprising thereof to the microorganisms and/or in their habitat.

More specifically, the present invention relates to curative or protective methods for controlling unwanted microorganisms, more specifically phytopathogenic fungi, which comprises the step of applying one or more compound of formula (I) or a composition comprising thereof to the seeds, the plants, the plant parts, the fruit or the soil in which the plants grow.

Typically, when the compounds of formula (I) or the compositions comprising thereof are intended to be used in curative or protective methods for controlling phytopathogenic fungi, an effective and non-phytotoxic amount of one or more compounds of formula (I) or a composition comprising thereof, is typically applied to the plant, plant part, fruit, seed or soil in which the plants grow. The expression "effective and non-phytotoxic amount" means an amount that is sufficient to control or destroy the fungi present or liable to appear on the cropland and that does not entail any appreciable symptom of phytotoxicity for said crops.

Such an amount can vary within a wide range depending on the fungus to be controlled, the type of crop, the climatic conditions and the compounds of formula (I). This amount can be determined by systematic field trials that are within the capabilities of a person skilled in the art.

The term "treatment" as used herein refers to the step of applying one or more compound of formula (I) or a composition comprising thereof to the plants, plant parts, fruits, seeds or soil that need(s) to be protected or cured.

Plants and Plant Parts

All plants and plant parts can be treated in accordance with the methods of the invention.

Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and the plant cultivars which are protectable and non-protectable by plant breeders' rights.

Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds. Plants which can be treated in accordance with the methods of the invention include the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); useful plants and ornamental plants for gardens and wooded areas; and genetically modified varieties of each of these plants.

In some preferred embodiments, wild plant species and plant cultivars, or those obtained by conventional biological breeding methods, such as crossing or protoplast fusion, and also parts thereof, are treated in accordance with the methods of the invention.

In some other preferred embodiments, transgenic plants and plant cultivars obtained by genetic engineering methods, if appropriate in combination with conventional methods (Genetically Modified Organisms), and parts thereof are treated in accordance with the methods of the invention. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The methods according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Plants and plant cultivars which can be treated by the above disclosed methods include all plants which have genetic material which impart particularly advantageous, useful traits to these plants (whether obtained by breeding and/or biotechnological means).

Plants and plant cultivars which can be treated by the above disclosed methods include plants and plant cultivars which are resistant against one or more biotic stresses, i.e. said plants show a better defense against animal and microbial pests, such as against nematodes, insects, mites, phytopathogenic fungi, bacteria, viruses and/or viroids.

Plants and plant cultivars which can be treated by the above disclosed methods include those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which can be treated by the above disclosed methods include those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants and plant cultivars which can be treated by the above disclosed methods include plants and plant cultivars which are hybrid plants that already express the characteristic of heterosis or hybrid vigor which results in generally higher yield, vigor, health and resistance towards biotic and abiotic stresses.

Plants and plant cultivars (obtained by plant biotechnology methods such as genetic engineering) which can be treated by the above disclosed methods include plants and plant cultivars which are herbicide-tolerant plants, i.e. plants made tolerant to one or more given herbicides. Such plants can be obtained either by genetic transformation, or by selection of plants containing a mutation imparting such herbicide tolerance.

Plants and plant cultivars (obtained by plant biotechnology methods such as genetic engineering) which can be treated by the above disclosed methods include plants and plant cultivars which are insect-resistant transgenic plants, i.e. plants made resistant to attack by certain target insects. Such plants can be obtained by genetic transformation, or by selection of plants containing a mutation imparting such insect resistance.

Plants and plant cultivars (obtained by plant biotechnology methods such as genetic engineering) which can be treated by the above disclosed methods include plants and plant cultivars which are tolerant to abiotic stresses. Such plants can be obtained by genetic transformation, or by selection of plants containing a mutation imparting such stress resistance.

Plants and plant cultivars (obtained by plant biotechnology methods such as genetic engineering) which can be treated by the above disclosed methods include plants and plant cultivars which show altered quantity, quality and/or storage-stability of the harvested product and/or altered properties of specific ingredients of the harvested product.

Plants and plant cultivars (obtained by plant biotechnology methods such as genetic engineering) which can be treated by the above disclosed methods include plants and plant cultivars, such as cotton plants, with altered fiber characteristics. Such plants can be obtained by genetic transformation, or by selection of plants contain a mutation imparting such altered fiber characteristics.

Plants and plant cultivars (obtained by plant biotechnology methods such as genetic engineering) which can be treated by the above disclosed methods include plants and plant cultivars, such as oilseed rape or related *Brassica* plants, with altered oil profile characteristics. Such plants can be obtained by genetic transformation, or by selection of plants contain a mutation imparting such altered oil profile characteristics.

Plants and plant cultivars (obtained by plant biotechnology methods such as genetic engineering) which can be treated by the above disclosed methods include plants and plant cultivars, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants and plant cultivars (obtained by plant biotechnology methods such as genetic engineering) which can be treated by the above disclosed methods include plants and plant cultivars, such as Tobacco plants, with altered post-translational protein modification patterns.

Pathogens and Diseases

The methods disclosed above can be used to control microorganisms, in particular phytopathogenic fungi, causing diseases, such as:

diseases caused by powdery mildew pathogens, such as *Blumeria* species (e.g. *Blumeria graminis*), *Podosphaera* species (e.g. *Podosphaera leucotricha*), *Sphaerotheca* species (e.g. *Sphaerotheca fuliginea*), *Uncinula* species (e.g. *Uncinula necator*);

diseases caused by rust disease pathogens, such as *Gymnosporangium* species (e.g. *Gymnosporangium sabinae*), *Hemileia* species (e.g. *Hemileia vastatrix*), *Phakopsora* species (e.g. *Phakopsora pachyrhizi* or *Phakopsora meibomiae*), *Puccinia* species (e.g. *Puccinia recondita*, *Puccinia graminis* or *Puccinia striiformis*), *Uromyces* species (e.g. *Uromyces appendiculatus*);

diseases caused by pathogens from the group of the Oomycetes, such as *Albugo* species (e.g. *Albugo candida*), *Bremia* species (e.g. *Bremia lactucae*), *Peronospora* species (e.g. *Peronospora pisi* or *P. brassicae*), *Phytophthora* species (e.g. *Phytophthora infestans*), *Plasmopara* species (e.g. *Plasmopara viticola*), *Pseudoperonospora* species (e.g. *Pseudoperonospora humuli* or *Pseudoperonospora cubensis*), *Pythium* species (e.g. *Pythium ultimum*);

leaf blotch diseases and leaf wilt diseases caused, for example, by *Alternaria* species (e.g. *Alternaria solani*), *Cercospora* species (e.g. *Cercospora beticola*), *Cladiosporium* species (e.g. *Cladiosporium cucumerinum*), *Cochliobolus* species (e.g. *Cochliobolus sativus* (conidial form: *Drechslera*, syn: *Helminthosporium*) or *Cochliobolus miyabeanus*), *Colletotrichum* species (e.g. *Colletotrichum lindemuthanium*), *Cycloconium* species (e.g. *Cycloconium oleaginum*), *Diaporthe* species (e.g. *Diaporthe citri*), *Elsinoe* species (e.g. *Elsinoe fawcettii*), *Gloeosporium* species (e.g. *Gloeosporium laeticolor*), *Glomerella* species (e.g. *Glomerella cingulate*), *Guignardia* species (e.g. *Guignardia bidwelli*), *Leptosphaeria* species (e.g. *Leptosphaeria maculans*), *Magnaporthe* species (e.g. *Magnaporthe grisea*), *Microdochium* species (e.g. *Microdochium nivale*), *Mycosphaerella* species (e.g. *Mycosphaerella graminicola*, *Mycosphaerella arachidicola* or *Mycosphaerella fijiensis*), *Phaeosphaeria* species (e.g. *Phaeosphaeria nodorum*), *Pyrenophora* species (e.g. *Pyrenophora teres* or *Pyrenophora tritici repentis*), *Ramularia* species (e.g. *Ramularia collo-cygni* or *Ramularia areola*), *Rhynchosporium* species (e.g. *Rhynchosporium secalis*), *Septoria* species (e.g. *Septoria apii* or *Septoria lycopersici*), *Stagonospora* species (e.g. *Stagonospora nodorum*), *Typhula* species (e.g. *Typhula incarnate*), *Venturia* species (e.g. *Venturia inaequalis*), root and stem diseases caused, for example, by *Corticium* species (e.g. *Corticium graminearum*), *Fusarium* species (e.g. *Fusarium oxysporum*), *Gaeumannomyces* species, (e.g. *Gaeumannomyces graminis*), *Plasmodiophora* species, (e.g. *Plasmodiophora brassicae*), *Rhizoctonia* species, (e.g. *Rhizoctonia solani*), *Sarocladium* species, (e.g. *Sarocladium oryzae*), *Sclerotium* species, (e.g. *Sclerotium oryzae*), *Tapesia* species, (e.g. *Tapesia acuformis*), *Thielaviopsis* species, (e.g. *Thielaviopsis basicola*); ear and panicle diseases (including corn cobs) caused, for example, by *Alternaria* species, (e.g. *Alternaria* spp.), *Aspergillus* species (e.g. *Aspergillus flavus*), *Cladosporium* species (e.g. *Cladosporium cladosporioides*, *Claviceps* species (e.g. *Claviceps purpurea*), *Fusarium* species, (e.g. *Fusarium culmorum*), *Gibberella* species (e.g. *Gibberella zeae*), *Monographella* species, (e.g. *Monographella nivalis*), *Stagnospora* species, (e.g. *Stagnospora nodorum*);

diseases caused by smut fungi, for example *Sphacelotheca* species (e.g. *Sphacelotheca reiliana*), *Tilletia* species (e.g. *Tilletia caries* or *Tilletia controversa*), *Urocystis* species (e.g. *Urocystis occulta*), *Ustilago* species (e.g. *Ustilago nuda*);

fruit rot caused, for example, by *Aspergillus* species (e.g. *Aspergillus flavus*), *Botrytis* species (e.g. *Botrytis cinerea*), *Penicillium* species (e.g. *Penicillium expansum* or *Penicillium purpurogenum*), *Rhizopus* species (e.g. *Rhizopus stolonifer*), *Sclerotinia* species (e.g. *Sclerotinia sclerotiorum*), *Verticilium* species (e.g. *Verticilium alboatrum*);

seed- and soil-borne rot and wilt diseases, and also diseases of seedlings, caused, for example, by *Alternaria* species (e.g. *Alternaria brassicicola*), *Aphanomyces* species (e.g. *Aphanomyces euteiches*), *Ascochyta* species (e.g. *Ascochyta lentis*), *Aspergillus* species (e.g. *Aspergillus flavus*), *Cladosporium* species (e.g. *Cladosporium herbarum*), *Cochliobolus* species (e.g. *Cochliobolus sativus* (conidial form: *Drechslera*, *Bipolaris* Syn: *Helminthosporium*)), *Colletotrichum* species (e.g. *Colletotrichum coccodes*), *Fusarium* species (e.g. *Fusarium culmorum*), *Gibberella* species (e.g. *Gibberella zeae*), *Macrophomina* species (e.g. *Macrophomina phaseolina*), *Microdochium* species (e.g. *Microdochium nivale*), *Monographella* species (e.g. *Monographella nivalis*), *Penicillium* species (e.g. *Penicillium expansum*), *Phoma* species (e.g. *Phoma lingam*), *Phomopsis* species (e.g. *Phomopsis sojae*), *Phytophthora* species (e.g. *Phytophthora cactorum*), *Pyrenophora* species (e.g. *Pyrenophora graminea*), *Pyricularia* species (e.g. *Pyricularia oryzae*), *Pythium* species (e.g. *Pythium ultimum*), *Rhizoctonia* species (e.g. *Rhizoctonia solani*), *Rhizopus* species (e.g. *Rhizopus oryzae*), *Sclerotium* species (e.g. *Sclerotium rolfsii*), *Septoria* species (e.g. *Septoria nodorum*), *Typhula* species (e.g. *Typhula incarnate*), *Verticillium* species (e.g. *Verticillium dahlia*);

cancers, galls and witches' broom caused, for example, by *Nectria* species (e.g. *Nectria galligena*); wilt diseases caused, for example, by *Monilinia* species (e.g. *Monilinia laxa*);

deformations of leaves, flowers and fruits caused, for example, by *Exobasidium* species (e.g. *Exobasidium vexans*), *Taphrina* species (e.g. *Taphrina deformans*);

degenerative diseases in woody plants, caused, for example, by *Esca* species (e.g. *Phaeomoniella chlamydospora*, *Phaeoacremonium aleophilum* or *Fomitiporia mediterranea*), *Ganoderma* species (e.g. *Ganoderma boninense*);

diseases of flowers and seeds caused, for example, by *Botrytis* species (e.g. *Botrytis cinerea*); diseases of plant tubers caused, for example, by *Rhizoctonia* species (e.g. *Rhizoctonia solani*), *Helminthosporium* species (e.g. *Helminthosporium solani*);

diseases caused by bacterial pathogens, for example *Xanthomonas* species (e.g. *Xanthomonas campestris* pv. *Oryzae*), *Pseudomonas* species (e.g. *Pseudomonas syringae* pv. *Lachrymans*), *Erwinia* species (e.g. *Erwinia amylovora*).

Seed Treatment

The method for controlling unwanted microorganisms may be used to protect seeds from phytopathogenic microorganisms, such as fungi.

The term "seed(s)" as used herein include dormant seed, primed seed, pregerminated seed and seed with emerged roots and leaves.

Thus, the present invention also relates to a method for protecting seeds and/or crops from unwanted microorganisms, such as bacteria or fungi, which comprises the step of treating the seeds with one or more compounds of formula (I) or a composition comprising thereof. The treatment of seeds with the compound(s) of formula (I) or a composition comprising thereof not only protects the seeds from phytopathogenic microorganisms, but also the germinating plants, the emerged seedlings and the plants after emergence.

The seeds treatment may be performed prior to sowing, at the time of sowing or shortly thereafter.

When the seeds treatment is performed prior to sowing (e.g. so-called on-seed applications), the seeds treatment may be performed as follows: the seeds may be placed into a mixer with a desired amount of compound(s) of formula (I) or a composition comprising thereof (either as such or after dilution), the seeds and the compound(s) of formula (I) or the composition comprising thereof are mixed until a homogeneous distribution on seeds is achieved. If appropriate, the seeds may then be dried.

The invention also relates to seeds treated with one or more compounds of formula (I) or a composition comprising thereof. As said before, the use of treated seeds allows not only protecting the seeds before and after sowing from unwanted microorganisms, such as phytopathogenic fungi, but also allows protecting the germinating plants and young seedlings emerging from said treated seeds. A large part of the damage to crop plants caused by harmful organisms is triggered by the infection of the seeds before sowing or after germination of the plant. This phase is particularly critical since the roots and shoots of the growing plant are particularly sensitive, and even small damage may result in the death of the plant.

Therefore, the present invention also relates to a method for protecting seeds, germinating plants and emerged seedlings, more generally to a method for protecting crop from phytopathogenic microorganisms, which comprises the step of using seeds treated by one or more compounds of formula (I) or a composition comprising thereof.

Preferably, the seed is treated in a state in which it is sufficiently stable for no damage to occur in the course of treatment. In general, seeds can be treated at any time between harvest and shortly after sowing. It is customary to use seeds which have been separated from the plant and freed from cobs, shells, stalks, coats, hairs or the flesh of the fruits. For example, it is possible to use seeds which have been harvested, cleaned and dried down to a moisture content of less than 15% by weight. Alternatively, it is also possible to use seeds which, after drying, for example, have been treated with water and then dried again, or seeds just after priming, or seeds stored in primed conditions or pre-germinated seeds, or seeds sown on nursery trays, tapes or paper.

The amount of compound(s) of formula (I) or composition comprising thereof applied to the seed is typically such that the germination of the seed is not impaired, or that the resulting plant is not damaged. This must be ensured particularly in case the active ingredients would exhibit phytotoxic effects at certain application rates. The intrinsic phenotypes of transgenic plants should also be taken into consideration when determining the amount of compound(s) of formula (I) or composition comprising thereof to be applied to the seed in order to achieve optimum seed and germinating plant protection with a minimum amount of compound(s) of formula (I) or composition comprising thereof being employed.

As indicated above, the compounds of the formula (I) can be applied, as such, directly to the seeds, i.e. without the use of any other components and without having been diluted, or a composition comprising the compounds of formula (I) can be applied. Preferably, the compositions are applied to the seed in any suitable form. Examples of suitable formulations include solutions, emulsions, suspensions, powders, foams, slurries or combined with other coating compositions for seed, such as film forming materials, pelleting materials, fine iron or other metal powders, granules, coating material for inactivated seeds, and also ULV formulations. The formulations may be ready-to-use formulations or may be concentrates that need to be diluted prior to use.

These formulations are prepared in a known manner, for instance by mixing the active ingredient or mixture thereof with customary additives, for example customary extenders and solvents or diluents, dyes, wetting agents, dispersants, emulsifiers, antifoams, preservatives, secondary thickeners, adhesives, gibberellins, and also water.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1. Useful wetting agents which may be present in the seed dressing formulations are all substances which promote wetting and which are conventionally used for the formulation of active agrochemical ingredients. Usable with preference are alkylnaphthalenesulphonates, such as diisopropyl- or diisobutylnaphthalenesulphonates. Useful dispersants and/or emulsifiers which may be present in the seed dressing formulations are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates. Antifoams which may be present in the seed dressing formulations are all foam-inhibiting substances conventionally used for the formulation of active agrochemical ingredients. Silicone antifoams and magnesium stearate can be used with preference. Preservatives which may be present in the seed dressing formulations are all substances usable for such purposes in agrochemical compositions. Examples include dichlorophene and benzyl alcohol hemiformal. Secondary thickeners which may be present in the seed dressing formulations are all substances usable for such purposes in agrochemical compositions. Preferred examples include cellulose derivatives, acrylic acid derivatives, xanthan, modified clays and finely divided silica. Adhesives which may be present in the seed dressing formulations are all customary binders usable in seed dressing products. Preferred examples include polyvinylpyrrolidone, polyvinyl acetate, polyvinyl alcohol and tylose.

The compounds of the formula (I) and the compositions comprising thereof are suitable for protecting seeds of any plant variety which is used in agriculture, in greenhouses, in forests or in horticulture. More particularly, the seed is that of cereals (such as wheat, barley, rye, millet, triticale, and oats), oilseed rape, maize, cotton, soybean, rice, potatoes, sunflower, beans, coffee, peas, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice. The compounds of formula (I) or the compositions comprising thereof can be used for treating transgenic seeds, in particular seeds of plants capable of expressing a protein which acts against pests, herbicidal damage or abiotic stress, thereby increasing the protective effect. Synergistic effects may also occur in interaction with the substances formed by expression.

Application

The active ingredient(s) can be applied as such, in the form of their formulations or in the use forms prepared from said formulations when these are not ready-to-use.

The application to the plant, plant part, fruit, seed or soil is accomplished in a customary manner, for example by watering, spraying, atomizing, broadcasting, dusting, foaming, spreading-on and the like. The active ingredients may also be applied by the ultra-low volume method or be injected into the soil.

The effective and non-phytotoxic amount of compounds of formula (I) or of a composition comprising thereof which is applied to the plant, plant part, fruit, seed or soil will depend on various factors, such as the compound/composition employed, the subject of the treatment (plant, plant part, fruit, seed or soil), the type of treatment (dusting, spraying, seed dressing), the purpose of the treatment (prophylactic or therapeutic) and the type of microorganisms.

When compounds of formula (I) are used as fungicides, the application rates can vary within a relatively wide range, depending on the kind of application. For instance, when compounds of formula (I) are used in the treatment of plant parts, such as leaves, the application rate may range from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used). When compounds of formula (I) are used in the treatment of seeds, the application rate may range from 0.1 to 200 g per 100 kg of seed, preferably from 1 to 150 g per 100 kg of seed, more preferably from 2.5 to 25 g per 100 kg of seed, even more preferably from 2.5 to 12.5 g per 100 kg of seed. When compounds of formula (I) are used in the treatment of soil, the application rate may range from 0.1 to 10 000 g/ha, preferably from 1 to 5000 g/ha.

These application rates are merely by way of example and are not limiting for the purposes of the invention.

Mycotoxins

In addition, the compounds of the formula (I) or compositions comprising thereof can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec. and others.

Material Protection

The compounds of the formula (I) and compositions comprising thereof can be used in the protection of materials, for instance industrial materials, from attack and destruction by microorganisms, such as fungi.

The terms "industrial materials" as used herein designate inanimate materials that may be used in industry. Examples of industrial materials include, but are not limited to, adhesives, glues, paper, wallpaper, board/cardboard, textiles, carpets, leather, wood, fibers, tissues, paints, plastic articles, cooling lubricants, heat transfer fluids and other materials which can be infected with or destroyed by microorganisms. Preferred industrial materials include adhesives, sizes, paper and card, leather, wood, paints, cooling lubricants and heat transfer fluids, more preferably wood. The compounds of the formula (I) and compositions comprising thereof may prevent adverse effects, such as rotting, decay, discoloration or formation of mould.

Further materials that can be protected by the compounds and compositions of the present invention include parts of production plants and buildings which may be impaired by the proliferation of microorganisms, for example coolingwater circuits, cooling and heating systems and ventilation and air-conditioning units.

In addition, the compounds of the formula (I) and compositions comprising thereof can be used to protect objects which come into contact with saltwater or brackish water, especially hulls, screens, nets, buildings, moorings and signalling systems, from fouling. Therefore, the compounds of the formula (I) and compositions comprising thereof can be used as antifouling agent, alone or in combinations with other active ingredients.

The compounds of the formula (I) and compositions comprising thereof may also be used to treat wood, in particular to treat wood against fungal diseases liable to grow on or inside timber. The term "timber" designates all types and species of wood and all types of construction timber, for example solid wood, high-density wood, laminated wood, and plywood. An exemplary method for treating timber comprises the step of contacting one or more compounds of formula (I) or a composition comprising thereof with the timber. The contacting step may be performed by direct application, spraying, dipping, injection or any other suitable means.

The compounds of the formula (I) and compositions comprising thereof can also be used for protecting storage goods. The terms "storage goods" as used herein designate natural substances of vegetable or animal origin or processed products thereof for which long-term protection is desired. Examples of storage goods of vegetable origin that can be protected include plants or plant parts, such as stems, leaves, tubers, seeds, fruits and grains. They can be protected in a freshly harvested state or after being processed, such as by (pre)drying, moistening, comminuting, grinding, pressing and/or roasting. Examples of storage goods of animal origin include hides, leather, furs and hairs. The compounds of the formula (I) or compositions comprising thereof may prevent adverse effects, such as rotting, decay, discoloration or formation of mould.

Microorganisms capable of degrading or altering the industrial materials include, for example, bacteria, fungi, yeasts, algae and slime organisms. The compounds of the formula (I) preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis*; *Aspergillus*, such as *Aspergillus niger Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor, Aureobasidium*, such as *Aureobasidium pullulans*; *Sclerophoma*, such as *Sclerophoma pityophila*; *Trichoderma*, such as *Trichoderma viride*; *Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli*; *Pseudomonas*, such as *Pseudomonas aeruginosa*; *Staphylococcus*, such as *Staphylococcus aureus, Candida* spp. and *Saccharomyces* spp., such as *Saccharomyces cerevisae*.

Aspects of the present teaching may be further understood in light of the following examples, which should not be construed as limiting the scope of the present teaching in any way.

EXAMPLES

Table 1 illustrates in a non-limiting manner examples of compounds of formula (I) according to the invention:

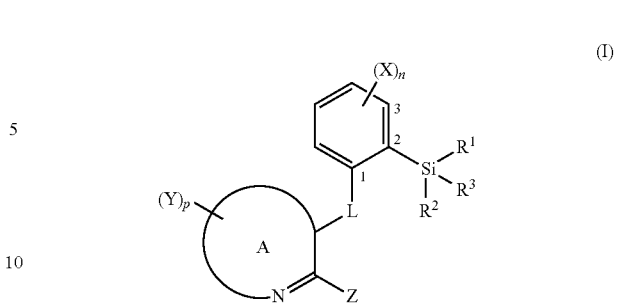

The compounds of formula (I) which are mentioned in table 1 hereinbelow were prepared in accordance with the procedures detailed hereinbelow in connection with specific examples and with the general description of the processes herein disclosed.

In table 1, unless otherwise specified, M+H (Apcl+) means the molecular ion peak plus 1 a.m.u. (atomic mass unit) as observed in mass spectroscopy via positive atmospheric pressure chemical ionisation.

In table 1, the log P values were determined in accordance with EEC Directive 79/831 Annex V.A8 by HPLC (High Performance Liquid Chromatography) on a reversed-phase column (C18), using the methods described below:

Method A: temperature: 40° C.; mobile phases: 0.1% aqueous formic acid and acetonitrile; linear gradient from 10% acetonitrile to 95% acetonitrile;

Method B: temperature: 40° C.; mobile phases: 0.001 molar ammonium acetate solution in water and acetonitrile; linear gradient from 10% acetonitrile to 95% acetonitrile.

Calibration was carried out using unbranched alkan-2-ones (comprising 3 to 16 carbon atoms) with known log P values (determination of the log P values by the retention times using linear interpolation between two successive alkanones). lambda-max-values were determined using UV-spectra from 200 nm to 400 nm and the peak values of the chromatographic signals.

In table 1, the point of attachment of the $(X)_n$ residue to the phenyl ring is based on the above numbering of the phenyl ring.

TABLE 1

| Example | $R^1$ | $R^2$ | $R^3$ | $(X)_n$ | L | | M + H | logP | logP Method |
|---|---|---|---|---|---|---|---|---|---|
| I.001 | Me | Me | Me | — | O | quinolin-3-yl | 294 | 5.17 | A |
| I.002 | Me | Me | OH | — | O | quinolin-3-yl | 296 | 2.82 | A |
| I.003 | Me | Me | OH | 3-F | O | quinolin-3-yl | 314 | 2.90 | A |
| I.004 | Me | Me | —OCH$_2$— | | O | quinolin-3-yl | 308 | 3.64 | A |
| I.005 | Me | Me | Et | 3-F | O | quinolin-3-yl | 326 | 5.47 | A |
| I.006 | Me | Me | vinyl | 3-F | O | quinolin-3-yl | 324 | 5.24 | A |
| I.007 | Me | Me | chloromethyl | 3-F | O | quinolin-3-yl | 346 | 5.00 | A |
| I.008 | —CH$_2$CH$_2$CH$_2$— | | Me | 3-F | O | quinolin-3-yl | 324 | 5.39 | A |
| I.009 | Me | Me | OH | — | NH | quinolin-3-yl | 295 | 3.20 | B |
| I.010 | Me | Me | —OCH$_2$— | | NH | quinolin-3-yl | 307 | 3.15 | B |
| I.011 | Me | Me | Me | — | NH | quinolin-3-yl | 293 | 3.46 | A |
| I.012 | Me | Me | Me | — | CH$_2$ | quinolin-3-yl | 292 | 4.06 | A |
| I.013 | Me | Me | phenyl | — | CH$_2$ | quinolin-3-yl | 354 | 4.20 | A |
| I.014 | Me | Me | 4-chlorophenyl | — | CH$_2$ | quinolin-3-yl | 388 | 4.74 | A |
| I.015 | Me | Me | 2-thienyl | — | CH$_2$ | quinolin-3-yl | 360 | 4.04 | A |
| I.016 | Me | Me | 4-phenoxyphenyl | — | CH$_2$ | quinolin-3-yl | 446 | 5.62 | A |

TABLE 1-continued

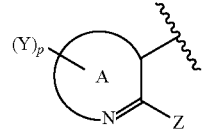

| Example | R¹ | R² | R³ | (X)$_n$ | L | ![ring] | M + H | logP | logP Method |
|---|---|---|---|---|---|---|---|---|---|
| I.017 | Me | Me | Me | 3-F | C=O | quinolin-3-yl | 324 | 4.49 | A |
| I.018 | Me | Me | OH | 4-F | O | 8-chloroquinolin-3-yl | 348 | 3.50 | A |
| I.019 | Me | Me | Me | 4-F | O | 8-chloroquinolin-3-yl | 346 | 5.62 | A |
| I.020 | Me | Me | Me | — | O | 7,8-difluoroquinolin-3-yl | 330 | 5.39 | A |
| I.021 | Me | Me | Me | 3-F | O | 7,8-difluoroquinolin-3-yl | 348 | 5.32 | A |
| I.022 | Me | Me | OH | 3-F | O | 7,8-difluoroquinolin-3-yl | 350 | 2.35 | A |
| I.023 | Me | Me | OH | — | O | 7,8-difluoroquinolin-3-yl | 332 | 3.27 | A |
| I.024 | Me | Me | Me | — | O | 7,8-difluoro-2-methylquinolin-3-yl | 344 | 6.01 | A |
| I.025 | Me | Me | OH | 3-F | O | 7,8-difluoro-2-methylquinolin-3-yl | 364 | 3.55 | A |
| I.026 | Me | Me | OH | — | O | 7,8-difluoro-2-methylquinolin-3-yl | 346 | 3.51 | A |
| I.027 | Me | Me | Me | 3-F | O | 7,8-difluoro-2-methylquinolin-3-yl | 362 | 5.54 | B |
| I.028 | Me | Me | phenyl | 3-F | O | 7,8-difluoro-2-methylquinolin-3-yl | 424 | 6.01 | A |
| I.029 | Me | Me | Me | 5-NH$_2$ | O | 7,8-difluoro-2-methylquinolin-3-yl | 359 | 4.59 | A |
| I.030 | Me | Me | 2-thienyl | 3-F | O | 7,8-difluoro-2-methylquinolin-3-yl | 430 | 5.65 | A |
| I.031 | Me | Me | Me | 5-NO$_2$ | O | 7,8-difluoro-2-methylquinolin-3-yl | 389 | 5.34 | A |
| I.032 | Me | Me | F | 3-F | O | 7,8-difluoro-2-methylquinolin-3-yl | 366 | 4.75 | A |
| I.033 | Me | Me | OH | 3-OMe | O | 7,8-difluoro-2-methylquinolin-3-yl | 376 | 3.69 | A |
| I.034 | Me | Me | OH | 3-Cl | O | 7,8-difluoro-2-methylquinolin-3-yl | 380 | 3.83 | A |
| I.035 | Me | Me | OH | 5-F | O | 7,8-difluoro-2-methylquinolin-3-yl | 364 | 3.55 | A |
| I.036 | Me | Me | OH | 3-OCF$_3$ | O | 7,8-difluoro-2-methylquinolin-3-yl | 430 | 4.20 | A |
| I.037 | Me | Me | OH | 4-F | O | 7,8-difluoro-2-methylquinolin-3-yl | 364 | 3.55 | A |
| I.038 | Me | Me | Me | 3-OMe | O | 7,8-difluoro-2-methylquinolin-3-yl | 374 | 5.85 | A |
| I.039 | Me | Me | Et | 3-CN | O | 7,8-difluoro-2-methylquinolin-3-yl | 383 | 5.22 | A |
| I.040 | Me | Me | Me | — | CH$_2$ | 7,8-difluoro-2-methylquinolin-3-yl | 342 | 5.54 | A |
| I.041 | Me | Me | Et | — | O | 5,6,7,8-tetrahydroquinolin-3-yl | 312 | 3.68 | A |
| I.042 | Me | Me | Me | 3-F | O | 4-methylquinolin-3-yl | 326 | 5.62 | A |
| I.043 | Me | Me | Et | 3-CN | O | 4-[ethyl(dimethyl)silyl]-7,8-difluoro-2-methylquinolin-3-yl | 469 | 7.36 | A |
| I.044 | Me | Me | Me | 3-F | O | 2-vinylquinolin-3-yl | 338 | 6.30 | A |
| I.045 | Me | Me | Me | 3-F | O | 2-phenylquinolin-3-yl | 388 | 6.40 | A |
| I.046 | Me | Me | Me | 3-F | O | 2-methylquinolin-3-yl | 326 | 5.08 | A |
| I.047 | Me | Me | Me | — | O | 2-methylquinolin-3-yl | 308 | 4.85 | A |
| I.048 | Me | Me | OH | — | O | 2-methylquinolin-3-yl | 310 | 2.16 | A |
| I.049 | Me | Me | OH | 3-F | O | 2-methylquinolin-3-yl | 328 | 2.41 | A |
| I.050 | Me | Me | OH | 3-OCF$_3$ | O | 2-methylquinolin-3-yl | 394 | 3.35 | A |
| I.051 | Me | Me | OH | 3-Cl | O | 2-methylquinolin-3-yl | 344 | 2.80 | A |
| I.052 | Me | Me | Et | 3-F | O | 2-methylquinolin-3-yl | 340 | 5.62 | A |
| I.053 | Me | Me | H | 3-F | O | 2-methylquinolin-3-yl | 312 | 4.56 | A |
| I.054 | Me | Me | Me | — | NH | 2-methylquinolin-3-yl | 307 | 2.46 | A |
| I.055 | Me | Me | Me | 4-F | NH | 2-methylquinolin-3-yl | 325 | 2.63 | A |
| I.056 | Me | Me | Me | — | NEt | 2-methylquinolin-3-yl | 335 | 3.16 | A |
| I.057 | Me | Me | Et | 3-F | O | 2-methyl-1-oxidoquinolin-3-yl | 356 | 4.54 | A |
| I.058 | Me | Me | Me | — | NH | 2-methyl-1-oxidoquinolin-3-yl | 323 | 3.62 | A |
| I.059 | Me | Me | Me | 3-F | O | 2-hydroxyquinolin-3-yl | 328 | 3.85 | A |
| I.060 | Me | Me | Me | 3-F | O | 2-ethoxyquinolin-3-yl | 356 | 6.79 | A |
| I.061 | Me | Me | Me | 3-F | O | 2-cyclopropylquinolin-3-yl | 352 | 6.90 | A |
| I.062 | Me | phenyl | H | 3-F | O | 2-chloroquinolin-3-yl | 394 | 5.78 | A |
| I.063 | Me | Me | Me | 3-F | O | 2-chloroquinolin-3-yl | 346 | 5.90 | A |
| I.064 | Me | Me | Me | 3-F | O | 2-(methylsulfanyl)quinolin-3-yl | 358 | 6.79 | A |
| I.065 | Me | Me | Me | 3-F | O | 2-(difluoromethyl)quinolin-3-yl | 362 | 5.45 | A |
| I.066 | Me | Me | Me | 3-F | NH | 2-(difluoromethyl)quinolin-3-yl | 361 | 5.68 | A |
| I.067 | Me | Me | Me | 3-F | O | 2-(3-thienyl)quinolin-3-yl | 394 | 6.66 | A |
| I.068 | Me | Me | Me | — | O | quinoxalin-2-yl | 295 | 5.05 | A |
| I.069 | Me | Me | Me | 3-F | O | quinoxalin-2-yl | 313 | 5.22 | A |
| I.070 | Me | Me | OH | — | O | quinoxalin-2-yl | 297 | 2.86 | A |
| I.071 | Me | Me | OH | 3-F | O | quinoxalin-2-yl | 315 | 3.01 | A |
| I.072 | Me | Me | ter-butyl | — | O | quinoxalin-2-yl | 337 | 6.30 | A |
| I.073 | Me | Me | isobutyl | — | O | quinoxalin-2-yl | 337 | 6.33 | A |
| I.074 | Et | Et | Et | — | O | quinoxalin-2-yl | 337 | 6.43 | A |
| I.075 | Me | Me | isopropyl | — | O | quinoxalin-2-yl | 323 | 5.91 | A |
| I.076 | Me | Me | Et | — | O | quinoxalin-2-yl | 309 | 5.48 | A |
| I.077 | Me | Me | Et | — | O | 5,6-difluoroquinoxalin-2-yl | 345 | 5.62 | A |
| I.078 | Me | Me | Me | 3-F | O | 5,6-difluoroquinoxalin-2-yl | 349 | 5.20 | A |
| I.079 | Me | Me | Me | — | O | 5,6-difluoroquinoxalin-2-yl | 331 | 5.28 | A |
| I.080 | Me | Me | cyclohexyl | — | O | 5,6-difluoroquinoxalin-2-yl | 399 | 6.94 | A |
| I.081 | Me | Me | OH | — | O | 5,6-difluoroquinoxalin-2-yl | 333 | 3.23 | A |
| I.082 | Me | Me | OH | 3-F | O | 5,6-difluoroquinoxalin-2-yl | 351 | 3.33 | A |
| I.083 | Me | Me | F | 3-F | O | 5,6-difluoroquinoxalin-2-yl | 353 | 5.01 | A |
| I.084 | Me | Me | Me | — | NH | 5,6-difluoroquinoxalin-2-yl | 330 | 4.49 | A |
| I.085 | Me | Me | OH | 3-F | O | 5,6-difluoro-3-methylquinoxalin-2-yl | 365 | 3.67 | A |
| I.086 | Me | Me | Me | — | O | 5,6-difluoro-3-methylquinoxalin-2-yl | 345 | 5.46 | A |
| I.087 | Me | Me | OH | — | O | 5,6-difluoro-3-methylquinoxalin-2-yl | 347 | 3.35 | A |

TABLE 1-continued

| Example | R¹ | R² | R³ | (X)ₙ | L | Z | M + H | logP | logP Method |
|---|---|---|---|---|---|---|---|---|---|
| I.088 | Me | Me | Me | 3-F | O | 5,6-difluoro-3-methylquinoxalin-2-yl | 363 | 5.65 | A |
| I.089 | Me | Me | OH | 6-F | O | 5,6-difluoro-3-methylquinoxalin-2-yl | 365 | 3.62 | A |
| I.090 | Me | Me | OH | 3-Cl | O | 5,6-difluoro-3-methylquinoxalin-2-yl | 381 | 3.94 | A |
| I.091 | Me | Me | vinyl | 3-F | O | 5,6-difluoro-3-methylquinoxalin-2-yl | 375 | 5.62 | A |
| I.092 | Me | Me | F | 3-F | O | 5,6-difluoro-3-methylquinoxalin-2-yl | 367 | 4.75 | A |
| I.093 | Me | Me | OH | 5-CN | O | 5,6-difluoro-3-methylquinoxalin-2-yl | 372 | 3.39 | A |
| I.094 | Me | Me | OH | 3-OMe | O | 5,6-difluoro-3-methylquinoxalin-2-yl | 377 | 3.60 | A |
| I.095 | Me | Me | OH | 3-OCF₃ | O | 5,6-difluoro-3-methylquinoxalin-2-yl | 431 | 4.34 | A |
| I.096 | Me | Me | OH | 5-Me | O | 5,6-difluoro-3-methylquinoxalin-2-yl | 361 | 3.76 | A |
| I.097 | Me | Me | OH | 5-Me | O | 5,6-difluoro-3-methylquinoxalin-2-yl | 361 | 3.76 | A |
| I.098 | Me | Me | OH | 4-F | O | 5,6-difluoro-3-methylquinoxalin-2-yl | 365 | 3.63 | A |
| I.099 | Me | Me | OH | 4-Me | O | 5,6-difluoro-3-methylquinoxalin-2-yl | 361 | 3.85 | A |
| I.100 | Me | Me | Me | 4-F | O | 5,6-difluoro-3-methylquinoxalin-2-yl | 363 | 5.57 | A |
| I.101 | Me | Me | Me | 4-Cl | O | 5,6-difluoro-3-methylquinoxalin-2-yl | 379 | 6.11 | A |
| I.102 | Me | Me | OH | 4-Cl | O | 5,6-difluoro-3-methylquinoxalin-2-yl | 381 | 4.01 | A |
| I.103 | Me | Me | OH | 6-Cl | O | 5,6-difluoro-3-methylquinoxalin-2-yl | 381 | 3.96 | A |
| I.104 | Me | Me | OH | 6-Me | O | 5,6-difluoro-3-methylquinoxalin-2-yl | 361 | 3.73 | A |
| I.105 | Me | Me | OH | 5-F | O | 5,6-difluoro-3-methylquinoxalin-2-yl | 365 | 3.58 | A |
| I.106 | Me | Me | Me | 6-Cl | O | 5,6-difluoro-3-methylquinoxalin-2-yl | 379 | 6.07 | A |
| I.107 | Me | Me | Me | 6-Me | O | 5,6-difluoro-3-methylquinoxalin-2-yl | 359 | 5.88 | A |
| I.108 | Me | Me | Me | 5-F | O | 5,6-difluoro-3-methylquinoxalin-2-yl | 363 | 5.57 | A |
| I.109 | Me | Me | OH | 3-F | O | 3-methylquinoxalin-2-yl | 329 | 3.25 | A |
| I.110 | Me | Me | Me | — | O | 3-methylquinoxalin-2-yl | 309 | 5.31 | A |
| I.111 | Me | Me | Me | 3-F | O | 3-methylquinoxalin-2-yl | 327 | 5.45 | A |
| I.112 | Me | Me | OH | — | O | 3-methylquinoxalin-2-yl | 311 | 3.01 | A |
| I.113 | Me | Me | 2-thienyl | 3-F | O | 3-methylquinoxalin-2-yl | 395 | 5.51 | A |
| I.114 | Me | Me | 4-methoxyphenyl | 3-F | O | 3-methylquinoxalin-2-yl | 419 | 5.35 | A |
| I.115 | Me | Me | phenyl | 3-F | O | 3-methylquinoxalin-2-yl | 389 | 5.59 | A |
| I.116 | Me | Me | Me | 3-F | O | 1,5-naphthyridin-3-yl | 313 | 4.15 | A |
| I.117 | Me | Me | OH | 3-F | O | thieno[3,2-b]pyridin-6-yl | 320 | 2.80 | A |
| I.118 | Me | Me | Me | 3-F | O | thieno[3,2-b]pyridin-6-yl | 318 | 5.22 | A |
| I.119 | Me | Me | OH | 3-F | O | thieno[2,3-b]pyridin-5-yl | 320 | 3.09 | A |
| I.120 | Me | Me | Me | 3-F | O | thieno[2,3-b]pyridin-5-yl | 318 | 5.45 | A |
| I.121 | Me | Me | OH | 3-F | O | pyrazolo[1,5-a]pyrimidin-6-yl | 304 | 2.07 | A |
| I.122 | Me | Me | Me | 3-F | O | pyrazolo[1,5-a]pyrimidin-6-yl | 302 | 4.23 | A |
| I.123 | Me | Me | Me | — | O | pyrazolo[1,5-a]pyrimidin-6-yl | 284 | 4.11 | A |
| I.124 | Me | Me | Me | — | O | imidazo[1,2-a]pyrimidin-6-yl | 284 | 2.78 | A |
| I.125 | Me | Me | OH | — | O | imidazo[1,2-a]pyrimidin-6-yl | 286 | 2.10 | A |
| I.126 | Me | Me | OH | — | O | 3-fluoropyrazolo[1,5-a]pyrimidin-6-yl | 304 | 2.50 | A |
| I.127 | Me | Me | OH | 3-F | O | 3-fluoropyrazolo[1,5-a]pyrimidin-6-yl | 322 | 2.60 | A |
| I.128 | Me | Me | Me | 3-F | O | 3-fluoropyrazolo[1,5-a]pyrimidin-6-yl | 320 | 4.61 | A |
| I.129 | Me | Me | Me | — | O | 3-fluoropyrazolo[1,5-a]pyrimidin-6-yl | 302 | 4.56 | A |
| I.130 | Me | Me | Me | — | CH₂ | 4-methylquinolin-3-yl | 306 | 3.19 | A |
| I.131 | Me | Me | Me | 3-F | S | quinolin-3-yl | 328 | 5.72 | A |
| I.132 | Me | Me | Me | 3-F | S(=O) | quinolin-3-yl | 344 | 3.63 | A |
| I.133 | Me | Me | Me | 3-F | CH(OH) | quinolin-3-yl | 326 | 4.16 | A |
| I.134 | Me | Me | Me | 4-Cl | O | 2-methylquinolin-3-yl | 342 | 5.68 | A |
| I.135 | Me | Me | Me | 4-phenyl | O | 2-methylquinolin-3-yl | 384 | 6.27 | A |
| I.136 | Me | Me | Me | 4-cyclopropyl | O | 2-methylquinolin-3-yl | 348 | 5.68 | A |
| I.137 | Me | Me | Me | 4-vinyl | O | 2-methylquinolin-3-y | 334 | 5.51 | A |
| I.138 | Me | Me | Me | 4-(3-thienyl) | O | 2-methylquinolin-3-yl | 390 | 5.85 | A |
| I.139 | Me | Me | Me | — | CH₂ | 2-methylquinolin-3-yl | 306 | 2.76 | A |
| I.140 | Me | Me | phenyl | — | CH₂ | 2-methylquinolin-3-yl | 368 | 2.88 | A |
| I.141 | Me | Me | phenyl | — | CH₂ | 1,5-naphthyridin-3-yl | 355 | 4.14 | A |
| I.142 | Me | Me | benzyl | — | CH₂ | quinolin-3-yl | 368 | 4.94 | A |
| I.143 | Me | Me | 4-benzylphenyl | — | CH₂ | quinolin-3-yl | 444 | 5.78 | A |

Note:
Me: methyl; Et: ethyl

Table 2 illustrates in a non-limiting manner examples of compounds of formula (IIa) according to the invention as well as their acceptable salts:

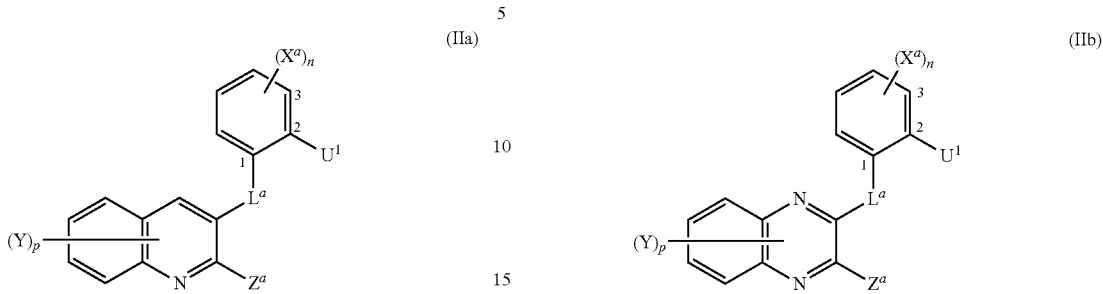
(IIa)

Table 3 illustrates in a non-limiting manner examples of compounds of formula (IIb) according to the invention as well as their acceptable salts:

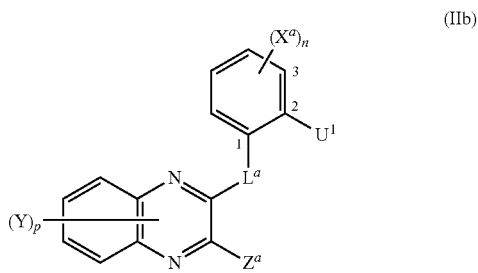
(IIb)

In table 2, M+H (Apcl+) and log P are defined as for table 1.

In table 2, the point of attachment of the $(X^a)_n$ residue to the phenyl ring is based on the above numbering of the phenyl ring.

In table 3, M+H (Apcl+) and log P are defined as for table 1.

In table 3, the point of attachment of the $(X^a)_n$ residue to the phenyl ring is based on the above numbering of the phenyl ring.

TABLE 2

| Example | $U^1$ | $(X^a)_n$ | $L^a$ | $Z^a$ | M + H | logP | logP Method |
|---|---|---|---|---|---|---|---|
| IIa.01 | I | 3-F | O | quinolin-3-yl | 366 | 3.71 | A |
| IIa.02 | I | — | O | quinolin-3-yl | 348 | 3.71 | A |
| IIa.03 | Br | — | O | quinolin-3-yl |  | 3.47 | A |
| IIa.04 | Br | — | O | 8-fluoroquinolin-3-yl | 318 | 3.61 | A |
| IIa.05 | Br | — | O | 8-fluoro-2-methyl quinolin-3-yl | 332 | 3.96 | A |
| IIa.06 | Br | — | O | 7,8-difluoroquinolin-3-yl | 336 | 3.92 | A |
| IIa.07 | Br | — | O | 7,8-difluoro-2-methylquinolin-3-yl | 350 | 4.25 | A |
| IIa.08 | Br | — | O | 2-methylquinolin-3-yl | 314 | 3.96 | A |
| IIa.09 | Br | 6-F | O | 7,8-difluoro-2-methylquinolin-3-yl | 368 | 4.25 | A |
| IIa.10 | Br | 5-F | O | 7,8-difluoro-2-methylquinolin-3-yl | 368 | 4.34 | A |
| IIa.11 | Br | 4-F | O | 8-chloroquinolin-3-yl | 352 | 4.18 | A |
| IIa.12 | Br | 4-F | O | 7,8-difluoro-2-methylquinolin-3-yl | 368 | 4.25 | A |
| IIa.13 | Br | 4-F | O | 2-methylquinolin-3-yl | 332 | 3.35 | A |
| IIa.14 | Br | 3-OMe | O | 7,8-difluoro-2-methylquinolin-3-yl | 380 | 4.11 | A |
| IIa.15 | Br | 3-F | O | 7,8-difluoroquinolin-3-yl | 354 | 3.90 | A |
| IIa.16 | Br | 3-F | O | 7,8-difluoro-2-methylquinolin-3-yl | 368 | 4.29 | A |
| IIa.17 | Br | 3-F | O | 4-methylquinolin-3-yl | 332 | 3.89 | A |
| IIa.18 | Br | 3-F | O | 2-methylquinolin-3-yl | 332 | 3.58 | A |
| IIa.19 | Br | 3-F | O | 2-(difluoromethyl) quinolin-3-yl | 368 | 3.99 | A |
| IIa.20 | Br | 3-Cl | O | 7,8-difluoro-2-methylquinolin-3-yl | 384 | 4.72 | A |
| IIa.21 | Br | 3-Cl | O | 2-methylquinolin-3-yl | 348 | 3.99 | A |
| IIa.22 | Br | 3-F | NH | 2-(difluoromethyl) quinolin-3-yl | 367 | 4.34 | A |
| IIa.23 | Cl | 4-F | O | 8-chloroquinolin-3-yl | 308 | 4.11 | A |
| IIa.24 | Br | 3-OCF$_3$ | O | 7,8-difluoro-2-methylquinolin-3-yl | 434 | 4.90 | A |
| IIa.25 | Br | 3-OCF$_3$ | O | 2-methylquinolin-3-yl | 398 | 4.30 | A |
| IIa.26 | Br | 4-Cl | O | 2-methylquinolin-3-yl | 348 | 4.13 | A |

Note:
Me: methyl

TABLE 3

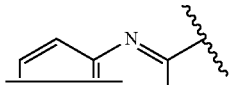

| Example | U¹ | $(X^a)_n$ | $L^a$ | $Z^a$ | M + H | logP | logP Method |
|---|---|---|---|---|---|---|---|
| IIb.01 | Br | — | O | 5,6-difluoroquinoxalin-2-yl | 337 | 3.92 | A |
| IIb.02 | Br | — | O | 5,6-difluoro-3-methylquinoxalin-2-yl | 351 | 4.38 | A |
| IIb.03 | Br | 6-Me | O | 5,6-difluoro-3-methylquinoxalin-2-yl | 365 | 4.80 | A |
| IIb.04 | Br | 6-F | O | 5,6-difluoro-3-methylquinoxalin-2-yl | 369 | 2.67 | A |
| IIb.05 | Br | 6-Cl | O | 5,6-difluoro-3-methylquinoxalin-2-yl | 385 | 4.87 | A |
| IIb.06 | Br | 5-Me | O | 5,6-difluoro-3-methylquinoxalin-2-yl | 365 | 4.85 | A |
| IIb.07 | Br | 5-F | O | 5,6-difluoro-3-methylquinoxalin-2-yl | 369 | 4.51 | A |
| IIb.08 | Br | 5-Cl | O | 5,6-difluoro-3-methylquinoxalin-2-yl | 385 | 5.05 | A |
| IIb.09 | Br | 4-Me | O | 5,6-difluoro-3-methylquinoxalin-2-yl | 365 | 4.92 | A |
| IIb.10 | Br | 4-F | O | 5,6-difluoro-3-methylquinoxalin-2-yl | 369 | 4.54 | A |
| IIb.11 | Br | 4-Cl | O | 5,6-difluoro-3-methylquinoxalin-2-yl | 385 | 5.16 | A |
| IIb.12 | Br | 3-Me | O | 5,6-difluoro-3-methylquinoxalin-2-yl | 365 | 4.85 | A |
| IIb.13 | Br | 3-OMe | O | 5,6-difluoro-3-methylquinoxalin-2-yl | 381 | 4.19 | A |
| IIb.14 | Br | 3-F | O | quinoxalin-2-yl | 319 | 3.78 | A |
| IIb.15 | Br | 3-F | O | 5,6-difluoroquinoxalin-2-yl | 355 | 3.97 | A |
| IIb.16 | Br | 3-F | O | 5,6-difluoro-3-methylquinoxalin-2-yl | 369 | 4.44 | A |
| IIb.17 | Br | 3-F | O | 3-methylquinoxalin-2-yl | 333 | 4.11 | A |
| IIb.18 | Br | 3-Cl | O | 5,6-difluoro-3-methylquinoxalin-2-yl | 385 | 4.82 | A |
| IIb.19 | Br | 4-CN-5-F | O | 5,6-difluoroquinoxalin-2-yl | 380 | 3.81 | A |
| IIb.20 | Br | 5-CN | O | 5,6-difluoro-3-methylquinoxalin-2-yl | 376 | 4.03 | A |
| IIb.21 | Br | 6-CN-3-F | O | 5,6-difluoroquinoxalin-2-yl | 380 | 3.72 | A |
| IIb.22 | Br | 3-CN | O | 5,6-difluoro-3-methylquinoxalin-2-yl | 376 | 3.83 | A |
| IIb.23 | Br | 3-OCF₃ | O | 5,6-difluoro-3-methylquinoxalin-2-yl | 435 | 5.08 | A |

Note:
Me: methyl

Table 4 illustrates in a non-limiting manner examples of compounds of formula (IVa) according to the invention, as well as their acceptable salts:

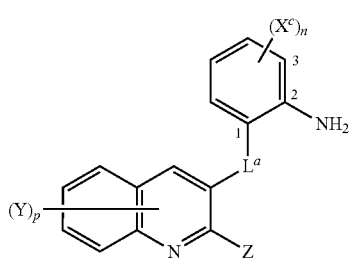

(IVa)

In table 4, M+H (Apcl+) and log P are defined as for table 1.

In table 4, the point of attachment of the $(X^c)_n$ residue to the phenyl ring is based on the above numbering of the phenyl ring.

TABLE 4

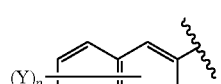

| Example | $(X^c)_n$ | $L^a$ | Z | M + H | logP | logP Method |
|---|---|---|---|---|---|---|
| IVa.01 | — | NH | quinolin-3-yl | 236 | 1.28 | A |
| IVa.02 | 3-F | O | 2-methylquinolin-3-yl | 269 | 2.15 | A |
| IVa.03 | — | O | 7,8-difluoroquinolin-3-yl | 273 | 2.71 | A |
| IVa.04 | 3-F | O | 7,8-difluoroquinolin-3-yl | 291 | 3.02 | A |
| IVa.05 | — | O | 7,8-difluoro-2-methylquinolin-3-yl | 287 | 2.99 | A |
| IVa.06 | 3-F | O | 7,8-difluoro-2-methylquinolin-3-yl | 305 | 3.27 | A |
| IVa.07 | — | O | 2-methylquinolin-3-yl | 251 | 1.66 | A |

Table 5 illustrates in a non-limiting manner examples of compounds of formula (Va) according to the invention, as well as their acceptable salts:

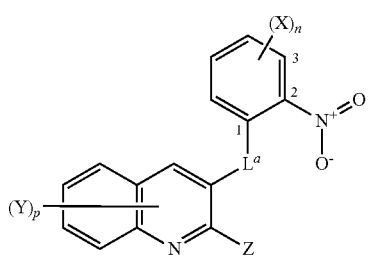

(Va)

In table 5, M+H (Apcl+) and log P are defined as for table 1.

In table 5, the point of attachment of the $(X)_n$ residue to the phenyl ring is based on the above numbering of the phenyl ring.

TABLE 5

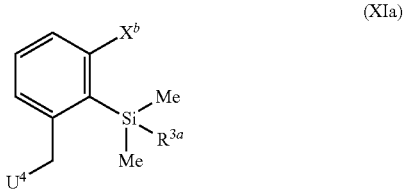

| Example | $(X)_n$ | $L^a$ | $(Y)_p$ ... | M + H | logP | logP Method |
|---------|---------|-------|-------------|-------|------|-------------|
| Va.01 | 3-F | O | 7,8-difluoroquinolin-3-yl | 321 | 3.35 | A |
| Va.02 | 3-F | O | 7,8-difluoro-2-methylquinolin-3-yl | 335 | 3.64 | A |
| Va.03 | — | O | 7,8-difluoroquinolin-3-yl | 303 | 3.06 | A |
| Va.04 | — | O | 7,8-difluoro-2-methylquinolin-3-yl | 317 | 3.42 | A |
| Va.05 | 3-F | O | quinolin-3-yl | 285 | 3.13 | A |
| Va.06 | 3-F | O | 2-methylquinolin-3-yl | 299 | 3.15 | A |
| Va.07 | — | O | quinolin-3-yl | 267 | 1.62 | A |
| Va.08 | — | O | 2-methylquinolin-3-yl | 281 | 2.64 | A |

Table 6 illustrates in a non-limiting manner examples of compounds of formula (IXa) according to the invention:

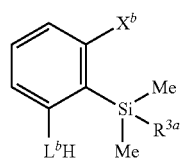

(IXa)

In table 6, M+H (Apcl+) and log P are defined as for table 1.

TABLE 6

| Example | $X^b$ | $L^b$ | $R^{3a}$ | M + H | logP | logP Method |
|---------|-------|-------|----------|-------|------|-------------|
| IXa.01 | 3-F | O | isopropyl | 169$^{(1)}$ | 4.27 | A |
| IXa.02 | — | O | isopropyl | 151$^{(1)}$ | 4.25 | A |
| IXa.03 | — | O | isobutyl | 151$^{(1)}$ | 4.67 | A |
| IXa.04 | — | O | ethyl | 180$^{(2)}$ | 3.90 | B |
| IXa.05 | — | O | cyclohexyl | 151$^{(1)}$ | 5.25 | A |
| IXa.06 | — | O | benzyl | 242$^{(2)}$ | 5.14 | A |

Note (1):
Mass M-$R^{3a}$ by GC-mass

Note (2):
Mass M by GC-mass

Table 7 illustrates in a non-limiting manner examples of compounds of formula (XIa) according to the invention:

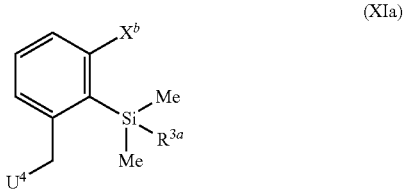

(XIa)

In table 7, M+H (Apcl+) and log P are defined as for table 1.

TABLE 7

| Example | $X^b$ | $U^4$ | $R^{3a}$ | M + H | logP | logP Method |
|---------|-------|-------|----------|-------|------|-------------|
| XIa.01 | — | Br | 6-chloropyridin-3-yl | 324$^{(1)}$ | 4.51 | A |
| XIa.02 | — | I | phenyl | 225$^{(2)}$ | 6.82 | A |
| XIa.03 | — | Br | phenyl | | 5.46 | A |
| XIa.04 | — | Br | 2-thienyl | 295$^{(1)}$ | 5.19 | A |
| XIa.05 | — | Br | 4-phenoxyphenyl | 381$^{(1)}$ | 6.43 | A |
| XIa.06 | — | Br | 4-chlorophenyl | 323$^{(1)}$ | 5.94 | A |
| XIa.07 | — | Br | benzyl | 238$^{(2)}$ | 5.59 | A |
| XIa.08 | — | Br | biphenyl-4-yl | 365$^{(1)}$ | 6.53 | A |
| XIa.09 | — | Br | 4-benzylphenyl | 314$^{(2)}$ | 6.50 | A |

Note (1):
Mass M-CH$_3$ by GC-mass

Note (2):
Mass M-$U^4$ by GC-mass

Table 8 illustrates in a non-limiting manner examples of compounds of formula (XIIa) according to the invention:

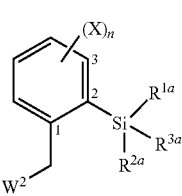

(XIIa)

In table 8, M+H (Apcl+) and log P are defined as for table 1.

In table 8, the point of attachment of the $(X)_n$ residue to the phenyl ring is based on the above numbering of the phenyl ring.

TABLE 8

| Example | W² | (X)ₙ | R¹ᵃ | R²ᵃ | R³ᵃ | M + H | logP | logP Method |
|---|---|---|---|---|---|---|---|---|
| XIIa.01 | 4,4,5,5-tetramethyl-1,3,2-dioxaborolan-2-yl | — | Me | Me | Me | —[1] | 5.68 | A |

Note:
Me: methyl
Note[1]:
no ionization

Table 9 illustrates in a non-limiting manner examples of compounds of formula (VIIa) according to the invention:

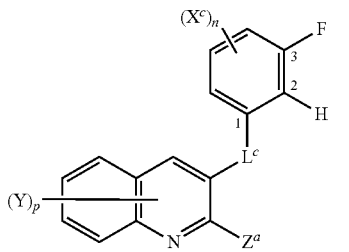

(VIIa)

In table 9, M+H (Apcl+) and log P are defined as for table 1.

In table 9, the point of attachment of the (X)ₙ residue to the phenyl ring is based on the above numbering of the phenyl ring.

TABLE 9

| Example | (Xᶜ)ₙ | Lᶜ | Zᵃ | M + H | logP | logP Method |
|---|---|---|---|---|---|---|
| VIIa.01 | — | O | 2-chloroquinolin-3-yl | 274 | 3.99 | A |
| VIIa.02 | — | O | 2-ethoxyquinolin-3-yl | 284 | 4.74 | A |
| VIIa.03 | — | O | 2-(methylsulfanyl)quinolin-3-yl | 286 | 4.92 | A |
| VIIa.04 | — | O | 2-methylquinolin-3-yl | 254 | 2.96 | A |
| VIIa.05 | — | O | quinolin-3-yl | 240 | 3.21 | A |
| VIIa.06 | — | O | 1-oxidoquinolin-3-yl | 256 | 2.14 | A |

Table 10 illustrates in a non-limiting manner examples of compounds of formula (XIV) according to the invention:

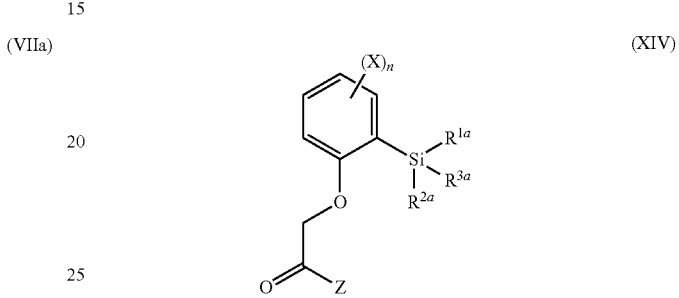

(XIV)

In table 10, M+H (Apcl+) and log P are defined as for table 1.

In table 10, the point of attachment of the (X)ₙ residue to the phenyl ring is based on the above numbering of the phenyl ring.

TABLE 10

| Example | Z | (X)ⁿ | R¹ᵃ | R²ᵃ | R³ᵃ | M + H | logP | logP Method |
|---|---|---|---|---|---|---|---|---|
| XIV.01 | CH₃ | — | Me | Me | Me | 222[1] | 1.39 | A |

Note:
Me: methyl
Note[1]:
Mass M by GC-mass

Table 11 illustrates other preferred compounds of formula (II), (VII) and (IX), according to the invention.

In table 11, M+H (Apcl+) and log P are defined as for table 1.

TABLE 11

| Example | Structure | M + H | logP | logP Method |
|---|---|---|---|---|
| II.01A | (structure shown) | 376 | 3.29 | A |

TABLE 11-continued

| Example | Structure | M + H | logP | logP Method |
|---------|-----------|-------|------|-------------|
| II.02A | 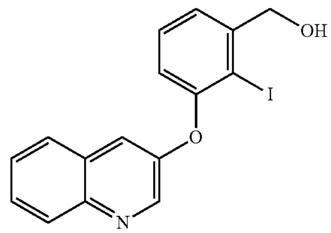 [SMILES: OCc1cccc(Oc2cnc3ccccc3c2)c1I] | 378 | 2.59 | A |
| II.03A | 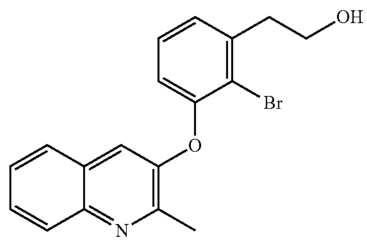 [SMILES: Cc1nc2ccccc2cc1Oc1cccc(CCO)c1Br] | 358 | 2.14 | A |
| II.04A | 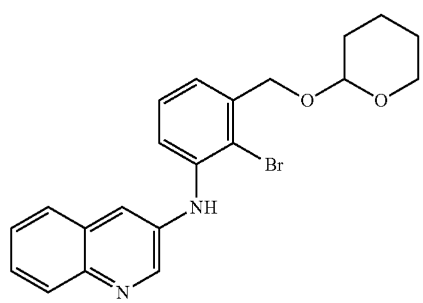 [SMILES: Brc1c(COC2CCCCO2)cccc1Nc1cnc2ccccc2c1] | 413 | 4.13 | B |
| II.05A | 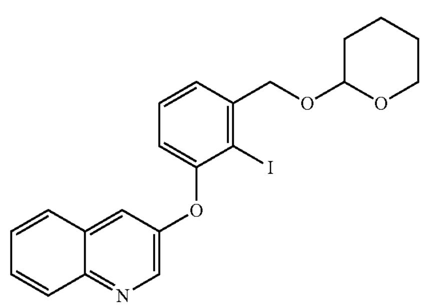 [SMILES: Ic1c(COC2CCCCO2)cccc1Oc1cnc2ccccc2c1] | 462 | 4.56 | B |
| II.06A | 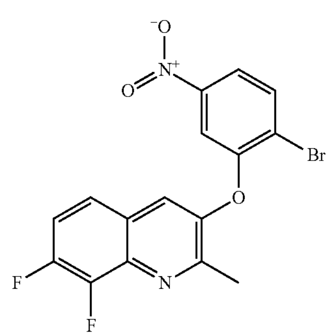 | 395 | 4.04 | A |

TABLE 11-continued

| Example | Structure | M + H | logP | logP Method |
|---|---|---|---|---|
| II.07A | 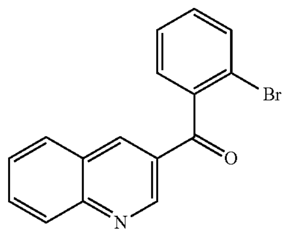 [SMILES: O=C(c1cnc2ccccc2c1)c1ccccc1Br] | | | |
| II.08A | 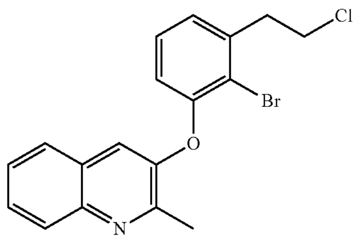 [SMILES: Cc1nc2ccccc2cc1Oc1cccc(CCCl)c1Br] | 376 | 3.99 | A |
| II.01B | 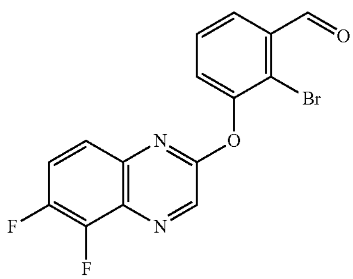 [SMILES: O=Cc1cccc(Oc2cnc3c(F)c(F)ccc3n2)c1Br] | 365 | 3.48 | A |
| VII.01A | 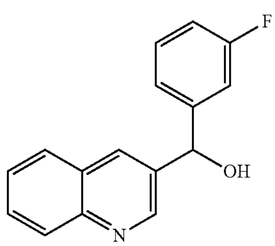 [SMILES: OC(c1cccc(F)c1)c1cnc2ccccc2c1] | 254 | 1.54 | A |
| VII.02A | 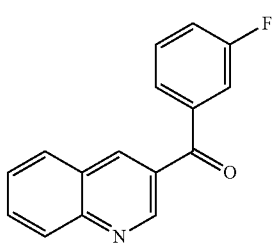 [SMILES: O=C(c1cccc(F)c1)c1cnc2ccccc2c1] | 252 | 2.73 | A |
| VII.03A | 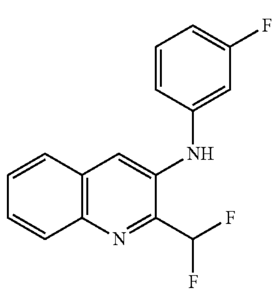 [SMILES: Fc1cccc(Nc2cc3ccccc3nc2C(F)F)c1] | 289 | 3.68 | A |

TABLE 11-continued

| Example | Structure | M + H | logP | logP Method |
|---|---|---|---|---|
| VII.04A | 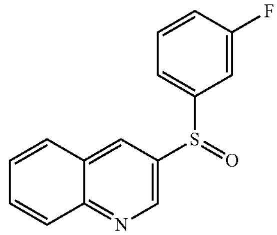 [SMILES: O=S(c1cccc(F)c1)c1cnc2ccccc2c1] | 2.10 | 272 | A |
| VII.05A | 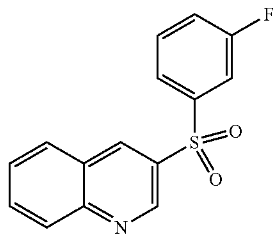 [SMILES: O=S(=O)(c1cccc(F)c1)c1cnc2ccccc2c1] | 2.68 | 288 | A |
| IX.01A | 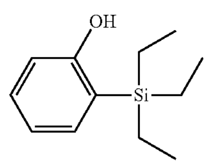 | 208[(1)] | 4.72 | A |
| IX.02A | 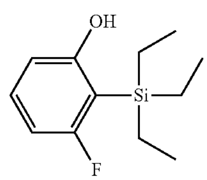 | 226[(1)] | 4.69 | A |

Note[(1)]:
Mass M (minor) by GC-mass together with M - Et, M - 2Et and M - 3Et.

Table 12 provides the NMR data ($^1$H) of a selected number of compounds from table 1, table 2, table 3, table 4, table 5, table 6, table 7, table 8, table 9, table 10 and table 11.

The $^1$H-NMR data of selected examples are stated in the form of $^1$H-NMR peak lists. For each signal peak, the λ value in ppm and the signal intensity in brackets are listed.

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

The $^1$H-NMR peak lists are similar to classical $^1$H-NMR prints and contain therefore usually all peaks, which are listed at classical NMR-interpretation. Additionally they can show like classical $^1$H-NMR prints signals of solvents, stereoisomers of the target compounds, which are also object of the invention, and/or peaks of impurities. To show compound signals in the delta-range of solvents and/or water the usual peaks of solvents, for example peaks of DMSO in d6-DMSO and the peak of water are shown in our $^1$H-NMR peak lists and have usually on average a high intensity.

The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values), can isolate the peaks of the target compounds as needed optionally using additional intensity filters. This isolation would be similar to relevant peak picking at classical $^1$H-NMR interpretation.

Further details of NMR-data description with peak lists can be found in the publication "Citation of NMR Peaklist Data within Patent Applications" of the Research Disclosure Database Number 564025.

TABLE 12

| | NMR peak lists |
|---|---|
| Example | $^1$H-NMR [CDCl$_3$ at 300 Mhz] |
| I.001 | 8.794 (0.71); 8.784 (0.72); 8.115 (0.34); 8.088 (0.38); 7.658 (0.44); 7.63 (0.37); 7.625 (0.4); 7.602 (0.33); 7.586 (0.36); 7.58 (0.37); 7.562 (0.41); 7.556 (0.42); 7.541 (0.34); 7.537 (0.33); 7.514 (0.42); 7.5 (0.55); 7.491 (0.69); 7.378 (0.33); 7.372 (0.32); 7.259 (1.34); 7.232 (0.32); 7.229 (0.32); 7.208 (0.51); 7.204 (0.49); 6.917 (0.47); 6.915 (0.45); 6.89 (0.42); 1.656 (0.42); 0.302 (0.58); 0.291 (16); 0.28 (0.78); 0 (0.96) |
| I.002 | 8.831 (0.95); 8.822 (0.95); 8.159 (0.5); 8.132 (0.56); 7.737 (0.46); 7.719 (0.64); 7.713 (1.1); 7.709 (1.01); 7.704 (0.49); 7.695 (0.65); 7.689 (0.7); 7.685 (0.68); 7.68 (0.63); 7.675 (0.33); 7.657 (0.48); 7.652 (0.37); 7.6 (0.81); 7.592 (1.2); 7.59 (1.09); 7.566 (0.6); 7.562 (0.38); 7.44 (0.49); 7.437 (0.47); 7.434 (0.49); 7.431 (0.4); 7.412 (0.45); 7.406 (0.41); 7.299 (6.28); 7.293 (0.72); 7.29 (0.59); 7.269 (0.78); 7.266 (0.73); 7.245 (0.33); 6.935 (0.71); 6.908 (0.64); 2.239 (0.61); 1.608 (3.75); 0.482 (0.68); 0.471 (16); 0.459 (0.73); 0.039 (6.19) |
| I.003 | 8.814 (2.06); 8.805 (2.11); 8.174 (1); 8.146 (1.13); 7.775 (0.91); 7.748 (1.32); 7.742 (0.8); 7.736 (0.69); 7.718 (1.07); 7.713 (1.19); 7.708 (0.62); 7.69 (0.95); 7.685 (0.76); 7.665 (1.63); 7.657 (1.56); 7.622 (0.91); 7.618 (0.92); 7.595 (1.21); 7.591 (0.75); 7.572 (0.53); 7.568 (0.49); 7.399 (0.59); 7.376 (0.73); 7.372 (1.31); 7.349 (1.34); 7.344 (0.84); 7.322 (0.8); 7.3 (16.11); 6.937 (0.88); 6.935 (0.85); 6.908 (1.53); 6.881 (0.78); 6.879 (0.72); 6.685 (1.63); 6.658 (1.5); 5.339 (1.16); 2.679 (1); 2.672 (0.95); 1.604 (15.76); 0.547 (0.88); 0.535 (16); 0.53 (15.95); 0.518 (0.69); 0.501 (0.5); 0.495 (0.46); 0.418 (0.46); 0.412 (0.44); 0.103 (0.7); 0.049 (0.44); 0.038 (10.86); 0.028 (0.42) |
| I.004 | 8.848 (1.07); 8.838 (1.11); 8.16 (0.55); 8.132 (0.64); 7.736 (0.48); 7.709 (1.02); 7.685 (0.57); 7.68 (0.61); 7.676 (0.34); 7.658 (0.48); 7.652 (0.37); 7.594 (0.48); 7.59 (0.5); 7.567 (0.66); 7.563 (0.48); 7.555 (0.9); 7.545 (1.06); 7.478 (0.55); 7.453 (1.06); 7.427 (0.7); 7.3 (2.82); 7.136 (0.76); 7.135 (0.76); 7.111 (0.66); 7.11 (0.66); 6.89 (0.75); 6.888 (0.75); 6.863 (0.7); 5.234 (3.08); 1.678 (0.33); 1.293 (0.44); 0.357 (0.54); 0.345 (16); 0.333 (0.8); 0.109 (0.33); 0.038 (1.27) |
| I.005 [1] | 8.757 (2.02); 8.751 (2.01); 8.12 (1.38); 8.099 (1.44); 7.706 (1.24); 7.685 (1.58); 7.664 (0.75); 7.66 (0.73); 7.646 (1.14); 7.643 (1.39); 7.626 (0.92); 7.622 (0.79); 7.553 (1.08); 7.551 (1.09); 7.533 (1.54); 7.517 (2.4); 7.512 (2.38); 7.329 (0.62); 7.312 (0.89); 7.309 (1.38); 7.292 (1.41); 7.289 (0.95); 7.272 (0.8); 7.259 (4.9); 6.871 (0.97); 6.849 (1.8); 6.829 (0.88); 6.673 (1.93); 6.653 (1.8); 1.602 (1.08); 1.256 (0.94); 0.982 (1.6); 0.962 (5.06); 0.953 (0.84); 0.944 (3.19); 0.869 (1.19); 0.85 (2.14); 0.831 (1.66); 0.811 (0.41); 0.472 (1.04); 0.338 (16); 0.333 (15.8); 0 (3.76) |
| I.006 | 8.783 (1.92); 8.774 (1.98); 8.16 (1.13); 8.132 (1.28); 7.744 (1.02); 7.717 (1.49); 7.711 (0.86); 7.706 (0.71); 7.687 (1.03); 7.682 (1.22); 7.678 (0.68); 7.659 (0.88); 7.654 (0.74); 7.597 (0.94); 7.594 (1.06); 7.57 (1.29); 7.544 (2.26); 7.535 (1.79); 7.391 (0.57); 7.369 (0.66); 7.364 (1.32); 7.342 (1.29); 7.337 (0.89); 7.314 (0.72); 7.298 (3.01); 6.924 (0.92); 6.896 (1.66); 6.868 (0.81); 6.721 (1.77); 6.694 (1.62); 6.471 (0.49); 6.467 (0.56); 6.423 (0.63); 6.418 (0.67); 6.404 (0.62); 6.399 (0.66); 6.355 (0.75); 6.351 (0.82); 5.993 (1.31); 5.982 (1.53); 5.945 (1.12); 5.933 (1.18); 5.789 (1.47); 5.778 (1.28); 5.722 (1.17); 5.71 (1.07); 1.292 (1.48); 0.568 (0.52); 0.493 (0.62); 0.482 (15.28); 0.475 (16); 0.037 (3) |
| I.007 | 8.813 (1.82); 8.804 (1.83); 8.186 (1.04); 8.158 (1.16); 7.774 (1.01); 7.747 (1.46); 7.738 (0.76); 7.733 (0.71); 7.714 (1.08); 7.71 (1.25); 7.705 (0.67); 7.686 (0.91); 7.682 (0.73); 7.675 (1.8); 7.642 (1.8); 7.621 (1.02); 7.617 (1.02); 7.594 (1.3); 7.57 (0.52); 7.567 (0.49); 7.408 (0.6); 7.386 (0.75); 7.381 (1.34); 7.359 (1.36); 7.354 (0.9); 7.331 (0.76); 7.297 (3.6); 6.929 (0.93); 6.9 (1.71); 6.872 (0.87); 6.694 (1.8); 6.667 (1.66); 3.258 (0.38); 3.194 (5.53); 3.191 (5.52); 1.469 (0.33); 1.323 (0.73); 1.291 (4.98); 0.916 (0.62); 0.892 (0.48); 0.878 (0.33); 0.863 (0.59); 0.69 (1.18); 0.552 (0.67); 0.54 (15.94); 0.535 (16); 0.109 (4.46); 0.036 (2.86) |
| I.008 | 8.796 (2.24); 8.788 (3.9); 8.781 (3.33); 8.154 (2.41); 8.127 (2.34); 7.738 (2.31); 7.71 (3.17); 7.687 (1.55); 7.675 (2.43); 7.659 (1.32); 7.652 (1.55); 7.588 (2.14); 7.564 (3.28); 7.553 (3.32); 7.545 (4.89); 7.538 (4.26); 7.439 (0.67); 7.431 (1.02); 7.404 (2.16); 7.389 (1.53); 7.382 (2.07); 7.362 (0.85); 7.354 (0.9); 7.301 (2.39); 7.294 (2.79); 7.208 (1.06); 6.952 (1.77); 6.931 (2.01); 6.925 (2.75); 6.905 (1.07); 6.898 (1.29); 6.784 (0.61); 6.771 (2.08); 6.764 (3.01); 6.744 (1.9); 6.737 (2.5); 2.668 (0.61); 2.268 (0.35); 2.253 (0.59); 2.242 (0.76); 2.234 (1.04); 2.219 (1.09); 2.213 (1.25); 2.2 (1.4); 2.192 (1.56); 2.18 (1.33); 2.171 (1.3); 2.164 (1.55); 2.158 (1.61); 2.146 (1.1); 2.139 (1.51); 2.132 (1.65); 2.115 (1.07); 2.107 (1.21); 2.1 (1.13); 2.091 (0.94); 2.084 (0.75); 2.076 (0.63); 2.066 (0.61); 1.709 (1.18); 1.701 (1.2); 1.642 (0.47); 1.491 (1.3); 1.466 (2.35); 1.46 (2.35); 1.449 (2.38); 1.442 (2.59); 1.416 (2.73); 1.384 (1.49); 1.289 (3); 1.261 (2.29); 1.25 (2.42); 1.239 (2.94); 1.231 (2.98); 1.218 (3.02); 1.211 (3.31); 1.192 (2.11); 1.168 (1.35); 1.16 (1.13); 0.89 (0.77); 0.581 (3.28); 0.568 (11.28); 0.561 (16); 0.305 (0.64); 0.298 (0.97); 0.234 (0.45); 0.216 (0.41); 0.208 (0.42); 0.191 (0.57); 0.175 (0.61); 0.167 (0.8); 0.115 (0.95); 0.108 (1.12); 0.054 (0.45); 0.041 (1.44); 0.034 (1.86) |
| I.009 | 8.69 (1.13); 8.681 (1.15); 8.023 (0.44); 8.018 (0.47); 7.993 (0.53); 7.849 (0.63); 7.763 (0.91); 7.754 (0.88); 7.669 (0.45); 7.664 (0.39); 7.66 (0.32); 7.644 (0.67); 7.637 (0.62); 7.552 (0.31); 7.535 (0.68); 7.529 (0.65); 7.525 (0.48); 7.515 (1.23); 7.511 (1.2); 7.502 (0.73); 7.49 (1.38); 7.463 (1.06); 7.46 (1.05); 7.45 (0.63); 7.445 (0.56); 7.427 (0.6); 7.422 (0.61); 7.3 (4.89); 7.12 (0.42); 7.115 (0.43); 7.096 (0.62); 7.092 (0.66); 7.072 (0.43); 7.068 (0.43); 1.295 (0.54); 0.692 (1.88); 0.506 (0.71); 0.495 (16); 0.484 (0.73); 0.111 (0.72); 0.04 (2.59) |
| I.010 | 8.739 (1.02); 8.73 (1.04); 8.072 (0.51); 8.045 (0.55); 7.681 (0.41); 7.677 (0.4); 7.655 (0.6); 7.65 (0.63); 7.613 (0.83); 7.603 (1.03); 7.598 (0.39); 7.58 (0.55); 7.575 (0.5); 7.553 (0.54); 7.547 (0.43); 7.538 (0.53); 7.533 (0.58); 7.511 (0.5); 7.508 (0.43); 7.453 (0.46); 7.427 (1.01); 7.402 (0.66); 7.3 (4.04); 7.227 (0.78); 7.201 (0.61); 7.032 (0.7); 7.007 (0.62); 5.711 (0.53); 5.214 (2.95); 1.658 (1.42); 0.442 (0.55); 0.43 (16); 0.419 (0.59); 0.039 (2.64) |
| I.011 | 8.655 (0.73); 8.646 (0.75); 8.045 (0.34); 8.019 (0.38); 7.613 (0.38); 7.607 (0.7); 7.6 (0.5); 7.589 (0.41); 7.584 (0.43); 7.527 (0.4); 7.521 (0.33); 7.5 (0.68); 7.493 (0.71); 7.469 (0.42); 7.444 (0.44); 7.439 (0.33); 7.423 (0.7); 7.416 (0.95); 7.392 (0.61); 7.298 (1.11); 7.226 (0.43); 7.222 (0.42); 5.792 (0.39); 0.375 (0.65); 0.365 (16); 0.354 (0.74); 0.041 (1.18) |

TABLE 12-continued

| | NMR peak lists |
|---|---|
| Example | $^1$H-NMR [CDCl$_3$ at 300 Mhz] |
| I.012 | 8.817 (0.63); 8.81 (0.65); 8.142 (0.39); 8.114 (0.45); 7.756 (0.91); 7.73 (0.71); 7.711 (0.36); 7.706 (0.4); 7.648 (0.35); 7.626 (0.46); 7.619 (0.41); 7.569 (0.33); 7.546 (0.46); 7.348 (0.35); 7.342 (0.39); 7.326 (0.67); 7.32 (0.61); 7.303 (0.44); 7.297 (1.51); 7.071 (0.38); 7.065 (0.41); 7.042 (0.33); 4.377 (1.9); 0.381 (0.68); 0.371 (16); 0.36 (0.85); 0.039 (1.08) |
| I.013 | 8.558 (0.94); 8.551 (0.91); 8.103 (0.64); 8.075 (0.75); 7.724 (0.55); 7.718 (0.47); 7.714 (0.44); 7.71 (0.45); 7.705 (0.56); 7.701 (0.76); 7.694 (0.67); 7.688 (0.53); 7.682 (0.74); 7.677 (0.39); 7.66 (0.75); 7.655 (0.54); 7.637 (0.86); 7.553 (0.77); 7.545 (1.45); 7.54 (0.9); 7.534 (1.3); 7.529 (0.7); 7.521 (1.5); 7.514 (0.55); 7.484 (0.95); 7.481 (0.91); 7.385 (0.59); 7.379 (0.62); 7.362 (1.28); 7.357 (1.33); 7.349 (2.34); 7.342 (2.71); 7.333 (1.48); 7.327 (1.13); 7.315 (0.47); 7.303 (1.23); 7.068 (0.61); 7.062 (0.62); 7.039 (0.51); 4.163 (3.02); 0.646 (0.8); 0.635 (16); 0.624 (0.62); 0.051 (0.9) |
| I.014 | 8.594 (1.07); 8.587 (1.08); 8.107 (0.62); 8.079 (0.73); 7.718 (0.35); 7.712 (0.39); 7.699 (0.62); 7.695 (0.94); 7.69 (0.85); 7.684 (0.44); 7.677 (0.73); 7.67 (0.74); 7.662 (0.81); 7.632 (0.84); 7.555 (0.59); 7.551 (0.53); 7.532 (0.52); 7.528 (0.68); 7.524 (0.36); 7.46 (0.9); 7.456 (0.88); 7.433 (0.46); 7.427 (1.74); 7.42 (0.61); 7.408 (0.89); 7.399 (2.3); 7.393 (0.47); 7.385 (0.71); 7.378 (0.92); 7.371 (0.62); 7.352 (0.64); 7.348 (0.57); 7.304 (1.26); 7.281 (2.36); 7.275 (0.66); 7.259 (0.64); 7.254 (1.5); 7.099 (0.63); 7.095 (0.63); 7.073 (0.54); 7.071 (0.53); 4.142 (2.9); 1.791 (1.56); 0.624 (0.69); 0.614 (16); 0.603 (0.66); 0.048 (1.14) |
| I.015 | 8.618 (1.04); 8.61 (1.05); 8.111 (0.64); 8.083 (0.62); 7.717 (0.32); 7.713 (0.44); 7.704 (0.59); 7.697 (1.06); 7.69 (1.24); 7.681 (0.79); 7.674 (0.79); 7.671 (0.8); 7.666 (1.51); 7.628 (0.91); 7.626 (0.84); 7.613 (0.97); 7.61 (0.87); 7.564 (0.88); 7.56 (0.89); 7.554 (0.81); 7.55 (0.57); 7.531 (0.45); 7.525 (0.73); 7.388 (0.58); 7.382 (0.6); 7.364 (0.64); 7.357 (0.94); 7.351 (0.62); 7.332 (0.6); 7.328 (0.57); 7.31 (1.09); 7.304 (2.38); 7.299 (1.21); 7.297 (1); 7.183 (0.82); 7.172 (0.79); 7.168 (0.82); 7.156 (0.66); 7.078 (0.6); 7.074 (0.63); 7.05 (0.53); 4.257 (2.91); 1.716 (1.83); 0.702 (0.64); 0.691 (16); 0.68 (0.63); 0.047 (1.89) |
| I.016 | 8.586 (1.13); 8.578 (1.12); 8.115 (0.64); 8.087 (0.78); 7.717 (0.93); 7.712 (0.53); 7.694 (1.48); 7.688 (1.55); 7.666 (0.69); 7.659 (0.93); 7.556 (0.59); 7.553 (0.54); 7.534 (0.58); 7.53 (0.69); 7.525 (0.5); 7.514 (0.98); 7.51 (1.04); 7.508 (1.02); 7.497 (0.35); 7.49 (1.96); 7.483 (0.65); 7.468 (0.76); 7.461 (2.03); 7.454 (0.33); 7.384 (0.7); 7.378 (1.27); 7.369 (0.41); 7.361 (1.29); 7.352 (1.9); 7.338 (0.71); 7.333 (0.74); 7.33 (0.66); 7.324 (1.12); 7.315 (0.36); 7.304 (4); 7.173 (0.37); 7.17 (0.57); 7.145 (0.85); 7.12 (0.37); 7.073 (0.63); 7.067 (0.66); 7.044 (0.55); 7.016 (1.34); 7.013 (1.54); 7.006 (0.38); 6.991 (0.86); 6.987 (1.32); 6.984 (1.01); 6.97 (0.33); 6.962 (2.16); 6.956 (0.66); 6.94 (0.71); 6.934 (1.81); 4.187 (3.01); 1.664 (4.76); 0.635 (0.8); 0.625 (16); 0.614 (0.67); 0.046 (3.58) |
| I.017 | 9.445 (1.37); 9.438 (1.4); 8.577 (1.33); 8.571 (1.32); 8.255 (0.83); 8.227 (1.06); 7.964 (0.83); 7.946 (0.63); 7.94 (1.09); 7.937 (1.14); 7.923 (0.77); 7.919 (0.83); 7.895 (0.54); 7.891 (0.44); 7.71 (0.63); 7.686 (0.97); 7.662 (0.43); 7.517 (0.35); 7.499 (0.39); 7.491 (0.67); 7.472 (0.66); 7.465 (0.56); 7.446 (0.51); 7.305 (1.8); 7.261 (0.63); 7.232 (1.01); 7.206 (1.65); 7.182 (1.09); 1.295 (0.41); 0.308 (0.38); 0.297 (15.16); 0.291 (16); 0.166 (0.79); 0.04 (1.36) |
| I.018 | 8.925 (1.19); 8.916 (1.23); 7.801 (0.62); 7.797 (0.69); 7.776 (0.76); 7.772 (0.8); 7.65 (0.55); 7.646 (0.59); 7.623 (0.83); 7.619 (0.78); 7.519 (1.23); 7.51 (1.38); 7.481 (0.92); 7.454 (0.5); 7.416 (0.66); 7.406 (0.66); 7.39 (0.61); 7.379 (0.63); 7.297 (3.58); 7.14 (0.37); 7.137 (0.46); 7.13 (0.36); 7.126 (0.43); 7.111 (0.41); 7.101 (0.37); 6.963 (0.67); 6.95 (0.69); 6.934 (0.51); 6.92 (0.5); 2.123 (0.65); 1.616 (3.17); 0.435 (0.59); 0.424 (16); 0.412 (0.62); 0.035 (3.15) |
| I.019 | 8.922 (0.78); 8.913 (0.78); 7.79 (0.44); 7.786 (0.45); 7.765 (0.51); 7.761 (0.52); 7.64 (0.36); 7.636 (0.37); 7.612 (0.53); 7.608 (0.49); 7.498 (0.55); 7.473 (0.61); 7.461 (0.79); 7.452 (0.79); 7.446 (0.38); 7.298 (7.2); 7.282 (0.43); 7.265 (0.37); 7.254 (0.4); 7.112 (0.32); 7.076 (0.38); 6.97 (0.45); 6.956 (0.57); 6.94 (0.36); 6.927 (0.43); 4.743 (0.65); 2.046 (0.33); 1.591 (8.01); 0.341 (7.36); 0.33 (1.15); 0.305 (0.58); 0.294 (16); 0.283 (0.63); 0.276 (0.32); 0.036 (7.02) |
| I.020 | 8.895 (0.62); 8.886 (0.62); 7.638 (0.35); 7.632 (0.37); 7.613 (0.41); 7.608 (0.42); 7.509 (0.48); 7.504 (0.53); 7.5 (0.54); 7.496 (0.46); 7.466 (0.76); 7.46 (0.66); 7.455 (0.49); 7.44 (1.42); 7.425 (0.38); 7.415 (0.32); 7.302 (1.74); 7.277 (0.53); 7.274 (0.51); 6.959 (0.51); 6.932 (0.46); 1.624 (1.12); 1.296 (0.49); 0.325 (0.68); 0.314 (16); 0.303 (0.65); 0.112 (5.48); 0.04 (1.32) |
| I.021 | 8.864 (1.17); 8.855 (1.2); 7.525 (0.89); 7.52 (0.96); 7.516 (1); 7.512 (0.87); 7.487 (1.63); 7.475 (0.76); 7.464 (1.7); 7.444 (0.68); 7.412 (0.45); 7.389 (0.46); 7.384 (0.88); 7.362 (0.88); 7.357 (0.54); 7.335 (0.48); 7.301 (2.28); 6.954 (0.55); 6.952 (0.55); 6.925 (0.98); 6.898 (0.5); 6.896 (0.47); 6.729 (1.05); 6.702 (0.98); 1.631 (1.95); 0.392 (0.64); 0.381 (16); 0.375 (15.93); 0.363 (0.67); 0.123 (0.64); 0.111 (16.17); 0.099 (0.59); 0.039 (2.07) |
| I.022 | 8.823 (2.03); 8.814 (1.98); 7.609 (1.56); 7.604 (1.78); 7.602 (1.75); 7.491 (0.51); 7.477 (2.37); 7.457 (2.07); 7.446 (1.18); 7.425 (1.25); 7.394 (1.61); 7.371 (1.45); 7.344 (0.69); 7.302 (0.6); 6.953 (1); 6.925 (1.81); 6.897 (0.89); 6.698 (1.98); 6.67 (1.75); 3.077 (0.98); 1.285 (0.62); 0.509 (16); 0.505 (15.33); 0.476 (0.88); 0.47 (0.81); 0.441 (0.46); 0.436 (0.45); 0.209 (0.72); 0.172 (0.84); 0.169 (0.87); 0.132 (0.45); 0.111 (3.35); 0.07 (1.08); 0.026 (0.45) |
| I.023 | 7.742 (0.67); 7.737 (0.64); 7.718 (0.76); 7.712 (0.69); 7.552 (0.9); 7.547 (0.96); 7.544 (0.96); 7.539 (0.72); 7.468 (0.44); 7.462 (0.38); 7.437 (2.31); 7.422 (0.94); 7.416 (1.57); 7.41 (1.18); 7.391 (0.58); 7.301 (0.48); 7.296 (0.62); 7.293 (0.54); 7.271 (1); 7.269 (0.84); 7.247 (0.43); 7.244 (0.36); 6.93 (0.95); 6.903 (0.86); 3.174 (0.7); 1.293 (1.21); 0.93 (0.41); 0.908 (1.13); 0.885 (0.45); 0.448 (0.91); 0.436 (16); 0.425 (0.69); 0.26 (0.4); 0.252 (0.38); 0.149 (0.34); 0.118 (1.78); 8.829 (1.15); 8.82 (1.12) |
| I.024 | 7.641 (0.34); 7.635 (0.37); 7.616 (0.39); 7.611 (0.42); 7.432 (0.32); 7.426 (0.33); 7.368 (0.45); 7.363 (0.46); 7.358 (0.6); 7.34 (0.94); 7.326 (0.98); 7.321 (0.76); 7.3 (1.8); 7.29 (0.34); 7.287 (0.34); 7.266 (0.5); 7.262 (0.5); 6.886 (0.47); 6.861 (0.43); 2.865 (4.23); 1.615 (1.09); 0.328 (0.6); 0.317 (16); 0.306 (0.62); 0.039 (1.81) |
| I.025 | 7.447 (2.44); 7.402 (0.37); 7.391 (0.44); 7.388 (0.41); 7.382 (1.15); 7.373 (1.78); 7.36 (0.86); 7.354 (1.03); 7.348 (0.79); 7.342 (1.02); 7.334 (1.01); 7.331 (1.41); 7.323 (0.49); 7.318 (1.42); 7.315 (0.89); 7.301 (0.72); 7.261 (2.63); 6.895 (0.93); 6.878 (1.75); 6.861 (0.91); 6.532 (1.86); |

TABLE 12-continued

| | NMR peak lists |
|---|---|
| Example | ¹H-NMR [CDCl₃ at 300 Mhz] |
| | 6.516 (1.82); 2.763 (12.8); 2.54 (1.78); 2.535 (1.68); 1.601 (1.87); 0.485 (16); 0.483 (15.55); 0.457 (0.4); 0.454 (0.37); 0 (2.55) |
| I.026 | 7.744 (0.52); 7.738 (0.57); 7.719 (0.6); 7.714 (0.61); 7.454 (0.48); 7.451 (0.47); 7.448 (0.5); 7.427 (0.45); 7.421 (0.44); 7.406 (1.12); 7.401 (1.11); 7.387 (1.11); 7.383 (0.71); 7.376 (0.61); 7.363 (1.61); 7.345 (0.51); 7.312 (0.54); 7.309 (0.56); 7.3 (4.96); 7.288 (0.8); 7.285 (0.78); 7.263 (0.33); 7.261 (0.32); 6.861 (0.74); 6.834 (0.68); 2.846 (6.46); 2.013 (1.74); 1.604 (3.87); 0.466 (0.53); 0.454 (16); 0.443 (0.62); 0.039 (5.04) |
| I.027 | 7.4 (0.33); 7.393 (1.9); 7.381 (0.9); 7.369 (2.3); 7.364 (1.32); 7.357 (0.51); 7.347 (1.68); 7.342 (2.27); 7.337 (0.81); 7.314 (0.52); 7.3 (3); 6.936 (0.55); 6.934 (0.55); 6.907 (0.99); 6.88 (0.5); 6.878 (0.47); 6.628 (1.05); 6.602 (0.98); 2.832 (8.27); 1.623 (3.11); 1.191 (2.86); 1.152 (2.86); 0.397 (0.66); 0.386 (16); 0.38 (15.97); 0.368 (0.74); 0.038 (2.65) |
| I.028 | 7.469 (1.99); 7.462 (1.9); 7.456 (1.58); 7.45 (2.65); 7.445 (2.18); 7.348 (0.67); 7.328 (1.53); 7.311 (1.95); 7.288 (1.35); 7.27 (1.37); 7.258 (22.84); 7.246 (1.06); 7.204 (0.86); 7.2 (0.89); 7.192 (0.93); 7.187 (0.94); 7.182 (0.66); 7.177 (0.63); 7.169 (0.57); 7.164 (0.67); 7.151 (0.76); 7.147 (0.63); 7.139 (2.58); 7.132 (1.73); 7.125 (4.35); 7.121 (4.26); 6.916 (3.14); 6.891 (2.05); 6.87 (1); 6.516 (2.17); 6.496 (2.07); 2.543 (14.72); 1.536 (13.75); 0.659 (15.74); 0.653 (16); 0.008 (1.01); 0 (22.32) |
| I.029 | 7.383 (1.89); 7.379 (1.53); 7.357 (1.36); 7.35 (0.45); 7.33 (0.36); 7.301 (0.77); 6.598 (0.49); 6.591 (0.49); 6.571 (0.46); 6.564 (0.46); 6.162 (0.88); 6.155 (0.84); 3.823 (0.35); 2.843 (4.65); 1.297 (0.32); 0.268 (0.61); 0.258 (16); 0.247 (0.85); 0.113 (4.59); 0.039 (0.54) |
| I.030 | 7.449 (1.75); 7.446 (1.72); 7.433 (1.88); 7.43 (1.84); 7.407 (0.73); 7.385 (1.17); 7.38 (1.53); 7.358 (1.78); 7.353 (1.72); 7.332 (1.51); 7.322 (1.03); 7.309 (1.42); 7.3 (19.81); 7.291 (1.62); 7.288 (1.41); 7.281 (2.05); 7.278 (2.02); 7.27 (1.99); 7.267 (1.79); 7.257 (0.4); 7.119 (2.29); 7.115 (2.3); 7.023 (1.67); 7.012 (1.66); 7.008 (1.66); 6.996 (1.43); 6.958 (0.95); 6.956 (0.92); 6.929 (1.67); 6.902 (0.85); 6.899 (0.78); 6.574 (1.77); 6.547 (1.66); 2.679 (13.51); 1.591 (11.36); 0.769 (0.74); 0.758 (16); 0.75 (15.89); 0.738 (0.72); 0.05 (0.75); 0.039 (20.83); 0.028 (0.77) |
| I.031 | 8.056 (0.44); 8.05 (0.44); 8.03 (0.54); 8.023 (0.54); 7.785 (0.95); 7.758 (0.8); 7.563 (0.9); 7.557 (0.86); 7.491 (0.93); 7.487 (0.87); 7.45 (0.99); 7.431 (0.77); 7.42 (0.4); 7.4 (0.37); 7.302 (0.46); 2.825 (4.68); 0.422 (0.73); 0.411 (16); 0.4 (0.71); 0.112 (3.57) |
| I.032 | 7.481 (0.7); 7.459 (0.83); 7.454 (1.54); 7.439 (0.37); 7.432 (1.72); 7.426 (1.11); 7.409 (6.92); 7.394 (1.6); 7.389 (2.01); 7.382 (1.57); 7.363 (1.22); 7.332 (0.34); 7.301 (5.85); 6.983 (1.12); 6.955 (2.09); 6.928 (1.01); 6.677 (2.19); 6.649 (2.04); 2.817 (16); 2.807 (0.92); 1.626 (1.47); 0.632 (0.36); 0.62 (10.09); 0.614 (10.13); 0.595 (10.12); 0.589 (10.08); 0.577 (0.47); 0.527 (0.64); 0.522 (0.64); 0.038 (5.95) |
| I.033 | 7.404 (1.08); 7.397 (1.91); 7.39 (2.46); 7.376 (2.46); 7.366 (1.52); 7.349 (1.17); 7.345 (0.77); 7.301 (2.1); 6.804 (1.26); 6.776 (1.15); 6.474 (1.29); 6.446 (1.22); 3.958 (9.47); 3.526 (1.28); 2.818 (8.49); 1.682 (0.71); 0.435 (0.78); 0.424 (16); 0.412 (0.85); 0.037 (1.54) |
| I.034 | 7.43 (1.42); 7.422 (2.08); 7.406 (0.73); 7.4 (0.88); 7.394 (0.63); 7.375 (0.54); 7.35 (0.51); 7.323 (1.34); 7.302 (1.85); 7.297 (1.2); 7.27 (1.1); 7.267 (1.16); 7.244 (0.54); 7.24 (0.43); 6.713 (0.81); 6.71 (0.78); 6.687 (0.76); 6.683 (0.71); 2.933 (0.97); 2.81 (6.81); 2.084 (0.37); 1.655 (0.67); 0.569 (0.67); 0.558 (16); 0.546 (0.64); 0.038 (1.39) |
| I.035 | 7.715 (0.57); 7.691 (0.68); 7.688 (0.7); 7.664 (0.6); 7.51 (1.1); 7.506 (1.09); 7.439 (1.01); 7.418 (0.94); 7.406 (0.52); 7.386 (0.48); 7.302 (1.95); 7.005 (0.34); 6.998 (0.35); 6.978 (0.66); 6.97 (0.67); 6.95 (0.33); 6.943 (0.32); 6.52 (0.59); 6.513 (0.58); 6.486 (0.6); 6.479 (0.57); 2.814 (6.33); 2.11 (0.47); 1.648 (0.45); 0.479 (0.58); 0.468 (16); 0.456 (0.62); 0.039 (1.55) |
| I.036 | 7.524 (1.29); 7.52 (1.21); 7.447 (1.16); 7.443 (1.11); 7.426 (1); 7.414 (1.93); 7.394 (0.58); 7.386 (0.89); 7.302 (3.6); 7.149 (0.49); 7.145 (0.5); 7.121 (0.41); 7.118 (0.41); 6.701 (1.01); 6.673 (0.93); 2.808 (6.85); 2.602 (0.82); 1.616 (1.93); 0.545 (0.7); 0.533 (16); 0.521 (0.66); 0.039 (2.88) |
| I.037 | 7.434 (0.59); 7.423 (0.63); 7.407 (0.63); 7.396 (0.64); 7.378 (0.8); 7.374 (0.82); 7.369 (0.91); 7.351 (1.59); 7.337 (0.55); 7.318 (1.26); 7.314 (1.21); 7.301 (1.11); 7.138 (0.43); 7.134 (0.46); 7.127 (0.41); 7.124 (0.42); 7.108 (0.41); 7.098 (0.37); 6.889 (0.64); 6.876 (0.67); 6.86 (0.53); 6.846 (0.51); 2.844 (6.65); 2.08 (0.43); 1.294 (0.36); 0.437 (0.71); 0.426 (16); 0.414 (0.65); 0.112 (2.23); 0.036 (0.83) |
| I.038 | 7.388 (0.4); 7.361 (0.85); 7.35 (0.43); 7.344 (0.44); 7.339 (0.62); 7.334 (0.58); 7.322 (0.86); 7.308 (0.36); 7.297 (3.89); 7.222 (0.66); 7.218 (0.67); 6.773 (0.53); 6.746 (0.48); 6.495 (0.52); 6.47 (0.5); 3.891 (4.62); 2.845 (3.99); 1.606 (3.21); 0.311 (0.54); 0.3 (16); 0.288 (0.51); 0.036 (3.62) |
| I.039 [2] | 7.571 (1.18); 7.556 (1.46); 7.438 (0.86); 7.422 (1.48); 7.406 (0.78); 7.365 (1.45); 7.353 (2.07); 7.344 (0.72); 7.28 (2.2); 7.261 (5.45); 6.98 (1.36); 6.964 (1.26); 2.788 (8.96); 1.559 (7.06); 1.256 (0.46); 0.984 (0.48); 0.976 (3.88); 0.971 (7.17); 0.958 (0.66); 0.465 (16); 0 (5.16) |
| I.040 | 7.646 (0.37); 7.514 (0.63); 7.384 (0.37); 7.367 (0.46); 7.36 (0.8); 7.349 (1); 7.337 (0.68); 7.331 (0.66); 7.304 (1.22); 6.966 (0.32); 4.293 (1.68); 2.776 (4.18); 1.668 (2.25); 0.334 (0.59); 0.323 (16); 0.312 (0.62); 0.115 (0.47); 0.043 (0.88) |
| I.041 | 8.173 (0.74); 8.164 (0.75); 7.536 (0.54); 7.53 (0.58); 7.512 (0.62); 7.506 (0.64); 7.354 (0.33); 7.335 (0.49); 7.333 (0.49); 7.33 (0.51); 7.327 (0.43); 7.308 (0.47); 7.302 (0.55); 7.298 (1.48); 7.166 (0.48); 7.163 (0.49); 7.142 (0.79); 7.139 (0.78); 7.118 (0.35); 7.115 (0.33); 7.013 (0.77); 7.004 (0.75); 6.804 (0.75); 6.803 (0.74); 6.777 (0.68); 2.964 (0.53); 2.943 (1.12); 2.922 (0.65); 2.793 (0.55); 2.772 (0.99); 2.751 (0.52); 1.958 (0.39); 1.941 (0.57); 1.927 (0.51); 1.921 (0.56); 1.851 (0.59); 1.844 (0.55); 1.83 (0.57); 1.824 (0.46); 1.814 (0.4); 1.478 (0.34); 1.466 (0.39); 1.426 (0.34); 1.414 (0.35); 1.304 (0.88); 1.293 (1.89); 1.282 (0.64); 1.016 (0.51); 1.011 (0.81); 1.007 (0.56); 0.983 (2.68); 0.971 (0.35); 0.959 (1.56); 0.862 (0.66); 0.857 (0.58); 0.836 (1.3); 0.831 (0.54); 0.811 (0.79); 0.809 (0.83); 0.32 (0.81); 0.311 (0.73); 0.301 (16); 0.29 (0.73); 0.037 (0.59) |

TABLE 12-continued

| | NMR peak lists |
|---|---|
| Example | $^1$H-NMR [CDCl$_3$ at 300 Mhz] |
| I.042 | 8.601 (2.65); 8.176 (0.7); 8.172 (0.78); 8.145 (0.84); 8.075 (0.71); 8.071 (0.71); 8.048 (0.85); 8.043 (0.85); 7.769 (0.34); 7.764 (0.4); 7.746 (0.65); 7.742 (0.83); 7.737 (0.39); 7.719 (0.6); 7.714 (0.56); 7.691 (0.6); 7.686 (0.66); 7.668 (0.4); 7.663 (0.8); 7.659 (0.6); 7.64 (0.32); 7.305 (1.47); 7.243 (0.39); 7.22 (0.45); 7.215 (0.88); 7.193 (0.87); 7.188 (0.56); 7.166 (0.67); 6.806 (0.63); 6.778 (1.13); 6.75 (0.55); 6.307 (1.22); 6.28 (1.15); 2.634 (9.67); 1.747 (0.62); 1.302 (0.46); 0.504 (0.62); 0.493 (15.63); 0.487 (16); 0.475 (0.69); 0.132 (0.35); 0.12 (8.56); 0.107 (0.32); 0.046 (1.1) |
| I.043 [2] | 7.562 (1.18); 7.547 (1.47); 7.431 (0.92); 7.415 (1.52); 7.399 (0.85); 7.383 (0.96); 7.377 (0.96); 7.291 (2.09); 7.261 (5.57); 6.972 (1.38); 6.956 (1.28); 2.78 (9.04); 1.563 (8.23); 1.256 (5.47); 1.218 (0.49); 0.994 (0.51); 0.985 (3.75); 0.979 (7.64); 0.963 (3.8); 0.948 (2.47); 0.894 (0.44); 0.882 (1.19); 0.868 (1.9); 0.852 (1.44); 0.836 (0.49); 0.469 (15.53); 0.4 (0.33); 0.357 (16); 0 (5.14) |
| I.044 | 8.146 (0.88); 8.118 (0.82); 7.692 (0.53); 7.687 (0.59); 7.665 (1.34); 7.641 (1.72); 7.528 (0.74); 7.525 (0.7); 7.506 (0.61); 7.5 (0.98); 7.478 (0.4); 7.475 (0.36); 7.448 (2.29); 7.392 (0.68); 7.356 (0.9); 7.334 (1.38); 7.304 (2.8); 7.298 (1.02); 7.282 (0.5); 6.909 (0.67); 6.88 (1.15); 6.853 (0.58); 6.773 (0.97); 6.767 (0.97); 6.716 (0.81); 6.709 (0.78); 6.615 (1.2); 6.587 (1.11); 5.727 (0.92); 5.72 (0.87); 5.691 (0.87); 5.684 (0.86); 1.666 (0.76); 1.301 (1.09); 0.41 (16); 0.404 (15.43); 0.118 (1.12); 0.046 (1.47) |
| I.045 | 8.238 (0.9); 8.21 (1); 8.008 (1.3); 8.001 (1.18); 7.981 (1.48); 7.976 (1.26); 7.735 (1.21); 7.71 (2.11); 7.681 (0.64); 7.606 (2.5); 7.582 (0.76); 7.557 (0.99); 7.532 (0.59); 7.524 (0.46); 7.518 (0.38); 7.506 (1.61); 7.484 (2.56); 7.468 (0.5); 7.36 (0.38); 7.333 (0.88); 7.305 (3.87); 7.283 (0.46); 6.881 (0.68); 6.852 (1.23); 6.824 (0.63); 6.727 (1.32); 6.7 (1.21); 1.677 (0.34); 1.301 (1.45); 0.907 (0.4); 0.887 (0.42); 0.281 (16); 0.275 (15.35); 0.118 (0.7); 0.046 (2.92) |
| I.046 | 8.088 (0.8); 8.058 (0.77); 7.675 (1.44); 7.649 (1.7); 7.645 (1.09); 7.627 (0.64); 7.622 (0.38); 7.522 (0.62); 7.519 (0.61); 7.5 (0.47); 7.495 (0.84); 7.472 (0.3); 7.469 (0.33); 7.402 (2.07); 7.36 (0.39); 7.338 (0.47); 7.333 (0.87); 7.311 (0.88); 7.306 (0.6); 7.3 (1.25); 7.284 (0.47); 6.905 (0.58); 6.903 (0.57); 6.876 (1.07); 6.849 (0.52); 6.847 (0.5); 6.613 (1.12); 6.586 (1.04); 2.781 (8.7); 0.418 (0.68); 0.407 (15.93); 0.401 (16); 0.39 (0.81); 0.115 (0.72); 0.04 (1.02) |
| I.047 | 8.08 (0.38); 8.05 (0.36); 7.647 (0.34); 7.642 (0.34); 7.631 (0.82); 7.625 (0.57); 7.621 (0.55); 7.615 (0.54); 7.607 (0.75); 7.601 (0.5); 7.476 (0.41); 7.401 (0.33); 7.38 (1.24); 7.374 (0.39); 7.3 (5.19); 7.258 (0.33); 7.236 (0.49); 7.233 (0.49); 6.874 (0.46); 6.847 (0.42); 5.339 (1.25); 2.81 (4.26); 1.609 (5.62); 0.348 (0.58); 0.337 (16); 0.326 (0.62); 0.039 (4.98) |
| I.048 | 7.639 (0.75); 7.629 (0.57); 7.522 (0.51); 7.518 (0.48); 7.5 (0.44); 7.494 (0.67); 7.464 (1.57); 7.452 (0.34); 7.427 (0.48); 7.425 (0.47); 7.422 (0.5); 7.4 (0.47); 7.394 (0.46); 7.302 (6.77); 7.282 (0.53); 7.279 (0.56); 7.258 (0.8); 7.255 (0.78); 7.234 (0.55); 6.842 (0.76); 6.814 (0.68); 2.791 (6.68); 2.554 (0.8); 2.142 (0.88); 1.623 (5.43); 1.306 (0.63); 1.027 (0.92); 0.989 (0.93); 0.922 (0.75); 0.489 (0.53); 0.478 (16); 0.466 (0.63); 0.295 (0.33); 0.276 (0.57); 0.177 (0.34); 0.04 (6.77); 8.089 (0.6); 8.06 (0.58); 7.73 (0.54); 7.724 (0.58); 7.706 (0.61); 7.7 (0.63); 7.676 (0.48); 7.672 (0.53); 7.666 (0.48); 7.659 (0.35); 7.654 (0.84); 7.644 (0.81) |
| I.049 | 8.104 (1.19); 8.076 (1.18); 7.717 (2.16); 7.692 (3.29); 7.666 (0.92); 7.661 (0.6); 7.555 (4); 7.529 (1.24); 7.505 (0.57); 7.374 (0.58); 7.346 (1.29); 7.323 (1.37); 7.319 (0.89); 7.304 (11.28); 7.296 (0.94); 6.918 (0.95); 6.889 (1.66); 6.862 (0.84); 6.555 (1.79); 6.527 (1.77); 2.775 (0.42); 2.767 (0.39); 2.75 (12.65); 2.694 (1.87); 2.684 (1.73); 1.625 (16); 1.31 (1.35); 0.946 (0.48); 0.924 (1.42); 0.902 (0.55); 0.55 (15.81); 0.545 (15.06); 0.515 (0.51); 0.51 (0.48); 0.476 (0.35); 0.471 (0.33); 0.297 (0.95); 0.278 (0.97); 0.234 (0.62); 0.216 (0.54); 0.179 (1); 0.098 (0.75); 0.053 (0.38); 0.042 (10.19); 0.032 (0.37) |
| I.050 | 8.107 (0.78); 8.079 (0.78); 7.724 (1.4); 7.698 (2.07); 7.673 (0.58); 7.574 (2.02); 7.56 (0.7); 7.534 (0.81); 7.51 (0.37); 7.405 (0.63); 7.378 (1.39); 7.35 (0.81); 7.303 (1.63); 7.115 (0.62); 7.112 (0.61); 7.088 (0.51); 7.084 (0.5); 6.677 (1.14); 6.649 (1.05); 2.8 (1.15); 2.748 (7.56); 1.697 (0.66); 0.553 (16); 0.041 (1.24) |
| I.051 | 8.095 (0.61); 8.066 (0.59); 7.703 (1.13); 7.698 (0.44); 7.679 (0.96); 7.676 (1.12); 7.671 (0.71); 7.655 (0.51); 7.546 (0.45); 7.542 (0.46); 7.524 (0.35); 7.518 (0.65); 7.491 (1.8); 7.312 (0.47); 7.302 (1.33); 7.286 (1.29); 7.259 (1.07); 7.234 (1.02); 7.23 (1.14); 7.208 (0.51); 7.204 (0.41); 6.687 (0.75); 6.683 (0.75); 6.66 (0.7); 6.657 (0.69); 2.75 (6.72); 2.084 (0.54); 1.298 (0.41); 0.593 (0.55); 0.581 (16); 0.569 (0.62); 0.113 (3.79); 0.039 (0.94) |
| I.052 | 8.086 (1.2); 8.057 (1.17); 7.674 (2.21); 7.668 (0.89); 7.65 (1.86); 7.646 (2.2); 7.642 (1.39); 7.626 (1); 7.621 (0.55); 7.521 (0.9); 7.517 (0.91); 7.499 (0.69); 7.493 (1.27); 7.471 (0.52); 7.468 (0.49); 7.404 (3.14); 7.353 (0.61); 7.331 (0.71); 7.326 (1.36); 7.304 (1.45); 7.298 (3.8); 7.277 (0.74); 6.898 (0.86); 6.896 (0.88); 6.869 (1.61); 6.842 (0.76); 6.84 (0.78); 6.599 (1.68); 6.572 (1.57); 2.773 (13.4); 1.72 (0.37); 1.292 (0.74); 1.043 (0.49); 1.035 (1.03); 1.03 (0.74); 1.019 (0.77); 1.008 (4.38); 0.985 (2.82); 0.93 (0.77); 0.926 (1.01); 0.921 (0.72); 0.903 (1.72); 0.893 (0.56); 0.878 (1.32); 0.868 (0.38); 0.393 (0.58); 0.382 (15.78); 0.376 (16); 0.365 (0.79); 0.128 (0.57); 0.036 (2.76) |
| I.053 | 8.09 (1.51); 8.06 (1.45); 7.673 (2.26); 7.666 (1.14); 7.651 (2.16); 7.644 (2.66); 7.639 (1.69); 7.626 (1.27); 7.621 (0.63); 7.523 (1.18); 7.52 (1.11); 7.501 (0.91); 7.496 (1.6); 7.473 (0.65); 7.47 (0.59); 7.421 (0.72); 7.398 (0.94); 7.394 (1.61); 7.371 (2.17); 7.365 (4.5); 7.344 (0.89); 7.304 (4.49); 6.952 (1.13); 6.925 (2.08); 6.898 (1); 6.692 (2.17); 6.665 (2.02); 4.605 (0.77); 4.592 (1.27); 4.58 (1.28); 4.567 (0.79); 2.785 (16); 2.752 (0.42); 1.336 (0.36); 1.298 (2.94); 0.922 (0.38); 0.905 (0.43); 0.899 (0.44); 0.884 (0.43); 0.551 (0.49); 0.546 (0.47); 0.436 (11.65); 0.432 (11.04); 0.423 (11.84); 0.419 (10.72); 0.115 (0.32); 0.042 (3.31) |
| I.054 [1] | 7.95 (0.44); 7.929 (0.47); 7.578 (0.41); 7.574 (0.44); 7.56 (0.46); 7.556 (0.47); 7.533 (0.39); 7.513 (0.51); 7.469 (0.38); 7.466 (0.48); 7.449 (0.33); 7.396 (1.67); 7.383 (0.41); 7.379 (0.61); 7.377 (0.57); 7.282 (0.63); 7.257 (2.25); 7.179 (0.54); 7.177 (0.52); 5.598 (0.43); 2.724 (4.45); 0.32 (1.05); 0.313 (16); 0.305 (0.94); 0 (1.84) |
| I.055 | 7.998 (0.34); 7.97 (0.38); 7.527 (0.6); 7.503 (0.37); 7.498 (0.34); 7.441 (0.33); 7.437 (0.35); 7.414 (0.37); 7.312 (0.45); 7.302 (1.81); 7.293 (0.34); 7.283 (0.51); 7.274 (0.46); 7.264 (0.4); |

TABLE 12-continued

| | NMR peak lists |
|---|---|
| Example | ¹H-NMR [CDCl₃ at 300 Mhz] |
| | 7.188 (1.02); 5.479 (0.4); 2.771 (3.98); 1.298 (0.62); 0.495 (0.4); 0.327 (0.61); 0.316 (16); 0.306 (0.68); 0.042 (1.16) |
| I.056 | 7.983 (0.39); 7.956 (0.44); 7.682 (0.72); 7.676 (0.51); 7.657 (0.87); 7.652 (0.78); 7.564 (0.36); 7.56 (0.44); 7.484 (0.33); 7.48 (0.33); 7.457 (0.47); 7.442 (1.09); 7.331 (0.39); 7.325 (0.38); 7.301 (1.51); 7.251 (0.34); 7.247 (0.35); 7.226 (0.51); 7.223 (0.49); 6.975 (0.48); 6.972 (0.47); 6.949 (0.42); 6.946 (0.4); 3.77 (0.93); 3.746 (0.95); 2.447 (4.5); 1.309 (1.25); 1.286 (2.36); 1.262 (1.03); 0.33 (0.68); 0.319 (16); 0.308 (0.72); 0.042 (1.33) |
| I.057 | 7.62 (1.07); 7.6 (1.02); 7.592 (0.51); 7.574 (0.44); 7.398 (0.59); 7.376 (0.76); 7.371 (1.32); 7.349 (1.38); 7.344 (0.83); 7.322 (0.72); 7.304 (3.43); 7.072 (2.78); 6.948 (0.95); 6.919 (1.72); 6.892 (0.85); 6.666 (1.82); 6.639 (1.7); 2.788 (10.53); 1.294 (1.88); 1.033 (0.58); 1.027 (1.19); 0.999 (4.43); 0.976 (2.93); 0.919 (0.38); 0.906 (1.14); 0.882 (1.92); 0.857 (1.42); 0.379 (0.72); 0.368 (16); 0.362 (15.77); 0.112 (0.69); 0.04 (2.95); 8.782 (1.18); 8.753 (1.29); 7.734 (0.52); 7.729 (0.59); 7.706 (1.98); 7.679 (2.92); 7.623 (1.12) |
| I.058 | 8.718 (0.38); 8.69 (0.43); 7.629 (0.38); 7.624 (0.41); 7.604 (0.7); 7.599 (0.8); 7.573 (1.06); 7.547 (0.47); 7.534 (0.47); 7.528 (0.48); 7.504 (0.33); 7.446 (0.41); 7.441 (0.39); 7.301 (1.12); 7.272 (0.33); 7.25 (0.52); 7.247 (0.54); 7.222 (0.79); 7.195 (0.47); 7.081 (1.05); 5.625 (0.5); 2.797 (4.17); 0.353 (0.78); 0.343 (16); 0.332 (0.82); 0.039 (1.13) |
| I.059 | 12.096 (0.48); 7.484 (0.76); 7.48 (0.75); 7.467 (1.03); 7.458 (1.05); 7.454 (1.03); 7.443 (0.93); 7.411 (1.19); 7.386 (0.82); 7.364 (0.52); 7.359 (0.84); 7.337 (0.86); 7.332 (0.55); 7.304 (3.38); 7.277 (0.6); 7.273 (0.54); 7.25 (0.85); 7.228 (0.4); 7.224 (0.35); 7.182 (2.57); 6.927 (0.59); 6.898 (1.07); 6.87 (0.53); 6.803 (1.18); 6.776 (1.09); 1.673 (0.92); 1.299 (1.14); 0.44 (16); 0.434 (15.53); 0.043 (2.55) |
| I.060 | 7.892 (0.75); 7.89 (0.75); 7.864 (0.95); 7.641 (0.73); 7.623 (0.67); 7.618 (1.08); 7.614 (1); 7.6 (0.83); 7.596 (0.74); 7.591 (0.39); 7.572 (0.55); 7.567 (0.38); 7.438 (2.35); 7.429 (0.76); 7.425 (0.63); 7.405 (0.8); 7.403 (0.88); 7.379 (0.43); 7.375 (0.35); 7.33 (0.39); 7.304 (1.79); 7.28 (0.91); 7.275 (0.53); 7.253 (0.48); 6.874 (0.63); 6.872 (0.52); 6.845 (1.06); 6.818 (0.56); 6.815 (0.45); 6.654 (1.18); 6.626 (1.13); 4.655 (0.73); 4.631 (2.31); 4.608 (2.34); 4.584 (0.75); 1.635 (0.52); 1.444 (2.4); 1.421 (4.9); 1.397 (2.33); 0.497 (1.44); 0.427 (0.78); 0.416 (16); 0.41 (14.91); 0.399 (0.61); 0.05 (1.02) |
| I.061 | 7.999 (0.7); 7.972 (0.85); 7.646 (0.69); 7.634 (0.53); 7.629 (0.5); 7.62 (1); 7.61 (0.84); 7.606 (0.74); 7.601 (0.42); 7.583 (0.57); 7.578 (0.43); 7.468 (0.6); 7.464 (0.61); 7.442 (0.87); 7.438 (0.54); 7.418 (0.37); 7.414 (0.36); 7.389 (2.15); 7.36 (0.4); 7.338 (0.46); 7.333 (0.88); 7.311 (0.93); 7.305 (1.97); 7.284 (0.48); 6.894 (0.57); 6.892 (0.56); 6.865 (1.04); 6.838 (0.52); 6.835 (0.49); 6.641 (1.1); 6.614 (1.03); 2.62 (0.34); 2.609 (0.37); 2.593 (0.72); 2.576 (0.4); 2.565 (0.38); 1.388 (0.34); 1.375 (0.99); 1.365 (1.21); 1.359 (1.11); 1.354 (0.78); 1.349 (1.11); 1.338 (0.44); 1.305 (0.62); 1.116 (0.37); 1.105 (1.1); 1.095 (0.97); 1.089 (0.55); 1.078 (1.07); 1.068 (0.95); 0.448 (0.63); 0.437 (16); 0.431 (15.91); 0.419 (0.69); 0.049 (1.4) |
| I.062 | 5.098 (3.96); 5.089 (2.9); 5.081 (0.99); 1.576 (10.29); 1.256 (1.43); 0.746 (14.93); 0.738 (16); 0.694 (0.38); 0.687 (0.33); 0.073 (0.71); 0 (6.18); 8.003 (4.72); 7.986 (5.18); 7.664 (0.4); 7.647 (1.92); 7.642 (2.08); 7.635 (2.33); 7.63 (3.97); 7.626 (2.16); 7.618 (2.2); 7.614 (2.32); 7.559 (0.38); 7.545 (4.84); 7.538 (7.32); 7.531 (6.78); 7.526 (5.43); 7.504 (1.61); 7.49 (10.93); 7.488 (10.37); 7.478 (4.86); 7.462 (1.27); 7.393 (1.81); 7.376 (4.07); 7.363 (4.23); 7.347 (2.1); 7.256 (8.03); 7.181 (0.45); 7.17 (2.54); 7.164 (8.83); 7.163 (8.66); 7.156 (13.45); 7.152 (12.4); 7.134 (12.55); 6.953 (3.07); 6.936 (5.9); 6.92 (3.02); 6.653 (6.11); 6.636 (5.94); 5.115 (0.81); 5.106 (2.78) |
| I.063 ⁽²⁾ | 8.048 (0.86); 8.03 (0.87); 7.679 (1.04); 7.666 (1.18); 7.662 (1.3); 7.651 (0.64); 7.553 (0.66); 7.536 (0.89); 7.522 (0.43); 7.506 (2.23); 7.33 (0.32); 7.316 (0.61); 7.314 (0.71); 7.3 (0.81); 7.284 (0.36); 7.259 (2.43); 6.886 (0.58); 6.869 (1.07); 6.852 (0.54); 6.604 (1.13); 6.588 (1.08); 1.55 (1.25); 0.377 (16); 0.374 (13.09); 0 (2.44) |
| I.064 | 8.045 (0.81); 8.018 (0.72); 8.016 (0.78); 7.652 (0.37); 7.647 (0.57); 7.639 (0.68); 7.633 (0.7); 7.629 (0.54); 7.624 (1.11); 7.618 (0.44); 7.612 (0.95); 7.607 (1); 7.6 (0.78); 7.468 (0.63); 7.464 (0.6); 7.446 (0.53); 7.44 (0.92); 7.418 (0.38); 7.414 (0.35); 7.364 (0.39); 7.342 (0.48); 7.336 (0.87); 7.314 (0.91); 7.309 (0.68); 7.304 (2.43); 7.287 (0.48); 7.253 (2.2); 6.914 (0.58); 6.912 (0.54); 6.885 (1.03); 6.858 (0.53); 6.855 (0.47); 6.692 (1.11); 6.664 (1.03); 2.75 (10.67); 1.598 (1.62); 0.46 (0.49); 0.44 (0.64); 0.429 (16); 0.423 (15.64); 0.412 (0.62); 0.047 (2.31) |
| I.065 | 8.245 (0.7); 8.217 (0.83); 7.769 (0.36); 7.764 (0.43); 7.741 (1.35); 7.714 (1.74); 7.65 (0.68); 7.629 (0.63); 7.621 (0.34); 7.547 (1.81); 7.405 (0.39); 7.382 (0.48); 7.377 (0.87); 7.355 (0.89); 7.35 (0.54); 7.328 (0.48); 7.304 (4.92); 7.252 (0.76); 7.072 (1.56); 6.958 (0.59); 6.956 (0.58); 6.93 (1.07); 6.902 (0.54); 6.9 (0.53); 6.892 (0.81); 6.71 (1.12); 6.683 (1.05); 1.604 (3.79); 0.411 (0.69); 0.4 (16); 0.394 (15.83); 0.382 (0.7); 0.044 (5.04) |
| I.066 | 8.044 (0.63); 8.018 (0.72); 7.631 (0.46); 7.614 (2.23); 7.607 (1.06); 7.6 (1.17); 7.58 (1.01); 7.574 (0.51); 7.569 (0.35); 7.555 (1.51); 7.55 (1.12); 7.532 (0.5); 7.526 (0.5); 7.421 (0.34); 7.394 (0.8); 7.372 (0.84); 7.367 (0.54); 7.345 (0.48); 7.304 (9.55); 7.183 (1.2); 7.156 (0.96); 7.129 (0.7); 6.947 (1.44); 6.916 (0.59); 6.886 (1.01); 6.858 (0.52); 6.766 (0.71); 6.395 (0.55); 1.597 (11.08); 0.412 (0.66); 0.401 (16); 0.394 (15.88); 0.383 (0.67); 0.054 (0.33); 0.044 (9.62); 0.032 (0.34) |
| I.067 | 8.289 (0.91); 8.285 (1.04); 8.279 (1.04); 8.275 (1.03); 8.182 (0.79); 8.154 (0.82); 8.098 (0.97); 8.094 (0.98); 8.081 (1.07); 8.077 (1.04); 7.706 (0.4); 7.702 (0.53); 7.684 (1.07); 7.679 (1.77); 7.653 (2.07); 7.541 (0.65); 7.538 (0.68); 7.519 (0.61); 7.514 (0.9); 7.494 (2.43); 7.447 (0.93); 7.437 (0.98); 7.43 (0.96); 7.42 (0.9); 7.381 (0.39); 7.358 (0.46); 7.354 (0.88); 7.331 (0.87); 7.326 (0.57); 7.305 (3.79); 6.933 (0.6); 6.906 (1.1); 6.877 (0.53); 6.718 (1.17); 6.691 (1.08); 1.301 (1.01); 0.908 (0.35); 0.901 (0.34); 0.887 (0.39); 0.38 (0.54); 0.369 (15.51); 0.363 (16); 0.118 (1.75); 0.046 (2.9) |
| I.068 | 8.662 (1.36); 8.063 (0.4); 8.057 (0.35); 7.795 (0.35); 7.776 (0.32); 7.773 (0.38); 7.769 (0.44); 7.669 (0.39); 7.663 (0.35); 7.642 (0.56); 7.635 (0.55); 7.614 (0.36); 7.609 (0.37); 7.602 (0.36); 7.597 (0.38); 7.578 (0.4); 7.572 (0.42); 7.464 (0.32); 7.462 (0.32); 7.438 (0.32); 7.31 (0.33); |

TABLE 12-continued

NMR peak lists

| Example | $^1$H-NMR [CDCl$_3$ at 300 Mhz] |
|---|---|
|  | 7.289 (0.49); 7.285 (0.51); 7.258 (1.33); 7.247 (0.53); 7.244 (0.48); 7.219 (0.4); 7.217 (0.37); 1.255 (0.49); 0.256 (0.6); 0.244 (16); 0.233 (0.75); 0 (0.82) |
| I.069 | 8.689 (2.64); 8.135 (0.59); 8.13 (0.49); 8.127 (0.43); 8.109 (0.78); 8.102 (0.66); 7.835 (0.46); 7.83 (0.66); 7.811 (0.61); 7.808 (0.71); 7.804 (0.85); 7.739 (0.38); 7.722 (0.77); 7.716 (0.68); 7.696 (1.32); 7.689 (1.18); 7.673 (0.38); 7.669 (0.65); 7.664 (0.63); 7.476 (0.39); 7.454 (0.45); 7.449 (0.88); 7.427 (0.88); 7.422 (0.54); 7.399 (0.47); 7.3 (3.24); 7.036 (0.95); 7.034 (1.04); 7.01 (1.27); 6.984 (0.94); 6.956 (0.49); 6.954 (0.44); 1.616 (4.92); 0.347 (0.7); 0.335 (16); 0.33 (15.83); 0.318 (0.74); 0.039 (2.67) |
| I.070 | 8.732 (2.12); 8.134 (0.47); 8.129 (0.38); 8.125 (0.32); 8.108 (0.62); 8.101 (0.53); 7.828 (0.37); 7.821 (0.52); 7.803 (0.48); 7.8 (0.57); 7.796 (0.7); 7.74 (0.66); 7.735 (0.72); 7.716 (1.19); 7.71 (1.12); 7.693 (0.78); 7.691 (0.68); 7.686 (0.74); 7.667 (0.52); 7.661 (0.51); 7.542 (0.5); 7.539 (0.49); 7.536 (0.5); 7.534 (0.41); 7.515 (0.46); 7.509 (0.42); 7.39 (0.49); 7.387 (0.48); 7.366 (0.79); 7.363 (0.75); 7.342 (0.34); 7.301 (4.81); 7.271 (0.79); 7.244 (0.65); 2.206 (1.55); 1.614 (4.15); 1.323 (0.36); 1.307 (1.19); 0.944 (0.43); 0.922 (1.35); 0.899 (0.5); 0.436 (0.55); 0.425 (16); 0.413 (0.61); 0.04 (5.01) |
| I.071 | 8.71 (4.25); 8.134 (0.93); 8.129 (0.76); 8.108 (1.2); 8.102 (1.06); 7.828 (0.71); 7.821 (0.94); 7.802 (0.95); 7.799 (1.1); 7.795 (1.39); 7.75 (0.48); 7.744 (0.58); 7.727 (1.22); 7.721 (1.05); 7.703 (1.58); 7.696 (1.46); 7.677 (0.98); 7.671 (0.96); 7.654 (0.43); 7.648 (0.35); 7.519 (0.56); 7.496 (0.7); 7.492 (1.1); 7.469 (1.28); 7.464 (0.8); 7.442 (0.69); 7.301 (3.7); 7.049 (3.19); 7.021 (3.34); 6.992 (0.87); 2.527 (0.49); 1.649 (1.8); 1.306 (0.77); 0.922 (0.86); 0.899 (0.33); 0.471 (0.59); 0.46 (16); 0.454 (15.75); 0.442 (0.77); 0.291 (1.39); 0.273 (1.42); 0.192 (1.03); 0.174 (1.47); 0.151 (0.56); 0.04 (3.69); −0.026 (1.46) |
| I.072 | 8.68 (1.77); 8.127 (0.43); 8.122 (0.38); 8.101 (0.56); 8.095 (0.5); 7.848 (0.43); 7.843 (0.46); 7.823 (0.44); 7.82 (0.5); 7.816 (0.59); 7.71 (0.49); 7.704 (0.46); 7.681 (0.62); 7.674 (0.59); 7.654 (0.45); 7.648 (0.46); 7.638 (0.42); 7.632 (0.59); 7.614 (0.46); 7.608 (0.57); 7.497 (0.42); 7.491 (0.46); 7.471 (0.39); 7.465 (0.35); 7.34 (0.37); 7.338 (0.44); 7.313 (1.22); 7.302 (1.35); 7.292 (0.32); 7.288 (0.41); 7.284 (0.6); 1.642 (0.76); 0.96 (16); 0.37 (0.89); 0.283 (0.62); 0.274 (11.93); 0.043 (1.07) |
| I.073 [3] | 8.653 (3.62); 7.892 (0.77); 7.887 (0.86); 7.878 (0.34); 7.868 (1.08); 7.549 (0.75); 7.543 (0.69); 7.531 (1.25); 7.527 (1.17); 7.515 (1.94); 7.512 (2.01); 7.508 (1.52); 7.502 (0.84); 7.498 (1.19); 7.493 (1); 7.488 (0.6); 7.482 (0.44); 7.477 (0.37); 7.374 (0.85); 7.37 (0.97); 7.356 (0.98); 7.352 (1.07); 7.333 (0.5); 7.329 (0.47); 7.313 (0.94); 7.31 (0.88); 7.295 (0.71); 7.29 (0.59); 7.135 (0.83); 7.117 (1.5); 7.11 (1.61); 7.101 (0.67); 7.099 (0.69); 7.09 (1.2); 3.351 (0.39); 3.341 (0.57); 3.218 (400.25); 3.163 (0.44); 2.309 (12.66); 2.305 (0.6); 2.301 (11.68); 1.436 (0.58); 1.42 (0.75); 1.403 (0.61); 0.651 (0.98); 0.635 (0.93); 0.503 (10.94); 0.486 (10.49); 0.454 (3.11); 0.437 (2.95); 0.031 (1.87); 0 (19.76) |
| I.074 [3] | 9.338 (0.57); 8.847 (5.15); 8.094 (1.09); 8.089 (1.22); 8.079 (0.47); 8.069 (1.49); 7.769 (0.38); 7.765 (0.44); 7.751 (1.25); 7.743 (0.8); 7.732 (1.73); 7.728 (1.62); 7.723 (1.04); 7.718 (1.9); 7.707 (2.22); 7.704 (2.99); 7.701 (2.45); 7.687 (1.28); 7.681 (0.85); 7.552 (1.15); 7.548 (1.48); 7.534 (1.85); 7.53 (1.83); 7.519 (1.52); 7.515 (1.15); 7.499 (1.06); 7.495 (0.8); 7.343 (1.17); 7.325 (1.96); 7.314 (2.18); 7.294 (1.69); 6.746 (0.38); 3.569 (0.33); 3.556 (0.41); 3.551 (0.53); 3.421 (561.36); 3.383 (0.78); 3.369 (0.41); 2.512 (16.49); 2.508 (21.21); 2.503 (15.55); 0.911 (0.87); 0.89 (2.65); 0.873 (1.8); 0.847 (5.15); 0.826 (16); 0.818 (2.3); 0.808 (9.79); 0.78 (1.42); 0.759 (1.03); 0.727 (3.33); 0.724 (3.3); 0.708 (8.05); 0.688 (5.7); 0.67 (1.33); 0.666 (1.28) |
| I.075 [3] | 8.708 (3.95); 7.956 (0.87); 7.951 (0.97); 7.941 (0.38); 7.931 (1.25); 7.63 (0.33); 7.615 (0.82); 7.608 (0.77); 7.597 (1.44); 7.593 (1.35); 7.582 (2.21); 7.579 (2.28); 7.575 (1.73); 7.57 (0.96); 7.565 (1.32); 7.56 (1.11); 7.556 (0.66); 7.549 (0.5); 7.544 (0.4); 7.43 (0.98); 7.426 (1.12); 7.412 (1.15); 7.408 (1.31); 7.401 (0.69); 7.397 (0.56); 7.381 (1.1); 7.362 (0.81); 7.358 (0.66); 7.203 (0.92); 7.185 (1.54); 7.17 (1.97); 7.151 (1.35); 3.411 (0.39); 3.285 (400.84); 2.376 (12.72); 2.372 (16); 2.367 (11.76); 0.863 (0.48); 0.845 (0.66); 0.832 (0.43); 0.826 (0.72); 0.809 (0.5); 0.766 (1.31); 0.748 (1.24); 0.726 (10.32); 0.708 (6.79); 0.044 (2.64); 0 (22.55) |
| I.076 [3] | 9.216 (0.43); 8.708 (4.28); 7.942 (0.92); 7.937 (1.06); 7.928 (0.42); 7.917 (1.35); 7.614 (0.35); 7.599 (0.87); 7.593 (0.82); 7.581 (1.54); 7.577 (1.47); 7.567 (2.37); 7.564 (2.47); 7.56 (1.88); 7.554 (1.02); 7.55 (1.42); 7.545 (1.21); 7.54 (0.72); 7.534 (0.53); 7.529 (0.44); 7.416 (1.03); 7.412 (1.23); 7.398 (1.23); 7.394 (1.44); 7.387 (0.78); 7.383 (0.62); 7.367 (1.18); 7.364 (1.06); 7.348 (0.88); 7.344 (0.73); 7.188 (1.01); 7.17 (1.66); 7.152 (2.39); 7.132 (1.45); 3.327 (1.57); 3.269 (403.6); 3.215 (0.53); 2.36 (12.5); 2.356 (16); 2.351 (11.82); 0.732 (0.73); 0.714 (0.51); 0.688 (1.92); 0.668 (5.14); 0.649 (3.02); 0.588 (0.37); 0.518 (1); 0.5 (2.56); 0.48 (2.02); 0.461 (0.46); 0.459 (0.46); 0.049 (3.73); 0 (25.64) |
| I.077 | 8.755 (2.01); 7.636 (0.58); 7.63 (0.63); 7.612 (0.72); 7.606 (0.78); 7.594 (0.83); 7.591 (0.88); 7.585 (0.88); 7.582 (0.78); 7.568 (1.69); 7.551 (0.56); 7.532 (0.33); 7.507 (0.59); 7.505 (0.58); 7.502 (0.57); 7.481 (0.52); 7.475 (0.45); 7.367 (0.54); 7.364 (0.54); 7.343 (0.84); 7.34 (0.82); 7.319 (0.37); 7.316 (0.35); 7.3 (1.83); 7.251 (0.88); 7.224 (0.72); 1.296 (1.23); 0.961 (0.89); 0.934 (2.71); 0.92 (0.41); 0.91 (1.7); 0.783 (0.55); 0.779 (0.52); 0.758 (1.4); 0.731 (1.03); 0.253 (0.87); 0.242 (16); 0.232 (0.83); 0.04 (1.75) |
| I.078 | 8.747 (2.13); 7.608 (0.76); 7.592 (1.85); 7.578 (0.98); 7.576 (1.07); 7.571 (0.89); 7.565 (0.82); 7.487 (0.42); 7.465 (0.47); 7.459 (0.89); 7.437 (0.81); 7.432 (0.59); 7.41 (0.49); 7.3 (5.67); 7.034 (0.5); 7.031 (0.61); 7.006 (1.91); 7.004 (1.89); 6.978 (1.36); 1.589 (2.42); 0.36 (0.48); 0.351 (0.33); 0.344 (0.38); 0.328 (0.95); 0.317 (16); 0.311 (15.98); 0.3 (0.87); 0.198 (0.56); 0.105 (0.4); 0.039 (6) |
| I.079 | 8.76 (1.23); 7.646 (0.35); 7.64 (0.37); 7.622 (0.41); 7.616 (0.44); 7.596 (0.49); 7.593 (0.52); 7.588 (0.47); 7.583 (0.42); 7.57 (1.11); 7.553 (0.34); 7.511 (0.33); 7.368 (0.33); 7.347 (0.5); 7.344 (0.49); 7.3 (2.96); 7.254 (0.5); 7.252 (0.48); 7.227 (0.41); 1.589 (2.17); 0.278 (0.57); 0.267 (16); 0.256 (0.61); 0.039 (3.17) |
| I.080 | 8.762 (1.91); 7.609 (0.56); 7.603 (0.61); 7.59 (0.75); 7.582 (1.15); 7.577 (1.67); 7.561 (1.33); 7.557 (0.77); 7.547 (0.58); 7.526 (0.33); 7.502 (0.54); 7.499 (0.53); 7.496 (0.5); 7.493 (0.45); |

TABLE 12-continued

| | NMR peak lists |
|---|---|
| Example | $^1$H-NMR [CDCl$_3$ at 300 Mhz] |
| | 7.475 (0.51); 7.469 (0.44); 7.361 (0.5); 7.358 (0.53); 7.337 (0.8); 7.333 (0.8); 7.312 (0.36); 7.309 (0.37); 7.3 (1.93); 7.24 (0.8); 7.238 (0.77); 7.213 (0.66); 7.211 (0.62); 1.656 (1.31); 1.619 (1.34); 1.604 (1.39); 1.108 (0.49); 1.071 (0.79); 1.053 (0.51); 1.027 (0.56); 1.022 (0.57); 0.229 (0.8); 0.219 (16); 0.208 (0.79); 0.04 (1.96) |
| I.081 | 8.778 (1.87); 7.741 (0.5); 7.736 (0.56); 7.717 (0.6); 7.711 (0.64); 7.594 (0.52); 7.579 (1.36); 7.569 (0.43); 7.564 (1); 7.558 (0.71); 7.551 (1.11); 7.544 (0.56); 7.523 (0.48); 7.518 (0.46); 7.405 (0.47); 7.402 (0.49); 7.38 (0.76); 7.378 (0.76); 7.356 (0.33); 7.301 (1.42); 7.253 (0.78); 7.252 (0.76); 7.226 (0.66); 1.655 (0.55); 0.416 (0.54); 0.404 (16); 0.393 (0.6); 0.188 (0.52); 0.04 (1.43) |
| I.082 | 8.765 (3.81); 7.611 (1.01); 7.59 (3.05); 7.58 (1.15); 7.571 (1.42); 7.567 (2.3); 7.559 (0.4); 7.536 (0.64); 7.513 (0.72); 7.508 (1.29); 7.486 (1.26); 7.481 (0.83); 7.459 (0.71); 7.302 (6.25); 7.07 (0.9); 7.041 (1.76); 7.035 (2.03); 7.013 (0.99); 7.008 (1.73); 5.34 (1.31); 1.626 (1.8); 1.34 (0.58); 1.324 (0.48); 1.306 (0.7); 1.293 (1.09); 0.919 (0.33); 0.449 (0.54); 0.438 (15.7); 0.433 (16); 0.421 (0.77); 0.271 (0.35); 0.264 (0.35); 0.039 (4.72) |
| I.083 | 8.77 (7.19); 8.763 (2.72); 7.621 (0.53); 7.605 (0.68); 7.588 (3.15); 7.574 (1.05); 7.565 (5.76); 7.561 (5.3); 7.543 (5.59); 7.538 (3.34); 7.533 (2.65); 7.51 (1.67); 7.504 (0.96); 7.482 (0.77); 7.477 (0.6); 7.454 (0.52); 7.297 (6.87); 7.091 (4.05); 7.064 (3.9); 7.057 (3.32); 7.032 (2.29); 7.03 (2.32); 7.006 (1.32); 1.618 (1.15); 1.29 (0.32); 1.244 (1.02); 1.212 (0.56); 0.545 (0.37); 0.533 (14.98); 0.527 (15.89); 0.507 (15.25); 0.501 (16); 0.49 (0.96); 0.448 (0.37); 0.436 (9.86); 0.43 (10.63); 0.419 (0.66); 0.108 (1.69); 0.035 (6.98); 0.024 (0.34) |
| I.084 | 8.392 (1.37); 7.651 (0.86); 7.625 (1.07); 7.622 (1.09); 7.539 (0.41); 7.522 (1.22); 7.505 (1.04); 7.499 (0.99); 7.365 (0.37); 7.362 (0.35); 7.34 (0.56); 7.3 (1.22); 1.294 (0.56); 0.371 (16); 0.111 (0.39); 0.039 (1.05) |
| I.085 | 7.531 (0.66); 7.504 (2.6); 7.497 (1.5); 7.492 (1.95); 7.481 (1.77); 7.476 (3.48); 7.461 (1.08); 7.454 (0.83); 7.302 (14.43); 7.066 (0.85); 7.064 (0.82); 7.036 (1.55); 7.009 (0.79); 7.007 (0.73); 6.97 (1.7); 6.942 (1.53); 2.907 (13.52); 2.14 (1.99); 2.131 (2.01); 1.595 (8.15); 1.373 (0.43); 1.35 (0.43); 0.421 (16); 0.416 (16); 0.404 (0.73); 0.262 (0.49); 0.257 (0.37); 0.247 (0.58); 0.237 (0.38); 0.15 (0.51); 0.139 (0.67); 0.092 (0.35); 0.051 (0.56); 0.04 (14.56); 0.029 (0.59); −0.042 (0.49); −0.072 (0.34) |
| I.086 | 7.649 (0.33); 7.643 (0.36); 7.624 (0.4); 7.619 (0.42); 7.509 (0.4); 7.506 (0.45); 7.503 (0.43); 7.501 (0.35); 7.492 (1.21); 7.482 (0.4); 7.475 (0.86); 7.464 (0.39); 7.443 (0.34); 7.367 (0.34); 7.364 (0.34); 7.342 (0.53); 7.339 (0.51); 7.3 (1.25); 7.188 (0.5); 7.186 (0.48); 7.16 (0.43); 7.158 (0.41); 2.931 (4.44); 2.916 (0.33); 1.613 (1.58); 0.268 (0.66); 0.257 (16); 0.246 (0.64); 0.04 (1.08) |
| I.087 | 7.74 (0.53); 7.734 (0.57); 7.716 (0.62); 7.71 (0.65); 7.553 (0.53); 7.551 (0.49); 7.547 (0.51); 7.526 (0.47); 7.52 (0.44); 7.49 (1.18); 7.485 (0.7); 7.476 (0.59); 7.466 (1.54); 7.445 (0.5); 7.403 (0.5); 7.4 (0.49); 7.379 (0.81); 7.376 (0.75); 7.355 (0.35); 7.301 (4.64); 7.211 (0.81); 7.184 (0.68); 5.341 (0.4); 2.932 (6.98); 1.925 (1.44); 1.604 (4.7); 0.408 (0.57); 0.397 (16); 0.385 (0.77); 0.04 (3.9) |
| I.088 | 7.504 (1.25); 7.498 (0.89); 7.491 (0.74); 7.48 (2.39); 7.46 (0.67); 7.456 (0.53); 7.451 (0.89); 7.429 (0.99); 7.424 (0.55); 7.401 (0.48); 7.301 (5.09); 7.029 (0.54); 7.027 (0.54); 7 (0.97); 6.973 (0.49); 6.97 (0.47); 6.911 (1.05); 6.884 (0.96); 2.909 (8.71); 1.597 (3.26); 0.306 (0.64); 0.294 (16); 0.288 (15.98); 0.277 (0.65); 0.04 (4.69) |
| I.089 | 7.473 (0.72); 7.468 (1.14); 7.463 (1.26); 7.461 (1.17); 7.446 (1.87); 7.438 (0.88); 7.43 (0.61); 7.375 (0.34); 7.363 (0.59); 7.348 (0.56); 7.339 (0.41); 7.324 (0.39); 7.314 (0.52); 7.308 (0.52); 7.297 (0.74); 7.28 (0.62); 7.274 (0.51); 5.331 (0.73); 2.936 (7.17); 2.218 (0.73); 0.398 (0.66); 0.386 (16); 0.375 (0.71); 0.034 (0.59) |
| I.090 | 7.488 (0.64); 7.481 (0.7); 7.476 (0.98); 7.46 (1.36); 7.454 (0.74); 7.445 (0.54); 7.427 (1.3); 7.4 (1.05); 7.369 (0.96); 7.365 (1.12); 7.342 (0.52); 7.339 (0.45); 7.297 (0.81); 7.027 (0.79); 7.023 (0.82); 7 (0.71); 6.997 (0.71); 2.89 (6.85); 2.485 (1.34); 0.453 (0.57); 0.441 (16); 0.429 (0.65); 0.034 (0.58) |
| I.091 | 7.506 (1.43); 7.501 (1.05); 7.494 (1.31); 7.482 (3.89); 7.466 (1.68); 7.463 (1.43); 7.453 (1.81); 7.431 (1.1); 7.426 (0.88); 7.403 (0.49); 7.304 (22.43); 7.049 (0.51); 7.032 (0.67); 7.02 (0.87); 7.002 (1.03); 6.992 (0.47); 6.975 (0.64); 6.933 (0.92); 6.912 (1.22); 6.886 (1.03); 6.275 (0.32); 6.227 (0.42); 6.208 (0.39); 6.159 (0.5); 6.156 (0.44); 5.796 (0.74); 5.785 (0.85); 5.748 (0.6); 5.736 (0.65); 5.594 (0.77); 5.582 (0.68); 5.526 (0.63); 5.514 (0.57); 2.911 (8.82); 2.876 (7.1); 1.599 (31.81); 1.52 (1.51); 0.382 (8.32); 0.375 (8.23); 0.308 (0.64); 0.296 (16); 0.291 (15.73); 0.053 (0.7); 0.042 (21.33); 0.032 (0.83); 0.016 (1.03); 0.004 (0.34) |
| I.092 | 7.592 (0.74); 7.568 (0.99); 7.564 (1.54); 7.542 (1.63); 7.537 (1); 7.514 (0.91); 7.49 (1.62); 7.483 (1.88); 7.478 (2.58); 7.462 (3.39); 7.447 (1.26); 7.304 (9.4); 7.083 (1.05); 7.061 (2.72); 7.035 (2.14); 7.027 (1); 3.476 (1.33); 3.456 (3.6); 3.438 (1.36); 2.896 (16); 1.682 (1.33); 1.672 (2.01); 1.662 (3.94); 1.653 (2.17); 1.642 (1.65); 1.621 (2.68); 1.523 (0.32); 1.475 (0.59); 0.526 (0.36); 0.514 (9.54); 0.508 (9.49); 0.489 (9.61); 0.482 (9.54); 0.042 (8.82); 0.031 (0.36) |
| I.093 | 7.865 (1.01); 7.84 (1.27); 7.654 (1.09); 7.65 (1.02); 7.629 (0.74); 7.625 (0.71); 7.538 (1.74); 7.518 (1.39); 7.508 (0.68); 7.494 (1.31); 7.304 (2.51); 2.927 (6.98); 2.918 (1.39); 2.073 (0.37); 2.05 (1.68); 1.635 (0.69); 0.425 (0.63); 0.414 (16); 0.402 (0.61); 0.041 (2.36) |
| I.094 | 7.504 (1.8); 7.498 (0.82); 7.485 (1.13); 7.47 (1.47); 7.453 (0.59); 7.443 (0.87); 7.304 (22.25); 6.894 (1.02); 6.866 (0.97); 6.772 (1.11); 6.744 (1.01); 3.967 (7.43); 3.253 (2.06); 2.909 (0.4); 2.896 (7.08); 1.595 (26.8); 1.309 (1.77); 1.102 (0.35); 1.064 (0.32); 0.946 (0.62); 0.924 (1.85); 0.902 (0.73); 0.387 (0.55); 0.339 (0.61); 0.327 (16); 0.298 (0.78); 0.292 (0.53); 0.278 (1.34); 0.268 (0.66); 0.256 (0.39); 0.249 (0.63); 0.238 (0.46); 0.198 (0.73); 0.185 (0.55); 0.179 (0.81); 0.155 (0.4); 0.128 (0.56); 0.112 (1.76); 0.104 (0.49); 0.053 (0.74); 0.042 (21.02); 0.031 (0.69); −0.066 (0.4) |
| I.095 | 7.57 (0.6); 7.543 (1.43); 7.515 (1.47); 7.506 (1.11); 7.501 (1.3); 7.485 (1.74); 7.47 (0.61); 7.304 (12.01); 7.269 (0.58); 7.266 (0.55); 7.244 (0.53); 7.106 (1.21); 7.079 (1.1); 2.913 (7.51); 2.109 (2.18); 1.596 (15.64); 0.468 (0.58); 0.451 (1.13); 0.432 (16); 0.42 (1.08); 0.216 (0.55); 0.202 |

TABLE 12-continued

NMR peak lists

| Example | ¹H-NMR [CDCl₃ at 300 Mhz] |
|---|---|
|  | (0.44);0.191 (0.34); 0.173 (0.44); 0.163 (0.39); 0.148 (0.63); 0.14 (0.68); 0.13 (0.78); 0.12 (1.31); 0.112 (1.26); 0.082 (0.54); 0.076 (0.6); 0.053 (0.63); 0.042 (11.6); 0.031 (0.74); 0.028 (0.72); 0.018 (1.45); 0.005 (0.4); −0.008 (0.74); −0.151 (0.62); −0.166 (1.55) |
| I.096 | 7.612 (1.07); 7.587 (1.23); 7.507 (1.09); 7.491 (0.69); 7.487 (0.76); 7.482 (0.6); 7.473 (0.6); 7.45 (0.58); 7.304 (3.38); 7.209 (0.72); 7.184 (0.65); 7 (1.27); 2.921 (7.42); 2.438 (5.71); 2.427 (0.73); 1.96 (1.52); 1.632 (6.29); 0.385 (0.9); 0.374 (16); 0.366 (1.66); 0.336 (0.57); 0.273 (0.54); 0.266 (0.85); 0.259 (1.22); 0.25 (0.78); 0.243 (0.64); 0.218 (0.33); 0.178 (0.5); 0.169 (1.28); 0.162 (0.41); 0.152 (0.59); 0.135 (0.39); 0.114 (0.77); 0.043 (2.39); −0.026 (0.99) |
| I.097 | 7.5 (1.58); 7.48 (1.11); 7.47 (0.6); 7.447 (0.55); 7.41 (0.55); 7.384 (1.05); 7.358 (0.73); 7.304 (1.96); 7.168 (0.87); 7.143 (0.71); 6.931 (0.8); 6.904 (0.72); 2.909 (7.57); 2.652 (0.57); 2.632 (5.79); 2.042 (1.61); 1.65 (2.68); 0.432 (0.61); 0.421 (16); 0.41 (0.73); 0.401 (1.54); 0.274 (0.64); 0.266 (1.02); 0.258 (1.85); 0.244 (0.58); 0.188 (0.46); 0.178 (0.69); 0.167 (1.24); 0.162 (0.52); 0.153 (0.49); 0.146 (0.56); 0.136 (0.52); 0.044 (2.7) |
| I.098 | 7.649 (0.35); 7.502 (0.76); 7.489 (1.34); 7.474 (1.39); 7.46 (0.68); 7.405 (0.47); 7.395 (0.58); 7.378 (0.48); 7.368 (0.61); 7.303 (67.28); 7.22 (0.61); 7.211 (0.61); 7.191 (1.19); 7.176 (0.93); 7.16 (0.39); 6.952 (0.38); 5.344 (0.7); 2.922 (7.25); 2.912 (1.24); 1.892 (2.03); 1.588 (62.91); 0.397 (0.63); 0.386 (16); 0.37 (0.91); 0.34 (2.26); 0.273 (1.56); 0.264 (1.86); 0.256 (1.23); 0.248 (1.66); 0.218 (0.67); 0.208 (0.69); 0.198 (2.48); 0.185 (0.52); 0.172 (0.56); 0.159 (0.77); 0.152 (0.67); 0.123 (0.46); 0.111 (0.87); 0.09 (2.24); 0.053 (2.16); 0.042 (64.21); 0.031 (2.36); 0.013 (0.89) |
| I.099 | 7.506 (1.02); 7.501 (1.05); 7.492 (1.84); 7.474 (1.19); 7.464 (0.58); 7.442 (0.51); 7.361 (0.45); 7.356 (0.42); 7.334 (0.57); 7.328 (0.54); 7.303 (10.52); 7.102 (1.13); 7.074 (0.91); 2.922 (7); 2.466 (5.28); 1.895 (1.63); 1.594 (7.73); 0.394 (0.63); 0.383 (16); 0.372 (0.61); 0.273 (1.1); 0.264 (1.16); 0.259 (0.86); 0.256 (0.79); 0.248 (0.79); 0.246 (0.77); 0.242 (0.71); 0.238 (0.67); 0.171 (0.39); 0.159 (0.43); 0.053 (0.41); 0.042 (10.76); 0.031 (0.38) |
| I.100 | 7.499 (0.53); 7.494 (0.48); 7.489 (0.46); 7.476 (1.15); 7.458 (0.34); 7.303 (6.66); 7.296 (0.44); 7.286 (0.39); 7.179 (0.4); 7.17 (0.37); 7.157 (0.61); 7.144 (0.64); 5.343 (0.96); 2.922 (4.68); 1.595 (5.01); 0.26 (0.52); 0.249 (16); 0.238 (0.66); 0.042 (5.65) |
| I.101 | 7.546 (0.74); 7.537 (0.9); 7.509 (0.47); 7.503 (0.5); 7.498 (0.62); 7.481 (1.01); 7.47 (0.62); 7.466 (0.47); 7.462 (0.46); 7.441 (0.6); 7.433 (0.51); 7.303 (13.77); 7.136 (0.89); 7.107 (0.72); 5.343 (1.23); 2.92 (4.6); 1.593 (15.41); 0.268 (0.65); 0.257 (16); 0.246 (0.59); 0.053 (0.41); 0.042 (11.29); 0.031 (0.38) |
| I.102 | 7.656 (1.29); 7.512 (0.89); 7.503 (0.83); 7.495 (1.36); 7.483 (1.09); 7.479 (1.28); 7.475 (1.45); 7.467 (0.65); 7.305 (4.54); 7.168 (1.32); 7.14 (1.12); 2.919 (6.99); 1.957 (1.46); 1.615 (7.36); 0.402 (0.57); 0.391 (16); 0.38 (0.66); 0.113 (0.66); 0.043 (4.13); 7.665 (1.16) |
| I.103 | 7.636 (1.55); 7.631 (1.67); 7.612 (1.84); 7.606 (2.03); 7.596 (1.83); 7.59 (1.45); 7.569 (2.36); 7.564 (1.59); 7.481 (1.2); 7.465 (3.39); 7.451 (1.92); 7.448 (2.02); 7.443 (1.84); 7.438 (1.51); 7.378 (1.96); 7.354 (2.41); 7.328 (1.34); 7.304 (6.64); 2.96 (16); 2.092 (1.53); 1.635 (9.77); 1.308 (0.51); 0.923 (0.54); 0.384 (13.68); 0.112 (1.04); 0.041 (4.38) |
| I.104 | 7.562 (0.99); 7.557 (1.1); 7.538 (1.25); 7.533 (1.31); 7.464 (1.36); 7.455 (1.7); 7.451 (2.72); 7.435 (3.04); 7.431 (2.34); 7.422 (1.84); 7.404 (1.55); 7.39 (0.34); 7.348 (1.88); 7.324 (2.41); 7.304 (6.08); 2.95 (16); 2.087 (0.47); 2.067 (12.15); 2.009 (0.56); 1.886 (1.37); 1.642 (9.21); 1.35 (0.55); 1.309 (3.52); 1.278 (0.37); 0.946 (1.25); 0.924 (3.9); 0.901 (1.47); 0.382 (0.33); 0.344 (15.2); 0.286 (0.54); 0.273 (2.52); 0.263 (1.96); 0.256 (1.38); 0.246 (1.68); 0.238 (1.14); 0.229 (0.37); 0.217 (0.64); 0.206 (0.42); 0.179 (0.52); 0.167 (0.44); 0.157 (1.05); 0.152 (0.55); 0.144 (0.52); 0.138 (0.38); 0.126 (0.67); 0.124 (0.8); 0.114 (1.21); 0.043 (4.26) |
| I.105 | 7.715 (0.55); 7.691 (0.67); 7.687 (0.68); 7.663 (0.61); 7.526 (1.28); 7.512 (0.57); 7.503 (1.23); 7.481 (0.5); 7.304 (6.93); 7.132 (0.34); 7.125 (0.37); 7.105 (0.64); 7.097 (0.69); 7.069 (0.33); 7 (0.64); 6.992 (0.56); 6.967 (0.65); 6.96 (0.56); 2.924 (6.88); 1.904 (0.98); 1.613 (14.91); 0.401 (0.62); 0.39 (16); 0.379 (0.61); 0.112 (1.08); 0.042 (5.44) |
| I.106 | 7.552 (0.32); 7.539 (0.32); 7.533 (0.36); 7.526 (0.45); 7.514 (0.45); 7.469 (0.39); 7.452 (0.59); 7.344 (0.35); 7.319 (0.54); 7.304 (5.13); 2.955 (2.82); 1.613 (16); 0.232 (0.4); 0.221 (10.04); 0.21 (0.36); 0.042 (3.12) |
| I.107 | 7.487 (1.01); 7.482 (1.14); 7.467 (3.11); 7.462 (2.8); 7.456 (2.22); 7.443 (4); 7.424 (1.14); 7.387 (0.75); 7.385 (0.78); 7.381 (0.84); 7.362 (1.63); 7.36 (1.65); 7.356 (1.39); 7.32 (2.02); 7.304 (6.53); 7.296 (2.38); 7.272 (0.8); 2.949 (16); 2.033 (12.63); 1.627 (14.05); 0.19 (2.26); 0.179 (57.05); 0.168 (2.13); 0.043 (4.16) |
| I.108 | 7.604 (0.38); 7.58 (0.49); 7.577 (0.47); 7.553 (0.43); 7.531 (1.17); 7.513 (0.76); 7.503 (0.38); 7.481 (0.34); 7.305 (4.27); 7.074 (0.43); 7.066 (0.46); 6.97 (0.44); 6.962 (0.38); 6.936 (0.44); 6.929 (0.37); 2.926 (4.62); 1.596 (3.09); 0.265 (0.65); 0.254 (16); 0.243 (0.63); 0.043 (4.36) |
| I.109 | 8.04 (0.88); 8.029 (0.74); 8.023 (0.67); 8.015 (0.61); 8.007 (1.02); 7.746 (0.73); 7.736 (0.57); 7.73 (0.6); 7.724 (0.98); 7.713 (1.29); 7.655 (0.44); 7.651 (0.38); 7.642 (2.49); 7.632 (1.33); 7.628 (1.52); 7.622 (1.5); 7.618 (1.05); 7.609 (2.06); 7.511 (0.58); 7.488 (0.72); 7.484 (1.31); 7.461 (1.35); 7.457 (0.84); 7.434 (0.75); 7.298 (10.36); 7.043 (0.81); 7.041 (0.84); 7.013 (1.49); 6.986 (0.75); 6.984 (0.76); 6.97 (1.7); 6.942 (1.49); 2.856 (14.43); 2.34 (0.83); 1.608 (6.51); 0.465 (0.64); 0.458 (0.72); 0.449 (0.85); 0.438 (16); 0.433 (15.98); 0.421 (0.64); 0.122 (0.51); 0.048 (0.37); 0.037 (10.34); 0.026 (0.37); −0.087 (1.53) |
| I.110 | 8.068 (0.37); 8.057 (0.36); 8.036 (0.43); 7.784 (0.34); 7.762 (0.42); 7.751 (0.51); 7.673 (0.43); 7.667 (0.46); 7.648 (0.58); 7.643 (0.66); 7.632 (1.1); 7.622 (0.63); 7.619 (0.62); 7.613 (0.64); 7.609 (0.49); 7.6 (0.88); 7.521 (0.42); 7.519 (0.42); 7.516 (0.41); 7.495 (0.38); 7.489 (0.33); 7.369 (0.43); 7.366 (0.42); 7.344 (0.68); 7.341 (0.67); 7.32 (0.35); 7.249 (0.65); 7.222 (0.54); 2.916 (5.48); 1.224 (1.68); 1.186 (1.66); 0.318 (0.95); 0.308 (16); 0.296 (0.92) |
| I.111 | 8.053 (0.62); 8.041 (0.62); 8.035 (0.48); 8.029 (0.45); 8.02 (0.71); 7.766 (0.54); 7.756 (0.45); 7.752 (0.47); 7.745 (0.75); 7.734 (0.85); 7.65 (0.35); 7.647 (0.33); 7.637 (1.83); 7.626 (1.11); 7.624 (1.13); 7.617 (1.11); 7.604 (1.44); 7.467 (0.4); 7.445 (0.53); 7.44 (0.89); 7.418 (0.93); 7.413 (0.6); 7.39 (0.53); 7.3 (0.37); 7.013 (0.58); 7.011 (0.6); 6.984 (1.06); 6.956 (0.58); 6.954 |

TABLE 12-continued

NMR peak lists

| Example | ¹H-NMR [CDCl₃ at 300 Mhz] |
|---|---|
| | (0.59); 6.944 (1.17); 6.917 (1.02); 2.872 (9.18); 1.204 (1.12); 1.166 (1.09); 0.327 (16); 0.321 (15.3) |
| I.112 | 8.038 (0.44); 8.028 (0.34); 8.022 (0.38); 8.006 (0.53); 7.742 (0.87); 7.735 (0.7); 7.726 (0.4); 7.717 (0.72); 7.71 (1.18); 7.629 (1.15); 7.62 (0.65); 7.614 (0.77); 7.61 (0.77); 7.604 (0.52); 7.596 (1.02); 7.544 (0.49); 7.541 (0.48); 7.538 (0.49); 7.536 (0.42); 7.517 (0.46); 7.511 (0.42); 7.388 (0.48); 7.385 (0.49); 7.364 (0.78); 7.361 (0.75); 7.34 (0.34); 7.301 (5.52); 7.221 (0.77); 7.194 (0.65); 2.885 (7.41); 2.12 (1.7); 1.611 (5.06); 0.426 (0.58); 0.415 (16); 0.403 (0.63); 0.175 (0.32); 0.041 (5.67) |
| I.113 | 7.99 (0.95); 7.978 (1.06); 7.971 (0.72); 7.967 (0.67); 7.958 (1.13); 7.698 (0.7); 7.686 (0.71); 7.677 (1.08); 7.665 (1.56); 7.653 (0.45); 7.629 (0.68); 7.618 (3.16); 7.606 (2.23); 7.597 (1.9); 7.585 (2.07); 7.511 (0.62); 7.489 (0.78); 7.484 (1.39); 7.462 (1.41); 7.457 (0.89); 7.434 (0.75); 7.402 (1.71); 7.4 (1.65); 7.387 (1.81); 7.385 (1.71); 7.302 (3.36); 7.14 (1.68); 7.137 (1.64); 7.128 (1.87); 7.126 (1.72); 7.051 (0.92); 7.049 (0.91); 7.021 (1.7); 6.994 (0.84); 6.992 (0.8); 6.926 (1.85); 6.914 (1.63); 6.898 (3.22); 6.887 (1.38); 2.608 (15.2); 1.299 (0.55); 0.674 (0.87); 0.662 (16); 0.654 (15.81); 0.643 (0.76); 0.044 (1.65) |
| I.114 | 7.96 (0.82); 7.95 (0.54); 7.946 (0.63); 7.939 (0.99); 7.928 (0.95); 7.663 (0.47); 7.65 (0.64); 7.645 (0.59); 7.638 (0.74); 7.63 (1.56); 7.621 (0.49); 7.614 (0.65); 7.61 (0.58); 7.601 (2.88); 7.591 (1.5); 7.588 (1.21); 7.579 (1.41); 7.568 (1.86); 7.497 (0.64); 7.475 (0.82); 7.47 (1.38); 7.448 (1.4); 7.443 (0.86); 7.42 (0.73); 7.325 (0.51); 7.318 (3.22); 7.311 (1.29); 7.302 (11.66); 7.297 (1.58); 7.289 (3.44); 7.281 (0.53); 7.046 (0.81); 7.044 (0.84); 7.017 (1.48); 6.99 (0.74); 6.987 (0.71); 6.904 (1.58); 6.877 (1.44); 6.57 (0.46); 6.563 (3.46); 6.556 (1.15); 6.54 (1.08); 6.534 (3.2); 6.526 (0.4); 3.557 (16); 2.542 (14.31); 1.608 (4.11); 1.524 (0.63); 1.478 (0.59); 1.13 (0.58); 1.085 (0.57); 0.613 (0.65); 0.601 (14.44); 0.594 (14.53); 0.582 (0.72); 0.111 (0.37); 0.052 (0.35); 0.041 (10.26); 0.03 (0.38) |
| I.115 | 7.958 (0.88); 7.948 (0.64); 7.944 (0.68); 7.937 (1.05); 7.926 (1.04); 7.68 (0.61); 7.668 (0.83); 7.661 (0.65); 7.656 (0.74); 7.647 (1.67); 7.637 (0.4); 7.619 (0.55); 7.616 (0.53); 7.607 (3.09); 7.596 (1.7); 7.584 (1.55); 7.574 (2.02); 7.508 (0.63); 7.485 (0.77); 7.48 (1.39); 7.458 (1.42); 7.453 (0.88); 7.431 (0.84); 7.416 (1.59); 7.41 (2.05); 7.401 (1.29); 7.395 (1.61); 7.385 (1.96); 7.301 (14.84); 7.097 (0.43); 7.091 (0.71); 7.081 (3.46); 7.076 (3.66); 7.067 (1.32); 7.063 (1.65); 7.061 (1.71); 7.058 (1.98); 7.052 (1.28); 7.049 (1.13); 7.041 (0.58); 7.023 (1.64); 6.996 (0.83); 6.993 (0.75); 6.918 (1.74); 6.891 (1.59); 2.469 (15.17); 1.605 (3.41); 1.473 (0.35); 1.295 (0.88); 0.618 (0.66); 0.607 (16); 0.599 (15.91); 0.588 (0.74); 0.128 (1.14); 0.123 (1.72); 0.111 (41.11); 0.098 (1.68); 0.086 (0.7); 0.051 (0.58); 0.041 (15); 0.03 (0.59) |
| I.116 | 8.951 (0.75); 8.945 (0.79); 8.937 (0.79); 8.931 (0.8); 8.891 (1.42); 8.882 (1.44); 8.444 (0.54); 8.442 (0.61); 8.439 (0.61); 8.437 (0.51); 8.416 (0.58); 8.414 (0.66); 8.411 (0.64); 8.409 (0.54); 7.699 (1); 7.697 (0.97); 7.69 (1.02); 7.609 (0.94); 7.595 (0.93); 7.581 (0.89); 7.566 (0.87); 7.419 (0.4); 7.397 (0.46); 7.392 (0.87); 7.37 (0.87); 7.365 (0.54); 7.343 (0.48); 7.302 (0.65); 6.964 (0.57); 6.961 (0.56); 6.935 (0.98); 6.907 (0.51); 6.905 (0.48); 6.824 (1.05); 6.797 (0.96); 0.372 (0.65); 0.361 (16); 0.355 (15.7); 0.344 (0.71); 0.108 (3.85); 0.028 (0.41) |
| I.117 | 8.538 (1.18); 7.825 (1.27); 7.735 (1.1); 7.717 (1.42); 7.683 (0.33); 7.665 (0.43); 7.645 (0.34); 7.637 (0.34); 7.589 (1.33); 7.57 (1.05); 7.558 (0.4); 7.367 (0.41); 7.34 (0.95); 7.317 (1.05); 7.304 (2.02); 7.289 (0.52); 6.898 (0.77); 6.87 (1.43); 6.842 (0.7); 6.606 (1.43); 6.579 (1.34); 0.556 (0.33); 0.544 (16); 0.539 (15.97); 0.528 (0.94); 0.438 (2.38); 0.432 (2.38); 0.114 (7.2); 0.101 (0.36); 0.039 (1.37) |
| I.118 | 8.542 (1.58); 8.533 (1.6); 7.766 (1.22); 7.765 (1.19); 7.758 (1.22); 7.702 (1.27); 7.683 (1.71); 7.584 (1.36); 7.566 (1); 7.564 (0.92); 7.348 (0.35); 7.325 (0.52); 7.321 (0.79); 7.304 (0.73); 7.298 (0.87); 7.294 (0.5); 7.271 (0.42); 6.881 (0.59); 6.852 (1.07); 6.825 (0.53); 6.642 (1.17); 6.615 (1.09); 0.42 (0.71); 0.409 (16); 0.403 (15.21); 0.392 (0.65); 0.12 (2.39); 0.041 (0.33) |
| I.119 | 8.453 (1.86); 8.444 (1.83); 7.728 (2.19); 7.72 (2.08); 7.661 (1.84); 7.641 (2.03); 7.357 (0.53); 7.334 (0.8); 7.33 (1.21); 7.307 (1.79); 7.304 (2.27); 7.28 (0.65); 7.252 (2.35); 7.232 (2.17); 6.889 (0.9); 6.86 (1.6); 6.833 (0.82); 6.59 (1.74); 6.563 (1.63); 1.297 (0.45); 0.557 (0.68); 0.546 (16); 0.54 (14.81); 0.529 (0.66); 0.445 (0.98); 0.439 (0.92); 0.115 (5.95); 0.04 (1.14) |
| I.120 | 8.441 (1.47); 8.432 (1.51); 7.661 (1.7); 7.653 (1.69); 7.638 (1.51); 7.618 (1.64); 7.339 (0.4); 7.316 (0.49); 7.312 (0.91); 7.304 (0.63); 7.29 (0.91); 7.285 (0.57); 7.262 (0.48); 7.241 (1.83); 7.222 (1.66); 6.872 (0.66); 6.844 (1.19); 6.816 (0.59); 6.624 (1.28); 6.597 (1.19); 0.425 (0.69); 0.415 (16); 0.409 (15.87); 0.398 (0.77); 0.123 (3.56) |
| I.121 | 8.522 (0.99); 8.516 (1.21); 8.458 (2.14); 8.449 (1.69); 8.16 (2.1); 8.152 (2.13); 7.403 (0.56); 7.38 (0.7); 7.376 (1.24); 7.353 (1.28); 7.348 (0.79); 7.326 (0.69); 7.301 (4.11); 6.934 (0.88); 6.932 (0.84); 6.906 (1.57); 6.878 (0.8); 6.876 (0.74); 6.803 (1.53); 6.801 (1.5); 6.795 (1.56); 6.793 (1.41); 6.654 (1.64); 6.626 (1.53); 2.724 (0.79); 1.659 (0.82); 0.567 (0.71); 0.555 (16); 0.55 (15.65); 0.538 (0.67); 0.477 (0.33); 0.037 (3) |
| I.122 | 8.445 (4.75); 8.142 (1.47); 8.134 (1.48); 7.37 (0.39); 7.348 (0.47); 7.343 (0.86); 7.321 (0.88); 7.316 (0.53); 7.301 (1.45); 7.294 (0.5); 6.906 (0.6); 6.877 (1.08); 6.85 (0.54); 6.79 (1.18); 6.782 (1.15); 6.657 (1.14); 6.63 (1.06); 2.082 (0.87); 2.045 (5.79); 1.708 (0.38); 1.296 (0.49); 0.432 (0.66); 0.421 (16); 0.415 (15.64); 0.404 (0.75); 0.108 (1.77); 0.035 (1.08) |
| I.123 | 8.476 (0.53); 8.468 (0.75); 8.432 (0.52); 8.425 (0.4); 8.13 (0.57); 8.123 (0.58); 7.594 (0.34); 7.589 (0.38); 7.57 (0.4); 7.564 (0.42); 7.399 (0.33); 7.393 (0.33); 7.301 (0.7); 7.249 (0.33); 7.225 (0.53); 7.222 (0.5); 6.884 (0.52); 6.856 (0.47); 6.79 (0.48); 6.783 (0.48); 0.372 (0.61); 0.37 (0.45); 0.361 (16); 0.352 (0.54); 0.35 (0.62); 0.039 (0.43) |
| I.124 | 8.369 (0.39); 8.363 (0.37); 8.347 (0.41); 8.341 (0.38); 7.557 (0.37); 7.539 (0.37); 7.533 (0.42); 7.403 (0.34); 7.38 (0.33); 7.301 (1.01); 7.259 (0.62); 7.247 (0.4); 7.234 (0.41); 7.232 (0.41); 7.223 (0.57); 7.22 (0.46); 6.938 (0.39); 6.931 (1.36); 6.925 (0.42); 6.916 (0.35); 0.335 (0.6); 0.333 (0.45); 0.324 (16); 0.313 (0.61); 0.037 (0.76) |
| I.125 | 8.46 (3.25); 8.113 (1.19); 8.104 (1.2); 7.688 (0.53); 7.682 (0.56); 7.664 (0.61); 7.658 (0.61); 7.415 (0.51); 7.413 (0.49); 7.41 (0.51); 7.407 (0.41); 7.388 (0.45); 7.382 (0.41); 7.301 (1); 7.262 (0.51); 7.26 (0.48); 7.238 (0.84); 7.236 (0.76); 7.214 (0.36); 7.211 (0.32); 6.868 (0.79); 6.841 |

TABLE 12-continued

NMR peak lists

| Example | $^1$H-NMR [CDCl$_3$ at 300 Mhz] |
|---|---|
| | (0.72); 6.765 (0.86); 6.757 (0.85); 4.186 (0.48); 4.162 (1.47); 4.139 (1.5); 4.115 (0.51); 2.076 (6.73); 2.039 (2.67); 1.313 (1.82); 1.289 (3.63); 1.265 (1.75); 0.496 (0.59); 0.484 (16); 0.473 (0.63); 0.031 (0.7) |
| I.126 | 7.431 (0.48); 7.428 (0.51); 7.426 (0.43); 7.407 (0.45); 7.401 (0.42); 7.297 (0.73); 7.282 (0.49); 7.279 (0.5); 7.258 (0.8); 7.255 (0.79); 7.233 (0.35); 7.231 (0.33); 6.885 (0.78); 6.858 (0.71); 0.485 (0.64); 0.474 (16); 0.462 (0.69); 0.031 (0.39); 8.431 (1.07); 8.423 (1.17); 8.267 (0.79); 8.263 (0.86); 8.259 (0.8); 8.255 (0.73); 7.982 (1.14); 7.97 (1.14); 7.691 (0.54); 7.685 (0.58); 7.667 (0.62); 7.661 (0.64); 7.434 (0.49) |
| I.127 | 8.952 (0.55); 8.419 (1.94); 8.411 (2.28); 8.324 (1.6); 8.32 (1.74); 8.316 (1.59); 8.312 (1.44); 8.025 (2.09); 8.014 (2.11); 7.419 (0.55); 7.396 (0.73); 7.391 (1.27); 7.369 (1.29); 7.364 (0.86); 7.341 (0.7); 7.297 (3); 6.948 (0.93); 6.92 (1.7); 6.892 (0.83); 6.664 (1.8); 6.637 (1.68); 2.64 (0.55); 1.67 (1.28); 0.539 (15.76); 0.534 (16); 0.46 (0.37); 0.453 (0.36); 0.032 (1.59) |
| I.128 | 8.409 (1.27); 8.401 (1.43); 8.25 (0.91); 8.246 (1.06); 8.242 (1); 8.238 (0.94); 8.009 (1.37); 7.997 (1.38); 7.386 (0.38); 7.364 (0.43); 7.359 (0.86); 7.337 (0.85); 7.332 (0.55); 7.31 (0.47); 7.298 (1.11); 6.923 (0.52); 6.921 (0.57); 6.893 (1.01); 6.867 (0.48); 6.865 (0.51); 6.667 (1.05); 6.64 (0.96); 0.421 (0.61); 0.41 (15.5); 0.404 (16); 0.392 (0.75); 0.107 (4.21); 0.033 (0.82); −0.02 (0.86) |
| I.129 | 8.438 (0.72); 8.43 (0.77); 8.231 (0.52); 8.228 (0.56); 8.223 (0.53); 8.22 (0.47); 7.991 (0.73); 7.979 (0.73); 7.596 (0.36); 7.59 (0.39); 7.572 (0.42); 7.566 (0.44); 7.41 (0.34); 7.408 (0.32); 7.404 (0.34); 7.297 (0.64); 7.264 (0.33); 7.261 (0.33); 7.24 (0.54); 7.237 (0.51); 6.892 (0.52); 6.864 (0.47); 0.357 (0.61); 0.346 (16); 0.335 (0.74); 0.034 (0.4) |
| IIa.01 [1] | 8.857 (15.86); 8.85 (16); 8.155 (7.5); 8.133 (8.31); 7.733 (6.71); 7.712 (9.11); 7.708 (5.64); 7.704 (4.73); 7.69 (7.03); 7.687 (8.77); 7.683 (4.5); 7.669 (6.06); 7.666 (4.98); 7.588 (5.87); 7.585 (6.24); 7.57 (5.13); 7.568 (8.92); 7.565 (5.62); 7.55 (3.62); 7.547 (3.63); 7.517 (11.38); 7.51 (11.17); 7.372 (4.33); 7.356 (4.69); 7.351 (9.41); 7.336 (9.46); 7.331 (5.5); 7.315 (5.15); 7.286 (8.11); 6.993 (5.14); 6.99 (5.62); 6.975 (5.92); 6.972 (9.43); 6.97 (6.33); 6.954 (4.76); 6.951 (4.96); 6.803 (5.81); 6.8 (10.37); 6.797 (6.24); 6.782 (5.53); 6.779 (9.68); 6.777 (5.75); 2.069 (0.61); 1.88 (1.76); 1.338 (0.85); 1.321 (1.94); 1.303 (2.51); 1.298 (2.52); 1.281 (9.73); 1.263 (1.64); 0.918 (4.82); 0.901 (15.32); 0.883 (6.33); 0.866 (0.35); 0.021 (7.33) |
| IIa.02 [1] | 8.862 (16); 8.855 (15.96); 8.143 (7.47); 8.123 (8.2); 8.122 (8.15); 7.966 (9.4); 7.962 (9.74); 7.946 (9.88); 7.942 (10.02); 7.703 (6); 7.7 (6.7); 7.68 (9.75); 7.678 (9.42); 7.674 (5.12); 7.66 (7.68); 7.656 (9.24); 7.652 (4.68); 7.639 (6.53); 7.635 (5.2); 7.56 (6.32); 7.558 (6.42); 7.543 (5.58); 7.54 (9.22); 7.537 (5.45); 7.523 (3.77); 7.52 (3.64); 7.423 (11.45); 7.416 (15.4); 7.412 (6.05); 7.397 (6.79); 7.395 (7.56); 7.393 (7.46); 7.391 (6.69); 7.377 (6.2); 7.373 (6.08); 7.284 (8.06); 7.063 (9.27); 7.06 (11.07); 7.043 (8.61); 7.039 (9.69); 7.026 (6.46); 7.022 (5.53); 7.007 (8.35); 7.006 (8.35); 7.003 (7.7); 6.987 (5.5); 6.984 (4.93); 2.017 (0.87); 1.798 (13.25); 1.282 (0.69); 0.026 (6.82) |
| IIa.03 [1] | 8.846 (15.65); 8.84 (16); 8.823 (0.92); 8.816 (0.63); 8.121 (10.46); 8.1 (11.28); 7.72 (8.59); 7.717 (9.63); 7.7 (9.24); 7.697 (10.31); 7.682 (9.51); 7.661 (13.02); 7.637 (9.4); 7.619 (5.98); 7.617 (5.8); 7.57 (0.44); 7.54 (8.43); 7.522 (10.63); 7.503 (4.73); 7.486 (0.46); 7.478 (0.44); 7.416 (0.5); 7.39 (13.54); 7.384 (13.8); 7.375 (5.56); 7.358 (9.17); 7.356 (9.52); 7.339 (6.02); 7.336 (6.09); 7.319 (0.52); 7.295 (0.39); 7.284 (0.37); 7.259 (52.44); 7.228 (0.47); 7.208 (0.51); 7.188 (0.34); 7.175 (0.57); 7.169 (0.65); 7.16 (5.08); 7.157 (6.29); 7.138 (10.57); 7.122 (4.74); 7.118 (6); 7.112 (11.34); 7.11 (10.65); 7.092 (9.06); 7.089 (8.92); 1.825 (0.34); 1.723 (1.36); 1.255 (0.47); −0.001 (54.77) |
| IIa.04 [4] | 8.942 (15.92); 8.933 (15.8); 8.919 (1.08); 8.901 (0.6); 8.892 (0.59); 8.054 (0.53); 8.05 (0.51); 8.028 (0.58); 8.023 (0.51); 7.879 (10.62); 7.874 (10.34); 7.852 (11.84); 7.848 (10.85); 7.787 (9.6); 7.761 (12.68); 7.719 (11.58); 7.714 (13.59); 7.711 (13.03); 7.706 (10.25); 7.671 (0.76); 7.666 (0.8); 7.63 (3.85); 7.613 (5.01); 7.604 (8.96); 7.587 (8.95); 7.578 (6.87); 7.568 (6.52); 7.562 (9.25); 7.56 (9.84); 7.556 (10.24); 7.551 (9.56); 7.543 (10.94); 7.54 (11.64); 7.538 (10.8); 7.53 (5.7); 7.516 (16); 7.493 (5.06); 7.402 (12.35); 7.397 (13.09); 7.374 (9.56); 7.37 (8.85); 7.341 (7.75); 7.336 (6.38); 7.316 (10.52); 7.314 (10.85); 7.311 (9.68); 7.29 (5.79); 7.285 (4.84); 7.256 (0.89); 7.23 (0.68); 7.174 (0.36); 7.148 (0.55); 7.123 (0.4); 5.789 (1.09); 3.366 (16.77); 3.342 (0.41); 2.676 (1.45); 2.539 (9.09); 2.533 (11.41); 2.527 (8.18); 2.47 (0.52); 0.022 (4.96) |
| IIa.05 [4] | 7.875 (1.88); 7.87 (1.8); 7.849 (2.07); 7.844 (1.89); 7.7 (1.27); 7.696 (1.04); 7.69 (0.85); 7.677 (1.6); 7.669 (1.57); 7.566 (0.96); 7.561 (0.91); 7.542 (1.65); 7.539 (1.85); 7.536 (1.78); 7.534 (1.73); 7.514 (2.3); 7.509 (2.58); 7.495 (4.67); 7.489 (5.56); 7.463 (1.86); 7.461 (1.87); 7.454 (1.53); 7.435 (0.59); 7.428 (0.41); 7.37 (2.07); 7.365 (2.36); 7.342 (1.8); 7.337 (2.1); 7.335 (1.87); 7.329 (1.13); 7.31 (1.79); 7.308 (1.83); 7.305 (1.52); 7.283 (1.04); 7.278 (0.83); 3.367 (12.9); 2.754 (16); 2.538 (0.99); 2.532 (1.14); 2.526 (0.79) |
| IIa.06 | 8.954 (9.73); 8.945 (9.78); 7.773 (6.63); 7.768 (6.86); 7.746 (7.32); 7.741 (7.46); 7.498 (0.63); 7.488 (0.5); 7.467 (7.94); 7.461 (8.77); 7.457 (13.7); 7.44 (16); 7.432 (8.43); 7.431 (8.49); 7.427 (11.88); 7.406 (5.16); 7.401 (4.91); 7.372 (7.78); 7.367 (8.52); 7.363 (8.42); 7.358 (7.29); 7.301 (16.65); 7.244 (4.25); 7.239 (5.07); 7.218 (5.82); 7.213 (7.09); 7.192 (4.28); 7.187 (12.17); 7.182 (7.08); 7.16 (6.99); 7.155 (5.8); 1.629 (6.36); 0.122 (0.96); 0.11 (21.08); 0.098 (0.84); 0.049 (0.72); 0.038 (17.4); 0.027 (0.68) |
| IIa.07 | 7.77 (1.56); 7.765 (1.55); 7.744 (1.72); 7.738 (1.68); 7.455 (0.76); 7.45 (0.74); 7.43 (1.5); 7.425 (1.44); 7.403 (1.2); 7.398 (1.12); 7.37 (1.8); 7.364 (1.98); 7.359 (2.61); 7.342 (3.53); 7.329 (1.35); 7.299 (5.45); 7.235 (1.03); 7.23 (1.11); 7.209 (1.46); 7.204 (1.56); 7.183 (0.82); 7.178 (0.84); 7.162 (3.01); 7.158 (2.86); 7.147 (2.05); 7.142 (1.69); 7.12 (1.63); 7.115 (1.42); 5.338 (0.61); 2.892 (16); 1.62 (4.22); 0.038 (4.56) |

TABLE 12-continued

| Example | $^1$H-NMR [CDCl$_3$ at 300 Mhz] |
|---|---|
| IIa.08 | 8.082 (1.52); 8.052 (1.42); 7.757 (1.54); 7.752 (1.56); 7.73 (1.7); 7.725 (1.7); 7.66 (0.72); 7.656 (0.97); 7.638 (2.1); 7.633 (2.16); 7.628 (0.86); 7.616 (1.75); 7.611 (2.54); 7.501 (1.17); 7.498 (1.14); 7.479 (0.99); 7.473 (1.68); 7.451 (0.67); 7.448 (0.62); 7.413 (0.73); 7.408 (0.73); 7.387 (1.41); 7.383 (1.4); 7.362 (1.12); 7.356 (1.04); 7.3 (1.26); 7.243 (3.87); 7.19 (0.98); 7.185 (1.09); 7.164 (1.43); 7.16 (1.53); 7.139 (0.77); 7.134 (0.78); 7.095 (1.87); 7.09 (1.66); 7.068 (1.56); 7.063 (1.4); 5.33 (3.52); 2.832 (16); 0.117 (0.4); 0.04 (1.3) |
| IIa.09 | 7.571 (0.77); 7.563 (1.07); 7.559 (0.94); 7.547 (0.85); 7.54 (1.53); 7.534 (0.99); 7.36 (1.34); 7.347 (3.47); 7.33 (2.62); 7.325 (2.11); 7.319 (2.15); 7.302 (2.91); 7.298 (1.84); 7.291 (1.39); 7.283 (1.49); 7.268 (1.66); 7.262 (2.21); 7.239 (1.14); 7.23 (0.43); 6.999 (2.88); 2.975 (16); 2.085 (1.11); 1.673 (0.63); 1.298 (0.69); 0.038 (2.32) |
| IIa.10 | 7.72 (1.51); 7.7 (1.55); 7.69 (1.65); 7.671 (1.61); 7.441 (0.32); 7.423 (0.5); 7.41 (4.13); 7.393 (2.5); 7.382 (1.43); 7.362 (1.27); 7.332 (0.36); 7.301 (2.13); 7.298 (2.97); 7.293 (2.72); 6.968 (0.84); 6.959 (0.96); 6.943 (1); 6.939 (0.92); 6.933 (1.14); 6.929 (0.99); 6.913 (0.78); 6.904 (0.87); 6.83 (1.66); 6.82 (1.43); 6.8 (1.66); 6.79 (1.41); 2.861 (0.46); 2.847 (16); 0.113 (2.6); 0.032 (0.93) |
| IIa.11 | 8.987 (15.81); 8.977 (16); 7.822 (0.32); 7.799 (9.03); 7.795 (9.47); 7.774 (10.69); 7.77 (10.86); 7.716 (0.75); 7.706 (0.68); 7.69 (0.73); 7.681 (0.87); 7.66 (0.33); 7.643 (1.41); 7.636 (7.02); 7.632 (7.3); 7.609 (10.74); 7.605 (10.05); 7.52 (5.69); 7.518 (6.1); 7.512 (6); 7.51 (6.47); 7.502 (11.72); 7.493 (7.05); 7.485 (7.05); 7.477 (11.92); 7.45 (6.62); 7.355 (0.4); 7.332 (15.98); 7.323 (15.67); 7.298 (146.91); 7.221 (1.81); 7.203 (2.64); 7.193 (10.97); 7.191 (10.53); 7.186 (9.67); 7.177 (10.06); 7.175 (11.85); 7.162 (8.51); 7.153 (7.46); 7.148 (1.86); 7.137 (1.03); 7.132 (1.72); 7.123 (1.98); 7.107 (0.37); 7.09 (0.43); 7.052 (0.33); 6.947 (0.76); 5.337 (2.74); 2.046 (0.36); 1.658 (0.43); 1.592 (181.38); 1.463 (0.59); 1.34 (0.71); 1.321 (0.88); 1.291 (1.59); 1.219 (3.23); 1.14 (1.67); 0.917 (0.53); 0.231 (0.58); 0.047 (4.51); 0.036 (138.67); 0.025 (4.76); −0.163 (0.48) |
| IIa.12 | 7.521 (1.11); 7.518 (1.09); 7.514 (1.19); 7.511 (0.94); 7.496 (0.99); 7.491 (1.39); 7.485 (0.89); 7.374 (1.44); 7.361 (3.36); 7.345 (2.61); 7.339 (1.82); 7.334 (1.7); 7.301 (4.16); 7.182 (1.82); 7.176 (3.24); 7.175 (3.24); 7.159 (3.04); 7.153 (3.28); 7.144 (0.39); 7.09 (3.1); 7.086 (2.89); 7.017 (0.55); 6.998 (0.38); 6.995 (0.37); 5.339 (0.4); 2.897 (16); 2.839 (1.05); 1.652 (1.95); 1.221 (0.43); 0.037 (3.75) |
| IIa.13 | 8.076 (1.66); 8.049 (1.75); 7.655 (0.83); 7.651 (0.97); 7.628 (3.23); 7.603 (3.74); 7.498 (2.68); 7.478 (2.43); 7.473 (2.92); 7.45 (0.74); 7.302 (0.83); 7.17 (0.42); 7.153 (4.47); 7.14 (1.75); 7.131 (2); 7.126 (2.54); 7.116 (1.89); 7.108 (3.6); 7.097 (0.5); 2.84 (16); 0.039 (0.52) |
| IIa.14 | 8.093 (0.7); 8.089 (0.72); 8.065 (0.76); 8.06 (0.77); 7.588 (0.32); 7.578 (0.33); 7.571 (0.34); 7.565 (0.45); 7.558 (0.46); 7.548 (0.42); 7.541 (0.43); 7.427 (0.46); 7.404 (0.51); 7.396 (1.82); 7.369 (3.72); 7.356 (1.63); 7.351 (1.72); 7.342 (3.45); 7.328 (3.27); 7.314 (1.19); 7.302 (2.41); 7.188 (2.41); 7.184 (2.46); 6.886 (1.43); 6.882 (1.58); 6.858 (1.32); 6.854 (1.37); 6.757 (1.65); 6.753 (1.64); 6.73 (1.53); 6.726 (1.45); 4.007 (16); 2.88 (14.38); 2.831 (8.68); 1.746 (2.78); 0.034 (1.93) |
| IIa.15 | 8.948 (7.36); 8.939 (7.42); 7.526 (0.35); 7.519 (0.51); 7.495 (6.95); 7.493 (7.18); 7.488 (6.17); 7.484 (5.96); 7.469 (16); 7.461 (7.39); 7.457 (7.88); 7.453 (8.82); 7.421 (2.94); 7.401 (2.87); 7.393 (5.84); 7.373 (5.88); 7.365 (3.8); 7.345 (3.51); 7.3 (35.3); 7.139 (3.36); 7.134 (3.56); 7.111 (4.76); 7.108 (5.24); 7.084 (2.86); 7.08 (2.85); 6.946 (3.7); 6.942 (6.46); 6.937 (3.48); 6.918 (3.27); 6.914 (5.67); 6.91 (3.08); 1.6 (35.18); 0.049 (1.32); 0.038 (34.78); 0.027 (1.3) |
| IIa.16 | 7.652 (0.45); 7.414 (0.83); 7.4 (2.84); 7.395 (2.07); 7.386 (2.27); 7.376 (4.09); 7.366 (1.85); 7.358 (2.28); 7.338 (1); 7.3 (7.59); 7.274 (2.7); 7.27 (2.72); 7.127 (0.93); 7.123 (1.02); 7.1 (1.44); 7.096 (1.57); 7.073 (0.79); 7.068 (0.8); 6.889 (1.01); 6.885 (1.81); 6.881 (1.04); 6.862 (0.91); 6.857 (1.62); 6.853 (0.91); 3.107 (2.2); 2.863 (16); 2.047 (1.06); 1.607 (3.56); 0.038 (7.28) |
| IIa.17 | 8.667 (1.28); 8.193 (1.27); 8.165 (1.44); 8.082 (1.23); 8.054 (1.42); 7.796 (0.6); 7.791 (0.69); 7.773 (1.1); 7.768 (1.44); 7.745 (0.96); 7.741 (0.9); 7.702 (1.23); 7.678 (1.46); 7.651 (0.68); 7.305 (6.67); 7.215 (0.73); 7.195 (0.78); 7.188 (1.68); 7.167 (1.69); 7.16 (1.06); 7.139 (0.98); 6.961 (0.98); 6.957 (1.09); 6.934 (1.59); 6.93 (1.75); 6.907 (0.84); 6.903 (0.87); 6.439 (1.01); 6.435 (1.85); 6.43 (1.15); 6.411 (0.95); 6.407 (1.72); 2.629 (16); 1.659 (5.22); 1.531 (0.87); 1.318 (0.36); 1.298 (1.55); 1.288 (0.84); 1.279 (0.47); 1.255 (0.35); 0.126 (1.36); 0.114 (32.76); 0.102 (1.25); 0.043 (4.69) |
| IIa.18 | 8.094 (1.44); 8.064 (1.41); 7.696 (0.62); 7.691 (1.36); 7.688 (1.4); 7.682 (1.15); 7.674 (0.78); 7.669 (2.05); 7.66 (2.1); 7.655 (1.75); 7.644 (1.33); 7.64 (0.64); 7.536 (1.1); 7.532 (1.14); 7.513 (0.84); 7.508 (1.54); 7.486 (0.6); 7.482 (0.59); 7.371 (1.12); 7.364 (3.73); 7.351 (0.85); 7.344 (1.62); 7.323 (1.62); 7.316 (1.04); 7.302 (4.09); 7.295 (1.1); 7.088 (0.92); 7.083 (0.99); 7.06 (1.47); 7.056 (1.57); 7.033 (0.78); 7.029 (0.79); 6.831 (1); 6.826 (1.77); 6.822 (1.01); 6.803 (0.91); 6.799 (1.6); 6.795 (0.9); 2.798 (16); 2.745 (0.34); 0.124 (0.34); 0.112 (8.71); 0.1 (0.34); 0.04 (3.93) |
| IIa.19 | 8.253 (6.5); 8.225 (7.63); 8.188 (0.38); 8.16 (0.41); 8.092 (0.83); 7.849 (0.41); 7.844 (0.42); 7.82 (0.49); 7.773 (3.45); 7.768 (3.92); 7.75 (5.18); 7.745 (7.76); 7.739 (6.03); 7.735 (5.84); 7.731 (5.37); 7.723 (3.72); 7.718 (6.34); 7.707 (9.76); 7.682 (0.54); 7.668 (1.94); 7.655 (6.53); 7.629 (5.59); 7.605 (2.38); 7.462 (0.47); 7.441 (6.13); 7.434 (16); 7.421 (3.82); 7.414 (7.76); 7.393 (7.22); 7.386 (4.88); 7.366 (4.32); 7.344 (6.5); 7.303 (10.28); 7.254 (0.65); 7.236 (0.46); 7.164 (13.77); 7.158 (5.23); 7.154 (4.65); 7.13 (7.14); 7.127 (7.01); 7.104 (3.78); 7.099 (3.52); 7.074 (1.26); 7.055 (0.83); 7.019 (0.5); 7.006 (5.47); 7.002 (8.24); 6.998 (4.41); 6.985 (7.59); 6.979 (5.25); 6.974 (7.43); 6.97 (4.11); 6.964 (0.94); 6.953 (0.36); 6.936 (0.5); 6.921 (0.61); 6.913 (0.52); 6.894 (0.81); 6.889 (0.46); 6.88 (0.68); 6.874 (0.65); 2.653 (4.35); 1.671 (12.51); 1.237 (1.05); 1.226 (7.18); 1.147 (3.7); 1.134 (0.43); 0.118 (0.92); 0.053 (0.37); 0.042 (9.69) |
| IIa.20 | 7.442 (1.15); 7.436 (1.3); 7.415 (2.68); 7.409 (2.46); 7.399 (0.33); 7.393 (0.69); 7.386 (3.51); 7.374 (3.61); 7.363 (2.96); 7.347 (3.62); 7.342 (1.54); 7.32 (1.41); 7.312 (0.35); 7.302 (1.29); |

TABLE 12-continued

NMR peak lists

| Example | $^1$H-NMR [CDCl$_3$ at 300 Mhz] |
|---|---|
|  | 7.222 (2.75); 7.217 (2.66); 7.011 (1.91); 7.006 (1.92); 6.984 (1.65); 6.979 (1.61); 2.861 (16); 2.079 (0.9); 1.774 (0.39); 1.293 (0.5); 0.032 (1.11) |
| IIa.21 | 8.089 (1.44); 8.073 (0.33); 8.06 (1.39); 7.689 (0.67); 7.684 (1.2); 7.679 (1.26); 7.674 (1.1); 7.661 (1.9); 7.652 (1.89); 7.647 (1.68); 7.637 (1.28); 7.632 (0.54); 7.53 (1.1); 7.527 (1.07); 7.508 (0.85); 7.502 (1.54); 7.48 (0.6); 7.477 (0.56); 7.412 (1.04); 7.407 (1.17); 7.385 (2.12); 7.38 (2.06); 7.372 (0.41); 7.366 (0.34); 7.354 (0.33); 7.336 (2.01); 7.329 (0.86); 7.315 (3.54); 7.309 (3.58); 7.302 (4.86); 7.282 (1.24); 6.949 (1.65); 6.944 (1.67); 6.922 (1.43); 6.917 (1.44); 4.197 (0.41); 4.173 (1.24); 4.149 (1.26); 4.126 (0.43); 2.804 (16); 2.086 (5.69); 1.69 (2.33); 1.323 (1.52); 1.299 (3.05); 1.275 (1.48); 0.039 (3.45) |
| IIa.22 | 8.119 (8.17); 8.098 (2.93); 8.075 (0.61); 7.819 (0.34); 7.767 (2.35); 7.742 (3.12); 7.738 (3.28); 7.718 (1.26); 7.713 (1.43); 7.695 (2.6); 7.69 (2.52); 7.668 (2.51); 7.662 (1.88); 7.648 (2.6); 7.644 (2.61); 7.621 (2.67); 7.597 (0.96); 7.474 (0.5); 7.464 (0.7); 7.454 (0.61); 7.304 (40.56); 7.289 (1.25); 7.282 (2.61); 7.262 (2.54); 7.254 (1.89); 7.234 (1.91); 7.193 (3.94); 7.165 (2.53); 7.135 (2.48); 7.124 (0.35); 7.111 (0.49); 7.104 (0.34); 7.097 (0.59); 7.076 (0.6); 7.07 (0.35); 6.954 (6.51); 6.864 (1.82); 6.859 (1.68); 6.837 (3.44); 6.832 (3.07); 6.81 (1.7); 6.805 (1.49); 6.773 (2.55); 6.593 (0.66); 6.578 (0.49); 6.566 (0.65); 6.55 (0.79); 6.522 (0.41); 5.344 (16); 4.258 (0.34); 2.053 (0.44); 1.594 (42.05); 0.113 (0.52); 0.054 (1.39); 0.043 (40.32); 0.032 (1.52) |
| IIa.23 | 8.988 (15.67); 8.979 (16); 7.796 (8.56); 7.792 (9.47); 7.772 (10.17); 7.767 (10.99); 7.643 (0.68); 7.634 (7.23); 7.63 (7.97); 7.607 (11.12); 7.603 (10.85); 7.5 (11.2); 7.475 (11.84); 7.448 (6.61); 7.358 (7.94); 7.349 (8.81); 7.33 (20.09); 7.321 (21.54); 7.297 (54.56); 7.237 (5.63); 7.22 (6.1); 7.207 (10.63); 7.19 (10.42); 7.145 (6.24); 7.135 (5.78); 7.12 (6.44); 7.115 (4.45); 7.11 (6.18); 7.105 (3.83); 7.09 (3.42); 7.08 (3.17); 2.392 (0.43); 1.597 (58.65); 1.29 (0.43); 1.218 (4.08); 1.14 (2.06); 0.046 (1.82); 0.035 (53.12); 0.024 (2.09) |
| IIa.24 | 7.463 (1.34); 7.435 (3.42); 7.416 (0.62); 7.407 (5.62); 7.393 (1.47); 7.384 (2.29); 7.381 (1.77); 7.362 (1.26); 7.331 (0.33); 7.302 (2.35); 7.298 (1.44); 7.293 (1.77); 7.284 (3.19); 7.28 (2.88); 7.27 (0.94); 7.266 (1.12); 7.261 (0.77); 7.026 (1.93); 7.022 (1.9); 6.999 (1.73); 6.994 (1.65); 2.859 (16); 1.292 (0.35); 0.113 (5.64); 0.036 (1.67) |
| IIa.25 | 8.337 (0.44); 8.111 (1.54); 8.082 (1.49); 7.702 (0.66); 7.697 (1.31); 7.693 (1.39); 7.688 (1.17); 7.675 (1.96); 7.666 (2.04); 7.661 (1.73); 7.65 (1.27); 7.646 (0.6); 7.54 (1.13); 7.537 (1.11); 7.518 (0.88); 7.512 (1.6); 7.49 (0.64); 7.487 (0.6); 7.415 (1.2); 7.387 (3.08); 7.377 (3.86); 7.36 (1.92); 7.302 (1.18); 7.259 (0.98); 7.254 (1.41); 7.25 (1.03); 7.231 (0.71); 7.226 (0.97); 7.222 (0.68); 6.964 (1.75); 6.96 (1.71); 6.936 (1.56); 6.932 (1.49); 2.8 (16); 0.119 (3.21); 0.039 (0.77) |
| IIb.01 | 8.874 (13.84); 7.751 (6.89); 7.746 (7.31); 7.724 (7.71); 7.719 (8.05); 7.617 (1.65); 7.596 (0.66); 7.585 (6.07); 7.564 (8); 7.56 (10.36); 7.554 (7.12); 7.538 (10); 7.527 (2.3); 7.509 (1.4); 7.503 (3.24); 7.498 (3.25); 7.478 (5.1); 7.476 (6.24); 7.474 (5.75); 7.471 (5.72); 7.452 (5.98); 7.447 (5.72); 7.37 (8.36); 7.364 (9.85); 7.342 (5.9); 7.337 (5.85); 7.3 (16.95); 7.288 (5.37); 7.283 (4.83); 7.264 (5.87); 7.262 (6.43); 7.258 (5.88); 7.257 (5.58); 7.237 (3.78); 7.232 (3.46); 3.32 (0.33); 2.084 (0.59); 1.614 (9.15); 1.322 (0.35); 1.293 (1.18); 0.11 (1.35); 0.049 (0.44); 0.038 (13.12); 0.027 (0.52) |
| IIb.02 | 7.737 (1.44); 7.732 (1.5); 7.71 (1.61); 7.705 (1.65); 7.503 (0.69); 7.498 (0.68); 7.48 (2.39); 7.476 (2.94); 7.471 (2.8); 7.467 (1.86); 7.453 (4.64); 7.447 (1.68); 7.437 (1.24); 7.392 (1.86); 7.386 (2.11); 7.365 (1.19); 7.36 (1.1); 7.298 (2.23); 7.275 (1.07); 7.269 (0.98); 7.25 (1.21); 7.248 (1.3); 7.245 (1.21); 7.243 (1.12); 7.224 (0.79); 7.218 (0.72); 2.96 (16); 1.63 (2.84); 0.111 (1.48); 0.037 (2.01) |
| IIb.03 | 7.559 (1.18); 7.556 (1.17); 7.533 (1.35); 7.53 (1.34); 7.478 (1.49); 7.47 (1.78); 7.466 (2.54); 7.449 (3.2); 7.435 (1.21); 7.332 (1.14); 7.33 (1.09); 7.304 (8.43); 7.185 (1.62); 7.159 (2.41); 7.133 (1.04); 2.981 (16); 2.262 (12.4); 1.609 (11.61); 0.113 (0.76); 0.042 (6.55) |
| IIb.04 | 7.535 (0.79); 7.53 (0.94); 7.522 (1.19); 7.515 (0.82); 7.506 (0.99); 7.502 (1.23); 7.498 (2.17); 7.489 (1.74); 7.484 (2.93); 7.469 (2.77); 7.464 (1.6); 7.455 (1.27); 7.302 (5.27); 7.294 (0.45); 7.274 (1.85); 7.271 (1.87); 7.266 (1.43); 7.248 (4.38); 7.236 (1.38); 7.228 (1.34); 2.984 (16); 1.603 (5.63); 0.112 (0.61); 0.04 (4.75) |
| IIb.06 | 7.594 (1.55); 7.566 (1.7); 7.509 (0.33); 7.496 (2.58); 7.478 (1.63); 7.469 (0.84); 7.447 (0.76); 7.304 (8.62); 7.183 (1.24); 7.178 (1.35); 7.078 (0.75); 7.073 (0.71); 7.051 (0.67); 7.046 (0.61); 5.455 (0.63); 5.343 (0.85); 2.95 (10.32); 2.436 (7.9); 2.325 (1.3); 1.604 (16); 0.112 (0.82); 0.042 (7.6) |
| IIb.07 | 7.705 (1.4); 7.685 (1.39); 7.675 (1.5); 7.656 (1.47); 7.521 (1.65); 7.516 (1.81); 7.511 (2.01); 7.508 (1.6); 7.494 (3.58); 7.478 (1.15); 7.304 (18); 7.215 (1.38); 7.205 (1.51); 7.186 (1.37); 7.176 (1.49); 7.053 (0.87); 7.044 (0.77); 7.027 (1.1); 7.024 (0.94); 7.018 (0.99); 7.014 (0.79); 6.998 (0.78); 6.988 (0.68); 2.959 (16); 1.598 (27.82); 0.112 (1.74); 0.053 (0.65); 0.042 (16.84); 0.031 (0.57) |
| IIb.08 | 7.664 (1.56); 7.636 (1.79); 7.522 (1.32); 7.516 (0.92); 7.51 (0.81); 7.498 (2.26); 7.479 (0.66); 7.434 (0.77); 7.424 (1.6); 7.416 (1.74); 7.406 (0.85); 7.304 (10.23); 7.269 (0.98); 7.261 (0.92); 7.241 (0.86); 7.233 (0.81); 7.086 (0.74); 7.078 (0.79); 6.876 (0.42); 6.869 (0.38); 6.848 (0.38); 6.84 (0.37); 5.613 (1.14); 5.344 (1.87); 2.952 (9.26); 1.6 (16); 0.112 (1); 0.053 (0.33); 0.042 (9.27); 0.032 (0.32) |
| IIb.09 | 7.539 (2.4); 7.496 (0.46); 7.487 (2.89); 7.473 (1.3); 7.464 (2.78); 7.441 (1.17); 7.305 (11.01); 7.29 (0.34); 7.261 (2.59); 7.255 (6.17); 7.228 (0.33); 5.345 (0.91); 2.955 (16); 2.453 (13.05); 1.598 (11.44); 0.055 (0.37); 0.044 (10.89); 0.034 (0.41) |
| IIb.10 | 7.503 (0.91); 7.488 (3.47); 7.478 (1.45); 7.472 (1.55); 7.469 (1.56); 7.464 (2.12); 7.453 (1.24); 7.373 (0.91); 7.356 (0.92); 7.343 (1.36); 7.326 (1.38); 7.303 (25.85); 7.231 (0.8); 7.221 (0.7); 7.205 (0.9); 7.201 (0.65); 7.195 (0.82); 7.191 (0.54); 7.175 (0.54); 7.166 (0.48); 5.343 (16); 2.956 (12.46); 2.052 (2.33); 1.591 (33.58); 0.112 (1.97); 0.053 (0.87); 0.042 (23.64); 0.031 (0.85) |
| IIb.11 | 7.737 (2.82); 7.729 (2.95); 7.51 (1.25); 7.494 (3.49); 7.476 (3.17); 7.472 (2.38); 7.468 (2.79); 7.447 (2.14); 7.439 (2.05); 7.338 (3.64); 7.304 (27.4); 5.344 (2.06); 2.954 (16); 2.053 (0.77); 1.595 (43.11); 1.579 (0.36); 0.112 (0.38); 0.054 (0.93); 0.043 (24.76); 0.032 (0.93) |

TABLE 12-continued

NMR peak lists

| Example | $^1$H-NMR [CDCl$_3$ at 300 Mhz] |
|---|---|
| IIb.12 | 7.65 (0.33); 7.492 (0.53); 7.483 (2.91); 7.469 (1.25); 7.46 (2.9); 7.438 (1.21); 7.393 (1.04); 7.367 (2.55); 7.341 (1.99); 7.304 (55.38); 7.267 (1.56); 7.243 (0.93); 7.212 (1.5); 7.185 (1.09); 6.953 (0.33); 5.63 (0.36); 5.344 (8.62); 2.968 (16); 2.531 (12.83); 2.443 (0.83); 2.053 (2.85); 1.596 (95.82); 0.112 (7.27); 0.054 (1.45); 0.043 (46.71); 0.032 (1.84) |
| IIb.13 | 7.48 (1.48); 7.474 (0.96); 7.466 (1); 7.462 (1.09); 7.455 (2.34); 7.435 (2.28); 7.407 (1.08); 7.304 (7.09); 7.024 (1.17); 7.02 (1.08); 6.997 (1.05); 6.992 (0.92); 6.943 (1.07); 6.939 (0.86); 6.915 (0.96); 6.911 (0.76); 4.009 (9.84); 3.934 (0.59); 2.964 (9.22); 1.607 (16); 0.042 (5.72) |
| IIb.14 | 8.829 (16); 8.159 (0.38); 8.148 (3.46); 8.142 (2.54); 8.136 (2.13); 8.124 (3.95); 8.116 (3.9); 8.102 (0.46); 7.787 (2.1); 7.779 (2.93); 7.765 (2.76); 7.759 (3.87); 7.754 (5.88); 7.743 (1.03); 7.735 (1.61); 7.728 (2.44); 7.712 (5.67); 7.705 (5.04); 7.7 (5.68); 7.689 (7.85); 7.678 (3.87); 7.674 (4.31); 7.667 (3.81); 7.651 (1.48); 7.645 (1.02); 7.474 (2.07); 7.453 (2.24); 7.446 (4.98); 7.426 (5.02); 7.418 (3.22); 7.398 (3.06); 7.3 (4.83); 7.213 (3.09); 7.209 (5.7); 7.204 (3.88); 7.186 (3.05); 7.181 (8.03); 7.177 (5.24); 7.154 (5.44); 7.15 (4.61); 7.127 (2.57); 7.122 (2.28); 1.672 (4.31); 1.304 (0.45); 1.298 (0.45); 0.921 (0.47); 0.116 (7.82); 0.04 (4.97) |
| IIb.15 | 8.886 (16); 7.631 (1.52); 7.608 (1.09); 7.599 (4.82); 7.576 (4.89); 7.567 (5.13); 7.563 (6.25); 7.559 (5.13); 7.546 (7.3); 7.544 (9.06); 7.532 (1.39); 7.528 (1.88); 7.511 (1.45); 7.485 (2.55); 7.465 (2.85); 7.458 (5.09); 7.438 (6.1); 7.43 (3.91); 7.41 (3.66); 7.298 (11.19); 7.2 (2.79); 7.196 (5.65); 7.192 (4.16); 7.187 (8.55); 7.182 (3.24); 7.173 (7); 7.168 (6.89); 7.16 (7.14); 7.156 (2.98); 7.145 (3.55); 7.141 (2.62); 1.607 (14.27); 0.12 (0.77); 0.108 (16.99); 0.096 (0.66); 0.046 (0.41); 0.036 (9.57); 0.025 (0.37) |
| IIb.16 | 7.496 (1.26); 7.488 (1.07); 7.481 (3.53); 7.467 (2.17); 7.463 (2.39); 7.46 (2.77); 7.453 (1.69); 7.44 (1.68); 7.433 (1.14); 7.413 (1); 7.298 (2.83); 7.217 (0.97); 7.212 (1.81); 7.208 (1.33); 7.19 (1.94); 7.185 (2.26); 7.181 (1.08); 7.163 (1.68); 7.158 (1.44); 7.136 (0.83); 7.131 (0.75); 2.961 (16); 1.618 (2.91); 1.296 (0.37); 0.11 (1.13); 0.036 (2.58) |
| IIb.17 | 8.048 (0.97); 8.04 (0.73); 8.035 (0.77); 8.023 (0.72); 8.016 (1.14); 7.723 (0.75); 7.716 (0.6); 7.706 (0.93); 7.7 (0.86); 7.691 (1.5); 7.653 (0.5); 7.638 (1.85); 7.633 (1.91); 7.63 (1.51); 7.62 (2.5); 7.609 (1.13); 7.605 (1.42); 7.602 (1.19); 7.477 (0.59); 7.457 (0.65); 7.45 (1.43); 7.429 (1.44); 7.422 (0.94); 7.402 (0.89); 7.298 (2); 7.242 (0.94); 7.238 (1.73); 7.234 (1.06); 7.215 (0.77); 7.21 (1.35); 7.206 (0.79); 7.172 (0.91); 7.168 (0.81); 7.145 (1.49); 7.141 (1.38); 7.118 (0.73); 7.113 (0.68); 2.914 (16); 1.656 (1.69); 0.113 (2.02); 0.039 (2.09) |
| IIb.18 | 7.51 (0.97); 7.503 (1.51); 7.501 (1.44); 7.485 (4.18); 7.478 (2.4); 7.47 (2.62); 7.465 (1.68); 7.458 (1.5); 7.448 (1.82); 7.421 (2.87); 7.394 (1.25); 7.302 (6.27); 7.301 (6.11); 7.294 (1.92); 7.273 (1.26); 7.267 (1.21); 2.962 (16); 1.599 (5.86); 0.112 (0.83); 0.041 (5.46) |
| IIb.19 | 10.183 (0.63); 8.922 (16); 8.022 (9.45); 8 (9.45); 7.706 (1.61); 7.681 (1.56); 7.674 (4.52); 7.65 (4.77); 7.642 (3.59); 7.62 (7.75); 7.615 (4.4); 7.603 (5.34); 7.598 (4.17); 7.589 (1.67); 7.583 (1.89); 7.571 (1.32); 7.567 (1.58); 7.41 (9.77); 7.38 (9.69); 7.304 (28.2); 5.343 (3.36); 1.598 (29.49); 1.306 (0.62); 0.923 (0.6); 0.111 (1.51); 0.052 (1.03); 0.041 (27.89); 0.03 (1.06) |
| IIb.20 | 7.881 (0.53); 7.853 (0.62); 7.727 (0.55); 7.721 (0.58); 7.557 (0.39); 7.55 (0.39); 7.529 (0.34); 7.523 (0.41); 7.51 (0.48); 7.492 (0.81); 7.304 (6.36); 2.968 (3.21); 1.603 (16); 0.111 (1.34); 0.041 (4.53) |
| IIb.21 | 10.185 (0.63); 9.013 (0.44); 8.995 (16); 7.982 (5.15); 7.963 (5.33); 7.952 (5.67); 7.933 (5.49); 7.68 (1.64); 7.654 (1.68); 7.648 (4.74); 7.623 (4.57); 7.616 (3.53); 7.592 (3.85); 7.583 (4.14); 7.577 (3.89); 7.566 (4.48); 7.561 (3.92); 7.551 (1.82); 7.545 (2.07); 7.534 (1.4); 7.529 (1.77); 7.304 (67.59); 7.244 (5.64); 7.218 (6.51); 7.214 (5.72); 7.188 (5.15); 6.953 (0.42); 5.344 (1.09); 1.595 (103.18); 1.303 (0.76); 0.924 (0.79); 0.112 (5.84); 0.053 (2.57); 0.042 (64.52); 0.032 (2.37) |
| IIb.22 | 7.718 (0.66); 7.708 (0.78); 7.696 (0.91); 7.686 (1.25); 7.639 (0.43); 7.621 (2.7); 7.618 (2.37); 7.612 (1.41); 7.596 (1.23); 7.525 (0.67); 7.502 (0.67); 7.493 (0.64); 7.487 (0.85); 7.483 (0.69); 7.472 (0.93); 7.468 (1.26); 7.304 (7.77); 2.974 (9.1); 1.604 (16); 0.041 (6.69) |
| IIb.23 | 7.548 (1.15); 7.522 (1.63); 7.519 (1.72); 7.508 (1.21); 7.493 (3.23); 7.49 (4.29); 7.478 (1.39); 7.471 (1.74); 7.466 (2.34); 7.372 (4.02); 7.347 (2.38); 7.344 (2.47); 7.304 (12.58); 2.972 (16); 1.592 (9.63); 0.053 (0.42); 0.043 (13.16); 0.032 (0.46) |
| IVa.01 | 8.679 (15.79); 8.67 (15.95); 8.039 (5.85); 8.034 (6.54); 8.009 (7.34); 7.622 (5.59); 7.617 (4.95); 7.614 (4.31); 7.597 (8.96); 7.59 (8.62); 7.567 (0.4); 7.532 (2.6); 7.526 (3.52); 7.509 (8.03); 7.503 (6.38); 7.499 (3.36); 7.484 (16); 7.477 (14.19); 7.457 (5.96); 7.453 (6.46); 7.434 (2.54); 7.43 (2.02); 7.3 (16.48); 7.232 (6.86); 7.228 (7.61); 7.206 (7.83); 7.202 (8.81); 7.181 (3.9); 7.176 (3.6); 7.156 (18.92); 7.149 (16.01); 7.13 (5.71); 7.125 (4.98); 6.928 (8.64); 6.924 (10.31); 6.901 (7.53); 6.897 (8.08); 6.883 (6.19); 6.878 (5.12); 6.858 (9.07); 6.853 (7.98); 6.832 (4.27); 6.828 (3.84); 6.754 (11.03); 5.565 (6.67); 3.852 (5.68); 3.447 (0.44); 2.039 (1.99); 1.768 (0.55); 1.297 (0.64); 0.054 (0.54); 0.043 (17.12); 0.032 (0.6) |
| IVa.02 | 8.072 (1.37); 8.044 (1.31); 7.658 (2.56); 7.632 (3.96); 7.607 (1.13); 7.602 (0.7); 7.507 (1.06); 7.503 (1.1); 7.48 (1.35); 7.457 (0.59); 7.453 (0.58); 7.36 (3.64); 7.298 (2.07); 6.991 (0.62); 6.984 (0.67); 6.967 (0.73); 6.959 (1.09); 6.943 (0.74); 6.94 (0.64); 6.925 (0.77); 6.76 (0.41); 6.732 (1.34); 6.716 (1.85); 6.711 (2.89); 6.703 (1.68); 6.697 (2.8); 6.683 (0.44); 3.896 (1.71); 2.816 (16); 0.113 (0.48); 0.038 (2.07) |
| IVa.03 | 8.97 (8.18); 8.961 (8.3); 7.473 (0.41); 7.464 (0.46); 7.442 (6.8); 7.438 (7.14); 7.434 (7.21); 7.431 (7.12); 7.415 (16); 7.407 (8.46); 7.402 (9.63); 7.37 (0.89); 7.3 (9.85); 7.169 (2.39); 7.164 (2.59); 7.143 (4.88); 7.139 (5.12); 7.118 (3.62); 7.114 (3.85); 7.019 (4.57); 7.015 (4.68); 6.992 (6.52); 6.988 (6.06); 6.957 (6.19); 6.952 (7.06); 6.93 (5.03); 6.925 (5.23); 6.861 (4.19); 6.856 (3.9); 6.836 (4.8); 6.834 (4.85); 6.831 (4.87); 6.81 (2.66); 6.804 (2.48); 3.87 (7.01); 1.659 (6.91); 0.11 (3.07); 0.048 (0.41); 0.037 (10.16); 0.026 (0.36) |
| IVa.04 | 8.962 (8.04); 8.953 (8.1); 7.492 (0.66); 7.467 (10.51); 7.461 (12.07); 7.456 (12.24); 7.452 (8.77); 7.447 (8.07); 7.442 (16); 7.425 (4.87); 7.395 (0.98); 7.3 (12.27); 7.028 (2.22); 7.02 (2.26); 7.003 (2.96); 6.995 (4.25); 6.988 (2.55); 6.967 (3.07); 6.962 (3); 6.817 (1.73); 6.812 (2.11); 6.789 (8.4); 6.781 (10.35); 6.764 (5.17); 6.756 (4.48); 6.737 (4.94); 6.729 (1.44); 6.71 (1.73); 3.91 (6.16); 1.641 (7.48); 0.109 (4.86); 0.047 (0.48); 0.036 (13.07); 0.025 (0.48) |

TABLE 12-continued

NMR peak lists

| Example | $^1$H-NMR [CDCl$_3$ at 300 Mhz] |
|---|---|
| IVa.05 | 7.356 (0.5); 7.35 (2.95); 7.346 (1.8); 7.337 (1.44); 7.325 (3.63); 7.307 (1.29); 7.3 (1.71); 7.254 (2.72); 7.249 (2.72); 7.164 (0.63); 7.159 (0.68); 7.137 (1.29); 7.134 (1.3); 7.113 (0.95); 7.108 (1.04); 6.962 (2.84); 6.957 (2.09); 6.94 (2.04); 6.935 (3.06); 6.931 (1.72); 6.86 (1.16); 6.855 (1.08); 6.835 (1.25); 6.83 (1.29); 6.809 (0.64); 6.804 (0.61); 3.84 (2.27); 2.89 (16); 1.736 (0.59); 0.037 (1.48) |
| IVa.06 | 7.386 (3.57); 7.372 (1.48); 7.362 (2.83); 7.341 (1.26); 7.311 (3.62); 7.3 (25.35); 7.023 (0.63); 7.016 (0.66); 6.998 (0.76); 6.99 (1.13); 6.975 (0.75); 6.971 (0.64); 6.957 (0.76); 6.789 (0.44); 6.761 (1.37); 6.744 (1.95); 6.738 (3.22); 6.726 (3.03); 6.711 (0.47); 3.872 (2.36); 2.88 (16); 1.592 (32.97); 0.049 (0.58); 0.038 (15.66); 0.028 (0.62) |
| IVa.07 | 8.064 (1.47); 8.034 (1.39); 7.627 (2.63); 7.622 (1.11); 7.604 (2.41); 7.6 (2.74); 7.596 (1.73); 7.58 (1.25); 7.575 (0.69); 7.481 (1.14); 7.477 (1.13); 7.459 (0.88); 7.453 (1.56); 7.431 (0.63); 7.427 (0.59); 7.304 (3.83); 7.137 (0.66); 7.132 (0.69); 7.11 (1.33); 7.107 (1.34); 7.086 (0.99); 7.081 (1.07); 6.948 (3.01); 6.944 (3.08); 6.922 (3.16); 6.917 (3.28); 6.84 (1.21); 6.835 (1.09); 6.815 (1.3); 6.813 (1.27); 6.81 (1.27); 6.789 (0.63); 6.784 (0.61); 3.862 (1.75); 2.839 (16); 0.12 (1.7); 0.042 (0.91) |
| IXa.04 | 7.421 (0.49); 7.415 (0.54); 7.397 (0.55); 7.391 (0.59); 7.308 (0.33); 7.3 (0.81); 7.283 (0.55); 7.277 (0.52); 7.256 (0.42); 7.251 (0.37); 6.998 (0.47); 6.995 (0.45); 6.974 (0.8); 6.971 (0.76); 6.949 (0.36); 6.947 (0.34); 6.729 (0.79); 6.703 (0.72); 4.826 (2.25); 1.665 (1.22); 1.038 (0.35); 1.031 (0.68); 1.027 (0.47); 1.012 (0.57); 1.004 (2.42); 0.981 (1.47); 0.899 (0.56); 0.894 (0.51); 0.874 (1.28); 0.869 (0.45); 0.864 (0.36); 0.848 (0.72); 0.846 (0.76); 0.346 (0.61); 0.335 (16); 0.324 (0.61); 0.182 (0.53); 0.049 (0.65) |
| Va.01 | 8.897 (14.04); 8.889 (14.22); 7.771 (10.43); 7.766 (11.48); 7.762 (11.51); 7.758 (9.94); 7.591 (2.65); 7.574 (3.27); 7.569 (2.94); 7.557 (10.36); 7.546 (11.49); 7.538 (8.76); 7.534 (6.74); 7.525 (16); 7.516 (8.73); 7.505 (10.41); 7.496 (11.11); 7.485 (2.76); 7.477 (5.7); 7.463 (2.75); 7.298 (6.03); 7.183 (6.14); 7.18 (6.22); 7.154 (10.96); 7.151 (10.92); 7.125 (5.3); 7.122 (5.16); 6.894 (10.22); 6.869 (6.43); 6.865 (9.36); 2.07 (0.61); 1.71 (6.24); 1.285 (0.37); 0.104 (6.74); 0.024 (5.73) |
| Va.02 | 7.655 (2.75); 7.651 (2.68); 7.523 (1.18); 7.504 (1.28); 7.495 (2.24); 7.488 (1.58); 7.475 (3.99); 7.469 (1.63); 7.467 (1.48); 7.454 (1.14); 7.446 (1.6); 7.444 (1.61); 7.423 (1.21); 7.414 (0.38); 7.392 (0.43); 7.3 (5.44); 7.163 (1.05); 7.16 (1.06); 7.134 (1.82); 7.131 (1.8); 7.105 (0.89); 7.102 (0.87); 6.77 (1.11); 6.766 (1.68); 6.762 (1.07); 6.742 (1.04); 6.738 (1.54); 6.734 (0.97); 5.338 (1.03); 2.772 (16); 1.618 (6.84); 0.036 (3.77) |
| Va.03 | 8.931 (10.31); 8.922 (10.43); 8.121 (6.58); 8.116 (6.86); 8.094 (7.2); 8.088 (7.35); 7.713 (3.71); 7.708 (3.77); 7.688 (5.47); 7.686 (5.8); 7.683 (5.96); 7.68 (5.22); 7.661 (5.08); 7.655 (4.86); 7.586 (8.19); 7.581 (8.41); 7.577 (8.88); 7.572 (7.58); 7.532 (1.02); 7.513 (2.27); 7.504 (16); 7.491 (6.93); 7.481 (12.42); 7.46 (6.44); 7.453 (5.34); 7.449 (5.59); 7.428 (6.51); 7.426 (7.27); 7.424 (7.06); 7.422 (6.21); 7.401 (3.95); 7.397 (3.97); 7.298 (10.79); 7.228 (8.18); 7.224 (8.01); 7.2 (7.26); 7.196 (7.05); 2.077 (0.32); 1.653 (9.38); 0.106 (2.37); 0.042 (0.44); 0.031 (10.9); 0.02 (0.37) |
| Va.04 | 8.144 (1.47); 8.138 (1.51); 8.116 (1.61); 8.111 (1.61); 7.709 (0.79); 7.704 (0.79); 7.684 (1.27); 7.682 (1.35); 7.679 (1.37); 7.657 (1.09); 7.651 (1.04); 7.446 (1.12); 7.442 (1.17); 7.413 (3.37); 7.407 (2.11); 7.402 (1.86); 7.387 (5.99); 7.381 (3.41); 7.372 (1.59); 7.341 (0.34); 7.3 (12.83); 7.163 (1.8); 7.16 (1.76); 7.136 (1.65); 7.132 (1.57); 2.849 (16); 1.602 (8.26); 0.048 (0.39); 0.038 (8.79); 0.027 (0.42) |
| Va.05 | 8.85 (11.05); 8.84 (11.18); 8.193 (5.64); 8.164 (6.43); 7.818 (5.29); 7.797 (12.25); 7.791 (16); 7.78 (4.45); 7.761 (5.91); 7.757 (6.85); 7.752 (3.54); 7.733 (4.88); 7.728 (3.96); 7.655 (4.91); 7.651 (5.06); 7.628 (6.89); 7.624 (4.38); 7.605 (2.68); 7.601 (2.62); 7.503 (3.3); 7.483 (3.54); 7.475 (7.39); 7.455 (7.4); 7.446 (4.35); 7.426 (4.12); 7.3 (8.33); 7.136 (4.36); 7.133 (4.54); 7.107 (7.39); 7.104 (7.51); 7.078 (3.81); 7.075 (3.76); 6.858 (4.67); 6.854 (7.03); 6.85 (4.67); 6.83 (4.32); 6.826 (6.44); 6.822 (4.23); 1.731 (6.41); 0.111 (3.2); 0.036 (8.64); 0.025 (0.28) |
| Va.06 | 8.104 (1.27); 8.076 (1.57); 8.074 (1.48); 7.757 (1.31); 7.747 (1.08); 7.742 (0.87); 7.731 (2); 7.724 (1.84); 7.719 (1.38); 7.714 (0.84); 7.696 (4.74); 7.578 (1.09); 7.575 (1.06); 7.552 (1.55); 7.528 (0.66); 7.524 (0.61); 7.469 (0.78); 7.449 (0.84); 7.44 (1.72); 7.42 (1.75); 7.412 (1); 7.392 (0.96); 7.3 (1.19); 7.105 (1.04); 7.102 (1.03); 7.076 (1.75); 7.073 (1.69); 7.047 (0.91); 7.044 (0.86); 6.725 (1.11); 6.721 (1.63); 6.717 (1.03); 6.696 (1.04); 6.692 (1.51); 6.688 (0.94); 2.704 (16); 1.862 (1.26); 0.032 (1.11) |
| Va.07 | 8.875 (13.29); 8.865 (13.52); 8.182 (6.53); 8.153 (7.51); 8.102 (7.08); 8.097 (7.46); 8.075 (7.7); 8.07 (7.97); 7.769 (6); 7.748 (8.44); 7.743 (12.23); 7.725 (7.35); 7.72 (7.33); 7.715 (3.93); 7.697 (5.84); 7.692 (4.41); 7.665 (4.02); 7.659 (4.19); 7.64 (16); 7.631 (15.87); 7.623 (7.01); 7.619 (6.75); 7.612 (6.04); 7.606 (5.77); 7.596 (8.05); 7.592 (5.09); 7.572 (3.09); 7.569 (3.01); 7.398 (5.17); 7.394 (5.57); 7.37 (7.76); 7.367 (6.69); 7.346 (4.17); 7.342 (4.22); 7.3 (13.25); 7.186 (8.74); 7.182 (8.7); 7.158 (7.75); 7.154 (7.66); 5.335 (0.56); 2.041 (0.37); 1.709 (10.32); 0.11 (3.34); 0.047 (0.49); 0.036 (13.62); 0.026 (0.47) |
| Va.08 | 8.114 (1.46); 8.109 (1.64); 8.102 (1.56); 8.087 (1.74); 8.082 (1.79); 8.074 (1.3); 8.072 (1.41); 7.711 (0.71); 7.706 (1.03); 7.695 (1.19); 7.689 (1.76); 7.683 (2.06); 7.678 (0.81); 7.668 (1.68); 7.663 (2.17); 7.659 (1.84); 7.654 (1.26); 7.649 (0.93); 7.629 (1.2); 7.627 (1.27); 7.624 (1.29); 7.621 (1.09); 7.602 (1.09); 7.596 (1.04); 7.543 (1.08); 7.54 (1.09); 7.521 (0.87); 7.515 (1.59); 7.493 (0.64); 7.49 (0.63); 7.472 (3.58); 7.384 (1.06); 7.38 (1.11); 7.359 (1.24); 7.357 (1.53); 7.356 (1.47); 7.353 (1.27); 7.332 (0.89); 7.328 (0.85); 7.3 (3.64); 7.107 (1.71); 7.103 (1.67); 7.079 (1.55); 7.075 (1.49); 2.782 (16); 1.7 (4.88); 0.037 (2.79) |
| XIa.01 | 8.479 (1); 8.477 (1.03); 8.473 (1.06); 7.752 (0.74); 7.745 (0.76); 7.725 (0.84); 7.718 (0.86); 7.538 (0.71); 7.515 (0.94); 7.499 (1.6); 7.494 (1.44); 7.477 (0.79); 7.382 (0.51); 7.374 (0.42); 7.359 (1.58); 7.333 (1.09); 7.304 (2.17); 4.507 (0.53); 4.436 (5.02); 1.629 (1.81); 0.746 (0.8); 0.735 (16); 0.723 (2.08); 0.042 (1.92) |
| XIa.02 | 7.551 (0.73); 7.544 (1); 7.536 (0.67); 7.528 (0.96); 7.519 (1.28); 7.512 (1.18); 7.508 (1.09); 7.482 (1.62); 7.422 (0.73); 7.417 (0.66); 7.409 (1.83); 7.405 (1.81); 7.398 (1.32); 7.391 (1.14); |

TABLE 12-continued

NMR peak lists

| Example | $^1$H-NMR [CDCl$_3$ at 300 Mhz] |
|---|---|
| | 7.386 (0.99); 7.373 (0.48); 7.368 (0.55); 7.298 (4.52); 7.275 (0.72); 7.271 (0.63); 4.433 (4.84); 1.583 (5.72); 0.704 (0.59); 0.694 (16); 0.683 (0.68); 0.039 (4.03) |
| XIa.03 | 7.528 (0.62); 7.527 (0.62); 7.506 (1.47); 7.501 (1.72); 7.492 (0.74); 7.491 (0.73); 7.484 (1.11); 7.476 (1.34); 7.466 (0.47); 7.461 (0.49); 7.44 (0.99); 7.436 (0.99); 7.423 (0.54); 7.419 (0.53); 7.399 (0.8); 7.395 (0.73); 7.378 (0.53); 7.375 (0.57); 7.362 (2.18); 7.353 (0.95); 7.343 (0.99); 7.339 (1.1); 7.322 (0.33); 7.31 (0.66); 7.305 (0.53); 7.286 (0.72); 7.281 (0.69); 7.243 (0.47); 6.809 (0.38); 6.808 (0.34); 4.41 (5.08); 1.523 (0.59); 1.265 (0.6); 0.881 (0.58); 0.654 (16); 0.643 (0.91); 0 (0.6) |
| XIa.04 | 7.7 (0.79); 7.698 (0.85); 7.685 (0.86); 7.683 (0.91); 7.58 (0.54); 7.558 (0.64); 7.555 (0.67); 7.522 (0.36); 7.5 (0.84); 7.496 (0.87); 7.482 (0.47); 7.478 (0.47); 7.458 (0.64); 7.454 (0.61); 7.362 (0.46); 7.357 (0.46); 7.344 (0.79); 7.342 (0.9); 7.333 (1.56); 7.305 (1.51); 7.261 (0.81); 7.25 (0.7); 7.246 (0.82); 7.235 (0.6); 4.544 (4.77); 1.597 (2.99); 0.777 (0.56); 0.766 (16); 0.755 (0.66); 0.05 (1.23) |
| XIa.05 | 7.583 (0.48); 7.58 (0.5); 7.559 (0.6); 7.555 (0.64); 7.516 (0.41); 7.504 (1.77); 7.497 (1.18); 7.491 (0.95); 7.482 (0.72); 7.476 (2.36); 7.452 (0.67); 7.447 (0.61); 7.426 (0.37); 7.418 (0.71); 7.41 (0.33); 7.393 (1.18); 7.39 (1.14); 7.371 (0.42); 7.365 (1.52); 7.36 (0.61); 7.34 (0.65); 7.335 (0.62); 7.304 (2.68); 7.19 (0.49); 7.166 (0.78); 7.141 (0.34); 7.097 (1.1); 7.093 (1.37); 7.086 (0.38); 7.071 (0.69); 7.067 (1.12); 7.065 (0.97); 7.05 (0.32); 7.042 (1.99); 7.036 (0.65); 7.02 (0.57); 7.014 (1.71); 4.484 (4.69); 1.59 (3.56); 0.704 (0.59); 0.694 (16); 0.683 (0.66); 0.048 (2.55) |
| XIa.06 | 7.559 (0.52); 7.535 (0.64); 7.532 (0.65); 7.498 (0.85); 7.492 (0.94); 7.486 (0.82); 7.48 (1.45); 7.474 (0.53); 7.463 (0.84); 7.459 (1.25); 7.452 (2.34); 7.446 (0.48); 7.438 (0.32); 7.391 (2.43); 7.385 (0.64); 7.37 (0.97); 7.364 (1.58); 7.346 (0.61); 7.34 (0.56); 7.304 (0.81); 4.438 (4.76); 1.595 (1.21); 0.707 (0.67); 0.696 (16); 0.685 (0.62); 0.052 (0.75) |
| VIIa.01 [3] | 2.503 (40.74); 8.849 (0.52); 8.162 (16); 8.015 (11.05); 7.992 (12.55); 7.809 (3.07); 7.806 (2.98); 7.792 (4.47); 7.788 (5); 7.77 (2.92); 7.767 (3.15); 7.684 (3.95); 7.682 (3.85); 7.664 (5.19); 7.646 (2.41); 7.644 (2.64); 7.511 (2.32); 7.491 (5.2); 7.473 (5.22); 7.453 (2.56); 7.13 (2.55); 7.124 (5.07); 7.118 (3.45); 7.099 (6.69); 7.093 (4.6); 7.079 (4.83); 7.074 (3.37); 7.058 (2.32); 7.054 (1.69); 7.009 (0.35); 6.99 (4.59); 6.984 (4.16); 6.969 (4.15); 6.964 (3.75); 3.486 (0.41); 3.415 (1.88); 3.359 (563.3); 2.677 (0.36); 2.512 (43.27); 2.508 (55.8) |
| VIIa.02 | 4.595 (5.17); 4.172 (2.77); 1.632 (0.35); 1.612 (7.11); 1.447 (16.57); 1.423 (33.47); 1.4 (16); 1.302 (0.61); 0.125 (0.78); 0.121 (1.05); 0.058 (0.43); 0.047 (12.42); 0.036 (0.42); 7.901 (4.46); 7.873 (5.48); 7.672 (4.45); 7.65 (7.37); 7.645 (8.3); 7.626 (4.67); 7.622 (4.98); 7.617 (2.66); 7.599 (3.36); 7.594 (2.65); 7.566 (14.03); 7.546 (0.64); 7.456 (0.33); 7.448 (3.71); 7.444 (3.75); 7.434 (0.53); 7.421 (5.56); 7.418 (3.57); 7.398 (2.53); 7.394 (2.52); 7.377 (2.19); 7.366 (0.35); 7.355 (2.56); 7.349 (4.87); 7.327 (4.97); 7.322 (3.11); 7.304 (12.88); 7.3 (3.55); 6.917 (1.63); 6.914 (1.87); 6.909 (1.98); 6.906 (2.19); 6.887 (3.83); 6.879 (7.26); 6.87 (4.46); 6.862 (1.87); 6.859 (2.06); 6.851 (4.56); 6.843 (3.93); 6.829 (0.42); 6.821 (3.35); 6.813 (4.65); 6.806 (1.97); 6.796 (0.39); 6.788 (3.21); 6.78 (4.82); 6.772 (2.12); 4.666 (4.98); 4.642 (15.74); 4.619 (15.97) |
| VIIa.03 | 8.057 (1.23); 8.03 (1.2); 7.679 (2.4); 7.654 (3.36); 7.629 (0.92); 7.624 (0.55); 7.492 (0.96); 7.489 (0.89); 7.466 (1.27); 7.442 (0.62); 7.439 (0.56); 7.419 (3.45); 7.392 (0.63); 7.387 (1.13); 7.364 (1.06); 7.359 (0.71); 7.337 (0.64); 7.304 (1.95); 6.96 (0.43); 6.958 (0.45); 6.952 (0.52); 6.95 (0.5); 6.931 (1.89); 6.923 (2.19); 6.903 (1.24); 6.895 (1.82); 6.874 (0.76); 6.866 (1.06); 6.858 (0.45); 6.841 (0.72); 6.833 (1.07); 6.825 (0.48); 3.002 (0.33); 2.744 (16); 1.616 (1.81); 0.048 (1.76) |
| VIIa.04 | 8.096 (0.33); 8.069 (0.39); 7.717 (0.34); 7.692 (0.5); 7.682 (0.45); 7.677 (0.38); 7.564 (0.95); 7.522 (0.4); 7.384 (0.36); 7.362 (0.4); 7.3 (7.66); 6.853 (0.33); 6.826 (0.32); 6.807 (0.35); 6.774 (0.38); 2.739 (4.27); 1.61 (16); 0.039 (5.49) |
| VIIa.05 [1] | 8.804 (16); 8.797 (15.96); 8.138 (9.46); 8.117 (10.23); 7.739 (8.32); 7.719 (10.35); 7.69 (5.26); 7.687 (5.12); 7.673 (7.98); 7.669 (10.22); 7.666 (5.46); 7.652 (7.23); 7.648 (6.89); 7.64 (14.18); 7.634 (13.75); 7.577 (7.23); 7.574 (7.05); 7.557 (10.29); 7.539 (4.39); 7.537 (4.09); 7.377 (4.19); 7.361 (5.34); 7.357 (9.21); 7.34 (9.38); 7.336 (5.83); 7.32 (4.9); 7.258 (22.46); 7.25 (5.82); 7.19 (1.06); 7.186 (0.72); 7.169 (2.35); 7.151 (3.08); 7.132 (1.48); 6.924 (3.65); 6.922 (3.9); 6.918 (4.22); 6.916 (4.16); 6.903 (6.74); 6.901 (7.25); 6.897 (7.77); 6.895 (7.67); 6.882 (10.03); 6.876 (11.51); 6.861 (6.2); 6.856 (7.67); 6.833 (6.2); 6.827 (8.97); 6.821 (4.32); 6.808 (5.93); 6.802 (9.03); 6.796 (4.31); 6.659 (2.6); 6.654 (2.95); 6.653 (2.93); 6.636 (4.08); 6.632 (3.9); 6.613 (6.22); 6.61 (5.49); 6.59 (4.25); 6.585 (3.21); 6.579 (1.16); 1.649 (8.11); 1.183 (2.5); 1.11 (0.74); 1.104 (3.72); 0.008 (1.21); 0 (20.49); −0.008 (1.03) |
| VIIa.06 [1] | E<br>8.693 (8.3); 8.671 (8.31); 8.471 (16); 8.466 (15.73); 8.042 (0.54); 7.951 (0.39); 7.932 (0.4); 7.75 (6.74); 7.732 (9.16); 7.729 (9.5); 7.702 (3.61); 7.698 (4); 7.685 (7.28); 7.681 (7.9); 7.677 (4.2); 7.663 (7.08); 7.659 (5.81); 7.645 (7.2); 7.642 (7.52); 7.625 (7.85); 7.608 (2.94); 7.605 (2.69); 7.493 (0.37); 7.407 (3.63); 7.39 (4.67); 7.386 (7.97); 7.37 (8.13); 7.366 (5.19); 7.349 (4.25); 7.341 (0.48); 7.263 (21.57); 7.244 (13.08); 7.239 (12.7); 6.971 (3.57); 6.965 (3.77); 6.95 (6.48); 6.944 (6.76); 6.93 (3.45); 6.924 (3.93); 6.916 (6.5); 6.911 (7.29); 6.895 (5.59); 6.89 (6.86); 6.867 (5.4); 6.861 (7.87); 6.856 (3.86); 6.843 (5.15); 6.837 (7.87); 6.832 (3.81); 5.298 (1.27); 1.717 (0.34); 1.677 (0.35); 1.64 (0.45); 1.256 (0.51); 0 (3.31) |
| II.01A | 10.257 (11.41); 10.255 (10.28); 10.106 (16); 10.105 (14.12); 8.979 (0.81); 8.974 (0.88); 8.965 (0.87); 8.959 (0.84); 8.907 (7.07); 8.898 (7.19); 8.28 (0.66); 8.253 (0.72); 8.192 (4.03); 8.164 (4.89); 7.91 (0.73); 7.883 (0.91); 7.823 (4.26); 7.818 (4.46); 7.807 (0.78); 7.798 (5.22); 7.792 (5.27); 7.784 (1.22); 7.755 (3.67); 7.743 (2.5); 7.738 (2.35); 7.728 (5.28); 7.72 (4.62); 7.715 (3.3); 7.71 (2); 7.692 (3.16); 7.687 (2.24); 7.649 (0.86); 7.646 (0.91); 7.624 (3.96); 7.621 (3.93); 7.598 (4.36); 7.574 (1.64); 7.57 (1.55); 7.539 (3.03); 7.537 (2.75); 7.513 (6.31); 7.501 (9.33); |

TABLE 12-continued

NMR peak lists

| Example | $^1$H-NMR [CDCl$_3$ at 300 Mhz] |
|---|---|
| | 7.494 (10.41); 7.487 (4.83); 7.476 (7.47); 7.47 (7.45); 7.393 (3.73); 7.367 (7.98); 7.342 (4.71); 7.328 (0.35); 7.313 (5.4); 7.308 (5.79); 7.3 (19.08); 7.296 (9.66); 7.287 (4.48); 7.281 (4.35); 7.275 (4.7); 7.27 (4); 7.108 (1.17); 5.335 (0.7); 2.443 (2.24); 2.085 (0.71); 1.724 (1.95); 1.304 (0.43); 1.297 (0.66); 1.281 (0.4); 0.917 (0.32); 0.046 (0.43); 0.036 (13.14); 0.025 (0.45) |
| II.01B | 15.065 (0.81); 10.458 (14.23); 8.942 (3.46); 7.976 (4.12); 7.963 (3.89); 7.958 (4.32); 7.945 (5.22); 7.93 (0.98); 7.646 (1.78); 7.639 (2.06); 7.613 (9.32); 7.608 (12.38); 7.595 (16); 7.582 (4.78); 7.575 (3.45); 7.55 (5.59); 7.533 (3.7); 7.519 (1.7); 7.5 (1.24); 7.368 (1.16); 7.3 (332.81); 7.258 (1.04); 7.237 (1.2); 6.949 (1.95); 4.172 (0.87); 3.483 (0.83); 2.998 (1.75); 2.924 (1.73); 2.085 (2.85); 1.653 (1.61); 1.586 (433.23); 1.52 (1.42); 1.322 (0.91); 1.299 (2.47); 1.274 (0.89); 1.254 (0.95); 0.235 (1.91); 0.107 (1.5); 0.049 (13.71); 0.038 (331.49); 0.028 (13.11); −0.027 (1.08); −0.159 (1.61); −0.285 (0.87); −1.452 (0.9) |
| II.02A | 8.969 (1.19); 8.963 (1.22); 8.955 (1.26); 8.949 (1.24); 8.872 (6.7); 8.863 (6.73); 8.748 (0.34); 8.25 (0.98); 8.246 (0.96); 8.222 (1.04); 8.181 (1.32); 8.166 (3.26); 8.155 (1.63); 8.139 (3.69); 7.893 (1.02); 7.867 (1.38); 7.802 (0.75); 7.797 (0.72); 7.779 (1.1); 7.774 (1.5); 7.769 (0.72); 7.75 (1.1); 7.745 (0.93); 7.724 (2.92); 7.708 (2.6); 7.702 (4.43); 7.698 (4.57); 7.684 (4.01); 7.68 (3.39); 7.674 (1.95); 7.657 (3.1); 7.651 (2.2); 7.634 (1.1); 7.63 (1.05); 7.607 (1.65); 7.604 (1.09); 7.593 (3.13); 7.588 (3.17); 7.581 (0.93); 7.566 (3.74); 7.562 (2.36); 7.542 (1.57); 7.539 (1.44); 7.488 (1.44); 7.474 (1.45); 7.466 (1.41); 7.46 (1.7); 7.446 (6.4); 7.44 (10.96); 7.429 (5.72); 7.419 (16); 7.404 (1.25); 7.3 (34.16); 7.287 (0.72); 7.278 (8.31); 7.252 (6.2); 7.081 (4.87); 7.078 (5.03); 7.076 (5.32); 7.056 (4.04); 7.053 (3.96); 7.051 (4.04); 7.037 (0.72); 7.022 (3.58); 7.012 (3.76); 6.998 (6.97); 6.993 (3.74); 6.971 (4.83); 6.966 (4.25); 6.104 (1.39); 5.051 (0.6); 4.847 (5.32); 4.838 (5.33); 4.732 (7.51); 4.722 (7.46); 4.172 (0.48); 4.149 (0.52); 2.442 (2.86); 2.373 (1.2); 2.31 (1.44); 2.154 (1.89); 2.085 (2.34); 1.671 (10.92); 1.47 (11.75); 1.322 (0.71); 1.298 (1.69); 1.274 (1.05); 0.049 (1.21); 0.038 (30.44); 0.027 (1.08) |
| II.03A | 5.339 (0.98); 4.036 (0.71); 4.014 (1.84); 3.994 (1.92); 3.973 (0.81); 3.21 (1.35); 3.188 (2.65); 3.166 (1.23); 2.832 (9.37); 2.085 (1.34); 2.048 (2.15); 1.606 (16); 1.533 (0.81); 1.514 (1.67); 1.494 (0.78); 1.322 (0.51); 1.299 (1.23); 1.275 (0.4); 0.92 (0.68); 0.049 (0.59); 0.038 (16.51); 0.028 (0.68); 8.08 (0.85); 8.05 (0.81); 7.664 (0.41); 7.659 (0.65); 7.651 (0.73); 7.646 (0.84); 7.642 (0.61); 7.636 (1.2); 7.63 (0.54); 7.625 (1.06); 7.619 (1.12); 7.612 (0.89); 7.508 (0.64); 7.504 (0.65); 7.486 (0.53); 7.48 (0.92); 7.458 (0.36); 7.362 (0.69); 7.336 (1.57); 7.309 (1.52); 7.3 (16.6); 7.253 (2.26); 7.242 (1.19); 7.222 (0.73); 7.216 (0.61); 6.983 (1.03); 6.978 (1); 6.957 (0.88); 6.951 (0.86) |
| II.04A | 17.544 (0.47); 9.388 (0.48); 8.833 (15.69); 8.824 (16); 8.1 (7.66); 8.073 (8.39); 7.842 (11.64); 7.833 (11.7); 7.739 (6.34); 7.717 (8.4); 7.712 (8.64); 7.653 (3.73); 7.648 (4.52); 7.63 (7.1); 7.625 (7.93); 7.62 (3.91); 7.603 (6.8); 7.598 (5.37); 7.572 (6.7); 7.568 (7.16); 7.545 (8.2); 7.522 (3.3); 7.518 (2.96); 7.481 (0.45); 7.366 (0.75); 7.327 (2.37); 7.312 (33.18); 7.3 (266.57); 7.293 (25.11); 7.266 (2.8); 7.227 (1.24); 7.213 (7.88); 7.202 (5.28); 7.194 (6.05); 7.183 (4.28); 7.17 (0.67); 6.949 (1.36); 6.392 (10.27); 6.004 (0.45); 4.938 (10.33); 4.894 (14.32); 4.873 (5.77); 4.861 (10.08); 4.85 (6.03); 4.688 (14.61); 4.644 (10.79); 4.05 (0.48); 4.037 (1.98); 4.027 (2.77); 4.01 (2.33); 3.999 (5.11); 3.99 (3.15); 3.972 (2.19); 3.961 (3.32); 3.673 (2.32); 3.654 (4.38); 3.639 (3.02); 3.617 (3.3); 3.603 (2.06); 3.562 (0.48); 3.458 (0.48); 2.016 (0.92); 1.972 (2.58); 1.947 (2.64); 1.92 (1.5); 1.888 (2.77); 1.878 (1.5); 1.857 (3.52); 1.846 (5.69); 1.835 (3.52); 1.804 (5.88); 1.789 (4.25); 1.746 (2.02); 1.733 (1.78); 1.717 (2.45); 1.703 (2.83); 1.687 (3.29); 1.666 (5.8); 1.653 (7.31); 1.64 (10.01); 1.624 (7.13); 1.599 (313.86); 0.233 (0.81); 0.117 (0.49); 0.105 (0.56); 0.049 (7.56); 0.038 (221.58); 0.027 (7.18); −0.029 (0.52); −0.161 (0.68) |
| II.05A | 8.889 (0.36); 8.88 (0.36); 7.432 (0.84); 7.424 (0.47); 7.417 (0.34); 7.41 (0.42); 7.3 (8.95); 5.004 (0.66); 4.994 (1.05); 4.987 (0.73); 4.978 (0.72); 4.885 (0.44); 4.863 (0.43); 4.855 (0.5); 4.847 (0.45); 4.654 (0.35); 4.609 (0.39); 4.603 (0.36); 3.956 (0.4); 3.946 (0.42); 3.932 (0.34); 3.919 (0.68); 3.908 (0.49); 3.897 (0.4); 3.884 (0.49); 3.62 (0.38); 3.594 (0.49); 3.582 (0.53); 3.576 (0.74); 3.564 (0.45); 3.558 (0.58); 3.544 (0.34); 3.538 (0.43); 3.534 (0.4); 1.943 (0.34); 1.925 (0.5); 1.912 (0.57); 1.899 (0.59); 1.888 (0.66); 1.875 (0.47); 1.866 (0.5); 1.854 (0.4); 1.844 (0.48); 1.834 (0.75); 1.824 (0.56); 1.804 (0.79); 1.792 (0.93); 1.783 (0.75); 1.766 (0.75); 1.734 (0.39); 1.724 (0.33); 1.703 (0.41); 1.695 (0.52); 1.67 (0.93); 1.658 (1.11); 1.653 (1.03); 1.641 (1.06); 1.627 (1.42); 1.612 (16); 1.603 (2.38); 1.602 (2.4); 1.6 (2.4); 1.584 (2.14); 1.571 (1.29); 1.566 (1.14); 1.559 (0.73); 1.546 (0.48); 1.47 (0.49); 0.037 (7.23) |
| II.06A [5] | 8.163 (1.72); 8.157 (0.66); 8.149 (0.85); 8.143 (3.4); 8.11 (1.67); 8.105 (3.03); 8.095 (2.92); 8.091 (5.57); 7.793 (3.52); 7.726 (0.58); 7.724 (0.58); 7.712 (0.69); 7.706 (1.2); 7.696 (1.07); 7.695 (1.07); 7.68 (0.85); 7.666 (0.86); 7.66 (1.06); 7.646 (0.97); 7.641 (0.58); 7.627 (0.46); 5.753 (0.54); 3.309 (1.51); 3.026 (1.58); 2.742 (16); 2.508 (1.59); 2.505 (2.15); 2.502 (1.61); 1.228 (0.43); 0 (1.31) |
| II.07A [2] | 9.38 (11.61); 9.375 (11.9); 8.514 (9.06); 8.51 (9.21); 8.222 (6.09); 8.205 (6.8); 7.935 (6.02); 7.918 (6.97); 7.911 (4.35); 7.908 (3.9); 7.897 (5.06); 7.894 (7.23); 7.891 (3.85); 7.88 (4.23); 7.877 (3.74); 7.754 (4.3); 7.752 (7.93); 7.74 (2.82); 7.736 (8.53); 7.673 (4.31); 7.67 (4.38); 7.656 (7.43); 7.642 (3.52); 7.64 (3.44); 7.544 (2.35); 7.542 (2.45); 7.532 (3.01); 7.527 (9.02); 7.515 (6.96); 7.513 (6.57); 7.494 (0.61); 7.485 (16); 7.47 (11.58); 7.468 (8.04); 7.456 (3.3); 7.452 (2.62); 7.288 (27.45); 5.325 (0.57); 1.6 (11.08); 1.217 (0.9) |
| II.08A | 8.082 (1.11); 8.053 (1.02); 7.67 (0.56); 7.665 (0.83); 7.656 (0.92); 7.65 (1.04); 7.642 (1.58); 7.636 (0.67); 7.629 (1.33); 7.624 (1.51); 7.617 (1.21); 7.512 (0.84); 7.508 (0.85); 7.49 (0.69); 7.484 (1.19); 7.462 (0.47); 7.459 (0.44); 7.373 (0.92); 7.347 (1.98); 7.321 (1.64); 7.3 (15.12); 7.257 (2.76); 7.24 (1.3); 7.235 (1.39); 7.214 (0.89); 7.209 (0.84); 7 (1.25); 6.995 (1.21); 6.974 (1.1); 6.968 (1.06); 5.339 (0.53); 3.878 (1.77); 3.854 (3.97); 3.83 (2.16); 3.385 (1.79); 3.361 (3.21); 3.337 (1.47); 2.827 (12.09); 1.609 (16); 0.05 (0.6); 0.039 (15.3); 0.028 (0.58) |
| VII.01A [3] | 8.904 (14.15); 8.899 (14.16); 8.311 (11.78); 8.306 (11.6); 7.998 (14.31); 7.977 (16); 7.747 (4.37); 7.744 (4.43); 7.73 (6.34); 7.726 (8.11); 7.723 (4.8); 7.709 (4.56); 7.705 (4.7); 7.618 (5.53); 7.615 (5.5); 7.598 (8.33); 7.595 (6.33); 7.578 (3.92); 7.409 (2.82); 7.389 (6.58); 7.374 (6.05); 7.37 (5.72); 7.354 (3.96); 7.325 (5.5); 7.321 (4.93); 7.301 (14.2); 7.298 (14.48); 7.28 |

TABLE 12-continued

NMR peak lists

| Example | $^1$H-NMR [CDCl$_3$ at 300 Mhz] |
|---|---|
| | (6.32); 7.093 (3.18); 7.088 (2.96); 7.072 (5.44); 7.068 (5.8); 7.05 (2.65); 7.046 (2.4); 6.36 (13.98); 6.349 (14.52); 6.018 (9.73); 6.009 (9.04); 3.322 (35.48); 2.508 (13.38); 2.504 (17.32); 2.499 (12.66); 1.991 (0.54); 0 (17.65); −0.008 (0.82) |
| VII.02A [3] | 9.845 (0.57); 9.225 (16); 9.219 (15.97); 8.788 (13.87); 8.783 (13.07); 8.223 (8.43); 8.204 (9.04); 8.154 (8.55); 8.133 (10.35); 7.974 (5.19); 7.97 (5.39); 7.957 (6.82); 7.953 (9.39); 7.95 (5.22); 7.936 (4.97); 7.932 (4.7); 7.761 (5.94); 7.758 (6.19); 7.741 (9.87); 7.723 (5.46); 7.721 (5.96); 7.715 (4.29); 7.711 (3.81); 7.699 (15.85); 7.696 (13.86); 7.689 (12.87); 7.682 (13.67); 7.668 (9.34); 7.664 (7.81); 7.661 (7.58); 7.651 (3.55); 7.631 (3.71); 7.625 (4.84); 7.618 (2.86); 7.608 (5.9); 7.605 (5.61); 7.602 (4.89); 7.589 (2.57); 7.585 (2.85); 7.579 (1.9); 7.565 (1); 7.53 (0.33); 7.525 (0.39); 7.51 (0.4); 7.237 (0.32); 3.319 (41.41); 2.508 (14.62); 2.504 (18.84); 2.5 (13.81); 1.236 (0.88); 0 (9.85); −0.008 (0.48) |
| VII.03A | 8.075 (15.43); 8.052 (4.15); 7.737 (2.95); 7.732 (2.61); 7.711 (4.93); 7.705 (4.75); 7.666 (1.37); 7.66 (1.84); 7.643 (4.08); 7.637 (3.22); 7.617 (7.9); 7.61 (6.77); 7.587 (3.37); 7.568 (1.14); 7.563 (0.96); 7.39 (1.78); 7.38 (0.43); 7.367 (2.28); 7.362 (3.9); 7.348 (0.78); 7.34 (4.24); 7.334 (2.61); 7.313 (2.64); 7.304 (14.74); 7.119 (4.13); 7.004 (6.73); 6.996 (4.39); 6.988 (3.74); 6.984 (3.68); 6.981 (3.73); 6.968 (2.77); 6.96 (4.11); 6.953 (2.09); 6.938 (8.39); 6.838 (1.68); 6.835 (1.71); 6.83 (1.66); 6.827 (1.53); 6.81 (3.3); 6.807 (3.26); 6.802 (3.11); 6.782 (1.61); 6.78 (1.58); 6.774 (1.54); 6.756 (4.2); 6.502 (2.58); 1.616 (16); 0.117 (0.48); 0.056 (0.47); 0.045 (14.74); 0.034 (0.5) |

Note [1]:
in CDCl$_3$ at 400 Mhz
Note [2]:
in CDCl$_3$ at 500 Mhz
Note [3]:
in d$_6$-DMSO at 400 Mhz
Note [4]:
in d$_6$-DMSO at 300 Mhz
Note [5]:
in d$_6$-DMSO at 500 Mhz The following examples illustrate in a non-limiting manner the preparation and efficacy of the compounds of formula (I) according to the invention.

Preparation Example 1: Preparation of 3-[2-(trimethylsilyl)phenoxy]quinoline (Compound I.001)

In a 5 mL microwave vial, 145 mg (0.68 mmol) of 3-bromoquinoline and 136 mg of 2-(trimethylsilyl)-phenol were dissolved in 4 mL of toluene. 300 mg (1.37 mmol) of potassium phosphate dihydrate were added, followed by 3 mg (0.014 mmol) of palladium (II) acetate and 9 mg (0.021 mol) of 2-di-tert-butyl-phosphino-2',4',6'-triisopropylbiphenyl. The mixture was heated under microwave [Biotage Initiator™] at 120° C. for 3 hours. The cooled reaction mixture was filtered off and the filtrate was diluted by ethyl acetate, washed by water and dried over magnesium sulfate. The organic phase was concentrated under vacuum to give 199 mg of the crude product as an orange oil. This residue was purified by preparative HPLC (gradient acetonitrile/water+0.1% HCO$_2$H) to yield 74 mg (37% yield) of 3-[2-(trimethylsilyl)phenoxy]quinoline as a pale orange oil. Log P=5.17 [Method A]. Mass (M+H)=294.

Preparation Example 2: Preparation of {2-[(7,8-difluoro-2-methylquinolin-3-yl)oxy]phenyl}(dimethyl)silanol (Compound I.026)

Step 1: Preparation of 7,8-difluoro-2-methyl-3-(2-nitrophenoxy)quinoline (Compound Va.04)

Under argon, 1 g (5.12 mmol) of 7,8-difluoro-2-methylquinolin-3-ol and 723 mg (5.12 mmol) of 1-fluoro-2-nitrobenzene were dissolved in 10 mL of DMF [N,N-dimethylformamide]. 1.10 g (5.63 mmol) of cesium carbonate was added and the reaction mixture was stirred at room temperature for 5 days. The reaction mixture was diluted by 500 mL of water. After 4 hours, the precipitate was filtered off and dried at 40° C. under vacuum to yield 1.33 g (82%) of pure 7,8-difluoro-2-methyl-3-(2-nitrophenoxy)quinoline used as such in the next step. Log P=3.37 [Method A]. Mass (M+H)=317.

Step 2: Preparation of 2-[(7,8-difluoro-2-methylquinolin-3-yl)oxy]aniline (Compound IVa.05)

A 0.05 molar solution of 1.25 g (3.95 mmol) of 7,8-difluoro-2-methyl-3-(2-nitrophenoxy)quinoline in ethyl acetate was reduced in a H-Cube™ [Continuous-flow Hydrogenation Reactor] over a cartridge of 10% Pd/C at a speed of 1 mL/min. Solvent evaporation has given 1.13 g (95%) of 2-[(7,8-difluoro-2-methylquinolin-3-yl)oxy]aniline as a solid of 95% purity used as such in the next step. Log P=2.99 [Method A]. Mass (M+H)=287.

Step 3: Preparation of 3-(2-bromophenoxy)-7,8-difluoro-2-methylquinoline (Compound IIa.07)

To a suspension of 630 mg (4.40 mmol) of copper (I) bromide, 955 mg (11 mmol) of lithium bromide and 0.630 mL (4.76 mmol) of tert-butyl nitrite in 20 mL of dry acetonitrile gently warmed at 60° C., was added dropwise over a period of 10 minutes, a solution of 1.05 g (3.66 mmol) of 2-[(7,8-difluoro-2-methylquinolin-3-yl)oxy]aniline in 20 mL of dry acetonitrile. After addition, the reaction mixture was stirred for further 30 minutes. The cooled reaction mixture was diluted by ethyl acetate and filtered over a cake of diatomaceous earth. The organic phase was concentrated under vacuum and the residue was purified by column chromatography on silica gel (gradient n-heptane/ethyl acetate) to yield 0.90 g (70%) of 3-(2-bromophenoxy)-7,8-difluoro-2-methylquinoline as a viscous oil which solidified. Log P=4.25 [Method A]. Mass (M+H)=350.

Step 4: Preparation of {2-[(7,8-difluoro-2-methylquinolin-3-yl)oxy]phenyl}(dimethyl)silanol (Compound I.026)

In a dried Radleys™ vial under argon, a mixture of 250 mg (0.71 mmol) of 3-(2-bromophenoxy)-7,8-difluoro-2-methylquinoline, 21 mg (0.071 mmol) of biphenyl-2-yl(di-tert-butyl)phosphine [Johnphos], 6.3 mg (0.036 mmol) of palladium (II) chloride and 0.37 mL (2.14 mmol) of N,N-diisopropylethylamine in 1.5 mL of dry NMP [N-methylpyrrolidone], was heated at 80° C. for 10 minutes. After further addition of 295 mg (1.42 mmol) of 1,2-diethoxy-1,1,2,2-tetramethyldisilane, the tube was sealed and stirred at 80° C. for 20 hours. To the cooled reaction mixture, were then added 1 mL of acetonitrile and 2 mL of an aqueous 1M acetic acid solution. The reaction mixture was vigorously stirred at room temperature for 2 hours. The reaction mixture was extracted by ethyl acetate (3×50 mL), and the organic extracts were washed by water then brine and dried over sodium sulfate. The organic phase was concentrated under vacuum and the residue was purified by column chromatography on silica gel (gradient n-heptane/ethyl acetate) to yield 101 mg (41%) of {2-[(7,8-difluoro-2-methylquinolin-3-yl)oxy]phenyl}(dimethyl)silanol as a solid. Log P=3.51 [Method A]. Mass (M+H)=346.

Preparation Example 3: Preparation of N-(1,1-dimethyl-1,3-dihydro-2,1-benzoxasilol-7-yl)quinolin-3-amine (Compound I.010)

Step 1: Preparation of 2-[(2-bromo-3-iodobenzyl)oxy]tetrahydro-2H-pyran

To a solution of 3.15 g (10 mmol) of (2-bromo-3-iodophenyl)methanol and 1.5 g (15 mmol) of 3,4-dihydro-2H-pyran in 15 mL of a 2:1 mixture of dichloromethane:tetrahydrofuran, were added 25 mg (0.1 mmol) of pyridinium p-toluenesulfonate. The reaction mixture was stirred at room temperature for 3 days. Solvents were removed under vacuum and the residue was dissolved in 200 mL of dichloromethane. The organic phase was washed by an aqueous saturated solution of NaHCO₃, dried and concentrated under vacuum to give 4.35 g (87%) of 2-[(2-bromo-3-iodobenzyl)oxy]tetrahydro-2H-pyran as a viscous oil of 80% purity used as such in the next step. GC-mass analysis: (M)=396.

Step 2: Preparation of N-{2-bromo-3-[(tetrahydro-2H-pyran-2-yloxy)methyl]phenyl}quinolin-3-amine (Compound II.04A)

In a dried Radleys™ vial sealed under argon, a mixture of 300 mg (2.03 mmol) of quinolin-3-amine, 962 mg (1.93 mmol) of 2-[(2-bromo-3-iodobenzyl)oxy]tetrahydro-2H-pyran, 127 mg (0.105 mmol) of 4,5-bis(diphenylphosphino)-9,9-dimethylxanthene [Xantphos] and 93 mg (0.102 mmol) of tris(dibenzylidene-acetone)dipalladium(0), were heated at 90° C. for 6 hours. The cooled reaction mixture was diluted by ethyl acetate and filtered over a cake of diatomaceous earth. The organic phase was concentrated under vacuum and the residue was purified by column chromatography on silica gel (gradient n-heptane/ethyl acetate) to yield 556 mg (66%) of N-{2-bromo-3-[(tetrahydro-2H-pyran-2-yloxy)-methyl]phenyl}quinolin-3-amine as a solid. Log P=4.13 [Method B]. Mass (M+H)=413.

Step 3: Preparation of N-(1,1-dimethyl-1,3-dihydro-2,1-benzoxasilol-7-yl)quinolin-3-amine (Compound I.010)

In a dried Radleys™ vial under argon, a mixture of 250 mg (0.60 mmol) of N-{2-bromo-3-[(tetrahydro-2H-pyran-2-yloxy)methyl]phenyl}quinolin-3-amine, 18 mg (0.06 mmol) of biphenyl-2-yl(di-tert-butyl)-phosphine, 5.3 mg (0.03 mmol) of palladium (II) chloride and 0.42 mL (2.42 mmol) of N,N-diisopropylethylamine in 1.5 mL of dry NMP, was heated at 80° C. for 10 minutes. After further addition of 374 mg (1.81 mmol) of 1,2-diethoxy-1,1,2,2-tetramethyldisilane, the tube was sealed and stirred at 80° C. for 36 hours. To the cooled reaction mixture, were then added 1 mL of acetonitrile and 2 mL of an aqueous 1M acetic acid solution. The reaction mixture was vigorously stirred at room temperature for 2 hours. The reaction mixture was extracted by ethyl acetate (3×50 mL), and the organic extracts were washed by water then brine and dried over sodium sulfate. The organic phase was concentrated under vacuum and the residue was purified by column chromatography on silica gel (gradient n-heptane/ethyl acetate) to give 150 mg of a viscous oil. This oily residue was dissolved in 40 mL of methanol and 230 mg (1.21 mmol) of 4-toluenesulfonic acid monohydrate were added. The reaction mixture was further stirred at room temperature for 4 days. The solvent was removed under vacuum and the residue was diluted by dichloromethane. The organic phase was washed by an aqueous saturated solution of NaHCO₃, dried and concentrated under vacuum to give 16 mg of a viscous oil. Purification by preparative HPLC (gradient acetonitrile/water+0.1% HCO₂H) yields 4 mg (2% yield) of N-(1,1-dimethyl-1,3-dihydro-2,1-benzoxasilol-7-yl)-quinolin-3-amine as a viscous oil. Log P=3.15 [Method B]. Mass (M+H)=307.

Preparation Example 4: Preparation of 3-[3-fluoro-2-(1-methylsiletan-1-yl)phenoxy]quinoline (Compound I.008)

To a solution of 100 mg (0.39 mmol) of 3-(3-fluorophenoxy)quinoline in 4 mL of tetrahydrofuran [THF] were added 122 mg (0.99 mmol) of 1-chloro-1-methylsiletane in solution in 4 mL of THF. The reaction mixture was cooled to −78° C. and 0.218 mL of a 2M solution of lithium diisopropylamine [LDA] in THF was slowly added. The reaction mixture was further stirred at −78° C. for 4 hours. The reaction mixture was brought up to room temperature, diluted by water and extracted by ethyl acetate. The organic phase was washed by water, dried over magnesium sulfate and concentrated under vacuum to give 170 mg of the crude product as an orange oil. This residue was purified by preparative HPLC (gradient acetonitrile/water+0.1% HCO₂H) to yield 30 mg (23% yield) of 3-[3-fluoro-2-(1-methylsiletan-1-yl)phenoxy]-quinoline as an orange oil. Log P=5.39 [Method A]. Mass (M+H)=324.

Preparation Example 5: Preparation of 3-{2-[(4-chlorophenyl)(dimethyl)silyl]benzyl}quinoline (Compound I.014)

Step 1: Preparation of [2-(bromomethyl)phenyl](4-chlorophenyl)dimethylsilane (Compound XIa.06)

To a mixture of 390 mg (1.40 mmol) of {2-[(4-chlorophenyl)(dimethyl)silyl]phenyl}methanol and 156 mg (1.55 mmol) of triethylamine in 10 mL of dichloromethane, were added 313 mg (1.4 mmol) of methanesulfonyl bromide. The reaction mixture was stirred for 4 hours at room temperature. Solvents were removed under vacuum, the residue was dissolved in a minimum amount of dichloromethane and purified by column chromatography on silica gel (n-heptane/ethyl acetate 95/5) to yield 399 mg (79%) of [2-(bromomethyl)-phenyl](4-chlorophenyl)dimethylsilane as a solid. Log P=5.94 [Method A]. GC-mass analysis: (M-CH$_3$)=323.

Step 2: Preparation of 3-{2-[(4-chlorophenyl)(dimethyl)silyl]benzyl}quinoline (Compound I.014)

In a 5 mL microwave vial, 100 mg (0.57 mmol) of 3-quinolylboronic acid were dissolved together with 196 mg (0.57 mmol) of [2-(bromomethyl)phenyl](4-chlorophenyl)dimethylsilane in 3 mL of 1-4-dioxane. 239 mg (1.73 mmol) of potassium carbonate in solution in 1 mL of water were added, and the reaction mixture been degassed with argon for a few minutes. 33 mg (0.029 mmole) of tetrakis(triphenyl-phosphine)palladium(0) were further added and the mixture was heated under microwave at 80° C. for 10 min. The cooled reaction mixture was filtered over a ChemElut™ cartridge (3 g) and the cartridge was further washed with 1-4-dioxane. The organic extracts were concentrated under vacuum and the residue was purified by column chromatography on silica gel (n-heptane/ethyl acetate 90/10) to yield 161 mg (68%) of 3-{2-[(4-chlorophenyl)(dimethyl)silyl]benzyl}quinoline. Log P=4.74 [Method A]. Mass (M+H)=388.

Preparation Example 6: Preparation of 7,8-difluoro-3-{3-fluoro-2-[fluoro(dimethyl)silyl]phenoxy}-2-methylquinoline (Compound I.032)

To a solution of 200 mg (0.519 mmol) of {2-[(7,8-difluoro-2-methylquinolin-3-yl)oxy]-6-fluorophenyl}-(dimethyl)silanol in 2 mL in dry THF, was added in one portion, 0.066 mL (0.519 mmol) of boron trifluoride diethyl etherate. The reaction mixture was stirred for 30 minutes and allowed to stand overnight at room temperature. The reaction mixture was diluted by a saturated aqueous solution of sodium bicarbonate and extracted by dichloromethane. The organic extracts were dried over sodium sulfate and the organic phase was concentrated under vacuum to give 275 mg of a viscous oil. This residue was purified by preparative HPLC (gradient acetonitrile/water+0.1% HCO$_2$H). Fractions were added to a saturated aqueous solution of sodium bicarbonate and extracted by dichloromethane. The combined organic extracts were dried over sodium sulfate and concentrated under vacuum to give 96 mg (45%) of 7,8-difluoro-3-{3-fluoro-2-[fluoro(dimethyl)silyl]phenoxy}-2-methylquinoline as an oil of 90% purity. Log P=4.75 [Method A]. Mass (M+H)=366.

Preparation Example 7: Preparation of 2-chloro-3-{3-fluoro-2-[methyl(phenyl)silyl]phenoxy}quinoline (Compound I.062)

Step 1: Preparation of 3-(3-fluorophenoxy)quinoline (Compound VIIa.05)

In a 10 mL microwave vial, 1 g (4.71 mmol) of 3-bromoquinoline, 0.566 g (4.94 mmol) of 3-fluorophenol and 174 mg (0.94 mmol) of dipivaloylmethane were dissolved in 5 mL of N,N-dimethylacetamide. 1 g (5.18 mmol) of copper (I) iodide and 1.697 g (5.18 mmol) of cesium carbonate were further added and the mixture was heated under microwave at 200° C. for 1 hour. The experiment was repeated three times. The combined reaction mixtures were diluted by ethyl acetate and filtered over a cake of diatomaceous earth. The organic phases were washed by water, dried over magnesium sulfate and concentrated under vacuum to give 6.76 g of a dark brown oil. This residue was purified by column chromatography on silica gel (n-heptane/ethyl acetate 95/5 to 85/15) to yield 3.03 g (64%) of 3-(3-fluorophenoxy)quinoline as an orange oil. Log P=3.21 [Method A]. Mass (M+H)=240.

Step 2: Preparation of 3-(3-fluorophenoxy)quinoline 1-oxide (Compound VIIa.06)

To a solution of 1.5 g (6.27 mmol) of 3-(3-fluorophenoxy)quinoline in 30 mL of chloroform, was slowly added at 0° C., a solution of 1.80 g (6.27 mmol) of meta-chloroperoxybenzoic acid [60% purity] in 30 mL of chloroform. The reaction mixture was stirred at room temperature for 90 minutes. The reaction mixture was poured over 100 mL of a 1M aqueous solution of sodium thiosulfate. The organic phase was separated, washed by water and dried over magnesium sulfate. Concentration under vacuum gave 2.40 g of an orange oil as a residue. This residue was purified by column chromatography on silica gel (n-heptane/ethyl acetate 65/35 to 50/50) to yield 1.30 g (78%) of 3-(3-fluorophenoxy)quinoline 1-oxide as an orange oil which crystallizes. Log P=2.14 [Method A]. Mass (M+H)=256.

Step 3: Preparation of 2-chloro-3-(3-fluorophenoxy)quinoline (Compound VIIa.01)

To a solution of 1.27 g (4.98 mmol) of 3-(3-fluorophenoxy)quinoline 1-oxide in 50 mL of dichloromethane, were added 182 mg (2.49 mmol) of DMF. The reaction mixture was cooled down to 0° C. and 917 mg (5.98 mmol) of phosphorous oxychloride were slowly added at 0° C. The reaction mixture was further stirred at room temperature for 8 hours. The reaction mixture was poured over 150 mL of a saturated aqueous solution of sodium bicarbonate and extracted by dichloromethane. The organic extracts were combined and dried over magnesium sulfate. Concentration under vacuum gave 1.40 g of an orange oil. This residue was purified by column chromatography on silica gel (n-heptane/ethyl acetate 80/20) to yield 1.27 g (93%) of 2-chloro-3-(3-fluorophenoxy)quinoline as an pale orange oil. Log P=3.99 [Method A]. Mass (M+H)=274.

Step 4: Preparation of 2-chloro-3-{3-fluoro-2-[methyl(phenyl)silyl]phenoxy}quinoline (Compound I.062)

To a solution of 100 mg (0.36 mmol) of 2-chloro-3-(3-fluorophenoxy)quinoline in 4 mL of THF were added 153 mg (0.91 mmol) of chloro(methyl)phenylsilane in solution in 4 mL of THF. The reaction mixture was cooled to −78° C. and 0.365 mL of a 2M solution of LDA in THF was slowly added. The reaction mixture was further stirred at −78° C. for 7 hours. The reaction mixture was brought up to room temperature, diluted by water and extracted by ethyl acetate. The organic phase was washed by water, dried over magnesium sulfate and concentrated under vacuum to give 243 mg of a yellow oil. This residue was purified by column chromatography on silica gel (n-heptane/ethyl acetate 96/4) to yield 58 mg (38%) of 2-chloro-3-{3-fluoro-2-[methyl (phenyl)silyl]phenoxy}quinoline as an pale orange oil. Log P=5.78 [Method A]. Mass (M+H)=394. Further purification of a second fraction yielded 17 mg (11%) of 2-chloro-3-(3-fluorophenoxy)-4-[methyl(phenyl)silyl]quinoline and 20 mg (13%) of 6-chloro-11-fluoro-12-methyl-12-phenyl-12H-[1,4]benz-oxasilino[2,3-c]quinoline. Log P=5.90 and 5.94 respectively [Method A].

Preparation Example 8: Preparation of 2-methyl-3-[2-(trimethylsilyl)phenoxy]quinoline (Compound I.047)

Step 1: preparation of 1-[2-(trimethylsilyl)phenoxy]acetone (Compound XIV.01)

To a solution of 1 g (6 mmol) of 2-trimethylsilylphenol in 50 mL of acetone, were added 1.2 g (11.6 mmol) of chloroacetone [of 90% purity] together with 100 mg (0.6 mmol) of potassium iodide and 1 g (7.21 mmol) of potassium carbonate. The reaction mixture was stirred at 50° C. for 7 hours. The cooled reaction was filtered over a sintered glass, washed by ethyl acetate and the solvents further removed under vacuum. The orange oily residue of 1.29 g was purified by column chromatography on silica gel (n-heptane/dichloromethane 75/25) to yield 924 mg (66%) of 1-[2-(trimethylsilyl)phenoxy]acetone as an orange oil. Log P=1.39 [Method A]. GC-mass analysis: mass (M)=322.

Step 2: Preparation of 2-methyl-3-[2-(trimethylsilyl)phenoxy]quinoline (Compound I.047)

In a 5 mL microwave vial, 100 mg (0.45 mmol) of 1-[2-(trimethylsilyl)phenoxy]acetone were mixed together with 56 mg (0.45 mmol) of 2-aminobenzaldehyde in 5 mL of acetic acid. The mixture was heated under microwave at 120° C. for 8 hours. The cooled reaction mixture was poured over 100 mL of an aqueous solution of 7 g of potassium bicarbonate and extracted by ethyl acetate. The organic extracts were concentrated under vacuum to leave 198 mg of a brownish residue. This residue was purified by column chromatography on silica gel (n-heptane/ethyl acetate 97/3 to 90/10) to yield 40 mg (21%) of 2-methyl-3-[2-(trimethylsilyl)phenoxy]quinoline as an orange oil. Log P=4.85 [Method A]. Mass (M+H)=308.

In the following:

CMP1 designates 7,8-difluoro-2-methyl-3-{2-[(trimethylsilyl)methyl]phenoxy}quinoline (prepared in accordance with the teaching of JP2014/166991).

CMP2 designates 8-chloro-4-[4-fluoro-2-(trimethylsilyl)phenoxy]quinoline (prepared in accordance with the teaching of EP 0326330).

CMP3 designates 7,8-difluoro-4-[3-fluoro-2-(trimethylsilyl)phenoxy]-2-methylquinoline (prepared in accordance with the teaching of EP 0326330).

CMP4 designates 4-[3-fluoro-2-(trimethylsilyl)-phenoxy]-1,5-naphthyridine (prepared in accordance with the teaching of EP 0410762).

Example A: In Vitro Cell Test on *Pyricularia oryzae*

Solvent: dimethyl sulfoxide
Culture medium: 14.6 g anhydrous D-glucose (VWR),
7.1 g mycological peptone (Oxoid),
1.4 g granulated yeast extract (Merck), QSP 1 liter
Inoculum: spore suspension The tested compounds were solubilized in dimethyl sulfoxide and the solution used to prepare the required range of concentrations. The final concentration of dimethyl sulfoxide used in the assay was ≤1%.

A spore suspension of *Pyricularia oryzae* was prepared and diluted to the desired spore density.

The compounds were evaluated for their ability to inhibit spore germination and mycelium growth in liquid culture assay. The compounds were added in the desired concentration to the culture medium with spores. After 5 days incubation, fungi-toxicity of compounds was determined by spectrometric measurement of mycelium growth. Inhibition of fungal growth was determined by comparing the absorbance values in wells containing the fungicides with the absorbance in control wells without fungicides.

In this test the following compounds according to the invention showed efficacy between 70% and 79% at a concentration of 20 ppm of active ingredient: I.125.

In this test the following compounds according to the invention showed efficacy between 80% and 89% at a concentration of 20 ppm of active ingredient: I.010; I.042; I.099; I.118; I.121; I.122.

In this test the following compounds according to the invention showed efficacy between 90% and 100% at a concentration of 20 ppm of active ingredient: I.001; I.002; I.003; I.004; I.005; I.006; I.007; I.008; I.009; I.011; I.012; I.013; I.017; I.018; I.019; I.020; I.021; I.022; I.023; I.024; I.025; I.026; I.027; I.028; I.029; I.030; I.031; I.032; I.033; I.034; I.035; I.036; I.037; I.038; I.039; I.041; I.044; I.045; I.046; I.047; I.049; I.050; I.051; I.052; I.053; I.054; I.056; I.057; I.059; I.062; I.063; I.065; I.066; I.067; I.069; I.070; I.071; I.072; I.073; I.074; I.075; I.076; I.077; I.078; I.081; I.082; I.084; I.085; I.086; I.087; I.088; I.089; I.090; I.091; I.093; I.094; I.095; I.096; I.097; I.098; I.100; I.109; I.110; I.111; I.112; I.113; I.114; I.115; I.116; I.120; I.123; I.124; I.127; I.129.

In this test the following compound according to the invention showed efficacy between 90% and 100% at a concentration of 4 ppm of active ingredient: I.119.

In this test, compound I.024 showed efficacy of at least 80% when tested at a dose of 0.25 ppm or 0.06 ppm whereas CMP1 (structurally close compound, not according to the invention) showed much lower efficacy at the same doses as shown in table A1.

TABLE A1

| Compound | dose (ppm) | Efficacy |
| --- | --- | --- |
| I.024 | 0.25 | 96 |
| I.024 | 0.06 | 89 |
| CMP1 | 0.25 | 56 |
| CMP1 | 0.06 | 1 |

In this test, compounds I.019, I.027 and I.116 showed efficacy of at least 90% when tested at a dose of 20 ppm or 4 ppm whereas the structurally close compounds CMP2, CMP3 and CMP4 (not according to the invention) showed much lower efficacy at a dose of 4 ppm, as shown in table A2.

TABLE A2

| Example | Efficacy | | |
|---|---|---|---|
| | 20 ppm | 4 ppm | 1 ppm |
| I.019 | 97 | 98 | 45 |
| CMP2 | 93 | 46 | 0 |
| I.027 | 100 | 94 | 85 |
| CMP3 | 96 | 25 | 0 |
| I.116 | 100 | 100 | 90 |
| CMP4 | 44 | 11 | 0 |

Example B: In Vivo Preventive Test on *Botrytis cinerea* (Grey Mould)

Solvent: 5% by volume of dimethyl sulfoxide
10% by volume of acetone
Emulsifier: 1 µL of Tween® 80 per mg of active ingredient The tested compounds were made soluble and homogenized in a mixture of dimethyl sulfoxide/acetone//Tween® 80 and then diluted in water to the desired concentration.

The young plants of gherkin were treated by spraying the tested compounds prepared as described above. Control plants were treated only with an aqueous solution of acetone/dimethyl sulfoxide/Tween® 80.

After 24 hours, the plants were contaminated by spraying the leaves with an aqueous suspension of *Botrytis cinerea* spores. The contaminated gherkin plants were incubated for 4 to 5 days at 17° C. and at 90% relative humidity.

The test was evaluated 4 to 5 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I.013; I.033; I.096; I.116.

In this test the following compounds according to the invention showed efficacy between 80% and 89% at a concentration of 500 ppm of active ingredient: I.005; I.053; I.056; I.069; I.089.

In this test the following compounds according to the invention showed efficacy between 90% and 100% at a concentration of 500 ppm of active ingredient: I.006; I.020; I.021; I.022; I.023; I.024; I.025; I.026; I.027; I.028; I.029; I.030; I.031; I.032; I.037; I.040; I.046; I.047; I.049; I.054; I.055; I.071; I.078; I.079; I.080; I.081; I.082; I.084; I.085; I.086; I.087; I.088; I.090; I.094; I.095; I.097; I.098; I.099; I.100.

In this test, compounds I.027 and I.116 showed efficacy of at least 70% when tested at a dose of 500 ppm whereas the structurally close compounds CMP3 and CMP4 (not according to the invention) showed no efficacy at a dose of 500 ppm, as shown in table B.

TABLE B

| Example | dose (ppm) | Efficacy |
|---|---|---|
| I.027 | 500 | 92 |
| CMP3 | 500 | 0 |
| I.116 | 500 | 73 |
| CMP4 | 500 | 0 |

Example C: In Vivo Preventive Test on *Leptosphaeria nodorum* (Wheat)

Solvent: 49 parts by weight of N,N-dimethylacetamide
Emulsifier: 1 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for preventive activity, young plants were sprayed with the preparation of active compound at the stated rate of application.

After the spray coating has been dried, the plants were sprayed with a spore suspension of *Leptosphaeria nodorum*. The plants remained for 48 hours in an incubation cabinet at approximately 20° C. and a relative atmospheric humidity of approximately 100%.

The plants were placed in the greenhouse at a temperature of approximately 25° C. and a relative atmospheric humidity of approximately 80%.

The test was evaluated 8 days after the inoculation. 0% means an efficacy which corresponds to that of the untreated control, while an efficacy of 100% means that no disease is observed.

In this test the following compounds according to the invention showed efficacy between 90% and 100% at a concentration of 500 ppm of active ingredient: I.025; I.026; I.085.

Example D: In Vivo Preventive Test on *Septoria tritici* (Leaf Spot on Wheat)

Solvent: 5% by volume of dimethyl sulfoxide
10% by volume of acetone
Emulsifier: 1 µL of Tween® 80 per mg of active ingredient The active compounds were made soluble and homogenized in a mixture of dimethyl sulfoxide/acetone//Tween® 80 and then diluted in water to the desired concentration.

The young plants of wheat were treated by spraying the active compound prepared as described above. Control plants were treated only with an aqueous solution of acetone/dimethyl sulfoxide/Tween® 80.

After 24 hours, the plants were contaminated by spraying the leaves with an aqueous suspension of *Septoria tritici* spores. The contaminated wheat plants were incubated for 72 hours at 18° C. and at 100% relative humidity and then for 21 days at 20° C. and at 90% relative humidity.

The test was evaluated 24 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I.048; I.109; I.112; I.116.

In this test the following compounds according to the invention showed efficacy between 80% and 89% at a concentration of 500 ppm of active ingredient: I.024; I.033; I.051.

In this test the following compounds according to the invention showed efficacy between 90% and 100% at a concentration of 500 ppm of active ingredient: I.025; I.026; I.030; I.032; I.034; I.049; I.081; I.082; I.085; I.087; I.090; I.091; I.094; I.095; I.097; I.117.

Under the same conditions, high (at least 80%) protection was observed at a dose of 500 ppm of compound I.024, whereas no protection was observed with compound CMP1, as shown in table D:

TABLE D

| Compound | dose (ppm) | Efficacy |
|---|---|---|
| I.024 | 500 | 81 |
| CMP1 | 500 | 0 |

Example E: In Vivo Preventive Test on *Venturia* Test (Apples)

Solvent: 24.5 parts by weight of acetone
24.5 parts by weight of N,N-dimethylacetamide
Emulsifier: 1 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for preventive activity, young plants were sprayed with the preparation of active compound at the stated rate of application. After the spray coating has dried on, the plants were inoculated with an aqueous conidia suspension of the causal agent of apple scab (*Venturia inaequalis*) and then remained for 1 day in an incubation cabinet at approximately 20° C. and a relative atmospheric humidity of 100%.

The plants were then placed in a greenhouse at approximately 21° C. and a relative atmospheric humidity of approximately 90%.

The test was evaluated 10 days after the inoculation. 0% means an efficacy which corresponds to that of the untreated control, while an efficacy of 100% means that no disease is observed.

In this test the following compounds according to the invention showed efficacy between 80% and 89% at a concentration of 250 ppm of active ingredient: I.031; I.032.

In this test the following compounds according to the invention showed efficacy between 90% and 100% at a concentration of 250 ppm of active ingredient: I.020; I.021; I.022; I.023; I.025; I.026; I.037; I.046; I.047; I.049; I.054; I.071; I.079; I.082; I.085; I.086; I.087; I.088; I.090.

The invention claimed is:
1. A compound of formula (I)

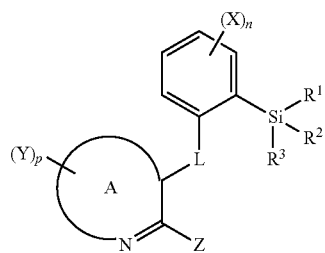

(I)

wherein
A represents a partially saturated or unsaturated fused bicyclic 9-, 10- or 11-membered heterocyclyl ring comprising at least 1 nitrogen atom and from 0 to 4 more heteroatoms independently selected from the group consisting of N, O and S;

Z is selected from the group consisting of hydrogen atom, halogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_4$-$C_7$-cycloalkenyl, hydroxyl, $C_1$-$C_8$-alkoxy, $C_1$-$C_8$-halogenoalkoxy comprising up to 9 halogen atoms that can be the same or different, aryl, heterocyclyl, formyl, $C_1$-$C_8$-alkylcarbonyl, (hydroxyimino)$C_1$-$C_8$-alkyl, ($C_1$-$C_8$-alkoxyimino)$C_1$-$C_8$-alkyl, carboxyl, $C_1$-$C_8$-alkoxycarbonyl, carbamoyl, $C_1$-$C_8$-alkylcarbamoyl, di-$C_1$-$C_8$-alkylcarbamoyl, amino, $C_1$-$C_8$-alkylamino, di-$C_1$-$C_8$-alkylamino, sulfanyl, $C_1$-$C_8$-alkylsulfanyl, $C_1$-$C_8$-alkylsulfinyl, $C_1$-$C_8$-alkylsulfonyl, $C_1$-$C_6$-trialkylsilyl, cyano and nitro;

n represents 0, 1, 2, 3 or 4;
p represents 0, 1, 2, 3, 4 or 5;
L represents O, S, SO, $SO_2$, $CR^4R^5$ or $NR^6$ wherein
$R^4$ and $R^5$ are independently selected from the group consisting of hydrogen atom, halogen atom, hydroxyl, $C_1$-$C_8$-alkoxy and $C_1$-$C_8$ alkyl, or they may form together with the carbon atom to which they are linked a carbonyl group;
$R^6$ is selected from the group consisting of hydrogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_3$-$C_8$-alkynyl, $C_3$-$C_8$-halogenoalkynyl comprising up to 9 halogen atoms that can be the same or different, $C_3$-$C_7$-cycloalkyl, $C_3$-$C_7$-halogenocycloalkyl comprising up to 9 halogen atoms that can be the same or different, $C_3$-$C_7$-cycloalkyl-$C_1$-$C_8$-alkyl, formyl, $C_1$-$C_8$-alkylcarbonyl, $C_1$-$C_8$-halogenoalkylcarbonyl comprising up to 9 halogen atoms that can be the same or different, $C_1$-$C_8$-alkoxycarbonyl, $C_1$-$C_8$-halogenoalkoxycarbonyl comprising up to 9 halogen atoms that can be the same or different, $C_1$-$C_8$-alkylsulfonyl, $C_1$-$C_8$-halogenoalkylsulfonyl comprising up to 9 halogen atoms that can be the same or different, aryl-$C_1$-$C_8$-alkyl and phenylsulfonyl;

X is independently selected from the group consisting of halogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_4$-$C_7$-cycloalkenyl, hydroxyl, $C_1$-$C_8$-alkoxy, $C_1$-$C_8$-halogenoalkoxy comprising up to 9 halogen atoms that can be the same or different, aryl, heterocyclyl, formyl, $C_1$-$C_8$-alkylcarbonyl, (hydroxyimino)$C_1$-$C_8$-alkyl, ($C_1$-$C_8$-alkoxyimino)$C_1$-$C_8$-alkyl, carboxyl, $C_1$-$C_8$-alkoxycarbonyl, carbamoyl, $C_1$-$C_8$-alkylcarbamoyl, di-$C_1$-$C_8$-alkylcarbamoyl, amino, $C_1$-$C_8$-alkylamino, di-$C_1$-$C_8$-alkylamino, sulfanyl, $C_1$-$C_8$-alkylsulfanyl, $C_1$-$C_8$-alkylsulfinyl, $C_1$-$C_8$-alkylsulfonyl, $C_1$-$C_6$-trialkylsilyl, cyano, nitro, hydroxymethyl and (tetrahydro-2H-pyran-2-yloxy) methyl;

Y is independently selected from the group consisting of halogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-halogenoalkenyl comprising up to 9 halogen atoms that can be the same or different, $C_2$-$C_8$-alkynyl, $C_2$-$C_8$-halogenoalkynyl comprising up to 9 halogen atoms that can be the same or different, $C_3$-$C_7$-cycloalkyl, $C_4$-$C_7$-cycloalkenyl, hydroxyl, $C_1$-$C_8$-alkoxy, $C_1$-$C_8$-halogenoalkoxy comprising up to 9 halogen atoms that can be the same or different, aryl, heterocyclyl, formyl, $C_1$-$C_8$-alkylcarbonyl, (hydroxyimino)$C_1$-$C_8$-alkyl, ($C_1$-$C_8$-alkoxyimino)$C_1$-$C_8$-alkyl, carboxyl, $C_1$-$C_8$-alkoxycarbonyl, carbamoyl, $C_1$-$C_8$-alkylcarbamoyl, di-$C_1$-$C_8$-alkylcarbamoyl, amino, $C_1$-$C_8$-alkylamino, di-$C_1$-$C_8$-alkylamino, sulfanyl, $C_1$-$C_8$-alkylsulfanyl, $C_1$-$C_8$-alkylsulfinyl, $C_1$-$C_8$-alkylsulfonyl, $C_1$-$C_6$-trialkylsilyl, cyano and nitro;

$R^1$ is selected from the group consisting of $C_1$-$C_8$-alkyl, $C_2$-$C_8$-alkenyl, $C_2$-$C_8$-alkynyl, $C_3$-$C_7$-cycloalkyl, $C_4$-$C_7$-cycloalkenyl, aryl and heterocyclyl;

$R^2$ is selected from the group consisting of hydroxyl, $C_1$-$C_8$-alkoxy, $C_1$-$C_8$-alkyl, $C_2$-$C_8$-alkenyl, $C_2$-$C_8$-alkynyl, $C_3$-$C_7$-cycloalkyl, $C_4$-$C_7$-cycloalkenyl, aryl and heterocyclyl;

when $R^1$ and $R^2$ represent a $C_1$-$C_8$ alkyl or a $C_2$-$C_8$ alkenyl, they can form, together with the silicon atom to which they are linked, a $C_3$-$C_8$-silacycloalkyl ring or a $C_4$-$C_8$-silacycloalkenyl ring;

$R^3$ is selected from the group consisting of hydrogen atom, halogen atom, $C_1$-$C_8$-alkyl, $C_1$-$C_8$-halogenoalkyl comprising up to 9 halogen atoms that can be the same or different, $C_2$-$C_8$-alkenyl, $C_2$-$C_8$-alkynyl, $C_3$-$C_7$-cycloalkyl, $C_4$-$C_7$-cycloalkenyl, hydroxyl, $C_1$-$C_8$-alkoxy, aryl, aryl-$C_1$-$C_8$-alkyl, heterocyclyl, heterocyclyl-$C_1$-$C_8$-alkyl, hydroxy-$C_1$-$C_8$-alkyl, $C_1$-$C_8$-alkoxy-$C_1$-$C_8$-alkyl, $C_1$-$C_8$-alkylcarbonyloxy-$C_1$-$C_8$-alkyl, aryloxy-$C_1$-$C_8$-alkyl, heterocyclyloxy-$C_1$-$C_8$-alkyl, amino-$C_1$-$C_8$-alkyl, $C_1$-$C_8$-alkylamino-$C_1$-$C_8$-alkyl, di-$C_1$-$C_8$-alkylamino-$C_1$-$C_8$-alkyl, arylamino-$C_1$-$C_8$-alkyl, di-arylamino-$C_1$-$C_8$-alkyl, heterocyclylamino-$C_1$-$C_8$-alkyl, $C_1$-$C_8$-alkylcarbonylamino-$C_1$-$C_8$-alkyl, $C_1$-$C_8$-alkoxycarbonylamino-$C_1$-$C_8$-alkyl, $C_1$-$C_8$-alkylsulfanyl-$C_1$-$C_8$-alkyl, $C_1$-$C_8$-alkylsulfinyl-$C_1$-$C_8$-alkyl, $C_1$-$C_8$-alkylsulfonyl-$C_1$-$C_8$-alkyl and cyano-$C_1$-$C_8$-alkyl;

$R^3$ and X, when said X is vicinal to $SiR^1R^2R^3$, may form, together with the silicon and carbon atoms to which they are respectively attached, an 5-, 6- or 7-membered, partially saturated, heterocycle;

when $R^2$ represents a $C_1$-$C_8$-alkoxy and $R^3$ represents a $C_1$-$C_8$-alkoxy or a $C_1$-$C_8$ alkyl, they can form, together with the silicon atom to which they are linked a 5-, 6- or 7-membered heterocycle;

and/or a salt, N-oxide, and/or an optically active isomer and/or geometric isomer.

2. The compound according to claim 1, wherein Y is independently selected from the group consisting of halogen atom, $C_1$-$C_6$-alkyl, $C_1$-$C_6$-halogenoalkyl comprising up to 9 halogen atoms that can be the same or different, $C_1$-$C_6$-alkoxy, $C_1$-$C_6$-halogenoalkoxy comprising up to 9 halogen atoms that can be the same or different and cyano.

3. The compound according to claim 1, wherein A is selected from the group consisting of:

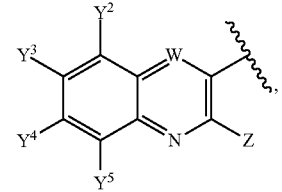
(A$^1$)

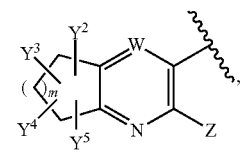
(A$^2$)

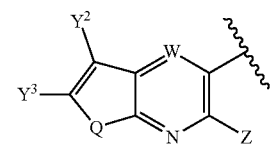
(A$^3$)

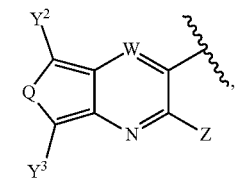
(A$^4$)

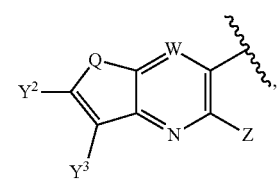
(A$^5$)

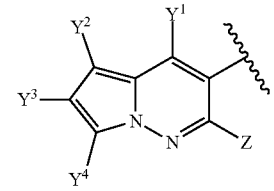
(A$^6$)

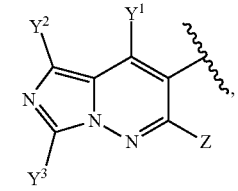
(A$^7$)

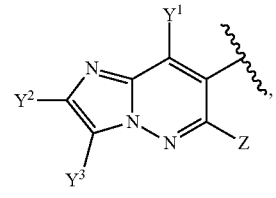
(A$^8$)

-continued

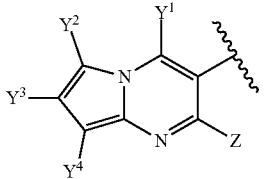
(A⁹)

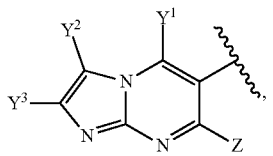
(A¹⁰)

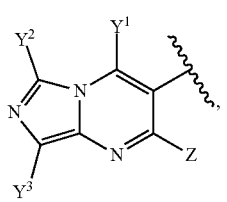
(A¹¹)

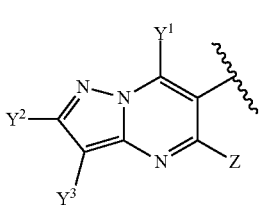
(A¹²)

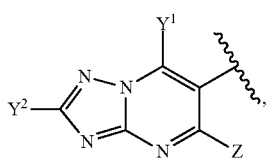
(A¹³)

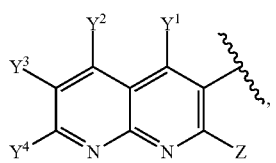
(A¹⁴)

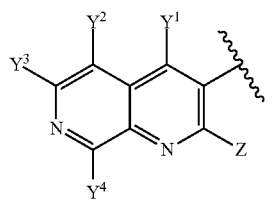
(A¹⁵)

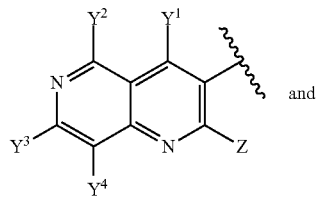
(A¹⁶)

and

-continued

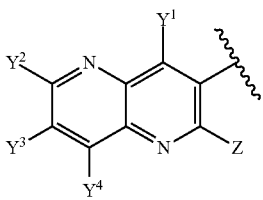
(A¹⁷)

wherein:

W is $CY^1$ or N;

Q is O, S or $NY^6$ with $Y^6$ being a hydrogen atom or a $C_1$-$C_8$-alkyl;

$Y^1$, $Y^2$, $Y^3$, $Y^4$ and $Y^5$ are independently a hydrogen atom or Y as recited in claim 1;

Z is as recited in claim 1; and m is 1, 2 or 3.

4. The compound according to claim 1, wherein Z is selected from the group consisting of hydrogen atom, halogen atom, hydroxyl, $C_1$-$C_6$-alkyl, $C_1$-$C_6$-halogenoalkyl comprising up to 9 halogen atoms that can be the same or different, $C_1$-$C_6$-alkoxy, $C_1$-$C_6$-halogenoalkoxy comprising up to 9 halogen atoms that can be the same or different and cyano.

5. The compound according to claim 1, wherein X is independently a halogen atom or a $C_1$-$C_6$-alkyl group.

6. The compound according to claim 1, wherein L is O or $CH_2$.

7. The compound according to claim 1, wherein n is 0 or 1.

8. The compound according to claim 1, wherein:

$R^1$ is a $C_1$-$C_6$-alkyl; and/or $R^2$ is a $C_1$-$C_6$-alkyl; and/or $R^3$ is selected from the group consisting of hydrogen atom, $C_1$-$C_6$-alkyl, $C_3$-$C_7$-cycloalkyl, aryl, aryl-$C_1$-$C_6$-alkyl, heterocyclyl, heterocyclyl-$C_1$-$C_6$-alkyl and hydroxyl.

9. The compound according to claim 3, wherein A is selected from the group consisting of $A^1$, $A^2$, $A^3$, $A^5$, $A^{10}$, $A^{12}$ and $A^{17}$.

10. The compound according to claim 3, wherein A represents a heterocycle of formula ($A^1$) wherein:

W is $CY^1$ or N;

$Y^1$ to $Y^5$ independently represent a hydrogen atom, a fluorine atom or a methyl group; and Z represents a hydrogen atom or a methyl group.

11. A fungicidal composition comprising one or more compounds of formula (I) according to claim 1 and one or more acceptable carriers.

12. A method for controlling unwanted phytopathogenic microorganisms which comprises applying one or more compounds according to claim 1 to the microorganisms and/or a habitat thereof.

13. A process for preparing the compound according to claim 1 which comprises:

reacting a halogenoaryl of formula (II) or a salt thereof:

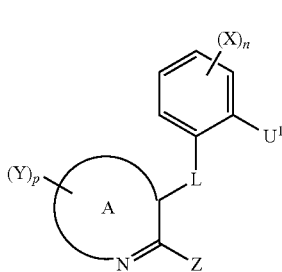

(II)

wherein U¹ represents a chlorine atom, a bromine atom, an iodine atom, a mesyl group, a tosyl group or a triflyl group, with a disilyl derivative of formula (IIIa):

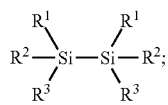

(IIIa)

or reacting a compound of formula (VI) or a salt thereof:

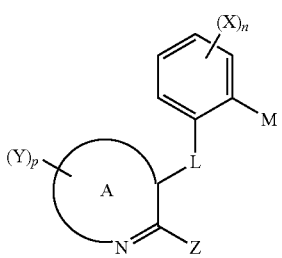

(VI)

wherein M represents an alkali metal that can be complexed by 1 to 2 ligands or a halogenomagnesium that can be complexed by 1 to 2 ligands, with a silyl derivative of formula (IIIb) or a silyl derivative of formula (IIIc):

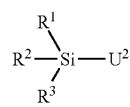

(IIIb)

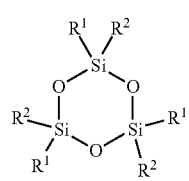

(IIIc)

wherein $U^2$ represents a chlorine atom, a bromine atom, an iodine atom or a $C_1$-$C_6$-alkoxy; or reacting a compound of formula (VIII) or a salt thereof with a compound of formula (IX):

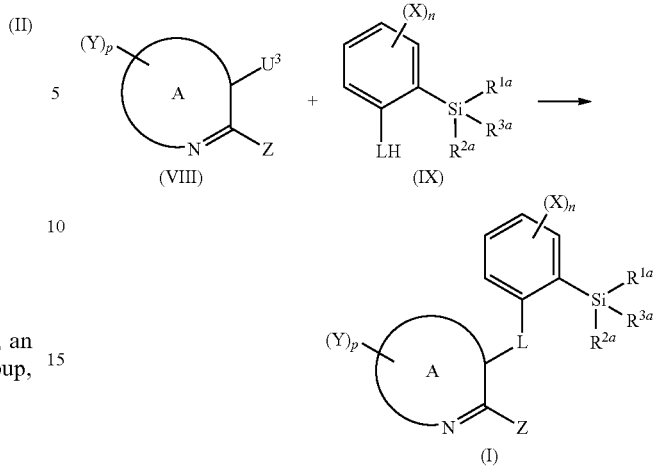

wherein L represents O, S or $NR^6$;

$U^3$ represents a chlorine atom, a bromine atom, an iodine atom, a mesyl group, a tosyl group or a triflyl group;

$R^{1a}$ and $R^{2a}$ independently represent a $C_1$-$C_8$-alkyl, a $C_2$-$C_8$-alkenyl, a $C_3$-$C_7$-cycloalkyl, an aryl or a heterocyclyl; and $R^{3a}$ represents a hydrogen atom, a $C_1$-$C_8$-alkyl, a $C_1$-$C_8$-halogenoalkyl comprising up to 9 halogen atoms that can be the same or different, a $C_2$-$C_8$-alkenyl, a $C_2$-$C_8$-alkynyl, a $C_3$-$C_7$-cycloalkyl, a $C_4$-$C_7$-cycloalkenyl, an aryl, an aryl-$C_1$-$C_8$-alkyl, a heterocyclyl, a heterocyclyl-$C_1$-$C_8$-alkyl, a hydroxy-$C_1$-$C_8$-alkyl, a $C_1$-$C_8$-alkoxy-$C_1$-$C_8$-alkyl, a $C_1$-$C_8$-alkylcarbonyloxy-$C_1$-$C_8$-alkyl, an aryloxy-$C_1$-$C_8$-alkyl, a heterocyclyloxy-$C_1$-$C_8$-alkyl, an amino-$C_1$-$C_8$-alkyl, a $C_1$-$C_8$-alkylamino-$C_1$-$C_8$-alkyl, a di-$C_1$-$C_8$-alkylamino-$C_1$-$C_8$-alkyl, an arylamino-$C_1$-$C_8$-alkyl, a di-arylamino-$C_1$-$C_8$-alkyl, a heterocyclylamino-$C_1$-$C_8$-alkyl, a $C_1$-$C_8$-alkylcarbonylamino-$C_1$-$C_8$-alkyl, a $C_1$-$C_8$-alkoxycarbonylamino-$C_1$-$C_8$-alkyl, a $C_1$-$C_8$-alkylsulfanyl-$C_1$-$C_8$-alkyl, a $C_1$-$C_8$-alkylsulfinyl-$C_1$-$C_8$-alkyl, a $C_1$-$C_8$-alkylsulfonyl-$C_1$-$C_8$-alkyl, or a cyano-$C_1$-$C_8$-alkyl; or reacting a compound of formula (X) or a salt thereof with a compound of formula (XI):

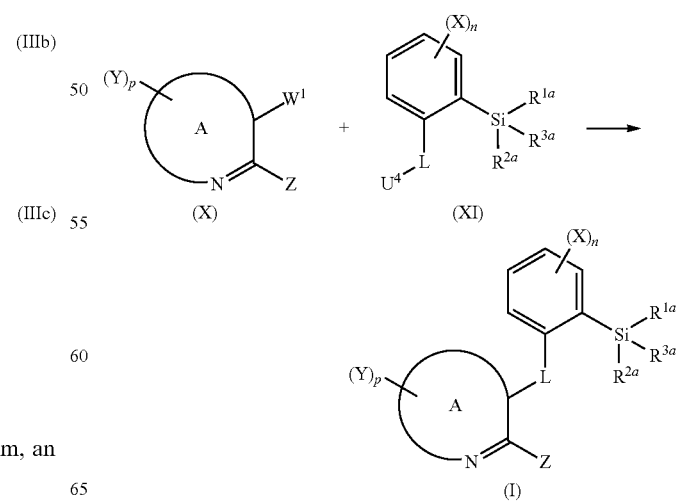

wherein L represents $CR^4R^5$;
R$^4$ and R$^5$ independently represent a hydrogen atom or a $C_1$-$C_8$ alkyl;
U$^4$ represents a bromine atom, a chlorine atom, an iodine atom, a mesyl group, a tosyl group or a triflyl group;
W$^1$ represents a boron derivative;
R$^{1a}$ and R$^{2a}$ independently represent a $C_1$-$C_8$-alkyl, a $C_2$-$C_8$-alkenyl, a $C_3$-$C_7$-cycloalkyl, an aryl or a heterocyclyl;
R$^{3a}$ represents a hydrogen atom, a $C_1$-$C_8$-alkyl, a $C_1$-$C_8$-halogenoalkyl comprising up to 9 halogen atoms that can be the same or different, a $C_2$-$C_8$-alkenyl, a $C_2$-$C_8$-alkynyl, a $C_3$-$C_7$-cycloalkyl, a $C_4$-$C_7$-cycloalkenyl, a aryl, a aryl-$C_1$-$C_8$-alkyl, a heterocyclyl, a heterocyclyl-$C_1$-$C_8$-alkyl, a hydroxy-$C_1$-$C_8$-alkyl, a $C_1$-$C_8$-alkoxy-$C_1$-$C_8$-alkyl, a $C_1$-$C_8$-alkylcarbonyloxy-$C_1$-$C_8$-alkyl, an aryloxy-$C_1$-$C_8$-alkyl, a heterocyclyloxy-$C_1$-$C_8$-alkyl, an amino-$C_1$-$C_8$-alkyl, a $C_1$-$C_8$-alkylamino-$C_1$-$C_8$-alkyl, a di-$C_1$-$C_8$-alkylamino-$C_1$-$C_8$-alkyl, an arylamino-$C_1$-$C_8$-alkyl, a di-arylamino-$C_1$-$C_8$-alkyl, a heterocyclylamino-$C_1$-$C_8$-alkyl, a $C_1$-$C_8$-alkylcarbonylamino-$C_1$-$C_8$-alkyl, a $C_1$-$C_8$-alkoxycarbonylamino-$C_1$-$C_8$-alkyl, a $C_1$-$C_8$-alkylsulfanyl-$C_1$-$C_8$-alkyl, a $C_1$-$C_8$-alkylsulfinyl-$C_1$-$C_8$-alkyl, a $C_1$-$C_8$-alkylsulfonyl-$C_1$-$C_8$-alkyl or a cyano-$C_1$-$C_8$-alkyl; or
reacting a compound of formula (VIII) or a salt thereof with a compound of formula (XII):

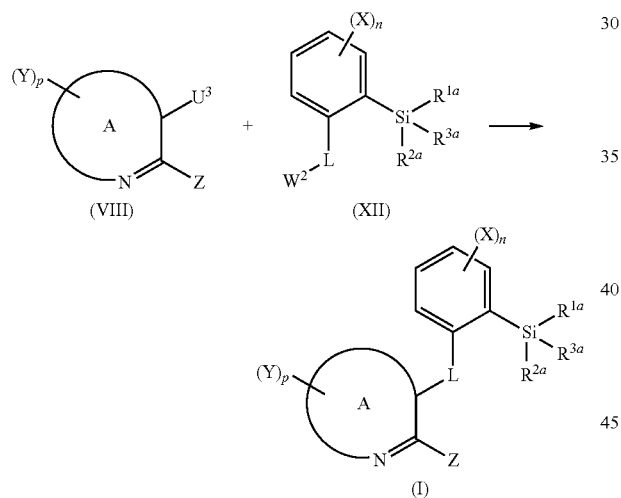

wherein L represents $CR^4R^5$;
R$^4$ and R$^5$ independently represent a hydrogen atom, a $C_1$-$C_8$-alkoxy or a $C_1$-$C_8$ alkyl;
U$^3$ represents a bromine atom, a chlorine atom, an iodine atom, a mesyl group, a tosyl group or a triflyl group;
W$^2$ represents a boron derivative;
R$^{1a}$ and R$^{2a}$ independently represent a $C_1$-$C_8$-alkyl, a $C_2$-$C_8$-alkenyl, a $C_3$-$C_7$-cycloalkyl, an aryl or a heterocyclyl;
R$^{3a}$ represents a hydrogen atom, a $C_1$-$C_8$-alkyl, a $C_1$-$C_8$-halogenoalkyl comprising up to 9 halogen atoms that can be the same or different, a $C_2$-$C_8$-alkenyl, a $C_2$-$C_8$-alkynyl, a $C_3$-$C_7$-cycloalkyl, a $C_4$-$C_7$-cycloalkenyl, an aryl, an aryl-$C_1$-$C_8$-alkyl, a heterocyclyl, a heterocyclyl-$C_1$-$C_8$-alkyl, a hydroxy-$C_1$-$C_8$-alkyl, a $C_1$-$C_8$-alkoxy-$C_1$-$C_8$-alkyl, a $C_1$-$C_8$-alkylcarbonyloxy-$C_1$-$C_8$-alkyl, an aryloxy-$C_1$-$C_8$-alkyl, a heterocyclyloxy-$C_1$-$C_8$-alkyl, an amino-$C_1$-$C_8$-alkyl, a $C_1$-$C_8$-alkylamino-$C_1$-$C_8$-alkyl, a di-$C_1$-$C_8$-alkylamino-$C_1$-$C_8$-alkyl, an arylamino-$C_1$-$C_8$-alkyl, a di-arylamino-$C_1$-$C_8$-alkyl, a heterocyclylamino-$C_1$-$C_8$-alkyl, a $C_1$-$C_8$-alkylcarbonylamino-$C_1$-$C_8$-alkyl, a $C_1$-$C_8$-alkoxycarbonylamino-$C_1$-$C_8$-alkyl, a $C_1$-$C_8$-alkylsulfanyl-$C_1$-$C_8$-alkyl, a $C_1$-$C_8$-alkylsulfinyl-$C_1$-$C_8$-alkyl, a $C_1$-$C_8$-alkylsulfonyl-$C_1$-$C_8$-alkyl or a cyano-$C_1$-$C_8$-alkyl; or
reacting a compound of formula (XIII) or a salt thereof with a compound of formula (XIV):

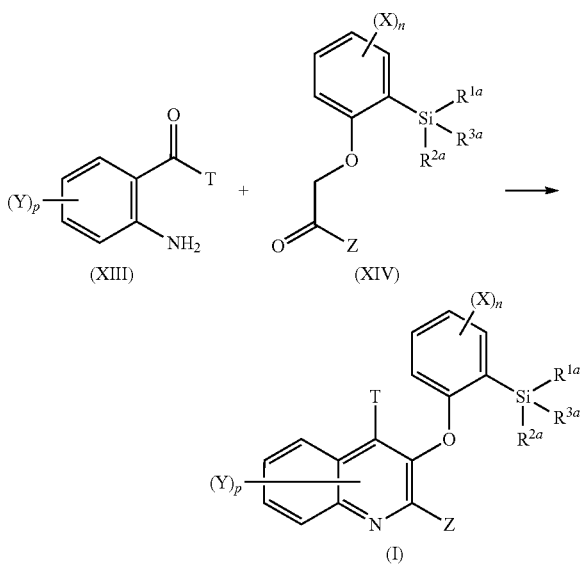

wherein T represents a hydrogen atom, a $C_1$-$C_8$ alkyl, a $C_3$-$C_7$-cycloalkyl, an aryl or a heterocyclyl;
p represents 0, 1, 2, 3 or 4;
Z represents a $C_1$-$C_8$-alkyl, a $C_3$-$C_7$-cycloalkyl, an aryl or a heterocyclyl;
R$^{1a}$ and R$^{2a}$ independently represent a $C_1$-$C_8$-alkyl, a $C_2$-$C_8$-alkenyl, a $C_3$-$C_7$-cycloalkyl, an aryl or a heterocyclyl;
R$^{3a}$ represents a hydrogen atom or a $C_1$-$C_8$-alkyl, a $C_1$-$C_8$-halogenoalkyl comprising up to 9 halogen atoms that can be the same or different, a $C_2$-$C_8$-alkenyl, a $C_2$-$C_8$-alkynyl, a $C_3$-$C_7$-cycloalkyl, a $C_4$-$C_7$-cycloalkenyl, an aryl, an aryl-$C_1$-$C_8$-alkyl, a heterocyclyl, a heterocyclyl-$C_1$-$C_8$-alkyl, a hydroxy-$C_1$-$C_8$-alkyl, a $C_1$-$C_8$-alkoxy-$C_1$-$C_8$-alkyl, a $C_1$-$C_8$-alkylcarbonyloxy-$C_1$-$C_8$-alkyl, an aryloxy-$C_1$-$C_8$-alkyl, a heterocyclyloxy-$C_1$-$C_8$-alkyl, an amino-$C_1$-$C_8$-alkyl, a $C_1$-$C_8$-alkylamino-$C_1$-$C_8$-alkyl, a di-$C_1$-$C_8$-alkylamino-$C_1$-$C_8$-alkyl, an arylamino-$C_1$-$C_8$-alkyl, a di-arylamino-$C_1$-$C_8$-alkyl, a heterocyclylamino-$C_1$-$C_8$-alkyl, a $C_1$-$C_8$-alkylcarbonylamino-$C_1$-$C_8$-alkyl, a $C_1$-$C_8$-alkoxycarbonylamino-$C_1$-$C_8$-alkyl, a $C_1$-$C_8$-alkylsulfanyl-$C_1$-$C_8$-alkyl, a $C_1$-$C_8$-alkylsulfinyl-$C_1$-$C_8$-alkyl, a $C_1$-$C_8$-alkylsulfonyl-$C_1$-$C_8$-alkyl or a cyano-$C_1$-$C_8$-alkyl.

14. The compound according to claim 3, wherein A is A$^1$.
15. The compound according to claim 10, wherein:
W is CY$^1$;
Y$^1$ is H;
Y$^2$ is H;
Y$^3$ is H;
Y$^4$ is F;
Y$^5$ is F;

Z is methyl;
L is O;
X is F attached to the phenyl ring in 3-position;
n is 1;
$R^1$ is methyl;
$R^2$ is methyl;
$R^3$ is hydroxyl;
and/or a salt, N-oxide, and/or an optically active isomer and/or geometric isomer.

16. The compound according to claim 1, wherein L is O.
17. The compound according to claim 1, wherein n is 1.
18. The compound according to claim 10, wherein W is $CY^1$.

\* \* \* \* \*